United States Patent
Anderson et al.

(10) Patent No.: US 11,957,695 B2
(45) Date of Patent: *Apr. 16, 2024

(54) METHODS AND COMPOSITIONS TARGETING GLUCOCORTICOID SIGNALING FOR MODULATING IMMUNE RESPONSES

(71) Applicants: The Broad Institute, Inc., Cambridge, MA (US); Massachusetts Institute of Technology, Cambridge, MA (US); The Brigham and Women's Hospital, Inc., Boston, MA (US)

(72) Inventors: Ana Carrizosa Anderson, Boston, MA (US); Asaf Madi, Boston, MA (US); Nandini Acharya, Boston, MA (US); Vijay K. Kuchroo, Boston, MA (US); Aviv Regev, Cambridge, MA (US)

(73) Assignees: The Broad Institute, Inc., Cambridge, MA (US); Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 409 days.

This patent is subject to a terminal disclaimer.

(21) Appl. No.: 16/396,461

(22) Filed: Apr. 26, 2019

(65) Prior Publication Data

US 2019/0365781 A1 Dec. 5, 2019

Related U.S. Application Data

(60) Provisional application No. 62/663,251, filed on Apr. 26, 2018, provisional application No. 62/663,520, filed on Apr. 27, 2018.

(51) Int. Cl.
| | | |
|---|---|---|
| *A61K 31/573* | (2006.01) | |
| *A61K 35/17* | (2015.01) | |
| *A61K 38/20* | (2006.01) | |
| *A61K 45/06* | (2006.01) | |
| *A61P 35/00* | (2006.01) | |

(52) U.S. Cl.
CPC ............ *A61K 31/573* (2013.01); *A61K 35/17* (2013.01); *A61K 38/20* (2013.01); *A61P 35/00* (2018.01); *A61K 45/06* (2013.01)

(58) Field of Classification Search
None
See application file for complete search history.

(56) References Cited

U.S. PATENT DOCUMENTS

| | | |
|---|---|---|
| 4,737,323 A | 4/1988 | Martin et al. |
| 4,837,028 A | 6/1989 | Allen |
| 5,143,854 A | 9/1992 | Fodor et al. |
| 5,288,644 A | 2/1994 | Beavis et al. |
| 5,324,633 A | 6/1994 | Fodor et al. |
| 5,432,049 A | 7/1995 | Fischer et al. |
| 5,470,710 A | 11/1995 | Weiss et al. |
| 5,492,806 A | 2/1996 | Drmanac et al. |
| 5,503,980 A | 4/1996 | Cantor |
| 5,510,270 A | 4/1996 | Fodor et al. |
| 5,525,464 A | 6/1996 | Drmanac et al. |
| 5,547,839 A | 8/1996 | Dower et al. |
| 5,580,732 A | 12/1996 | Grossman et al. |
| 5,580,737 A | 12/1996 | Polisky et al. |
| 5,641,870 A | 6/1997 | Rinderknecht et al. |
| 5,660,985 A | 8/1997 | Pieken et al. |
| 5,661,028 A | 8/1997 | Foote |
| 5,686,281 A | 11/1997 | Roberts |
| 5,800,992 A | 9/1998 | Fodor et al. |
| 5,811,097 A | 9/1998 | Allison et al. |
| 5,843,728 A | 12/1998 | Seed et al. |
| 5,851,828 A | 12/1998 | Seed et al. |
| 5,858,358 A | 1/1999 | June et al. |
| 5,869,326 A | 2/1999 | Hofmann |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,040,177 A | 3/2000 | Riddell et al. |
| 6,284,240 B1 | 9/2001 | Seed et al. |
| 6,352,694 B1 | 3/2002 | June et al. |
| 6,392,013 B1 | 5/2002 | Seed et al. |

(Continued)

FOREIGN PATENT DOCUMENTS

| | | |
|---|---|---|
| AU | 2015101792 A4 | 1/2016 |
| CA | 3 028 158 A1 | 12/2017 |

(Continued)

OTHER PUBLICATIONS

Castinetti et al. Neuroendocrinology, 92, 125-130, 2010. (Year: 2010).*
https://en.wikipedia.org/wiki/List_of_cancer_types—accessed May 22, 2020; https://www.cancer.gov/about-cancer/understanding/what-is-cancer). (Year: 2020).*
Anonymous Steroidogenesis inhibitors. Wikipedia, retrieved on Jun. 21, 2023. (Year: 2023).*

(Continued)

*Primary Examiner* — Elly-Gerald Stoica

(74) *Attorney, Agent, or Firm* — F. Brent Nix, Esq.; Johnson, Marcou, Isaacs & Nix, LLC; Michael B. Scher, Esq.

(57) ABSTRACT

The subject matter disclosed herein is generally directed to modulating T cell dysfunctional and effector states by modulating glucocorticoid and IL-27 signaling. The invention further relates to modulating immune states, such as CD8 T cell immune states, in vivo, ex vivo and in vitro. The invention further relates to diagnostic and screening methods.

12 Claims, 64 Drawing Sheets

Specification includes a Sequence Listing.

(56) References Cited

U.S. PATENT DOCUMENTS

| | | |
|---|---|---|
| 6,410,014 B1 | 6/2002 | Seed et al. |
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Cox et al. |
| 6,607,882 B1 | 8/2003 | Cox et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B2 | 6/2005 | June et al. |
| 6,905,874 B2 | 6/2005 | Berenson et al. |
| 6,933,113 B2 | 8/2005 | Case |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,637,307 B2 | 1/2014 | June et al. |
| 8,697,359 B1 | 4/2014 | Zhang |
| 8,697,854 B2 | 4/2014 | Schendel et al. |
| 8,735,553 B1 | 5/2014 | Li et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,062,111 B2 | 6/2015 | Nichol et al. |
| 9,101,584 B2 | 8/2015 | June et al. |
| 9,102,760 B2 | 8/2015 | June et al. |
| 9,102,761 B2 | 8/2015 | June et al. |
| 9,132,281 B2 | 9/2015 | Zeng et al. |
| 9,181,527 B2 | 11/2015 | Sentman |
| 9,233,125 B2 | 1/2016 | Davila et al. |
| 9,320,811 B2 | 4/2016 | Jure-kunkel |
| 9,327,014 B2 | 5/2016 | Gurney et al. |
| 2004/0171156 A1 | 9/2004 | Hartley et al. |
| 2004/0224402 A1 | 11/2004 | Bonyhadi et al. |
| 2010/0104509 A1 | 4/2010 | King et al. |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2013/0071414 A1 | 3/2013 | Dotti et al. |
| 2013/0236946 A1 | 9/2013 | Gouble |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0206749 A1* | 7/2014 | Gelfand ............... A61K 31/451 514/44 A |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0060691 A1 | 3/2016 | Giresi et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |
| 2016/0184362 A1* | 6/2016 | Duchateau ............ C12N 15/90 435/456 |
| 2016/0208243 A1 | 7/2016 | Zhang et al. |
| 2016/0208323 A1 | 7/2016 | Bernstein et al. |
| 2017/0211142 A1 | 7/2017 | Smargon et al. |
| 2017/0283504 A1 | 10/2017 | Wiltzius et al. |
| 2018/0085444 A1 | 3/2018 | Morgan et al. |
| 2018/0112255 A1 | 4/2018 | Chen et al. |
| 2021/0100774 A1 | 4/2021 | Anderson et al. |

FOREIGN PATENT DOCUMENTS

| | | |
|---|---|---|
| EP | 0 404 097 A2 | 12/1990 |
| EP | 0 785 280 A2 | 7/1997 |
| EP | 0 373 203 B2 | 2/2007 |
| EP | 2 764 103 A2 | 8/2014 |
| EP | 2 771 468 B1 | 2/2015 |
| EP | 2 784 162 B1 | 4/2015 |
| EP | 3 009 511 A2 | 4/2016 |
| WO | 92/15322 A1 | 9/1992 |
| WO | 93/11161 A1 | 6/1993 |
| WO | 95/21265 A1 | 8/1995 |
| WO | 96/31622 A1 | 10/1996 |
| WO | 96/40281 A2 | 12/1996 |
| WO | 97/10365 A1 | 3/1997 |
| WO | 97/27317 A1 | 7/1997 |
| WO | 97/49450 A1 | 12/1997 |
| WO | 98/52609 A1 | 11/1998 |
| WO | 03/020763 A2 | 3/2003 |
| WO | 03/057171 A2 | 7/2003 |
| WO | 2004/005229 A1 | 1/2004 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |

(56) References Cited

FOREIGN PATENT DOCUMENTS

| | | |
|---|---|---|
| WO | 2006/125962 A2 | 11/2006 |
| WO | 2008/038002 A2 | 4/2008 |
| WO | 2008/039818 A2 | 4/2008 |
| WO | 2009/012418 A2 | 1/2009 |
| WO | 2011/146862 A1 | 11/2011 |
| WO | 2012/058460 A2 | 5/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |
| WO | 2014/059173 A2 | 4/2014 |
| WO | 2014/070874 A1 | 5/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/089351 A1 | 6/2015 |
| WO | 2015/089354 A1 | 6/2015 |
| WO | 2015/089364 A1 | 6/2015 |
| WO | 2015/089419 A1 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/120096 A2 | 8/2015 |
| WO | 2015/142675 A2 | 9/2015 |
| WO | 2015/158671 A1 | 10/2015 |
| WO | 2015/187528 A1 | 12/2015 |
| WO | 2016/000304 A1 | 1/2016 |
| WO | 2016/011210 A2 | 1/2016 |
| WO | 2016/014789 A2 | 1/2016 |
| WO | 2016/028682 A1 | 2/2016 |
| WO | 2016/040476 A1 | 3/2016 |
| WO | 2016/049024 A2 | 3/2016 |
| WO | 2016/049163 A2 | 3/2016 |
| WO | 2016/049258 A2 | 3/2016 |
| WO | 2016/070061 A1 | 5/2016 |
| WO | 2016/089920 A1 | 6/2016 |
| WO | 2016/094867 A1 | 6/2016 |
| WO | 2016/094872 A1 | 6/2016 |
| WO | 2016/094874 A1 | 6/2016 |
| WO | 2016/094880 A1 | 6/2016 |
| WO | 2016/100974 A1 | 6/2016 |
| WO | 2016/106236 A1 | 6/2016 |
| WO | 2016/106244 A1 | 6/2016 |
| WO | 2016/161516 A1 | 10/2016 |
| WO | 2016/168584 A1 | 10/2016 |
| WO | 2016/191756 A1 | 12/2016 |
| WO | 2016/196388 A1 | 12/2016 |
| WO | 2016/205749 A1 | 12/2016 |
| WO | 2016/205759 A1 | 12/2016 |
| WO | 2017/004916 A1 | 1/2017 |
| WO | 2017/011804 A1 | 1/2017 |
| WO | 2017/031370 A1 | 2/2017 |
| WO | 2017/069958 A2 | 4/2017 |
| WO | 2017/070395 A1 | 4/2017 |
| WO | 2017/070605 A1 | 4/2017 |
| WO | 2017/075478 A2 | 5/2017 |
| WO | 2017/106290 A1 | 6/2017 |
| WO | 2017/156336 A1 | 9/2017 |
| WO | 2017/164936 A1 | 9/2017 |
| WO | 2017/211900 A1 | 12/2017 |
| WO | 2017/219027 A1 | 12/2017 |
| WO | 2018/005873 A1 | 1/2018 |
| WO | 2018/028647 A1 | 2/2018 |
| WO | 2018/035250 A1 | 2/2018 |
| WO | 2018/049025 A2 | 3/2018 |
| WO | 2018/170333 A1 | 9/2018 |
| WO | 2019/005866 A1 | 1/2019 |
| WO | 2019/014581 A1 | 1/2019 |
| WO | 2019/068099 A1 | 4/2019 |
| WO | 2020/006036 A1 | 1/2020 |

OTHER PUBLICATIONS

Acharya, et al., 2019, An endogenous glucocorticoid-cytokine signaling circuit promotes CD8+ T cell dysfunction in the tumor microenvironment, bioRxiv 799759; doi: doi.org/10.1101/799759, supplemental table S1, 104 pages, Oct. 10, 2019.

Barrat et al., "In Vitro Generation of Interleukin 10-producing Regulatory CD4(+) T Cells is Induced by Immunosuppressive drugs and Inhibited by T helper type 1 (Th1)- and Th2-inducing Cytokines", Journal of Experimental Medicine, vol. 195, No. 5, Mar. 4, 2002, 603-616.

Brattsand et al., "Cytokine Modulation by Glucocorticoids: Mechanisms and Actions in Cellular Studies", Alimentary Pharmacology & Therapeutics, vol. 10, Issue Suppl 2, 1996, 81-90.

Carey et al., "Nfil3 is a Glucocorticoid-egulated Gene Required for Glucocorticoid-induced Apoptosis in Male Murine T Cells", Endocrinology, vol. 154, No. 4, Apr. 2013, 1540-1552.

Chen et al., "Glucocorticoid Amplifies IL-2-Dependent Expansion of Functional FoxP3(+)CD4(+)CD25(+) T Regulatory Cells in Vivo and Enhances their Capacity to Suppress EAE", European Journal of Immunology, vol. 36, No. 8, Aug. 2006, 2139-2149.

Chihara et al., "Induction and Transcriptional Regulation of the Co-Inhibitory Gene Module in T Cells", Nature, vol. 558, No. 7710, Jun. 2018, 36 pages.

Fourcade et al., "Upregulation of Tim-3 and PD-1 Expression is Associated with Tumor Antigen-specific CD8+ T Cell Dysfunction in Melanoma Patients", Journal of Experimental Medicine, vol. 207, No. 10, Sep. 27, 2010, 2175-2186.

Hu et al., "Function of Regulatory T-cells Improved by Dexamethasone in Graves Disease", European Journal of Endocrinology, vol. 166, No. 4, Apr. 2012, 641-646.

Im et al., "Defining CD8+ T Cells that provide the Proliferative Burst after PD-1 Therapy", Nature, vol. 537, No. 7620, Sep. 15, 2016, 30 pages.

Jin et al., "Cooperation of Tim-3 and PD-1 in CD8 T-cell Exhaustion During Chronic Viral Infection", Proceedings of the National Academy of Sciences of the United States of America, vol. 107, No. 33, Aug. 17, 2010, 14733-14738.

Jubb et al., "Glucocorticoid Receptor Binding Induces Rapid and Prolonged Large-Scale Chromatin Decompaction at Multiple Target Loci", Cell Reports, vol. 21, No. 11, Dec. 12, 2017, 3022-3031.

Karin et al., "Dexamethasone Stimulation of Metallothionein Synthesis in HeLa Cell Cultures", Science, vol. 204, No. 4389, Apr. 13, 1979, 176-177.

(56) References Cited

OTHER PUBLICATIONS

Karwacz et al., "Critical Role of IRF1 and BATF in Forming Chromatin Landscape During Type 1 Regulatory Cell Differentiation", Nature Immunology, vol. 18, No. 4, Feb. 6, 2017, 12 pages.
Kurtulus et al., "Checkpoint Blockade Immunotherapy Induces Dynamic Changes in PD-1(−)CD8(+) Tumor-Infiltrating T Cells", Immunity, vol. 50, No. 1, Jan. 2019, 21 pages.
Le et al., "Glucocorticoid Receptor-Dependent Gene Regulatory Networks", PLOS Genetics, vol. 1, No. 2, Aug. 2005, 0159-0170.
Ling et al., "Circulating Dendritic Cells Subsets and CD4+Foxp3+ Regulatory T Cells in Adult Patients with Chronic ITP Before and After Treatment with High-dose Dexamethasome", European Journal of Endocrinology, vol. 79, No. 4, Oct. 2007, 310-316.
Petta et al., "The Interactome of the Glucocorticoid Receptor and Its Influence on the Actions of Glucocorticoids in Combatting Inflammatory and Infectious Diseases", Microbiology and Molecular Biology Reviews, vol. 80, No. 2, Jun. 2016, 495-522.
Piemonti et al., "Glucocorticoids Affect Human Dendritic Cell Differentiation and Maturation", Journal of Immunology, vol. 162, No. 11, Jun. 1, 1999, 6473-6481.
Quatrini et al., "Endogenous Glucocorticoids Control Host Resistance to Viral Infection Through the Tissue-specific Regulation of PD-1 Expression on NK cells", Nature Immunology, vol. 19, No. 9, Sep. 2018, 28 pages.
Rhen et al., "Antiinflammatory Action of Glucocorticoids—new Mechanisms for Old Drugs", The New England Journal of Medicine, vol. 353, No. 16, Oct. 20, 2005, 1711-1723.
Rutishauser et al., "Transcriptional Repressor Blimp-1 Promotes CD8(+) T Cell Terminal Differentiation and Represses the Acquisition of Central Memory T Cell Properties", Immunity, vol. 31, No. 2, Aug. 21, 2009, 296-308.
Sade-Feldman et al., "Defining T Cell States Associated with Response to Checkpoint Immunotherapy in Melanoma", Cell, vol. 175, No. 4, Nov. 1, 2018, 37 pages.
Sakuishi et al., "Targeting Tim-3 and PD-1 Pathways to Reverse T cell Exhaustion and Restore Anti-Tumor Immunity", Journal of Experimental Medicine, vol. 207, No. 10, Sep. 2010, 2187-2194.
Shin et al., "A Role for the Transcriptional Repressor Blimp-1 in CD8 T Cell Exhaustion During Chronic Viral Infection", Immunity, vol. 31, No. 2, Aug. 21, 2009, 21 pages.
Siddiqui et al., "Intratumoral Tcf1+ PD-1+ CD8+ T Cells with Stem-like Properties Promote Tumor Control in Response to Vaccination and Checkpoint Blockade Immunotherapy", Immunity, vol. 50, No. 1, Jan. 15, 2019, 28 pages.
Sidler et al., "Colon Cancer Cells Produce Immunoregulatory Glucocorticoids", Oncogene, vol. 30, No. 21, May 26, 2011, 2411-2419.
Singer et al., "A Distinct Gene Module for Dysfunction Uncoupled from Activation in Tumor-Infiltrating T Cells", Cell, vol. 171, No. 5, Nov. 16, 2017, 4 pages.
Singer et al., "A Distinct Gene Module for Dysfunction Uncoupled from Activation in Tumor-Infiltrating T Cells", Cell, vol. 166, No. 6, Sep. 8, 2016, 32 pages.
Suarez et al., "Enrichment of CD4+ CD25high T Cell Population in Patients with Systemic Lupus Erythematosus Treated with Glucocorticoids", Annals of the Rheumatic Diseases, vol. 65, No. 11, Nov. 2006, 1512-1517.
Wherry et al., "Molecular and Cellular Insights into T Cell Exhaustion", Nature Reviews Immunology, vol. 15, No. 8, Aug. 2015, 29 pages.
Zhu et al., "An IL-27/NFIL3 Signalling Axis Drives Tim-3 and IL-10 Expression and T-cell Dysfunction", Nature Communications, vol. 6, No. 6072, Jan. 23, 2015, 11 pages.
Wherry, et al., "Viral Persistence Alters CD8 T-Cell Immunodominance and Tissue Distribution and Results in Distinct Stages of Functional Impairment", Journal of Virology, vol. 77, No. 8, Apr. 2003, 4911-4927.
The Broad Institute, Inc., Final Office Action for U.S. Appl. No. 17/065,328, dated Feb. 7, 2023, 12 pages.
Azner et al, "Intratumoral Delivery of Immunotherapy—Act Locally, Think Globally", Journal of Immunology, 2017, 198(i), pp. 31-39, 2017.
Rettura et al., "Brief Communication: Metyrapone-Inhibited Oncogenesis in Mice Inoculated with a Murine Sarcoma Virus", Journal of the National Cancer Institute, vol. 51, No. 6, 1973, 3 pages.
Seifter et al., "Effect of Metyrapone and Aminoglutethimide on the Murine Sarcoma (MiSV-M) and Breast Adenocarcinoma (C3HBA)", Journal of Surgical Oncology, 12, pp. 281-288, 1979.
Acharya N, Madi A, Zhang H, et al. "Endogenous Glucocorticoid Signaling Regulates CD8+ T Cell Differentiation and Development of Dysfunction in the Tumor Microenvironment", Immunity. 2020;53(3):658-671.e6.

* cited by examiner

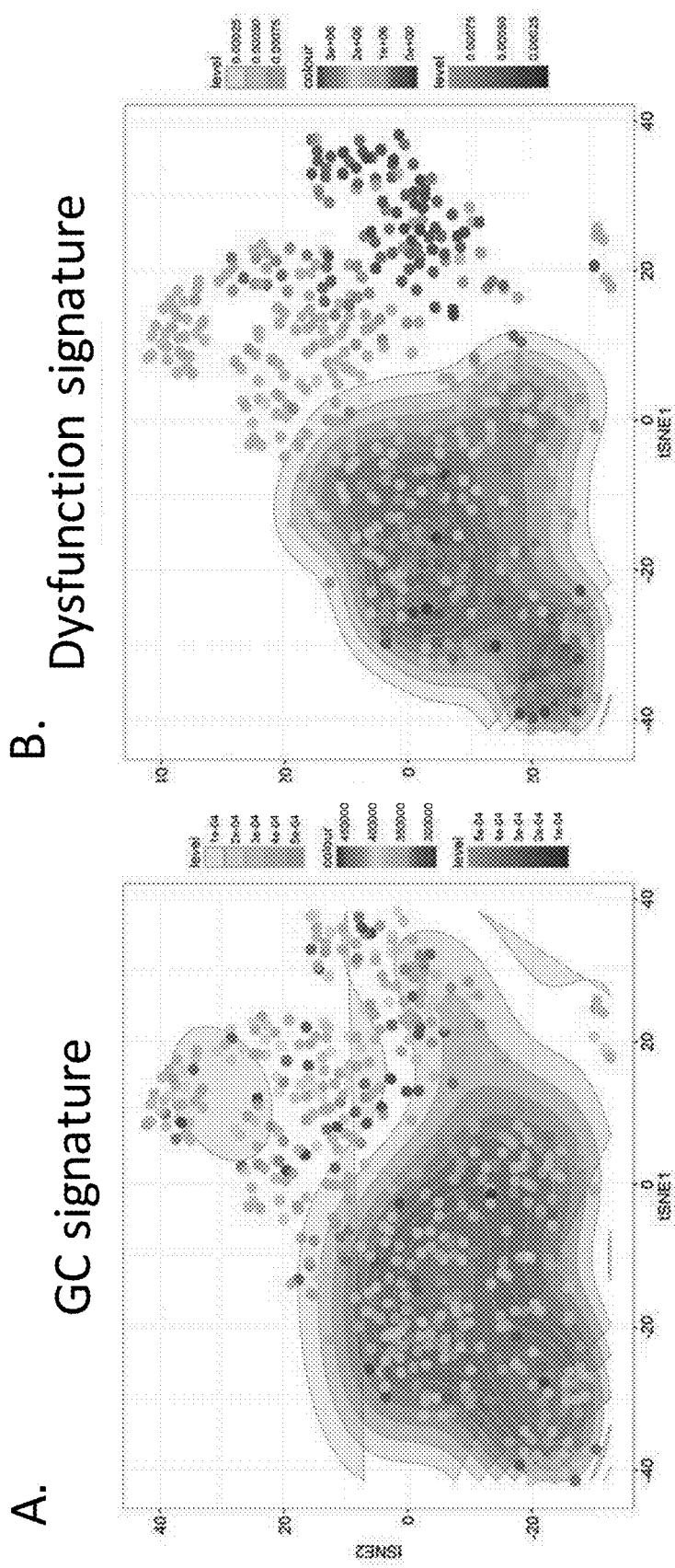
FIG. 1A-B

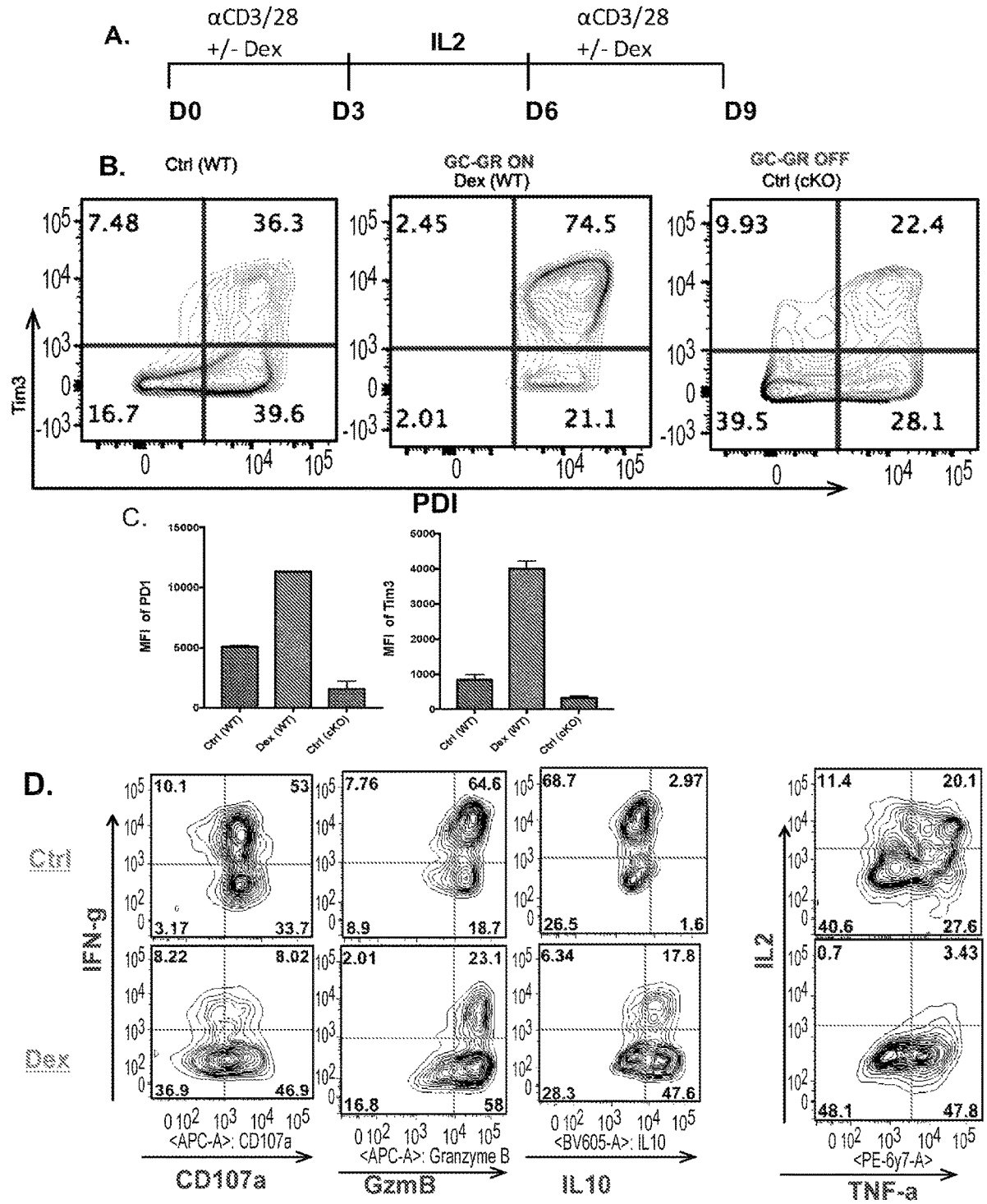
FIG. 3A-D

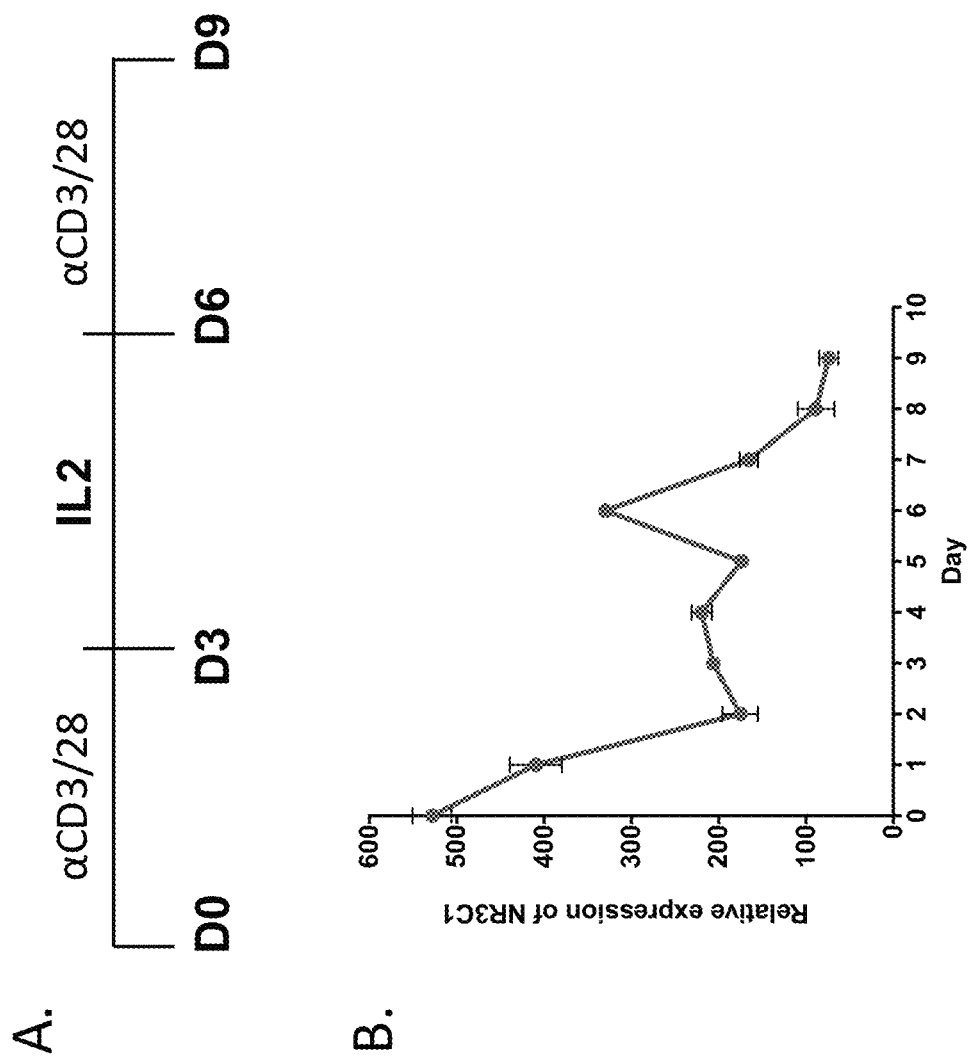
FIG. 4A-B

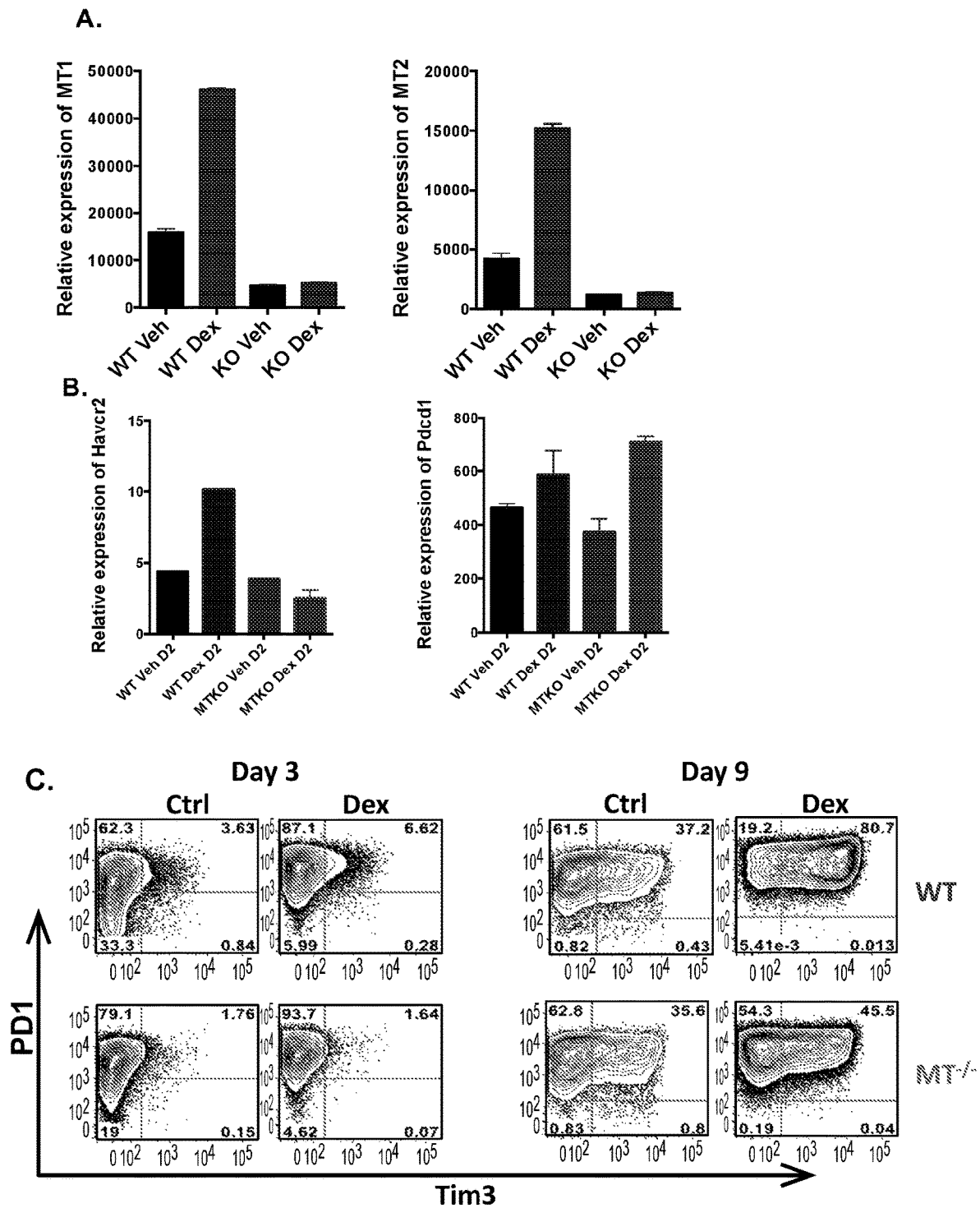
FIG. 5A-C

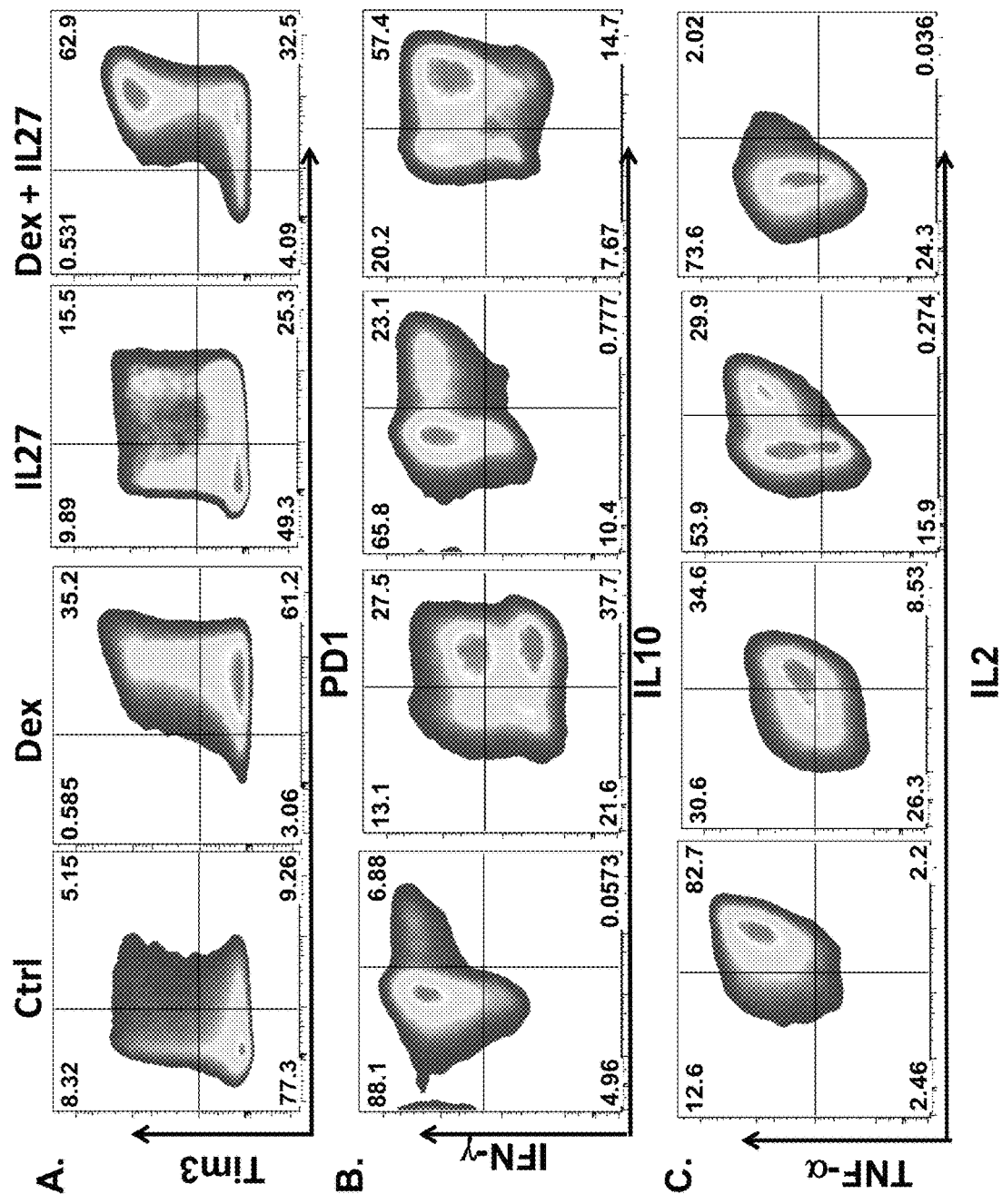
FIG. 10A-C

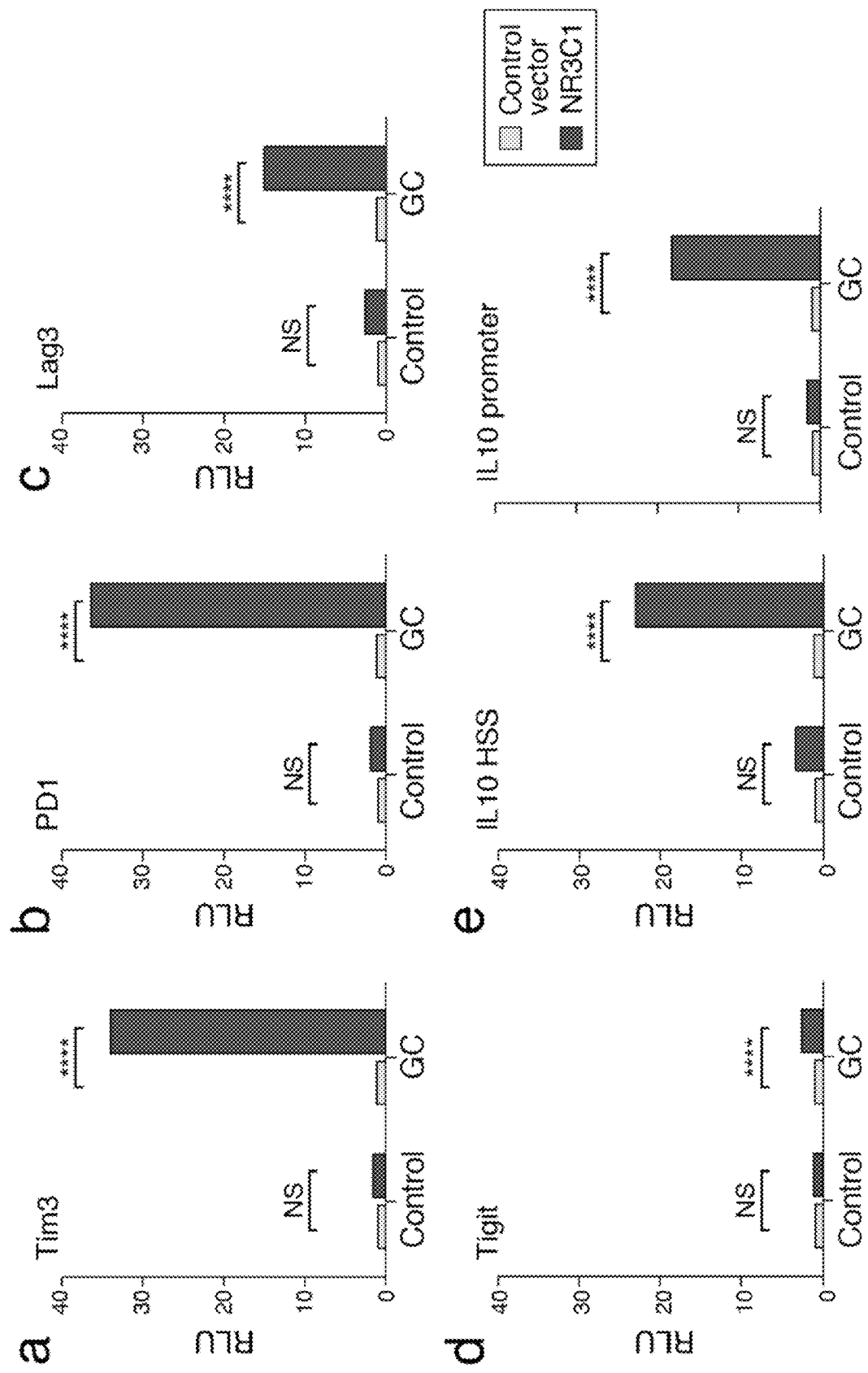
FIG. 21A-E

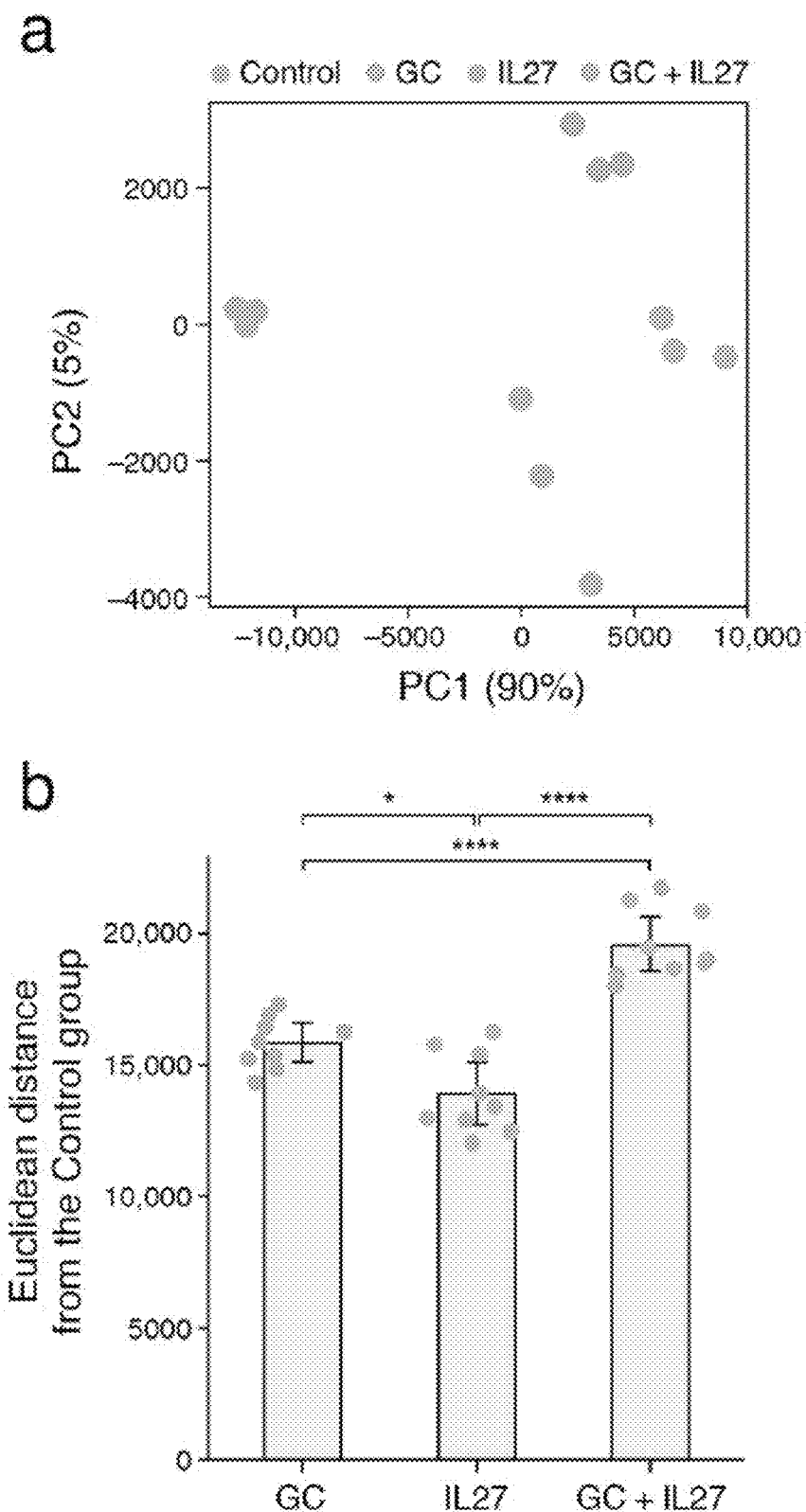
FIG. 22A-B

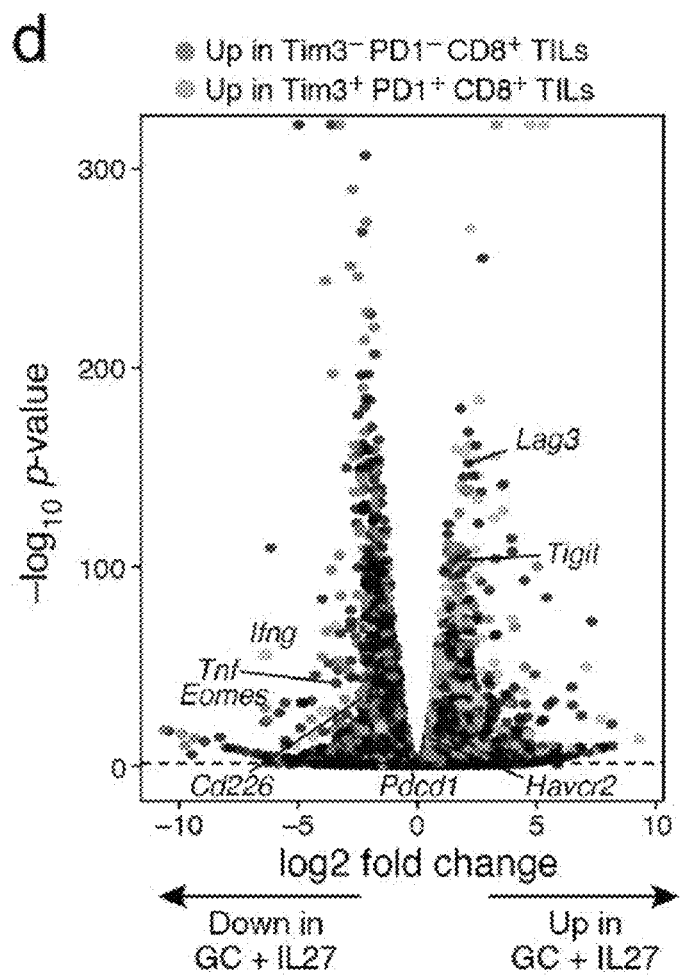
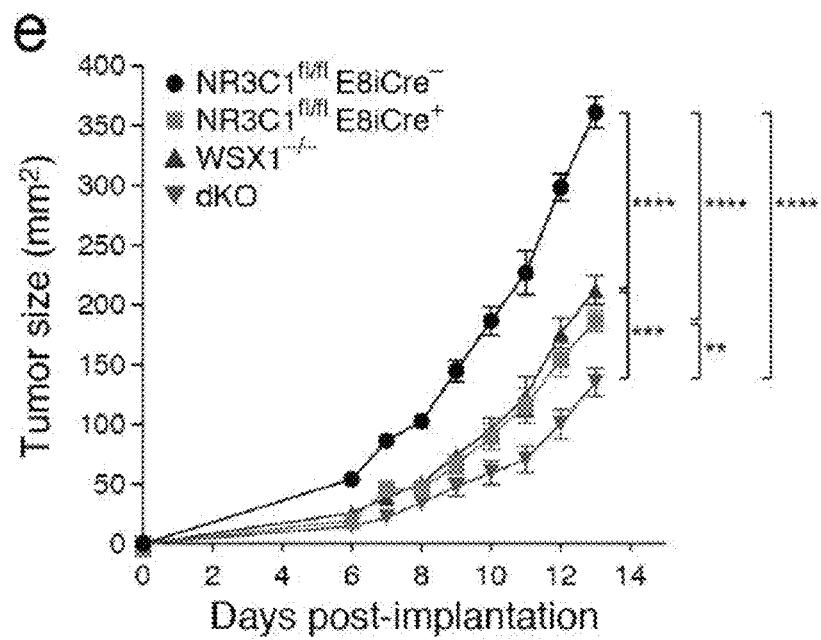
FIG. 22D-E

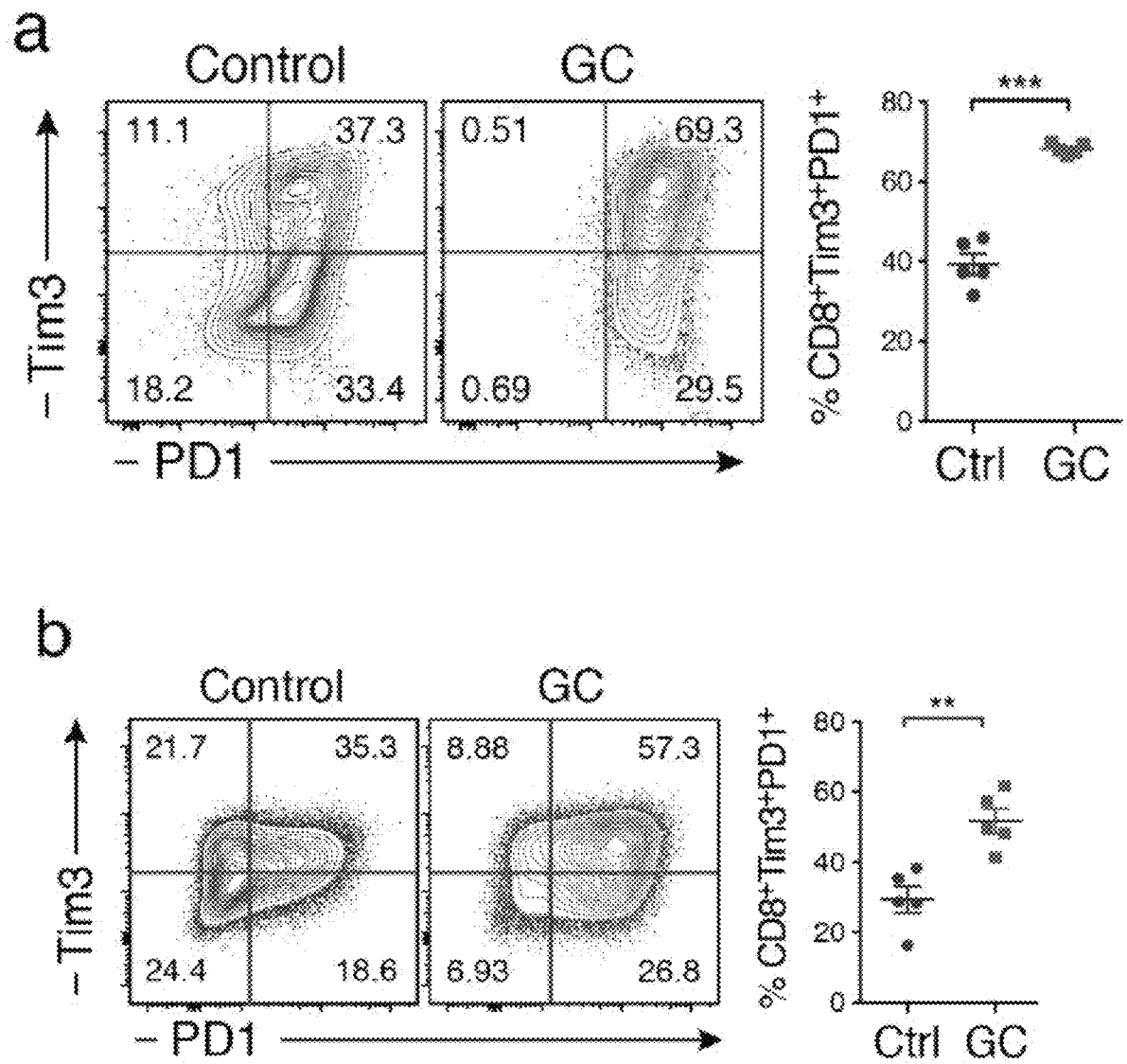
FIG. 25A-B

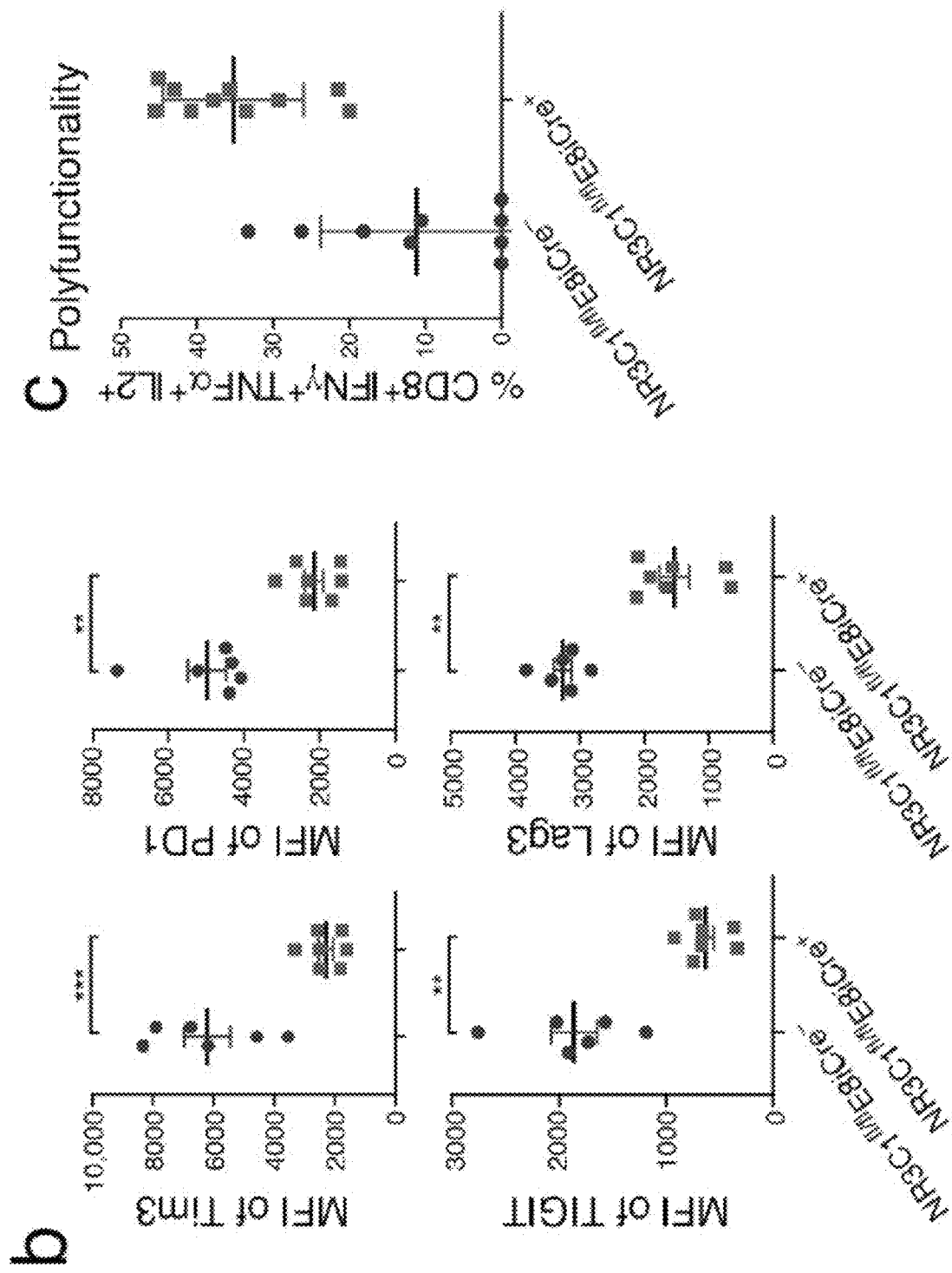
FIG. 26B-C

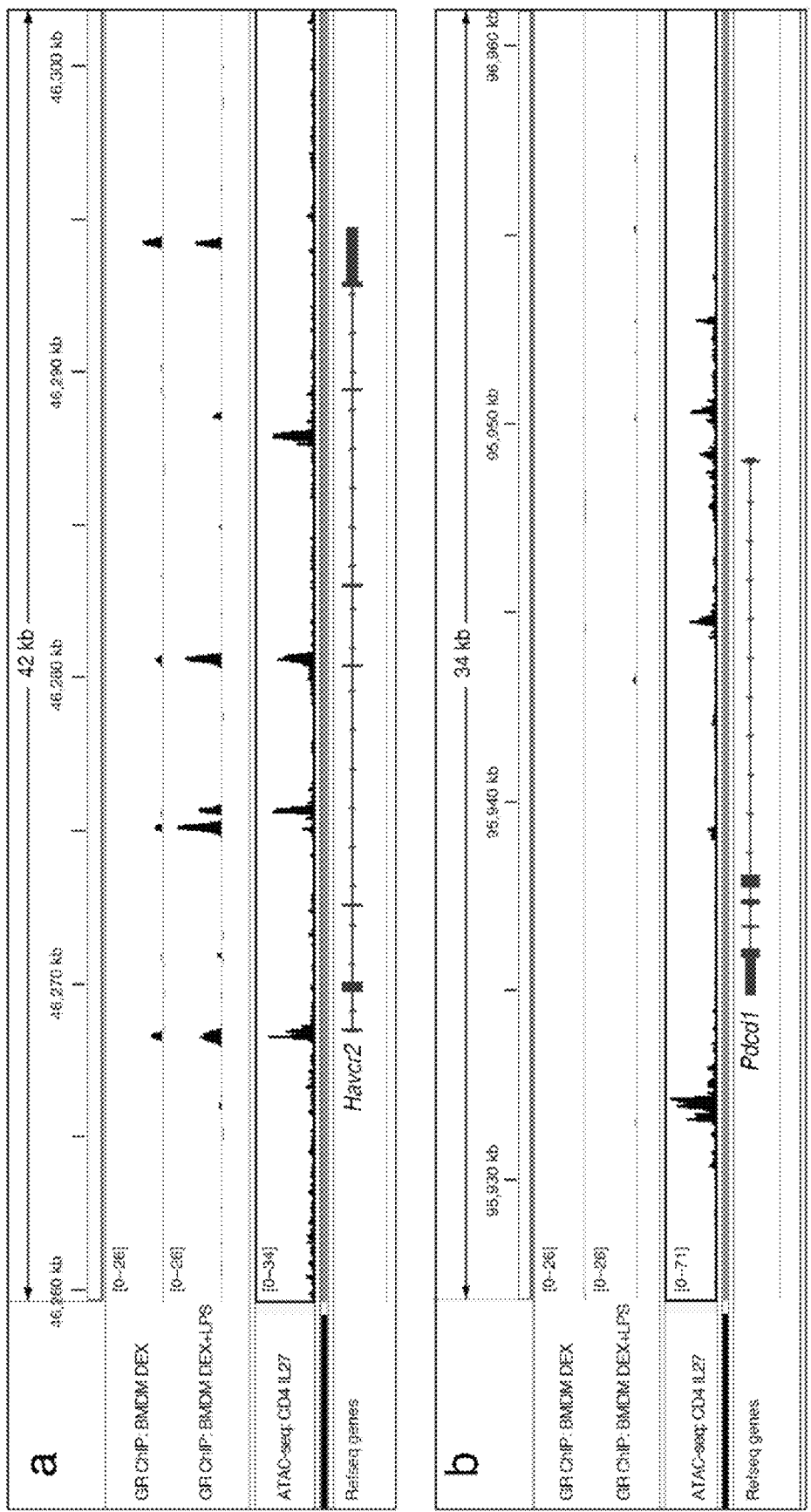
FIG. 27A-B

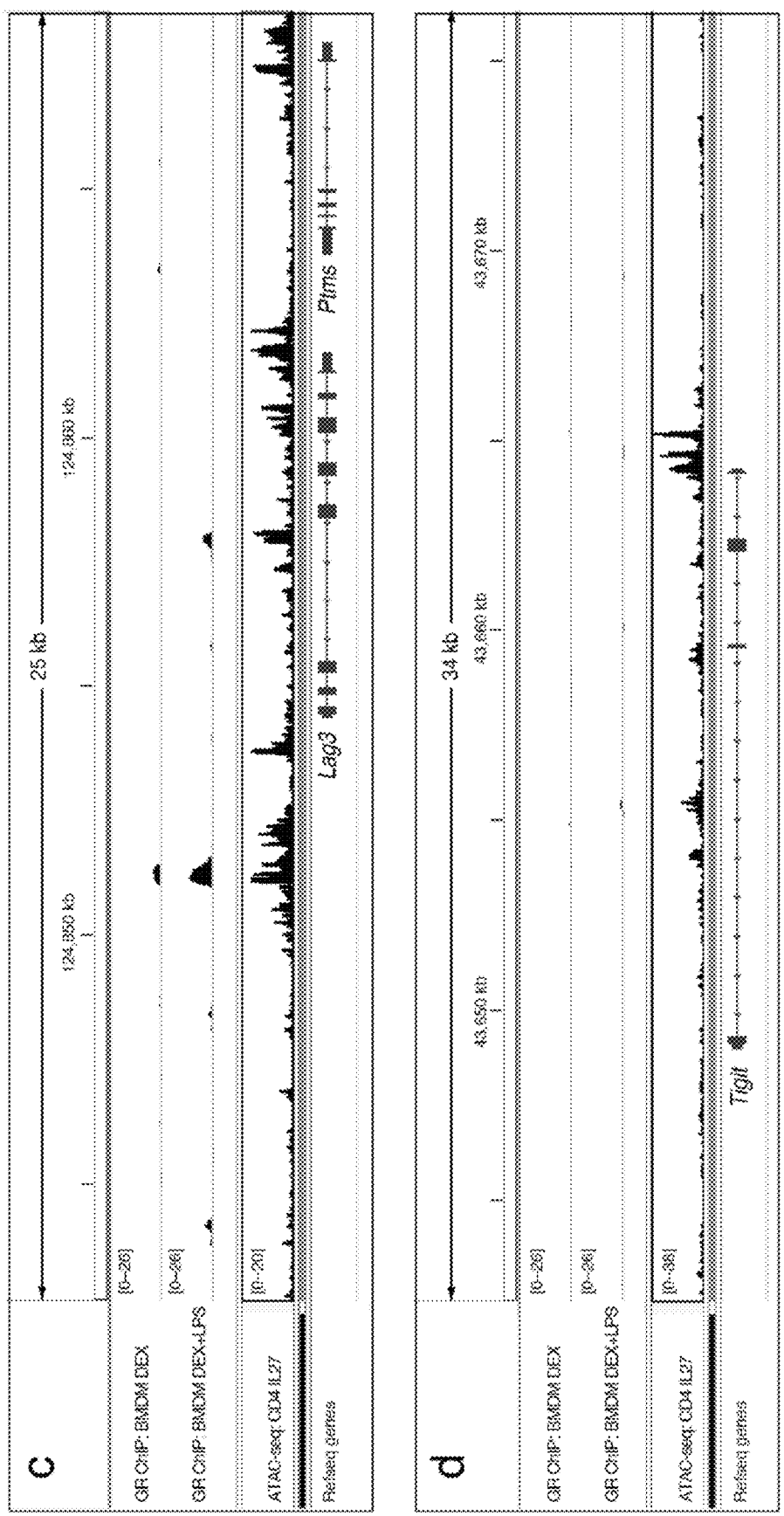
FIG. 27C-D

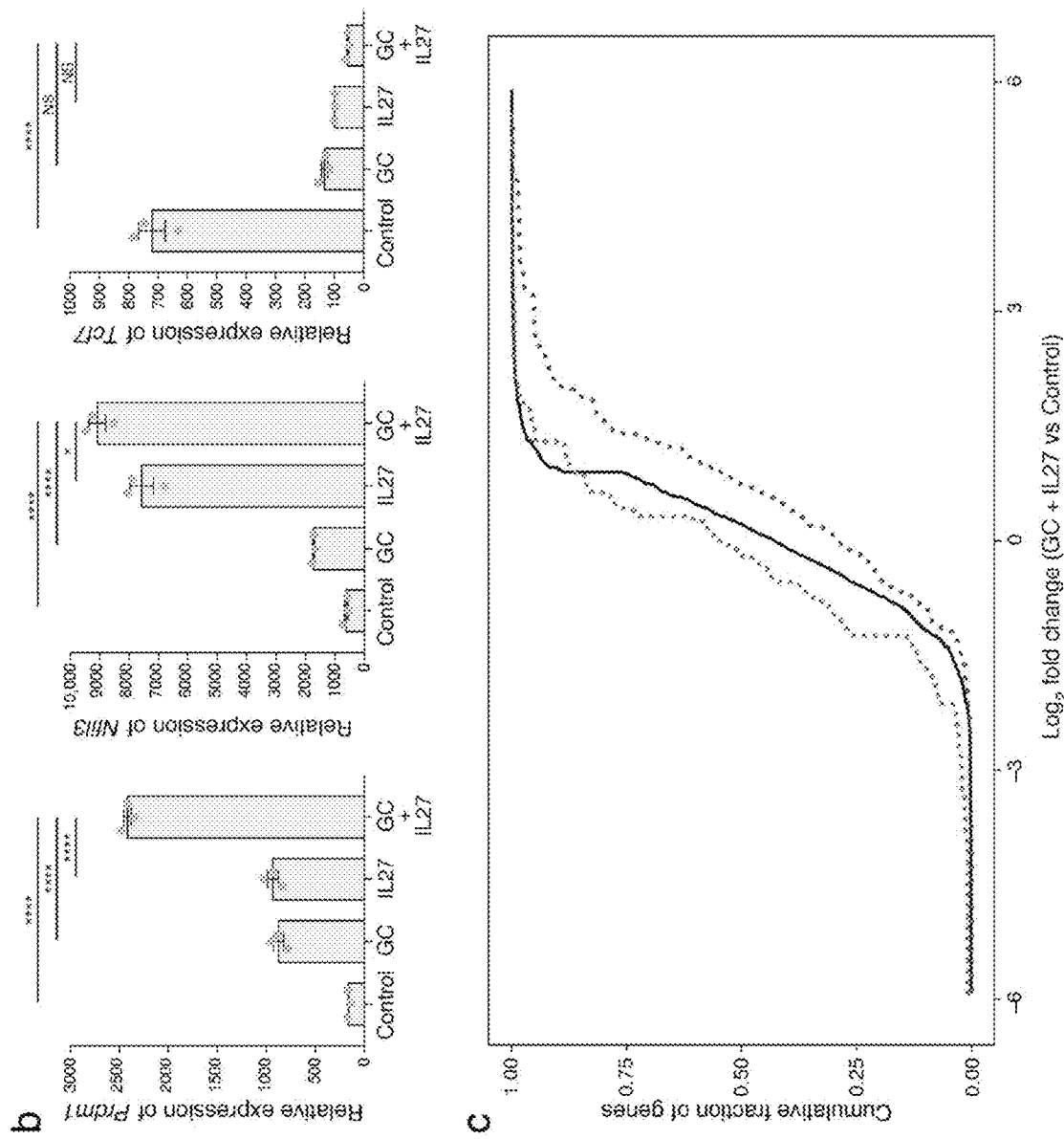
FIG. 28B-C

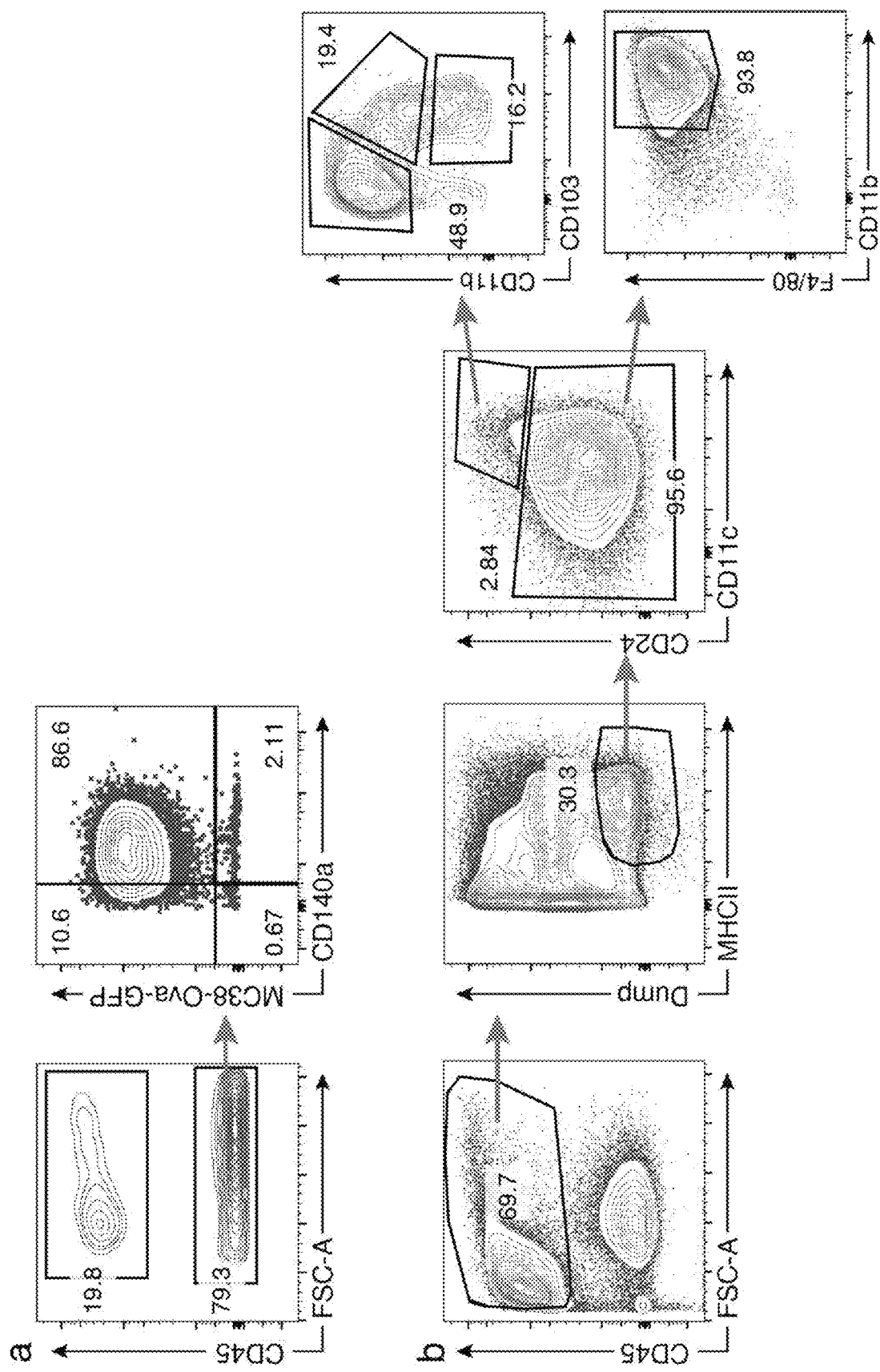
FIG. 29A-B

METHODS AND COMPOSITIONS TARGETING GLUCOCORTICOID SIGNALING FOR MODULATING IMMUNE RESPONSES

CROSS-REFERENCE TO RELATED APPLICATIONS

This application claims the benefit of U.S. Provisional Application Nos. 62/663,251, filed Apr. 26, 2018 and 62/663,520, filed Apr. 27, 2018. The entire contents of the above-identified applications are hereby fully incorporated herein by reference.

STATEMENT REGARDING FEDERALLY SPONSORED RESEARCH

This invention was made with government support under Grant No.(s) CA187975 AI073748, NS045937 and CA229400 awarded by the National Institutes of Health. The government has certain rights in the invention.

REFERENCE TO AN ELECTRONIC SEQUENCE LISTING

The contents of the electronic sequence listing (BROD_2485US_ST25.txt"; Size is 7 Kilobytes and it was created on Apr. 26, 2019) is herein incorporated by reference in its entirety.

REFERENCE TO AN ELECTRONIC TABLE

The instant application contains a "lengthy" Table which has been submitted electronically in ASCII format and is hereby incorporated by reference in its entirety. Said ASCII format, created on Apr. 22, 2019, is named Table_1.txt and is 1,900,000 bytes in size.

LENGTHY TABLES

The patent contains a lengthy table section. A copy of the table is available in electronic form from the USPTO web site (https://seqdata.uspto.gov/?pageRequest=docDetail&DocID=US11957695B2). An electronic copy of the table will also be available from the USPTO upon request and payment of the fee set forth in 37 CFR 1.19(b)(3).

TECHNICAL FIELD

The subject matter disclosed herein is generally directed to modulating T cell dysfunctional and effector states by modulating glucocorticoid and IL-27 signaling.

BACKGROUND

Although the immune system has the capacity to fight cancer, signals present within the tumor microenvironment (TME) actively suppress anti-tumor immune responses. In particular, CD8$^+$ T cells, key mediators of anti-tumor immunity, develop a dysfunctional or "exhausted" state in the highly immunosuppressive TME[1], but the key mechanisms and factors in the TME that promote T cell dysfunction have not been identified. Dysfunctional CD8$^+$ T cells exhibit defective cytolytic activity, loss of pro-inflammatory cytokines, and induction of the immunosuppressive cytokine IL-10[2]. Accordingly, dysfunctional CD8$^+$ T cells are not only poor mediators of tumor clearance but also contribute to the suppressive microenvironment within the tumor. Therefore, understanding the signals, both T cell intrinsic and extrinsic, that contribute to the development of T cell dysfunction is of key importance in devising effective therapies to improve anti-tumor CD8$^+$ T cell responses.

Consequently, there exists a continuous need to provide additional and preferably improved markers, products and methods allowing to determine and modulate the functional state of immune cells. Likewise, there exists a continuous need to provide additional and preferably improved molecular targets involved in immune responses, as well as therapeutically useful substances and compositions impinging on such molecular targets to modulate immune responses.

SUMMARY

In certain example embodiments, the present invention provides for modulating T cell dysfunctional and effector immune states by modulating glucocorticoid and IL-27 signaling in T cells. The present invention may be advantageous for use in generating in vitro models, cells for adoptive transfer and for treatment of diseases requiring modulation of an immune response.

In one aspect, the present invention provides for a method of altering T cell dysfunction in a subject in need thereof comprising administering to the subject one or more agents capable of modulating glucocorticoid signaling, wherein a dysfunctional immune state in the subject is increased when glucocorticoid signaling is enhanced, or wherein a dysfunctional immune state in the subject is decreased when glucocorticoid signaling is reduced. In certain embodiments, the method further comprises administering to the subject one or more agents capable of modulating IL-27 signaling, wherein a dysfunctional immune state in the subject is increased when both glucocorticoid signaling and IL-27 signaling are enhanced, or wherein a dysfunctional immune state in the subject is decreased when both glucocorticoid signaling and IL-27 signaling are reduced.

In certain embodiments, the one or more agents capable of modulating glucocorticoid signaling comprise a glucocorticoid or a glucocorticoid agonist in an amount sufficient to increase dysfunction. In certain embodiments, the glucocorticoid agonist binds glucocorticoid and enhances its binding to glucocorticoid receptor. In certain embodiments, the glucocorticoid agonist increases expression of glucocorticoid receptor. In certain embodiments, the glucocorticoid agonist increases expression or activity of an enzyme of steroid biogenesis in macrophages. In certain embodiments, the enzyme is Cyp11a1.

In certain embodiments, the one or more agents capable of modulating glucocorticoid signaling comprise a glucocorticoid antagonist in an amount sufficient to decrease dysfunction. In certain embodiments, the glucocorticoid antagonist binds glucocorticoid and decreases its binding to glucocorticoid receptor. In certain embodiments, the glucocorticoid antagonist decreases expression of glucocorticoid receptor. In certain embodiments, the glucocorticoid antagonist decreases expression or activity of an enzyme of steroid biogenesis in macrophages. In certain embodiments, the enzyme is Cyp11a1.

In certain embodiments, the one or more agents capable of modulating IL-27 signaling comprise IL-27 or an IL-27 agonist in an amount sufficient to increase dysfunction. In certain embodiments, the IL-27 agonist binds IL-27 and enhances its binding to IL-27R. In certain embodiments, the IL-27 agonist increases expression of IL-27Ra. In certain embodiments, the IL-27 agonist increases expression of IL-27 or an IL-27 subunit in dendritic cells.

In certain embodiments, the one or more agents capable of modulating IL-27 signaling comprise an IL-27 antagonist in an amount sufficient to decrease dysfunction. In certain embodiments, the IL-27 antagonist binds IL-27 and reduces its binding to IL-27R. In certain embodiments, the IL-27 antagonist decreases expression of IL-27Ra. In certain embodiments, the IL-27 antagonist decreases expression of IL-27 or an IL-27 subunit in dendritic cells.

In another aspect, the present invention provides for a method of altering T cell dysfunction in a subject in need thereof comprising administering to the subject one or more T cells contacted with one or more agents capable of modulating glucocorticoid signaling, wherein the dysfunctional state of the one or more T cells is increased when glucocorticoid signaling is enhanced, or wherein the dysfunctional state of the one or more T cells is decreased when glucocorticoid signaling is reduced. In certain embodiments, the one or more T cells are further contacted with one or more agents capable of modulating IL-27 signaling, wherein the dysfunctional state of the one or more T cells is increased when both glucocorticoid signaling and IL-27 signaling are enhanced, or wherein the dysfunctional state of the one or more T cells is decreased when both glucocorticoid signaling and IL-27 signaling are reduced.

In certain embodiments, the one or more T cells administered to the subject are in vitro differentiated in a culture media comprising IL-27 and a glucocorticoid. In certain embodiments, the T cells are CD8+ T cells or naïve T cells.

In certain embodiments, the one or more agents capable of modulating glucocorticoid signaling comprise a glucocorticoid or a glucocorticoid agonist in an amount sufficient to increase dysfunction. In certain embodiments, the glucocorticoid agonist binds glucocorticoid and enhances its binding to glucocorticoid receptor. In certain embodiments, the glucocorticoid agonist increases expression of glucocorticoid receptor.

In certain embodiments, the one or more agents capable of modulating glucocorticoid signaling comprise a glucocorticoid antagonist in an amount sufficient to decrease dysfunction. In certain embodiments, the glucocorticoid antagonist binds glucocorticoid and decreases its binding to glucocorticoid receptor. In certain embodiments, the glucocorticoid antagonist decreases expression of glucocorticoid receptor.

In certain embodiments, the one or more agents capable of modulating IL-27 signaling comprise IL-27 or an IL-27 agonist in an amount sufficient to increase dysfunction. In certain embodiments, the IL-27 agonist binds IL-27 and enhances its binding to IL-27R. In certain embodiments, the IL-27 agonist increases expression of IL-27Ra.

In certain embodiments, the one or more agents capable of modulating IL-27 signaling comprise an IL-27 antagonist in an amount sufficient to decrease dysfunction. In certain embodiments, the IL-27 antagonist binds IL-27 and reduces its binding to IL-27R. In certain embodiments, the IL-27 antagonist decreases expression of IL-27Ra.

In another aspect, the present invention provides for a method of altering T cell dysfunction in a subject in need thereof comprising administering to the subject one or more agents capable of modulating the expression, activity or function of one or more glucocorticoid+IL-27 signature genes or gene products; or administering one or more T cells contacted with the one or more agents, wherein the one or more genes are selected from the group consisting of: Lilrb4, Bcl2, Nupr1, Tgfb3, Tnfrsf4, Il24, Ramp1, Klf10, Cd27, Cd28, Tle2, Btla, Xcl1, Egr2, Entpd1, Tcf7, Nfil3, Prdm1, Mt1, Mt2, Stat3, Tigit, Havcr2, Lag3, Itga7, Acvrl1, Gpr125, Aqp11, Kit, Trip6, Il10, Enpp2, Asb2, Jag2, Tnfrsf18, Smyd3, Dbp, Ddit3, Tnfrsf14, Zfp467, Crebl2, Hif1a, Irf6, Alcam, Bach1, Pdcd1, Ctla4, Epcam, Gpld1, Cd68, Prnp, Gab2, Vldlr, Il10, Il1r2, Nt5e, Itgae, C1qtnf4, Ccr7, Cd226, Ifng, Ccl4, Spp1, Ccl3, Cd48, Cxcr3, Nanog, Tfrc, Hmgn2, Ptrf, Icam2, Cd40lg and Il1a; or Table 7A and Table 7B; or Table 5A and Table 5B; or Table 6A and Table 6B; or Table 3; or Table 2A and Table 2B; or Table 1, wherein modulating the expression, activity or function comprises increasing the expression, activity or function of glucocorticoid+IL-27 signature genes that are downregulated as compared to the control according to Table 1 and decreasing the expression, activity or function of glucocorticoid+IL-27 signature genes that are upregulated as compared to the control according to Table 1, whereby dysfunction is decreased, or wherein modulating the expression, activity or function comprises decreasing the expression, activity or function for glucocorticoid+IL-27 signature genes that are downregulated as compared to the control according to Table 1 and increasing the expression, activity or function for glucocorticoid+IL-27 signature genes that are upregulated as compared to the control according to Table 1, whereby dysfunction is increased. In certain embodiments, Epcam, Gpld1, Cd68, Prnp, Gab2, Vldlr, Il10, Il1r2, Nt5e, Itgae, C1qtnf4, Tgfb3, Itga7, Acvrl1, Gpr125, Aqp11, Ramp1, Kit, Trip6, Il10, Enpp2, Asb2, Jag2, Tnfrsf18, Prdm1, Smyd3, Tigit, Dbp, Tle2, Ddit3, Klf10, Tnfrsf14, Zfp467, Entpd1, Nfil3, Crebl2, Hif1a, Irf6, Lag3, Alcam, Mt2, Stat3, Mt1, Bach1, Cd28, Havcr2, Pdcd1, Ctla4 and Cd27 are upregulated in glucocorticoid+IL-27 as compared to the control. In certain embodiments, Ifng, Ccl4, Bcl2, Spp1, Btla, Ccl3, Cd48, Cxcr3, Nanog, Tfrc, Xcl1, Lilrb4, Nupr1, Hmgn2, Il24, Ptrf, Icam2, Cd40lg, Il1a, Tcf7, Tnfrsf4, Egr2, Ccr7 and Cd226 are downregulated in glucocorticoid+IL-27 as compared to the control.

In certain embodiments, the T cells are in vitro differentiated in a culture media comprising the one or more agents. In certain embodiments, the T cells are CD8+ T cells or naïve T cells.

In certain embodiments, the agent is: capable of targeting or binding to one or more cell surface exposed gene products; or capable of targeting or binding to one or more receptors or ligands specific for a cell surface exposed gene product; or capable of targeting or binding to one or more secreted gene products; or capable of targeting or binding to one or more receptors specific for a secreted gene product. In certain embodiments, the one or more agents comprise an antibody, antibody fragment, intrabody, antibody-like protein scaffold, aptamer, polypeptide, small molecule, small molecule degrader, genetic modifying agent, or any combination thereof.

In certain embodiments, the genetic modifying agent comprises a CRISPR system, RNAi system, a zinc finger nuclease system, a TALE, or a meganuclease. In certain embodiments, the CRISPR system comprises Cas9, Cas12, or Cas14. In certain embodiments, the CRISPR system comprises a dCas fused or otherwise linked to a nucleotide deaminase. In certain embodiments, the nucleotide deaminase is a cytidine deaminase or an adenosine deaminase. In certain embodiments, the dCas is a dCas9, dCas12, dCas13, or dCas14. In certain embodiments, the CRISPR system is administered as a ribonucleoprotein (RNP) complex.

In certain embodiments, the method is for treating an autoimmune disease in a subject in need thereof. In certain embodiments, the autoimmune disease is selected from Multiple Sclerosis (MS), Irritable Bowel Disease (IBD), Crohn's disease, spondyloarthritides, Systemic Lupus Erythematosus (SLE), Vitiligo, rheumatoid arthritis, psoriasis, Sjögren's syndrome, and diabetes. In certain embodiments, the method is for treating an inflammatory disorder in a subject in need thereof. In certain embodiments, the inflammatory disorder is selected from psoriasis, inflammatory bowel diseases (IBD), allergic asthma, food allergies and rheumatoid arthritis. In certain embodiments, the method is for inducing immune tolerance or preventing graft versus host disease in a subject having received an organ transplant.

In certain embodiments, the method is for treating cancer in a subject in need thereof, whereby a tumor specific immune response is enhanced. In certain embodiments, the treatment is a cancer adjuvant therapy comprising administering glucocorticoid therapy and one or more agents capable of modulating one or more genes or gene products according to claim 37, whereby the subject maintains T cell immunity against tumor cells. In certain embodiments, the adjuvant therapy is administered to a subject having received chemotherapy. In certain embodiments, the one or more genes or gene products are selected from the group consisting of PD-1, TIM3, TIGIT, LAG3, MT1, MT2, and IL-10. In certain embodiments, the agent is an antibody or fragment thereof selected from the group consisting of anti-PD1, anti-TIM3, anti-TIGIT, anti-LAG3 and anti-IL-10. In certain embodiments, the agent is an MT1/2 antagonist. In certain embodiments, the glucocorticoid is dexamethasone (Dex).

In another aspect, the present invention provides for an isolated T cell modified to comprise altered IL-27 and glucocorticoid signaling. In certain embodiments, the T cell is in vitro differentiated in a culture media comprising IL-27 and a glucocorticoid, whereby dysfunction is increased. In certain embodiments, the T cell is modified to comprise decreased IL-27 signaling and glucocorticoid signaling, whereby dysfunction is decreased. In certain embodiments, the T cell comprises decreased or abolished expression or activity of the IL-27 receptor and the glucocorticoid receptor. In certain embodiments, the isolated T cell is modified to comprise modulated expression or activity of one or more genes or gene products according to claim 37. In certain embodiments, the T cell comprises a genetic modifying agent. In certain embodiments, the genetic modifying agent comprises a CRISPR system, RNAi system, a zinc finger nuclease system, a TALE, or a meganuclease. In certain embodiments, the CRISPR system comprises Cas9, Cas12, or Cas14. In certain embodiments, the CRISPR system comprises a dCas fused or otherwise linked to a nucleotide deaminase. In certain embodiments, the nucleotide deaminase is a cytidine deaminase or an adenosine deaminase. In certain embodiments, the dCas is a dCas9, dCas12, dCas13, or dCas14.

In certain embodiments, the T cell is obtained from PBMCs. In certain embodiments, the T cell is a tumor infiltrating lymphocyte (TIL). In certain embodiments, the T cell expresses an endogenous T cell receptor (TCR) or chimeric antigen receptor (CAR) specific for a tumor antigen. In certain embodiments, the T cell is expanded. In certain embodiments, the T cell is modified to express a suicide gene, wherein the T cell can be eliminated upon administration of a drug. In certain embodiments, the glucocorticoid is dexamethasone (Dex).

In another aspect, the present invention provides for a pharmaceutical composition comprising one or more isolated T cells according to any embodiment herein. In another aspect, the present invention provides for a method of treating cancer in a subject in need thereof comprising administering a pharmaceutical composition comprising one or more isolated T cells according to any embodiment herein where dysfunction is decreased. In another aspect, the present invention provides for a method of treating an autoimmune disease or inflammatory disorder, or for inducing immune tolerance in a subject in need thereof comprising administering a pharmaceutical composition comprising one or more isolated T cells according to any embodiment herein where dysfunction is increased.

In another aspect, the present invention provides for a method of generating an in vitro T cell that faithfully recapitulates an in vivo dysfunctional T cell comprising culturing a T cell in a culture media comprising IL-27 and a glucocorticoid.

In another aspect, the present invention provides for a method of detecting a checkpoint blockade (CPB) therapy non-responder gene signature in a subject in need thereof comprising detecting in T cells obtained from a pre-treatment biological sample from the subject the expression or activity of one or more glucocorticoid+IL-27 signature genes or gene products selected from the group consisting of: Table 2A and Table 2B; or Lilrb4, Bcl2, Nupr1, Tgfb3, Tnfrsf4, Il24, Ramp1, Klf10, Cd27, Cd28, Tle2, Btla, Xcl1, Egr2, Entpd1, Tcf7, Nfil3, Prdm1, Mt1, Mt2, Stat3, Tigit, Havcr2, Lag3, Itga7, Acvrl1, Gpr125, Aqp11, Kit, Trip6, Il10, Enpp2, Asb2, Jag2, Tnfrsf18, Smyd3, Dbp, Ddit3, Tnfrsf14, Zfp467, Crebl2, Hif1a, Irf6, Alcam, Bach1, Pdcd1, Ctla4, Epcam, Gpld1, Cd68, Prnp, Gab2, Vldlr, Il10, Il1r2, Nt5e, Itgae, C1qtnf4, Ccr7, Cd226, Ifng, Ccl4, Spp1, Ccl3, Cd48, Cxcr3, Nanog, Tfrc, Hmgn2, Ptrf, Icam2, Cd40lg and Il1a; or Table 7A and Table 7B; or Table 5A and Table 5B; or Table 6A and Table 6B; or Table 3; or Table 1, wherein Epcam, Gpld1, Cd68, Prnp, Gab2, Vldlr, Il10, Il1r2, Nt5e, Itgae, C1qtnf4, Tgfb3, Itga7, Acvrl1, Gpr125, Aqp11, Ramp1, Kit, Trip6, Il10, Enpp2, Asb2, Jag2, Tnfrsf18, Prdm1, Smyd3, Tigit, Dbp, Tle2, Ddit3, Klf10, Tnfrsf14, Zfp467, Entpd1, Nfil3, Crebl2, Hif1a, Irf6, Lag3, Alcam, Mt2, Stat3, Mt1, Bach1, Cd28, Havcr2, Pdcd1, Ctla4 and Cd27 are upregulated in glucocorticoid+IL-27 as compared to the control, and wherein Ifng, Ccl4, Bcl2, Spp1, Btla, Ccl3, Cd48, Cxcr3, Nanog, Tfrc, Xcl1, Lilrb4, Nupr1, Hmgn2, Il24, Ptrf, Icam2, Cd40lg, Il1a, Tcf7, Tnfrsf4, Egr2, Ccr7 and Cd226 are downregulated in glucocorticoid+IL-27 as compared to the control. In certain embodiments, the method further comprises treating the subject wherein if a non-responder signature is detected treating the subject according to any embodiment herein where dysfunction is decreased. In certain embodiments, the method further comprises administering checkpoint blockade (CPB) therapy. In certain embodiments, the CPB therapy comprises anti-PD-1, anti-CTLA4+PD-1, or anti-CTLA4.

In another aspect, the present invention provides for a method of determining a prognosis for cancer survival in a subject in need thereof comprising detecting the expression of Cyp11a1 in CD45+ cells obtained from a tumor sample of the subject, wherein low Cyp11a1 levels compared to a reference level indicates increased survival. In certain embodiments, expression is detected in CD11b+F4/80+ macrophages. In certain embodiments, the method further comprises treating the subject wherein if high Cyp11a1 levels are detected treating the subject according to any embodiment herein where dysfunction is decreased.

In another aspect, the present invention provides for a method of screening for one or more agents capable of modulating a glucocorticoid+IL-27 gene signature according to claim 83 comprising administering to a population of T cells one or more agents; and detecting expression, activity or function of one or more genes or gene products in the signature. In certain embodiments, the one or more genes detected are selected from the group consisting of PD-1, TIM3, LAG3, MT1, MT2, and IL-10. In certain embodiments, the population of cells express one or more reporter genes. In certain embodiments, the one or more agents bind to glucocorticoid receptor and/or IL-27 receptor. In certain embodiments, the one or more agents modify chromatin structure at one or more of the signature genes.

In another aspect, the present invention provides for a method of decreasing inflammation in a subject in need thereof comprising administering to the subject IL-27 and a glucocorticoid.

In another aspect, the present invention provides for a method of decreasing inflammation in a subject in need thereof comprising administering to the subject immune cells in vitro differentiated in a culture media comprising IL-27 and a glucocorticoid.

In another aspect, the present invention provides for a method of inducing immune tolerance in a subject having received an organ transplant comprising administering to the subject IL-27 and a glucocorticoid.

In another aspect, the present invention provides for a method of inducing immune tolerance in a subject having received an organ transplant comprising administering to the subject immune cells in vitro differentiated in a culture media comprising IL-27 and a glucocorticoid.

In another aspect, the present invention provides for a method of treating cancer in a subject in need thereof comprising administering one or more agents capable of inhibiting IL-27 signaling and glucocorticoid signaling.

In another aspect, the present invention provides for a method of administering cancer adjuvant glucocorticoid therapy to a subject in need thereof comprising measuring a T cell receptor (TCR) activation and/or T cell resting state in the subject and administering adjuvant glucocorticoid therapy to the subject when the subject has a TCR activation state and/or stopping adjuvant glucocorticoid therapy when the subject has a T cell resting state.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1A-1B—tSNE analysis comparing expression of a glucocorticoid signature and dysfunction signature.

FIG. 3A-3D—a. Schematic of a time course experiment activating T cells+/−Dex, b. FACS in WT and GR KO cells measuring PD1 and Tim3, c. bar graphs showing expression of PD1 and Tim3, d. FACS in cells+/−Dex and measuring IFNg, CD107a, Granzyme B, IL-10, IL-2, and TNFa.

FIG. 4A-4B—a. Schematic of a time course experiment activating T cells and allowing the T cells to rest, b. NR3C1 expression over the time course.

FIG. 5A-5C—a. Bar graphs showing expression of MT1/2 in WT and GR KO cells treated with vehicle or Dex, b. Bar graphs showing expression of PD1 and Tim3 in WT and MT KO cells treated with vehicle or Dex, c. FACS in WT and MT KO cells treated with +/−Dex and measuring PD1 and Tim3.

FIG. 10A-10C. FACS experiments detecting the indicated target after treatment with control, Dex, IL27 and Dex+IL27.

FIG. 21A-21E—Transactivation of checkpoint receptors and IL-10 by GR. Luciferase activity in 293T cells transfected with pGL4.23 or pGL4.10 reporters for the loci of a) Havcr2 (Tim3), b) Pdcd1 (PD1), c) Lag3 d) Tigit, and e) IL10 together with either empty vector (control) or constructs encoding Nr3c1. Cells were treated with GC after 24 h. Firefly luciferase activity was measured 48 h after transfection and is presented relative to constitutive Renilla luciferase activity. ****p<0.0001, Two-way ANOVA (Tukey's multiple comparisons test). Data are mean S.E.M. The data are representative of 2 independent experiments.

FIG. 22A-22F—The glucocorticoid and IL-27 pathways co-operate to promote dysfunction in CD8+ T cells. a-c) Naïve CD8+ T cells were cultured in vitro with anti CD3/28 in the presence of Dex (GC), IL-27, or GC+IL-27. Cells were harvested on Day 9 and gene expression analyzed by RNA sequencing. a) Principle component analysis (PCA) of Ctrl, GC, IL-27, and GC+IL-27 treated CD8+ T, the percentage of explained variance for each principal component is indicated. b) Bar graph shows the mean delta Euclidean distance between the GC, IL-27, or GC+IL-27 treated groups to the control group, adjusted p-values were calculated using one-way ANOVA (p-value=9.89e-09), followed by Tukey HSD, *p<0.05, **p<0.001. c) Heatmap of DE genes between Ctrl and GC+IL-27 treatment. Tick marks indicate selected genes associated with T cell dysfunction. d) Volcano plot showing overlap of genes down-regulated by IL-27+GC with genes expressed in Tim-3−PD-1− CD8+ TILs (p=2.1×10$^{-10}$, Mean-rank Gene Set Test), and genes up-regulated by IL-27+GC with Tim-3+PD-1+ CD8+ TILs (p=4.3×10$^{-05}$, Mean-rank Gene Set Test). e) CD8 T cells from either WT (E8i-Cre−Nr3c1$^{fl/fl}$), E8i-Cre+Nr3c1$^{fl/fl}$, WSX1$^{-/-}$ or and E8i-Cre+Nr3c1$^{fl/fl}$ WSX1$^{-/-}$ (DKO) mice and CD4+ T cells from WT mice were transferred to Rag$^{-/-}$ mice (n=5/group) that were implanted with MC38-Ova cells two days later. Mean tumor growth is shown p<0.01, *p<0.001, **p<0.0001, linear regression. Data are representative of 2 independent experiments. f) tSNE plot of single-cell RNA profiles of TILs from melanoma patients. I) CD8 expression, II) CD4 expression, III) pre- (orange) versus post- (purple) treatment samples, IV) Responder (red) versus non-responder (blue), V) Projection of CD8+ TILs dysfunction signature, VI) Projection of the GC+IL-27 signature. Box plots show the GC+IL-27 signature score in responder versus non-responders in pre- and post-treatment samples, p-value=4.048e-09 and p-value=5.028e-05, respectively (Welch Two Sample t-test).

FIG. 25A-25D—Glucocorticoid-mediated effects on CD8+ T cells requires Nr3c1. Naïve CD8+ T cells from wild type mice (n=5) (a) or from human samples (n=5) (b) were activated in the presence or absence of Dex (GC) as in FIG. 19a and harvested on Day 9. Representative flow cytometry data of Tim-3 and PD-1 expression. P<0.01, *p<0.001. Student's t-test. Mean±SEM are shown. c) Expression of Nr3c2 on T cells was quantified by qPCR. MC38-Ova cells were used as the positive control. Data are representative of 2 independent experiments. d) Heatmap of differentially expressed genes in wild type (E8i-Cre⁻Nr3c1$^{fl/fl}$) or E8i-Cre⁺Nr3c1$^{fl/fl}$ CD8⁺ T cells+/−GC treatment. Tick marks indicate selected known GC target genes.

FIG. 26A-26F—Glucocorticoid signaling dampens effector function of CD8⁺ T cells. a) B16F10 was implanted into wild type (E8i-Cre⁻Nr3c1$^{fl/fl}$) and E8i-Cre⁺Nr3c1$^{fl/fl}$ mice (n=5). Mean tumor growth is shown. **p<0.0001, linear regression. Data are representative of 2 independent experiments. b-f) MC38-Ova was implanted into wild type (E8i-Cre⁻Nr3c1$^{fl/fl}$) and E8i-Cre⁺Nr3c1$^{fl/fl}$ mice. b) Expression level of Tim-3, PD-1, Lag-3 and Tigit as indicated by mean fluorescence intensity (MFI) in CD8⁺ T cells from wild type (E8i-Cre⁻Nr3c1$^{fl/fl}$) and E8i-Cre⁺Nr3c1$^{fl/fl}$ mice (n=6-7). Data are representative of 3 independent experiments. c,d) TILs were isolated and activated with OVA$_{257-264}$ (SIINFEKL) in the presence of Golgi Plug and Golgi Stop for 4 hr prior to extracellular and intracellular staining and analysis by flow cytometry. (c) Summary plot showing polyfunctionality of CD8⁺ TILs from wild type (E8i-Cre⁻Nr3c1$^{fl/fl}$) and E8i-Cre⁺Nr3c1$^{fl/fl}$ mice (n=9-10). Data are pooled from 2 independent experiments. d) Summary plots representing cytokine production in Tim3⁺PD1⁺CD8⁺ TILs from WT and cKO mice. Data are pooled from 2 independent experiments (n=9-10). e) Summary plots representing the frequency of CD4⁺ T cells expressing checkpoint receptors in wild type (E8i-Cre⁻Nr3c1$^{fl/fl}$) and E8i-Cre⁺Nr3c1$^{fl/fl}$ mice (n=6-7). f) Summary plots of the MFI of checkpoint receptors on CD4⁺ T cells in WT and E8i-Cre⁺Nr3c1$^{fl/fl}$ mice (n=6-7). p<0.01, ***p<0.001, Student's t-test. Mean±SEM are shown.

FIG. 27A-27E—GR binding sites and open chromatin in the loci of checkpoint receptors and IL10. Overlay of ChIP-seq data of GR24 and ATAC-seq data of naive CD4⁺ cells induced with IL-2725 in the loci of (a) Havcr2 (Tim3) (b) Pdcd1 (PD1) (c) Lag3 (d) Tigit and (e) Il10.

FIG. 28A-28C—Effects of glucocorticoid and IL-27 in CD8⁺ T cells. a,b) Naïve CD8⁺ T cells were cultured in vitro with anti CD3/CD28 in the presence of Dex (GC), IL-27, or GC+IL-27. Cells were harvested on Day 9 for analysis. a) Heatmap display of the pairwise Euclidean distance between samples calculated for all genes. b) Quantitative RT-PCR analysis of Prdm1, Nfil3, and Tcf7 mRNA expression in the Ctrl, GC, IL-27, or GC+IL-27 treated cells. *p<0.05, ****p<0.0001. Ordinary one way ANOVA (Tukey's multiple comparisons test). Mean±SEM are shown. c) Kolmogorov Smirnov one-sample curve47 showing overlap of genes down-regulated by GC+IL-27 with genes expressed in Tim-3⁻PD-1⁻ CD8+ TILs (p=5.5×10⁻¹⁶), and genes up-regulated by GC+IL-27 with Tim-3⁺PD-1⁺CD8⁺ TILs (p=7.7×10⁻¹⁶).

FIG. 29A-29B—Gating strategy for isolation of cell populations from tumors. a) Wild type mice were implanted with MC38-OVA-GFP cells. Ex vivo tumor cells CD45⁻ GFP⁺) and cancer-associated fibroblasts (CD45⁻GFP⁻CD140a⁺) were gated as shown. b) WT mice were implanted with MC38-Ova and the tumor-associated dendritic cells (Dump⁻MHCII⁺CD11c⁻ CD24⁺) and macrophages (Dump⁻MHCII⁺CD24⁻F4/80⁺) were flow cytometry-sorted as per the gates shown in the representative plots. Dump gate includes CD3, CD19, NK1.1, Ly6G, Ly6C and SiglecF.

Figure 2B:
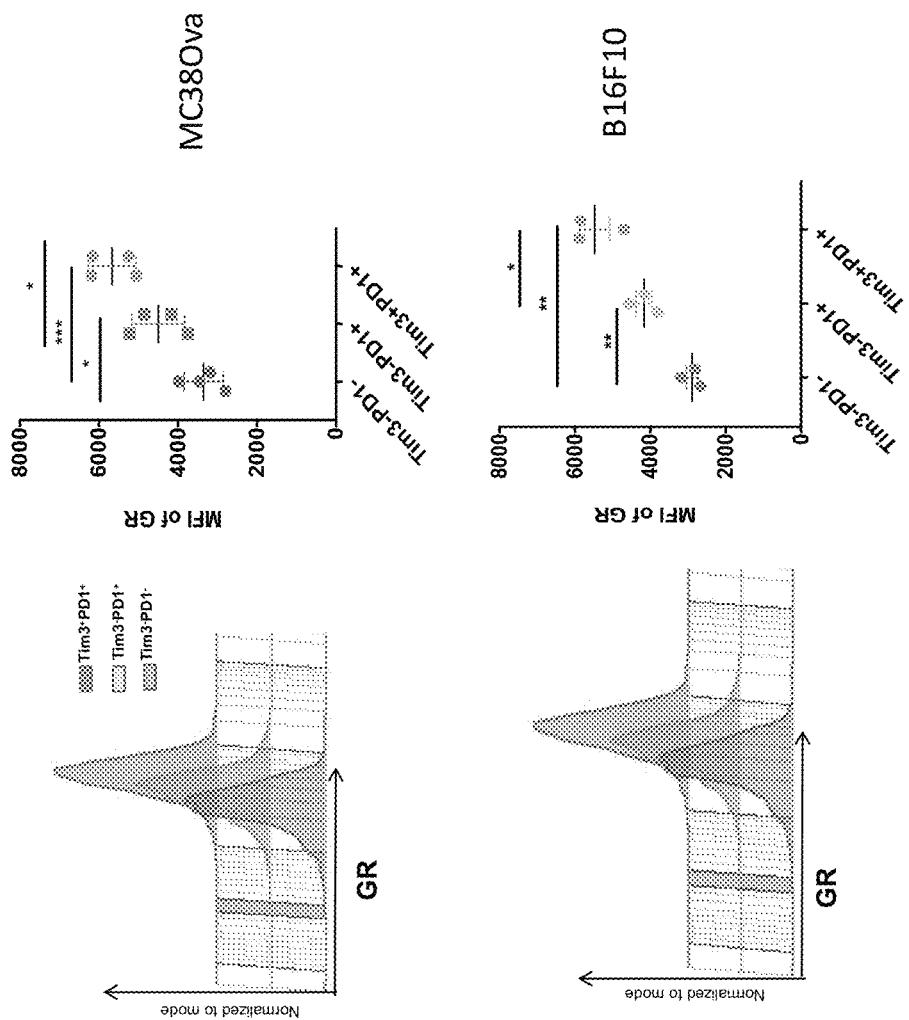
FIG. 2A-2B—(left) adapted from Singer et al., 2016, showing expression of cluster 1 genes (including Nr3c1) across Tim-3-PD-1− (DN), Tim-3-PD-1+(SP), and Tim-3+ PD-1+(DP) CD8+ TILs. (right) Glucocorticoid receptor expression across Tim-3-PD-1− (DN), Tim-3-PD-1+(SP), and Tim-3+PD-1+(DP) CD8+ TILs.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies, A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.). The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2$^{nd}$ed., J. Wiley & Sons (New York, N.Y. 1994), March, Advanced Organic Chemistry Reactions, Mechanisms and Structure 4$^{th}$ ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to PCT/US2013/067481, filed Oct. 30, 2013 and published as WO2014070874A1; PCT/US2016/056177, filed Oct. 7, 2016 and published as WO2017069958A2; PCT/US2016/059507, filed Oct. 28, 2016 and published as WO2017075478A2; PCT/US2017/050469, filed Sep. 7, 2017 and published as WO2018049025A2; PCT/US2018/042069, filed Jul. 13, 2018 and published as WO2019/014581; and PCT/US2018/053791, filed Oct. 1, 2018 and published as WO2019068099A1.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods and compositions for modulating immune responses and immune states. Specifically, Applicants have identified pathways for modulating T cell balance between dysfunctional and/or exhaustive T cell states and activated T cell states. Embodiments disclosed herein also provide for methods of detecting gene signatures and biomarkers for use in diagnostic assays or for screening of therapeutic agents. Embodiments disclosed herein also provide for cell compositions for use in screening of therapeutic agents and identifying therapeutic targets for modulating T cell dysfunction.

Identifying signals in the tumor microenvironment (TME) that promote CD8$^+$ T cell dysfunction can inform improved therapeutic approaches for cancer. Applicants previously defined a gene signature for dysfunctional CD8$^+$ tumor-infiltrating lymphocytes (TILs) based on the differential gene expression of CD8$^+$ TIL populations that exhibit distinct effector capacities[3,4]. Specifically, the expression of the checkpoint receptors Tim-3 and PD-1 distinguishes CD8$^+$ TILs subsets with different degrees of function: Tim-3$^+$PD-1$^+$CD8$^+$ TILs are severely dysfunctional, Tim-3$^+$PD-1$^+$CD8$^+$ TILs are partially dysfunctional with intermediate effector function, and Tim-3$^-$PD-1$^-$ CD8$^+$ TILs exhibit strong effector function[4,5], with each of these populations exhibiting distinct transcriptional profiles[3].

From the transcriptome data of these subsets of CD8$^+$ TILs, Applicants identified Nr3c1, the gene encoding the glucocorticoid receptor (GR), as being highly expressed in severely dysfunctional Tim-3$^+$PD-1$^+$CD8$^+$ tumor-infiltrating lymphocytes (TILs). Glucocorticoids (GC), steroid hormones derived from the metabolic breakdown of cholesterol, bind to the GR, which resides in the cytosol in its inactivate state and translocates to the nucleus upon ligand binding. In the nucleus, the GR can regulate gene expression either directly by binding to the promoter of a given target gene or indirectly by affecting the binding of other transcription factors (TFs) to the promoter regions of their respective targets[6]. Both natural and synthetic glucocorticoids suppress a number of inflammatory indices and have been used clinically since the 1950s for treating excessive inflammation in patients with asthma, autoimmune diseases, and sepsis. Currently, glucocorticoids are routinely used to manage excessive inflammation in cancer patients treated with checkpoint blockade[7].

Despite their widespread use, surprisingly little is known regarding the molecular circuitry by which glucocorticoids suppress immune responses[8]. The prevailing dogma attributes the anti-inflammatory effects of glucocorticoids to transrepression, whereby the GR inhibits the function of TFs that have key roles in driving pro-inflammatory responses. The GR binds to and directly interferes with AP-1[9,10]. The GR can also interfere with NF-κB either directly or indirectly by modulating IκBα[11, 12, 13, 14]. However, glucocorticoids have also been associated with enhanced expression of anti-inflammatory cytokines, such as IL10[15], raising the possibility that in addition to actively repressing pro-inflammatory gene expression, they may also promote suppression via transactivation of immune-suppressive genes.

Applicants show that activation of GR signaling in CD8$^+$ T cells promotes T cell dysfunction in the TME and that the GR transactivates the expression of the checkpoint receptors Tim-3, PD-1, and Lag-3, and of the anti-inflammatory cytokine IL-10. Accordingly, loss of GR in CD8$^+$ T cells limits dysfunctional phenotype in CD8$^+$ TILs resulting in tumor growth inhibition. Reduced steroidogenic capacity is also correlated with better survival in cancer patients. Applicants further show that the effects of glucocorticoid signaling are conserved in human T cells and that glucocorticoid signaling co-operates with IL-27 signaling to form an immunoregulatory circuit that promotes T cell dysfunction in the TME. Applicants show that glucocorticoids are synthesized de novo in the TME where they co-operate with the immunosuppressive cytokine IL-27 to promote the dysfunction gene program in CD8$^+$ T cells. High expression of a glucocorticoid+IL-27 specific gene signature in CD8$^+$ TILs correlates with failure to respond to checkpoint blockade in melanoma patients, highlighting the relevance of these two pathways in human disease.

Glucocorticoid and IL-27 Signaling in T Cell Dysfunction

Applicants found high expression of glucocorticoid receptor on dysfunctional cells, thus providing a link of glucocorticoid signaling to dysfunction. As used herein the terms "dysfunctional" and "exhausted" are used interchangeably. Applicants also discovered a synergistic relationship between glucocorticoid signaling and IL-27 signaling, such that activation of both pathways in certain embodiments may result in T cells having a dysfunctional phenotype that recapitulates the most dysfunctional cells in vivo. Applicants have also discovered downstream targets of glucocorticoid and IL-27 activation that are transcriptionally distinct to the combination.

As used herein "glucocorticoid signaling" refers to glucocorticoid binding to and activating glucocorticoid receptor (GR), as well as, all downstream targets activated or repressed as a result of the binding. Modulating glucocorticoid signaling encompasses modulating glucocorticoid binding to and activating glucocorticoid receptor, as well as, modulating any downstream targets activated or repressed as a result of activated GR. As used herein "IL-27 signaling" refers to IL-27 binding to IL-27 receptor and the activation of all signaling pathways as a result of the binding. Modulating IL-27 signaling encompasses modulating IL-27 binding to IL-27 receptor, as well as, modulating any downstream targets activated or repressed as a result. As used herein "modulating glucocorticoid and IL-27 signaling" may refer to modulation of either pathway individually, but also modulating the targets specific to the combination.

In certain embodiments, modulating glucocorticoid signaling, IL-27 signaling and/or the expression or activity of downstream targets can be used to modulate an immune state. In certain embodiments, modulation of T cell dysfunction as described herein can promote tolerance or dampen an inappropriate, unwanted, or undesirable immune response, thereby permitting treatment of autoimmune disease and/or conditions associated with transplants (e.g., graft vs. host disease). In certain embodiments, modulation of T cell dysfunction as described herein can promote an enhanced immune response, thereby permitting treatment of chronic disease and/or conditions (e.g., cancer, infection). In certain embodiments, modulation of glucocorticoid and IL-27 signaling and/or downstream targets are used to treat diseases requiring a shift in T cell balance. In certain embodiments, modulation of glucocorticoid and IL-27 signaling and/or downstream targets are used to generate cells for adoptive cell transfer. In certain embodiments, immune cells are modulated, such that upon transfer an immune response is dampened (e.g., treating autoimmune diseases). In certain embodiments, immune cells are modulated, such that upon transfer an immune response is enhanced.

In certain embodiments, modulation of glucocorticoid and IL-27 signaling and/or downstream targets are used to generate dysfunctional cells that recapitulate in vivo dysfunctional cells. Embodiments disclosed herein provide for in vitro cell-based systems that faithfully recapitulate an in vivo dysfunctional phenotype and methods of generating and using the cell-based systems. In certain embodiments, dysfunctional cells are characterized by assaying dysfunctional markers as described herein. In certain embodiments, the cells can be used to screen for immunomodulators as described further herein.

Applicants have further discovered that the glucocorticoid receptor, Nr3C1, is dynamically regulated with TCR activation, i.e. downregulated with TCR activation and re-expressed when T cells return to resting state. In certain embodiments, glucocorticoid administration can be adjusted based on the T cell state. In certain embodiments, glucocorticoid administration is coordinated in cancer patients to ameliorate the effects of a cancer treatment and to avoid dampening an anti-tumor adaptive immune response. In certain embodiments, glucocorticoids can be administered when the glucocorticoid receptor is downregulated on T cells.

Functional T Cell Immune States

In certain embodiments, the present invention provides for modulating immune states. The immune state can be modulated by modulating T cell dysfunction. In particular embodiments, T cell dysfunction is modulated by targeting glucocorticoid and IL-27 signaling. In certain embodiments, T cells can affect the overall immune state, such as other immune cells in proximity.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells (including, e.g., thymocytes, Th or Tc; Th1, Th2, Th17, Thαβ, CD4$^+$, CD8$^+$, effector Th, memory Th, regulatory Th, CD4$^+$/CD8$^+$ thymocytes, CD4−/CD8− thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

As used throughout this specification, "immune response" refers to a response by a cell of the immune system, such as a B cell, T cell (CD4$^+$ or CD8$^+$), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4$^+$ response or a CD8$^+$ response. Such responses by these cells can include, for example, cytotoxicity, proliferation, cytokine or chemokine production, trafficking, or phagocytosis, and can be dependent on the nature of the immune cell undergoing the response.

T cell response refers more specifically to an immune response in which T cells directly or indirectly mediate or otherwise contribute to an immune response in a subject. T cell-mediated response may be associated with cell mediated effects, cytokine mediated effects, and even effects associated with B cells if the B cells are stimulated, for example, by cytokines secreted by T cells. By means of an example but without limitation, effector functions of NHC class I restricted Cytotoxic T lymphocytes (CTLs), may include cytokine and/or cytolytic capabilities, such as lysis of target cells presenting an antigen peptide recognized by the T cell receptor (naturally-occurring TCR or genetically engineered TCR, e.g., chimeric antigen receptor, CAR), secretion of cytokines, preferably IFN gamma, TNF alpha and/or or more immunostimulatory cytokines, such as IL-2, and/or antigen peptide-induced secretion of cytotoxic effector molecules, such as granzymes, perforins or granulysin. By means of example but without limitation, for NMC class II restricted T helper (Th) cells, effector functions may be antigen peptide-induced secretion of cytokines, preferably, IFN gamma, TNF alpha, IL-4, IL5, IL-10, and/or IL-2. By means of example but without limitation, for T regulatory (Treg) cells, effector functions may be antigen peptide-induced secretion of cytokines, preferably, IL-10, IL-35, and/or TGF-beta. B cell response refers more specifically to an immune response in which B cells directly or indirectly mediate or otherwise contribute to an immune response in a subject. Effector functions of B cells may include in particular production and secretion of antigen-specific antibodies by B cells (e.g., polyclonal B cell response to a plurality of the epitopes of an antigen (antigen-specific antibody response)), antigen presentation, and/or cytokine secretion.

During persistent immune activation, such as during uncontrolled tumor growth or chronic infections, subpopulations of immune cells, particularly of CD8+ or CD4+ T cells, become compromised to different extents with respect to their cytokine and/or cytolytic capabilities. Such immune cells, particularly CD8+ or CD4+ T cells, are commonly referred to as "dysfunctional" or as "functionally exhausted" or "exhausted". As used herein, the term "dysfunctional" or "functional exhaustion" refer to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation (e.g., in response to a cytokine, such as IFN-gamma) or cell division, entrance into the cell cycle, cytokine production, cytotoxicity, migration and trafficking, phagocytotic activity, or any combination thereof. Normal input signals can include, but are not limited to, stimulation via a receptor (e.g., T cell receptor, B cell receptor, co-stimulatory receptor). Unresponsive immune cells can have a reduction of at least 10%, 20%, 30%, 40%, 50%, 60%, 70%, 80%, 90%, 95%, or even 100% in cytotoxic activity, cytokine production, proliferation, trafficking, phagocytotic activity, or any combination thereof, relative to a corresponding control immune cell of the same type. In some particular embodiments of the aspects described herein, a cell that is dysfunctional is a CD8+ T cell that expresses the CD8+ cell surface marker. Such CD8+ cells normally proliferate and produce cell killing enzymes, e.g., they can release the cytotoxins perforin, granzymes, and granulysin. However, exhausted/dysfunctional T cells do not respond adequately to TCR stimulation, and display poor effector function, sustained expression of inhibitory receptors and a transcriptional state distinct from that of functional effector or memory T cells. Dysfunction/exhaustion of T cells thus prevents optimal control of infection and tumors. Exhausted/dysfunctional immune cells, such as T cells, such as CD8+ T cells, may produce reduced amounts of IFN-gamma, TNF-alpha and/or one or more immunostimulatory cytokines, such as IL-2, compared to functional immune cells. Exhausted/dysfunctional immune cells, such as T cells, such as CD8+ T cells, may further produce (increased amounts of) one or more immunosuppressive transcription factors or cytokines, such as IL-10 and/or Foxp3, compared to functional immune cells, thereby contributing to local immunosuppression. Dysfunctional CD8+ T cells can be both protective and detrimental against disease control. As used herein, a "dysfunctional immune state" refers to an overall suppressive immune state in a subject or microenvironment of the subject (e.g., tumor microenvironment). For example, increased IL-10 production leads to suppression of other immune cells in a population of immune cells.

CD8+ T cell function is associated with their cytokine profiles. It has been reported that effector CD8+ T cells with the ability to simultaneously produce multiple cytokines (polyfunctional CD8+ T cells) are associated with protective immunity in patients with controlled chronic viral infections as well as cancer patients responsive to immune therapy (Spranger et al., 2014, J. Immunother. Cancer, vol. 2, 3). In the presence of persistent antigen CD8$^+$ T cells were found to have lost cytolytic activity completely over time (Moskophidis et al., 1993, Nature, vol. 362, 758-761). It was subsequently found that dysfunctional T cells can differentially produce IL-2, TNFa and IFNg in a hierarchical order (Wherry et al., 2003, J. Virol., vol. 77, 4911-4927). Decoupled dysfunctional and activated CD8+ cell states have also been described (see, e.g., Singer, et al. (2016). A Distinct Gene Module for Dysfunction Uncoupled from Activation in Tumor-Infiltrating T Cells. Cell 166, 1500-1511 e1509; WO/2017/075478; and WO/2018/049025

Genes and Polypeptides

All gene name symbols as disclosed herein refer to the gene as commonly known in the art. The examples described herein that refer to the mouse gene names are to be understood to also encompasses human genes, as well as genes in any other organism (e.g., homologous, orthologous genes). The term, homolog, may apply to the relationship between genes separated by the event of speciation (e.g., ortholog). Orthologs are genes in different species that evolved from a common ancestral gene by speciation. Normally, orthologs retain the same function in the course of evolution. Gene symbols may be those referred to by the HUGO Gene Nomenclature Committee (HGNC) or National Center for Biotechnology Information (NCBI). Any reference to the gene symbol is a reference made to the entire gene or variants of the gene, as well as the gene products (e.g., proteins, non-coding RNA), including all modifications or variants of the gene products (e.g., splice variants, protein modifications, edited RNA). The signature as described herein may encompass any of the genes or gene products described herein.

The gene name NR3C1, Nr3c1 or Nr3C1 may refer to the glucocorticoid receptor gene or polypeptide according to NCBI Reference Sequence accession numbers NM_001204264.1, NM_001204263.1, NM 001204262.1, NM_001204261.1, NM 001204260.1, NM_001204259.1, NM 001204258.1, NM 001024094.1, NM 001018077.1, NM 001018076.1, NM_001018075.1, NM_001018074.1, NM_000176.2, NM_001204265.1, NM_001020825.1 and NM_008173.3.

Interleukin 27 (IL-27) is a member of the IL-12 cytokine family. It is a heterodimeric cytokine that is composed of two distinct genes, Epstein-Barr virus-induced gene 3 (EBI3) and IL-27p28. The IL-27 receptor (IL-27R) consists of two proteins, IL-27α and gp130.

The gene name EBI3 may refer to the Epstein-Barr virus-induced gene 3 gene or polypeptide according to NCBI Reference Sequence accession numbers NM_005755.2 and NM_015766.2.

The gene name IL27, IL-27, p28, IL-27A, IL27A, IL27p28 and IL30 may refer to the interleukin 27 gene or polypeptide according to NCBI Reference Sequence accession numbers NM_145659.3 and NM_145636.1.

The gene name IL27RA, CRL1, IL-27RA, IL27R, TCCR, WSX1, and zcytor1 may refer to the interleukin 27 receptor subunit alpha gene or polypeptide according to NCBI Reference Sequence accession numbers NM_004843.3 and NM_016671.3.

Methods of Modulating T Cell Dysfunction

The following section provides multiple example embodiments for inducing, increasing or enhancing T cell dysfunction or for suppressing, decreasing or reducing T cell dysfunction. The compositions of the methods may be administered to subjects having aberrant activation and/or expansion of T cells or subjects requiring an enhanced immune response. Thus, the embodiments may be used to prevent and/or treat diseases and disorders characterized by aberrant activation, expansion or suppression of immune cells.

In certain embodiments, a glucocorticoid and IL-27 are administered to a subject or a population of immune cells to increase dysfunction. In certain embodiments, glucocorticoid and IL-27 agonists are administered to a subject or a population of immune cells to increase dysfunction. In certain embodiments, glucocorticoid and IL-27 antagonists are administered to a subject or a population of immune cells to decrease dysfunction.

In certain embodiments, a method of increasing or decreasing T cell dysfunction comprises administering or more agents capable of modulating expression, activity, or function of glucocorticoid receptor, IL-27, IL-27 receptor or one or more biomarkers of the glucocorticoid+IL-27 gene signature as defined herein.

As used herein, "modulating" or "to modulate" generally means either reducing or inhibiting the expression or activity of, or alternatively increasing the expression or activity of a target (e.g., Nr3C1, IL-27 receptor, downstream target of glucocorticoid and IL-27 signaling described herein). In particular, "modulating" or "to modulate" can mean either reducing or inhibiting the activity of, or alternatively increasing a (relevant or intended) biological activity of, a target or antigen as measured using a suitable in vitro, cellular or in vivo assay (which will usually depend on the target involved), by at least 5%, at least 10%, at least 25%, at least 50%, at least 60%, at least 70%, at least 80%, at least 90%, or more, compared to activity of the target in the same assay under the same conditions but without the presence of an agent. An "increase" or "decrease" refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more. "Modulating" can also involve effecting a change (which can either be an increase or a decrease) in affinity, avidity, specificity and/or selectivity of a target or antigen, such as glucocorticoid or IL-27. "Modulating" can also mean effecting a change with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target or antigen involved.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can, for example, also involve effecting a change in respect of the folding or confirmation of the target, or in respect of the ability of the target to fold, to change its conformation (for example, upon binding of a ligand), to associate with other (sub)units, or to disassociate. Modulating can, for example, also involve effecting a change in the ability of the target to signal, phosphorylate, dephosphorylate, and the like.

Biomarkers and Expression Signatures

In certain example embodiments, the therapeutic, diagnostic, and screening methods disclosed herein target, detect, or otherwise make use of one or more biomarkers of an expression signature. As used herein, the term "biomarker" can refer to a gene, an mRNA, cDNA, an antisense transcript, a miRNA, a polypeptide, a protein, a protein fragment, or any other nucleic acid sequence or polypeptide sequence that indicates either gene expression levels or protein production levels. Accordingly, it should be understood that reference to a "signature" in the context of those embodiments may encompass any biomarker or biomarkers whose expression profile or whose occurrence is associated with a specific cell type, subtype, or cell state of a specific cell type or subtype within a population of cells (e.g., dysfunctional T cells) or a specific biological program. As used herein the term "module" or "biological program" can be used interchangeably with "expression program" and refers to a set of biomarkers that share a role in a biological function (e.g., a dysfunction program, activation program, cell differentiation program, proliferation program). Biological programs can include a pattern of biomarker expression that result in a corresponding physiological event or phenotypic trait. Biological programs can include up to several hundred biomarkers that are expressed in a spatially and temporally controlled fashion. Expression of individual biomarkers can be shared between biological programs. Expression of individual biomarkers can be shared among different single cell types; however, expression of a biological program may be cell type specific or temporally specific (e.g., the biological program is expressed in a cell type at a specific time). Expression of a biological program may be regulated by a master switch, such as a nuclear receptor (e.g., (GR) or transcription factor.

The invention further relates to various biomarkers for detecting CD8+ and/or CD4+ T cell subpopulations. In certain example embodiments, these CD8+ and/or CD4+ T cell populations are tumor infiltrating lymphocytes (TIL). The methods may comprise detecting a first population of CD8+ and/or CD4+ T cell population as described further below, a second population of CD8+ and/or CD4+ T cell population as described further below, a third population of CD8+ and/or CD4+ T cell population as described further below or any combination of two subtypes or all three subtypes. The first, second and third CD8+ and/or CD4+ T cell populations may be detected by detecting one or more biomarkers in a sample.

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of $\geq 5$ consecutive amino acids, or $\geq 10$ consecutive amino acids, or $\geq 20$ consecutive amino acids, or $\geq 30$ consecutive amino acids, e.g., $\geq 40$ consecutive amino acids, such as for example $\geq 50$ consecutive amino acids, e.g., $\geq 60$, $\geq 70$, $\geq 80$, $\geq 90$, $\geq 100$, $\geq 200$, $\geq 300$, $\geq 400$, $\geq 500$ or $\geq 600$ consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of $\geq 5$ consecutive nucleotides, or $\geq 10$ consecutive nucleotides, or $\geq 20$ consecutive nucleotides, or $\geq 30$ consecutive nucleotides, e.g., $\geq 40$ consecutive nucleotides, such as for example $\geq 50$ consecutive nucleotides, e.g., $\geq 60$, $\geq 70$, $\geq 80$, $\geq 90$, $\geq 100$, $\geq 200$, $\geq 300$, $\geq 400$, $\geq 500$ or $\geq 600$ consecutive nucleotides of the corresponding full-length nucleic acid.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

Gene Signatures

The present invention is also directed to signatures and uses thereof. As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., tumor infiltrating lymphocytes). In certain embodiments, the expression of the CD8+ and/or CD4+ TIL signatures are dependent on epigenetic modification of the genes or regulatory elements associated with the genes. Thus, in certain embodiments, use of signature genes includes epigenetic modifications that may be detected or modulated. For ease of discussion, when discussing gene expression, any gene or genes, protein or proteins, or epigenetic element(s) may be substituted. Reference to a gene name throughout the specification encompasses the human gene, mouse gene and all other orthologues as known in the art in other organisms. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular immune cell or immune cell (sub)population if it is upregulated or only present, detected or detectable in that particular immune cell or immune cell (sub)population, or alternatively is downregulated or only absent, or undetectable in that particular immune cell or immune cell (sub)population. In this context, a signature consists of one or more differentially expressed genes/proteins or differential epigenetic elements when comparing different cells or cell (sub)populations, including comparing different immune cell or immune cell (sub)populations, as well as comparing immune cell or immune cell (sub)populations with non-immune cell or non-immune cell (sub) populations. It is to be understood that "differentially expressed" genes/proteins include genes/proteins which are up- or down-regulated as well as genes/proteins which are turned on or off. When referring to up-or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population or subpopulation level, refer to genes that are differentially expressed in all or substantially all cells of the population or subpopulation (such as at least 80%, preferably at least 90%, such as at least 95% of the individual cells). This allows one to define a particular subpopulation of immune cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least two, at least three, at least four, at least five, at least six, or all genes/proteins and/or epigenetic elements of the signature.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In certain example embodiments, the signature genes may be used to deconvolute the network of cells present in a tumor based on comparing them to data from bulk analysis of a tumor sample. In certain example embodiments, the presence of specific immune cells and immune cell subtypes may be indicative of tumor growth, invasiveness and/or resistance to treatment. In one example embodiment, detection of one or more signature genes may indicate the presence of a particular cell type or cell types. In certain example embodiments, the presence of immune cell types within a tumor may indicate that the tumor will be sensitive to a treatment (e.g., checkpoint blockade therapy). In one embodiment, the signature genes of the present invention are applied to bulk sequencing data from a tumor sample obtained from a subject, such that information relating to disease outcome and personalized treatments is determined.

Glucocorticoid+IL-27 Signature

In certain embodiments, a glucocorticoid+IL-27 (GC+IL-27) signature comprises one or more genes that are differentially expressed in T cells in response to combined glucocorticoid signaling and IL-27 signaling activation as compared to a control not activated. In certain embodiments, the glucocorticoid+IL-27 signature comprises one or more genes selected from Table 1 (submitted as text file electronically).

Table 1 is divided into genes that are non-additive (first 3416 genes) and genes that are additive (last 3396 genes) pertaining to differential expression of the genes after the combination GC+IL-27 treatment. Non-additive means that GC+IL-27 does not equal GC+IL-27, meaning that the effect of the combination cannot be predicted by the sum of each individual condition. The non-additive effect can be either positive or negative. It is important to note that non-additive does not mean synergy (e.g., it does not mean that GC+IL-27 combination>GC+IL-27). Additive means that GC+IL-27 combination equals GC+IL-27, meaning that the effect of the combination is the sum of the effect of each individual condition.

In certain embodiments, the signature comprises the non-additive genes (Table 1). In certain embodiments, the signature comprises the additive genes. In preferred embodiments, non-additive genes are used as biomarkers and therapeutic targets.

In one example embodiment, the glucocorticoid+IL-27 signature comprises any gene in Table 1 and at least N additional biomarkers selected in Table 1, wherein N equals 1, 2, 3, 4, . . . , or up to 6811. In certain embodiments, the genes are non-additive.

In preferred embodiments, the GC+IL-27 signature comprises a subset of genes in Table 1, wherein the genes are filtered based on a threshold of adjusted p-value<0.01 and the additional threshold of fold change>2 resulting in a subset of 1558 genes downregulated (e.g., Tcf7) (Table 2A) and 1592 genes upregulated (e.g., Prdm1, Nfil3, and Entpd1) (Table 2B) in response to glucocorticoid and IL-27 treatment. Table 2A and B genes are ranked based on their adjusted p-value (from low to high). Therefore, the signature may include one or more of the ranked genes starting from the first ranked genes for the upregulated and/or downregulated genes. In certain embodiments, the signature includes the top 5, 10, 20, 30, 40, 50, 60, 70, 80, 90, 100 or up to 3150 top ranking genes. Note, Table 2 shows the glucocorticoid+IL-27 signature used for FIGS. 18C and 22F.

In certain embodiments, the glucocorticoid+IL-27 signature comprises one or more genes overlapping with a dysfunction signature (Table 3). In certain embodiments, the dysfunction signature comprises one or more genes in Table 4. The dysfunction signature in Table 4 is a CD8+ T cell dysfunction signature that includes genes differentially expressed in Tim-3$^+$PD-1$^+$CD8$^+$ TILs (tumor infiltrating lymphocytes) as compared to Tim-3$^-$ PD-1$^-$ CD8$^+$ TILs isolated from MC38-OVA tumor-bearing C57BL/6 mice (see, e.g., Kurtulus, S. et al. Checkpoint Blockade Immunotherapy Induces Dynamic Changes in PD-1(−)CD8(+) Tumor-Infiltrating T Cells. *Immunity* 50, 181-194 e186 (2019); and WO2019/014581).

In certain embodiments, the glucocorticoid+IL-27 signature comprises one or more genes differentially expressed after GC+IL27 treatment and overlapping with the MC38 dysfunction signature (Table 4) and a CT26 dysfunction signature previously obtained by a similar method as for MC38 (see, e.g., Singer, M. et al. A Distinct Gene Module for Dysfunction Uncoupled from Activation in Tumor-Infiltrating T Cells. *Cell* 171, 1221-1223 (2017); and WO2017075478A2).

In certain embodiments, the glucocorticoid+IL-27 signature comprises one or more non-additive genes differentially expressed after GC+IL27 treatment and overlapping with the MC38 dysfunction signature and the CT26 dysfunction signature (Table 5 and 6). The gene signatures are induced by GC+IL27 treatment, indicating the most dysfunctional cells, as discovered in the present invention. The gene signatures also include the genes that are non-additive when induced by GC+IL27 treatment indicating that the response is not predictable. In certain embodiments, the genes in Tables 5 and 6 indicate the genes in the dysfunction signatures most strongly associated with dysfunction. In certain embodiments, these genes are used as biomarkers and therapeutic targets.

TABLE 5A

Non-additive genes downregulated following DEX + IL27 treatment and downregulated in both exhaustion models.

| Tcf7 | Cmah | Rras2 | Icam2 | Abcc4 |
|---|---|---|---|---|
| St6gal1 | Rbm38 | Ptcra | Pim2 | Adk |
| Iigp1 | Slfn5 | Ifrigr2 | Fgr | Pepd |
| Fads2 | Slco3a1 | Stk38 | Top1mt | Pde7a |
| Btla | Hs3st3b1 | Zdhhc13 | Ehd3 | Lrrc33 |
| Dnajc7 | Socs1 | Gpx1 | Tnfsf8 | Nxf1 |
| Gpd1l | Tlr1 | | | |

TABLE 5B

Non-additive genes upregulated following DEX + IL27 treatment and upregulated in both exhaustion models.

| Entpd1 | 5330426P16Rik | Filip1 | Syngr3 | Oit3 |
|---|---|---|---|---|
| Prdm1 | Arsb | Pmaip1 | Uhrf2 | Tmem159 |
| Cysltr2 | Il1r2 | Lgals3 | Dapk2 | Aldoc |
| Aplp1 | Ppp1r3b | Gdpd5 | Hip1r | Ephb6 |
| Gpr160 | Samsn1 | BC068157 | Amigo1 | Dkkl1 |
| Tmem171 | Tmbim4 | Arhgef9 | Acadl | Abhd4 |
| Plekhb2 | Casp4 | Nrn1 | Scy12 | Impa2 |
| Sdf4 | Tnfrsf18 | AA467197 | 1110007C09Rik | Farp1 |
| Ndrg1 | Ndfip2 | Polk | Icos | Hif1a |
| Chst12 | Gm11110 | Zfp52 | Itgay | Stab1 |
| Ccdc109b | Arhgap18 | Dynlt3 | Apbb1 | |

TABLE 6A

Non-additive genes downregulated following DEX + IL27 treatment and downregulated in both exhaustion models (different threshold used).

| Dnajc7 | Slco3a1 | Sema4f | Ptcra | Traf4 |
|---|---|---|---|---|
| Fas | Ddr1 | Pde4b | Ifrigr2 | Lpin1 |
| Samhd1 | Ctsl | Aldh6a1 | Stk38 | Ipcef1 |
| Lrp12 | Btla | Socs1 | Zdhhc13 | Top1mt |
| Rftn1 | Epcam | Tlr1 | Arid5a | Chst15 |
| Il4ra | Gramd4 | Camkk1 | Phc1 | Ehd3 |
| Idua | Atp1Od | Tspan13 | Gtf2i | Rcn3 |
| Psap | Rere | Vmac | Gpx1 | Tnfsf8 |
| Bcl3 | Hs3st3b1 | Fads2 | Icam2 | Abcc4 |
| Zscan12 | St6gal1 | Kbtbd11 | Irf7 | Ephx1 |
| Gpd1l | Mbp | AB124611 | Utrn | P2rx4 |
| Tmem50b | Arhgef3 | Sesn3 | Zfp260 | Socs3 |
| Tcp1l2 | Satb1 | Serinc5 | Trib2 | Zeb1 |
| Atp2a1 | Acss2 | FosI2 | Klhdc1 | Tcf7 |
| Vdr | Iigp1 | Map4k4 | Pim2 | Adk |
| Cmah | 2610035D17Rik | Rras2 | Osbp19 | Cyp2s1 |
| Npc1 | Als2c1 | Rgs10 | Cdc14b | Pepd |
| Gpr18 | Jhdm1d | Ifnar2 | Tom1 | Pde7a |
| Rbm38 | Tpd52 | Ccpg1 | Fgr | St8sia1 |
| Gimap6 | Ralgps2 | Dzip1 | Slamf6 | Pik3ip1 |

TABLE 6A-continued

Non-additive genes downregulated following DEX + IL27 treatment and downregulated in both exhaustion models (different threshold used).

| | | | | |
|---|---|---|---|---|
| Cd24a | Itgae | Prcp | Sgip1 | Lrrc33 |
| Slfn5 | Atp1b3 | Zcchc11 | Uvrag | Nxf1 |

TABLE 6B

Non-additive genes upregulated following DEX + IL27 treatment and upregulated in both exhaustion models (different threshold used).

| | | | | |
|---|---|---|---|---|
| Chst12 | Tmem-171 | Lgals3 | Cenpp | Ccdc14 |
| Cysltr2 | Casp4 | Gdpd5 | Degs1 | Apbb1 |
| Alg8 | Tnfrsf18 | Ccdc50 | Cdca5 | Oit3 |
| Aplp1 | Ube2i | Zbtb32 | Dapk2 | Hmmr |
| Kif22 | Plekhb2 | BC068157 | Hip1r | Tmem159 |
| Ccdc109b | Sdf4 | Arhgef9 | Amigo1 | Cenph |
| Nup107 | Ccl3 | Nrn1 | Ctsc | Kdm2b |
| Ifng | Anapc4 | Tacc3 | Mrps36 | Ptplad1 |
| Rabgef1 | Ndfip2 | Spry2 | Acadl | Aldoc |
| 5330426P16Rik | Stard4 | Nr4a2 | Nqo2 | Mmd |
| Ccl4 | Fasl | Trappc4 | Scy12 | Ephb6 |
| Gpr160 | Tmem48 | AA467197 | Myo1e | Nedd9 |
| Serpine2 | Cenpt | Polk | Tmem39a | Dkk11 |
| Rpa2 | Gm-11110 | Ndrg1 | Nuf2 | Abhd4 |
| Arsb | Ttk | Sh2d2a | Rnaseh2c | Exo1 |
| Cdca3 | Arhgap-18 | Cox17 | Atad5 | Slc37a2 |
| Il1r2 | Mlf1 | Zfp52 | Ncaph | Impa2 |
| Shcbp1 | Cenpa | Dynlt3 | 2610318N02Rik | Farp1 |
| Dclk1 | Nrp1 | Syngr3 | Traip | Tmem126a |
| Esco2 | Sephs1 | Uhrf2 | Gem | Fam188a |
| Ppp1r3b | Prdm1 | Ino80c | Elk3 | Huila |
| Eno3 | Sh3bgrl | Ttc39c | Egr1 | Mtmr7 |
| Abcb1b | Filip1 | Usp46 | 1110007C09Rik | Casp3 |
| Birc5 | Plek | B4galt5 | Icos | Dut |
| Magohb | Kif20a | Gzmc | Tbc1d7 | Stab1 |
| Samsn1 | Idh3a | Tk1 | Itgay | 2810417H1-3Rik |
| Zwilch | Pmaip1 | Osbp13 | C330027C09Rik | Pilra |
| Tmbim4 | Prf1 | Smc2 | Entpd1 | Tnirsi4 |

In certain embodiments, the glucocorticoid+IL-27 signature comprises one or more genes in Table 7. The genes in Table 7 are highlighted in FIGS. 13, 14 and 22C. In certain embodiments, the genes in Table 7 are used as biomarkers and therapeutic targets.

TABLE 7A

Genes upregulated following DEX + IL27 treatment.

Upregulated after combo

| | | | | |
|---|---|---|---|---|
| Epcam | C1qtnf4 | Asb2 | Tnfrsf14 | Stat3 |
| Gpld1 | Tgfb3 | Jag2 | Zfp467 | Mt1 |
| Cd68 | Itga7 | Tnfrsf8 | Entpd1 | Bach1 |
| Prnp | Acyrl1 | Prdm1 | Nfil3 | Cd28 |
| Gab2 | Gpr125 | Smyd3 | Crebl2 | Havcr2 |
| Vldlr | Aqp11 | Tigit | Hif1a | Pdcd1 |
| Il10 | Ramp1 | Dbp | Irf6 | Ctla4 |
| Il1r2 | Kit | Tle2 | Lag3 | Cd27 |
| Nt5e | Trip6 | Ddit3 | Alcam | |
| Itgae | Enpp2 | Klf10 | Mt2 | |

TABLE 7B

Genes downregulated following DEX + IL27 treatment.

Downregulated after combo

| | | | | |
|---|---|---|---|---|
| Ifng | Ccl3 | Xcl1 | Ptrf | Tnfrsf4 |
| Ccl4 | Cd48 | Lilrb4 | Icam2 | Egr2 |
| Bcl2 | Cxcr3 | Nupr1 | Cd40lg | Ccr7 |
| Spp1 | Nanog | Hmgn2 | Il1a | Cd226 |
| Btla | Tfrc | Il24 | Tcf7 | |

In certain embodiments, the one or more glucocorticoid+IL-27 signature genes are upregulated or downregulated in response to activation of glucocorticoid signaling or IL-27 signaling separately or only one of glucocorticoid signaling and IL-27 signaling, however, the differential expression is enhanced when both glucocorticoid and IL-27 signaling is activated, such that a downregulated gene is further downregulated and an upregulated gene is further upregulated (see, Table 1).

In certain embodiments, the signature includes genes whose expression is further enhanced by the combination. For example, Tgfb3 expression is further enhanced, where the control cells show expression levels of 0.1, 0.12, 0.03, the Dex only cells show expression levels of 8.53, 5.51, 5.9, the IL-27 only cells show expression levels of 3.6, 1.14, 2.06, and the combo cells show expression levels of 12.08, 11.67, 16.33. Also, CD28 expression is further enhanced, where the control cells show expression levels of 19.54, 18.14, 18.29, the Dex only cells show expression levels of 31.98, 33.89, 35.83, the IL-27 only cells show expression levels of 48.93, 37.2, 39.84, and the combo cells show expression levels of 61.19, 60.85, 56.07. In certain embodiments, genes in Table 1 having enhanced expression in response to both glucocorticoid signaling and IL-27 signaling activation are used as biomarkers and therapeutic targets.

In certain embodiments, the signature includes genes whose expression is further reduced by the combination. For example, Il24 expression is further reduced, where the control cells show expression levels of 280.07, 260.93, 314.42, the Dex only cells show expression levels of 156.6, 224.35, 191, the IL-27 only cells show expression levels of 86.97, 190.89, 192.77, and the combo cells show expression levels of 12.82, 44.26, 14.08. Also, Tcf7 expression is further reduced, where the control cells show expression levels of 9.93, 8.28, 11.45 the Dex only cells show expression levels of 9.54, 8.42, 8.72, the IL-27 only cells show expression levels of 5.37, 7.39, 5.57, and the combo cells show expression levels of 1.62, 1.39, 3.32. In certain embodiments, genes in Table 1 having reduced expression in response to both glucocorticoid signaling and IL-27 signaling activation are used as biomarkers and therapeutic targets.

In certain embodiments, the gene signature includes genes that are upregulated or downregulated in response to activation of only one of glucocorticoid signaling and IL-27 signaling, but are downregulated or upregulated when the combination is activated (e.g., the response is reversed from either single treatment). For example, Lilrb4 expression is reversed, where the control cells show expression levels of 87.12, 92.82, 96.51, the Dex only cells show expression levels of 179.28, 174.41, 160.09 (increased as compared to control), the IL-27 only cells show expression levels of 73.62, 94.25, 105.87 (increased as compared to control), and the combo cells show expression levels of 31.55, 29.82, 27.03 (decreased as compared to control). Also, Nupr1 expression is reversed, where the control cells show expression levels of 12.77, 13.57, 13.47, the Dex only cells show expression levels of 11.81, 14.26, 21.7, the IL-27 only cells show expression levels of 11.93, 21.86, 19.79, and the combo cells show expression levels of 3.56, 7.19, 3.68. Differential expression of the genes in this group as compared to the control after the combination treatment indicates genes that have differential expression in the most dysfunctional cells. Based on the change in direction of expression as compared to either Dex or IL-27 alone, these genes are unexpected targets for modulation of T cell dysfunction (e.g., the direction of modulation is unexpected). In certain embodiments, based on the differential expression as compared to control, these genes are used as biomarkers and therapeutic targets.

In certain embodiments, the glucocorticoid+IL-27 signature is referred to as a checkpoint blockade (CPB) therapy non-responder signature. The presence of dysfunctional T cells having the signature correlate with non-response to CPB therapy.

Immunotherapy can include checkpoint blockers (CPB), chimeric antigen receptors (CARs), and adoptive T-cell therapy. Antibodies that block the activity of checkpoint receptors, including CTLA-4, PD-1, Tim-3, Lag-3, and TIGIT, either alone or in combination, have been associated with improved effector $CD8^+$ T cell responses in multiple pre-clinical cancer models (Johnston et al., 2014. The immunoreceptor TIGIT regulates antitumor and antiviral CD8(+) T cell effector function. Cancer cell 26, 923-937; Ngiow et al., 2011. Anti-TIM3 antibody promotes T cell IFN-gamma-mediated antitumor immunity and suppresses established tumors. Cancer research 71, 3540-3551; Sakuishi et al., 2010. Targeting Tim-3 and PD-1 pathways to reverse T cell exhaustion and restore anti-tumor immunity. The Journal of experimental medicine 207, 2187-2194; and Woo et al., 2012. Immune inhibitory molecules LAG-3 and PD-1 synergistically regulate T-cell function to promote tumoral immune escape. Cancer research 72, 917-927). Similarly, blockade of CTLA-4 and PD-1 in patients (Brahmer et al., 2012. Safety and activity of anti-PD-L1 antibody in patients with advanced cancer. The New England journal of medicine 366, 2455-2465; Hodi et al., 2010. Improved survival with ipilimumab in patients with metastatic melanoma. The New England journal of medicine 363, 711-723; Schadendorf et al., 2015. Pooled Analysis of Long-Term Survival Data From Phase II and Phase III Trials of Ipilimumab in Unresectable or Metastatic Melanoma. Journal of clinical oncology: official journal of the American Society of Clinical Oncology 33, 1889-1894; Topalian et al., 2012. Safety, activity, and immune correlates of anti-PD-1 antibody in cancer. The New England journal of medicine 366, 2443-2454; and Wolchok et al., 2017. Overall Survival with Combined Nivolumab and Ipilimumab in Advanced Melanoma. The New England journal of medicine 377, 1345-1356) has shown increased frequencies of proliferating T cells, often with specificity for tumor antigens, as well as increased $CD8^+$ T cell effector function (Ayers et al., 2017. IFN-gamma-related mRNA profile predicts clinical response to PD-1 blockade. The Journal of clinical investigation 127, 2930-2940; Das et al., 2015. Combination therapy with anti-CTLA-4 and anti-PD-1 leads to distinct immunologic changes in vivo. Journal of immunology 194, 950-959; Gubin et al., 2014. Checkpoint blockade cancer immunotherapy targets tumour-specific mutant antigens. Nature 515, 577-581; Huang et al., 2017. T-cell invigoration to tumour burden ratio associated with anti-PD-1 response. Nature 545, 60-65; Kamphorst et al., 2017. Proliferation of PD-1+ CD8 T cells in peripheral blood after PD-1-targeted therapy in lung cancer patients. Proceedings of the National Academy of Sciences of the United States of America 114, 4993-4998; Kvistborg et al., 2014. Anti-CTLA-4 therapy broadens the melanoma-reactive $CD8^+$ T cell response. Science translational medicine 6, 254ra128; van Rooij et al., 2013. Tumor exome analysis reveals neoantigen-specific T-cell reactivity in an ipilimumab-responsive melanoma. Journal of clinical oncology: official journal of the American Society of Clinical Oncology 31, e439-442; and Yuan et al., 2008. CTLA-4 blockade enhances polyfunctional NY-ESO-1 specific T cell responses in metastatic melanoma patients with clinical benefit. Proceedings of the National Academy of Sciences of the United States of America 105, 20410-20415). Accordingly, the success of checkpoint receptor blockade has been attributed to the binding of blocking antibodies to checkpoint receptors expressed on dysfunctional $CD8^+$ T cells and restoring effector function in these cells. The check point blockade therapy may be an inhibitor of any check point protein described herein. The checkpoint blockade therapy may comprise anti-TIM3, anti-CTLA4, anti-PD-L1, anti-PD1, anti-TIGIT, anti-LAG3, or combinations thereof. Anti-PD1 antibodies are disclosed in U.S. Pat. No. 8,735,553. Antibodies to LAG-3 are disclosed in U.S. Pat. No. 9,132,281. Anti-CTLA4 antibodies are disclosed in U.S. Pat. Nos. 9,327,014; 9,320,811; and 9,062,111. Specific check point inhibitors include, but are not limited to anti-CTLA4 antibodies (e.g., Ipilimumab and tremelimumab), anti-PD-1 antibodies (e.g., Nivolumab, Pembrolizumab), and anti-PD-L1 antibodies (e.g., Atezolizumab).

Detection and Isolation Using Biomarkers

A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., $\pm 1 \times SD$ or $\pm 2 \times SD$ or $\pm 3 \times SD$, or $1 \times SE$ or $\pm 2 \times SE$ or $\pm 3 \times SE$). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

The method may allow to detect or conclude the presence or absence of the specified immune cells in a tested object (e.g., in a cell population, tissue, organ, organism, or in a biological sample of a subject). The method may also allow to quantify the specified immune cells in a tested object (e.g., in a cell population, tissue, organ, organism, or in a biological sample of a subject). The quantity of the specified immune cells in the tested object such as the biological sample may be suitably expressed for example as the number (count) of the specified immune cells per standard unit of volume (e.g., ml, µl or nl) or weight (e.g., g or mg or ng) of the tested object such as the biological sample. The quantity of the specified immune cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of white blood cells, peripheral blood mononuclear cells, immune cells, antigen presenting cells, or dendritic cells comprised in the tested object such as the biological sample. The quantity of the specified immune cells in the tested object such as the biological sample may also be suitably represented by an absolute or relative quantity of a suitable surrogate analyte, such as a peptide, polypeptide, protein, or nucleic acid expressed or comprised by the specified immune cells.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

In certain embodiments, the CD8+ and/or CD4+ T cell subtypes may be detected, quantified or isolated using a technique selected from the group consisting of flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH), Flow-FISH and combinations thereof. The technique may employ one or more agents capable of specifically binding to one or more gene products expressed or not expressed by the CD8$^+$ T cells, preferably on the cell surface of the CD8$^+$ T cells. The one or more agents may be one or more antibodies. Other methods including absorbance assays and colorimetric assays are known in the art and may be used herein.

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

Immunoassays

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

In other example embodiments, detection of a marker may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In certain example embodiments, detection of a marker or signature may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

MS Methods

Biomarker detection may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')$_2$ fragment, a single chain antibody fragment, an Fv fragment, a single chain Fv fragment, a nucleic acid, a lectin, a ligand-binding receptor, affibodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

In other example embodiments, detection of a marker may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

Separation

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

In certain embodiments, further techniques for separating, detecting and/or quantifying markers may be used in conjunction with any of the above described detection methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (sc-RNA seq), or the like. By means of an example, methods to profile the RNA content of large numbers of individual cells have been recently developed.

Hybridization Assays

Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324, 633; 5,432,049; 5,470,710; 5,492,806; 5,503,980; 5,510, 270; 5,525,464; 5,547,839; 5,580,732; 5,661,028; 5,800, 992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

Sequencing and Single Cell Sequencing

In certain embodiments, the invention involves targeted nucleic acid profiling (e.g., sequencing, quantitative reverse transcription polymerase chain reaction, and the like) (see e.g., Geiss G K, et al., Direct multiplexed measurement of gene expression with color-coded probe pairs. Nat Biotechnol. 2008 March; 26(3):317-25). In certain embodiments, a target nucleic acid molecule (e.g., RNA molecule), may be sequenced by any method known in the art, for example, methods of high-throughput sequencing, also known as next generation sequencing or deep sequencing. A nucleic acid target molecule labeled with a barcode (for example, an origin-specific barcode) can be sequenced with the barcode to produce a single read and/or contig containing the sequence, or portions thereof, of both the target molecule and the barcode. Exemplary next generation sequencing technologies include, for example, Illumina sequencing, Ion Torrent sequencing, 454 sequencing, SOLiD sequencing, and nanopore sequencing amongst others.

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p 666-673, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In certain embodiments, the invention involves the Assay for Transposase Accessible Chromatin using sequencing (ATAC-seq) as described. (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. *Nature* 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. *Science.* 2015 May 22; 348(6237): 910-4. doi: 10.1126/science.aab1601. Epub 2015 May 7; US20160208323A1; US20160060691A1; and WO2017156336A1).

T cell Modulating Agents

In certain embodiments T cell dysfunction is modulated in a population of cells or in a subject in need thereof by contacting with one or more agents. As used herein, an "agent" can refer to a protein-binding agent that permits modulation of activity of proteins or disrupts interactions of proteins and other biomolecules, such as but not limited to disrupting protein-protein interaction, ligand-receptor interaction, or protein-nucleic acid interaction. Agents can also refer to DNA targeting or RNA targeting agents. In certain embodiments, the one or more agents comprise an antibody, antibody fragment, intrabody, antibody-like protein scaffold, aptamer, polypeptide, small molecule, small molecule degrader (PROTAC), genetic modifying agent, or any combination thereof.

In certain embodiments, the agent is a therapeutic agent used for treating a subject in need thereof. The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein "treating" includes ameliorating, curing, preventing it from becoming worse, slowing the rate of progression, or preventing the disorder from re-occurring (i.e., to prevent a relapse). In certain embodiments, the present invention provides for one or more therapeutic agents against combinations of targets identified. Targeting the identified combinations may provide for enhanced or otherwise previously unknown activity in the treatment of disease.

IL-27

In certain embodiments, agents can refer to proteins, such as IL-27. IL-27 is a heterodimeric cytokine and a member of the IL-12 family of cytokines that is produced by antigen presenting cells. Although IL-27 was initially shown to promote pro-inflammatory Type 1 immune responses, emerging evidence suggests that this cytokine plays an important role in the resolution of tissue inflammation (Yoshida and Hunter, (2015) *Annual review of immunology* 33, 417-443). IL-27 administration in vivo suppresses the pathogenicity of primed effector T cells and inhibits the development of autoimmunity (Fitzgerald et al., (2007a) *Journal of immunology* 179, 3268-3275). Consistent with a suppressive function for IL-27, IL-27ra (WSX-1) deficient mice exhibit increased inflammation during *Toxoplasma gondii* infection and exacerbated disease in a model of central nervous system autoimmunity (Awasthi et al., (2007) *Nature immunology* 8, 1380-1389; Hirahara et al., (2012) *Immunity* 36, 1017-1030; Villarino et al., (2003) *Immunity* 19, 645-655). Indeed, Applicants (Awasthi et al., 2007) and others (Fitzgerald et al., 2007a; Stumhofer et al., (2007) *Nature immunology* 8, 1363-1371) have shown that exposure of naïve T cells to IL-27 induces IL-10-secreting Type 1 regulatory (Tr1) cells that are immune suppressive. Moreover, Applicants have recently shown that IL-27 induces Tim-3 (Zhu et al., (2015) Nature communications 6, 6072), which has been shown to cooperate with PD-1 in promoting a dysfunctional phenotype in T cells (Sakuishi et al., 2010, *The Journal of experimental medicine* 207, 2187-2194). Applicants, previously used a systems biology approach to find that IL-27 signaling drives the expression of a gene module that includes not only Tim-3, but also Lag-3, TIGIT, and IL-10, all molecules that are associated with T cell dysfunction (see, e.g., WO/2017/069958).

The present invention provides methods of using agonists and antagonists of IL-27. An agonist of IL-27 encompasses, e.g., IL-27, an IL-27 variant, hyperkine, or peptide mimetic thereto, agonistic antibodies to WSX-1/TCCR or gp130, and nucleic acids encoding these agonists. Antagonists of IL-27 include, e.g., antibodies to IL-27, antibodies to p28 or EBI3, blocking antibodies to WSX-1/TCCR or gp130, a soluble receptor based on the extracellular region of a subunit of WSX-1/TCCR or gp130, peptide mimetics thereto, and nucleic acids encoding these antagonists. Anti-idiotypic antibodies may also be used.

The present invention provides methods of using agonists and antagonists of p28, agonists and antagonists of the complex of p28 and EBI3, agonists and antagonists of WSX-1/TCCR, agonists and antagonists of gp130, and agonists and antagonists of the complex of WSX-1/TCCR and gp130.

An IL-27 hyperkine encompasses, e.g., a fusion protein comprising the polypeptide sequence of p28 and EBI3, where p28 and EBI3 occur in one continuous polypeptide chain. The sequences of p28 and EBI3 may be in either order in the continuous polypeptide chain. The fusion protein may contain a linker sequence, residing in between the sequences of p28 and EBI3, in one continuous polypeptide chain.

Antibodies to p28, EBI3, WSX-1/TCCR, and gp130 are available (see, e.g., Pflanz, et al. (2004) J. Immunol. 172: 2225-2231; Larousserie, et al. (2004) J. Pathol. 202:164-171; Devergne, et al. (2001) Am. J. Pathol. 159:1763-1776; Autissier, et al. (1998) Int. Immunol. 10:1881-1889). Also contemplated are antibodies that specifically bind the complex of p28 and EBI3, and antibodies that specifically bind to the complex of WSX-1/TCCR and gp130.

Also provided are soluble receptors corresponding to an extracellular domain of WSX-1/TCCR and gp130. The extracellular domain of mature human WSX-1/TCCR comprises amino acids 33 to 514 of the amino acid sequence of GenBank BC028003 or NM 004843. This extracellular domain includes a classical cytokine binding domain, and also three fibronectin (FN) domains. The invention contemplates a soluble receptor comprising the cytokine binding domain and none, one, or, or three of the FN domains. Soluble gp130 is available (see, e.g., Hui, et al. (2000) Cytokine 12:151-155).

Glucocorticoids

In certain embodiments, methods of increasing T cell dysfunction may comprise contacting a population of cells with a glucocorticoid or administering a glucocorticoid to a subject in need thereof. In certain embodiments, a glucocorticoid and IL-27 is contacted or administered. Glucocorticoids (GCs) are a class of corticosteroids, which are a class of steroid hormones. Glucocorticoids are corticosteroids that bind to the glucocorticoid receptor (GR) that is present in almost every vertebrate animal cell. The name glucocorticoid (glucose+cortex+steroid) is composed from its role in regulation of glucose metabolism, synthesis in the adrenal cortex, and its steroidal structure. The glucocorticoid receptor (GR, or GCR) also known as NR3C1 (nuclear receptor subfamily 3, group C, member 1) is the receptor to which cortisol and other glucocorticoids bind. Example glucocorticoids applicable to the present invention include, but are not limited to:

| Name | Glucocorticoid potency | Mineralocorticoid potency | Terminal half-life (hours) |
| --- | --- | --- | --- |
| Cortisol (hydrocortisone) | 1 | 1 | 8 |
| Cortisone | 0.8 | 0.8 | 8 |
| Prednisone | 3.5-5 | 0.8 | 16-36 |
| Prednisolone | 4 | 0.8 | 16-36 |
| Methylprednisolone | 5-7.5 | 0.5 | 18-40 |
| Dexamethasone | 25-80 | 0 | 36-54 |
| Betamethasone | 25-30 | 0 | 36-54 |
| Triamcinolone | 5 | 0 | 12-36 |
| Fludrocortisone acetate | 15 | 200 | 24 |
| Deoxycorticosterone acetate | 0 | 20 | — |

In certain embodiments, the agent modulates glucocorticoid signaling. In certain embodiments, the agent is an agonist or antagonist of glucocorticoid receptor activity. Agonists and antagonists of the glucocorticoid receptor have been described and are applicable to the present invention (see, e.g., WO2004005229A1).

Steroidogenesis Inhibitors

In certain embodiments, the agent prevents production of glucocorticoids. A steroidogenesis inhibitor, also known as a steroid biosynthesis inhibitor, is a type of drug which inhibits one or more of the enzymes that are involved in the process of steroidogenesis, the biosynthesis of endogenous steroids and steroid hormones. They may inhibit the production of cholesterol and other sterols, sex steroids such as androgens, estrogens, and progestogens, corticosteroids such as glucocorticoids and mineralocorticoids, and neurosteroids. They are currently used in the treatment of a variety of medical conditions that depend on endogenous steroids. Non-limiting examples of inhibitors useful in the present invention are provided herein.

Cholesterol side-chain cleavage enzyme (P450scc, CYP11A1) inhibitors such as aminoglutethimide, ketoconazole, and mitotane inhibit the production of pregnenolone from cholesterol and thereby prevent the synthesis of all steroid hormones. They have been used to inhibit corticosteroid synthesis in the treatment of Cushing's syndrome and adrenocortical carcinoma. Ketoconazole has also been used to inhibit androgen production in the treatment of prostate cancer. Other inhibitors of Cyp11a1 applicable to the present invention include, but are not limited to 22-ABC, 3,3'-Dimethoxybenzidine, 3-Methoxybenzidine, Aminoglutethimide, Amphenone B, Canrenone, Cyanoketone, Danazol, Etomidate, Ketoconazole, Levoketoconazole, Mitotane, Spironolactone and Trilostane.

3β-Hydroxysteroid dehydrogenase (3β-HSD) inhibitors such as amphenone B, azastene, cyanoketone, epostane, mitotane, and trilostane inhibit the conversion of Δ$^5$-3β-hydroxysteroids into Δ$^4$-3-ketosteroids and thereby inhibit the production of most of the steroid hormones. Trilostane was formerly used to inhibit corticosteroid synthesis in the treatment of Cushing's syndrome.

17α-Hydroxylase/17,20-lyase (CYP17A1) inhibitors such as abiraterone acetate, etomidate, galeterone, ketoconazole, and orteronel inhibit the production of androgens and glucocorticoids and are used to reduce androgen levels in the treatment of prostate cancer.

21-Hydroxylase (CYP21A2) inhibitors prevent the production of corticosteroids from progesterone and 17α-hydroxyprogesterone. Non-limiting examples include Aminoglutethimide, Amphenone B, Bifonazole, Canrenone, Clotrimazole, Diazepam, Econazole, Genistein, Isoconazole, Ketoconazole, Levoketoconazole, Metyrapone, Miconazole, Midazolam, Spironolactone, Abiraterone, Abiraterone acetate, and Tioconazole.

11β-Hydroxylase (CYP11B1) inhibitors such as amphenone B, etomidate, ketoconazole, metyrapone, mitotane, and osilodrostat inhibit the production of the potent corticosteroids cortisol, corticosterone, and aldosterone from the less potent corticosteroids 11-deoxycorticosterone and 11-deoxycortisol and are used in the diagnosis and treatment of Cushing's syndrome.

Additional Classes of Agents

Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs; recombinant antibodies; chimeric antibodies; humanized antibodies; nanobodies; tribodies; midibodies; or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof. An "agent" as used herein, may also refer to an agent that inhibits expression of a gene, such as but not limited to a DNA targeting agent (e.g., CRISPR system, TALE, Zinc finger protein) or RNA targeting agent (e.g., inhibitory nucleic acid molecules such as RNAi, miRNA, ribozyme).

The composition of the invention can also advantageously be formulated in order to release an agent in the subject in a timely controlled fashion. In certain embodiments, the agent is a time released agent. The active agent may be released upon contact with a certain pH. The agent may be administered in a time release device.

The agents of the present invention may be modified, such that they acquire advantageous properties for therapeutic use (e.g., stability and specificity), but maintain their biological activity.

It is well known that the properties of certain proteins can be modulated by attachment of polyethylene glycol (PEG) polymers, which increases the hydrodynamic volume of the protein and thereby slows its clearance by kidney filtration. (See, e.g., Clark et al., J. Biol. Chem. 271: 21969-21977 (1996)). Therefore, it is envisioned that certain agents can be PEGylated (e.g., on peptide residues) to provide enhanced therapeutic benefits such as, for example, increased efficacy by extending half-life in vivo. In certain embodiments, PEGylation of the agents may be used to extend the serum half-life of the agents and allow for particular agents to be capable of crossing the blood-brain barrier. Thus, in one embodiment, PEGylating the agonists or antagonists improve their pharmacokinetics and pharmacodynamics.

In regards to peptide PEGylation methods, reference is made to Lu et al., Int. J. Pept. Protein Res. 43: 127-38 (1994); Lu et al., Pept. Res. 6: 140-6 (1993); Felix et al., Int. J. Pept. Protein Res. 46: 253-64 (1995); Gaertner et al., Bioconjug. Chem. 7: 38-44 (1996); Tsutsumi et al., Thromb. Haemost. 77: 168-73 (1997); Francis et al., hit. J. Hematol. 68: 1-18 (1998); Roberts et al., J. Pharm. Sci. 87: 1440-45 (1998); and Tan et al., Protein Expr. Purif. 12: 45-52 (1998). Polyethylene glycol or PEG is meant to encompass any of the forms of PEG that have been used to derivatize other proteins, including, but not limited to, mono-(C1-10) alkoxy or aryloxy-polyethylene glycol. Suitable PEG moieties include, for example, 40 kDa methoxy poly(ethylene glycol) propionaldehyde (Dow, Midland, Mich.); 60 kDa methoxy poly(ethylene glycol) propionaldehyde (Dow, Midland, Mich.); 40 kDa methoxy poly(ethylene glycol) maleimidopropionamide (Dow, Midland, Mich.); 31 kDa alpha-methyl-w-(3-oxopropoxy), polyoxyethylene (NOF Corporation, Tokyo); mPEG2-NHS-40k (Nektar); mPEG2-MAL-40k (Nektar), SUNBRIGHT GL2-400MA ((PEG)240 kDa) (NOF Corporation, Tokyo), SUNBRIGHT ME-200MA (PEG20 kDa) (NOF Corporation, Tokyo). The PEG groups are generally attached to the peptide via acylation or alkylation through a reactive group on the PEG moiety (for example, a maleimide, an aldehyde, amino, thiol, or ester group) to a reactive group on the peptide (for example, an aldehyde, amino, thiol, a maleimide, or ester group).

The PEG molecule(s) may be covalently attached to any Lys, Cys, or K(CO(CH2)2SH) residues at any position in a peptide. In certain embodiments, the agents described herein can be PEGylated directly to any amino acid at the N-terminus by way of the N-terminal amino group. A "linker arm" may be added to a peptide to facilitate PEGylation. PEGylation at the thiol side-chain of cysteine has been widely reported (see, e.g., Caliceti & Veronese, Adv. Drug Deliv. Rev. 55: 1261-77 (2003)). If there is no cysteine residue in the peptide, a cysteine residue can be introduced through substitution or by adding a cysteine to the N-terminal amino acid. In certain embodiments, protein agents are PEGylated through the side chains of a cysteine residue added to the N-terminal amino acid.

In exemplary embodiments, the PEG molecule(s) may be covalently attached to an amide group in the C-terminus of a peptide. In preferred embodiments, there is at least one PEG molecule covalently attached to the agent. In certain embodiments, the PEG molecule used in modifying an agent of the present invention is branched while in other embodiments, the PEG molecule may be linear. In particular aspects, the PEG molecule is between 1 kDa and 100 kDa in molecular weight. In further aspects, the PEG molecule is selected from 10, 20, 30, 40, 50, 60, and 80 kDa. In further still aspects, it is selected from 20, 40, or 60 kDa. Where there are two PEG molecules covalently attached to the agent of the present invention, each is 1 to 40 kDa and in particular aspects, they have molecular weights of 20 and 20 kDa, 10 and 30 kDa, 30 and 30 kDa, 20 and 40 kDa, or 40 and 40 kDa. In particular aspects, the agent (e.g., neuromedin U receptor agonists or antagonists) contain mPEG-cysteine. The mPEG in mPEG-cysteine can have various molecular weights. The range of the molecular weight is preferably 5 kDa to 200 kDa, more preferably 5 kDa to 100 kDa, and further preferably 20 kDa to 60 kDA. The mPEG can be linear or branched.

In particular embodiments, the agents (e.g., agonist or antagonists) include a protecting group covalently joined to the N-terminal amino group. In exemplary embodiments, a protecting group covalently joined to the N-terminal amino group of the agent reduces the reactivity of the amino terminus under in vivo conditions. Amino protecting groups include —C1-10 alkyl, —C1-10 substituted alkyl, —C2-10 alkenyl, —C2-10 substituted alkenyl, aryl, —C1-6 alkyl aryl, —C(O)—(CH2)1-6-COOH, —C(O)—C1-6 alkyl, —C(O)-aryl, —C(O)—O—C1-6 alkyl, or —C(O)—O-aryl. In particular embodiments, the amino terminus protecting group is selected from the group consisting of acetyl, propyl, succinyl, benzyl, benzyloxycarbonyl, and t-butyloxycarbonyl. In other embodiments, deamination of the N-terminal amino acid is another modification that may be used for reducing the reactivity of the amino terminus under in vivo conditions.

Chemically modified compositions of the agents wherein the agent is linked to a polymer are also included within the scope of the present invention. The polymer selected is usually modified to have a single reactive group, such as an active ester for acylation or an aldehyde for alkylation, so that the degree of polymerization may be controlled. Included within the scope of polymers is a mixture of polymers. Preferably, for therapeutic use of the end-product preparation, the polymer will be pharmaceutically acceptable. The polymer or mixture thereof may include but is not limited to polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (for example, glycerol), and polyvinyl alcohol.

In other embodiments, the agents are modified by PEGylation, cholesterylation, or palmitoylation. The modification can be to any amino acid residue. In preferred embodiments, the modification is to the N-terminal amino acid of the agent (e.g., agonist or antagonists), either directly to the N-terminal amino acid or by way coupling to the thiol group of a cysteine residue added to the N-terminus or a linker added to the N-terminus such as trimesoyl tris(3,5-dibromosalicylate (Ttds). In certain embodiments, the N-terminus of the agent comprises a cysteine residue to which a protecting group is coupled to the N-terminal amino group of the cysteine residue and the cysteine thiolate group is derivatized with N-ethylmaleimide, PEG group, cholesterol group, or palmitoyl group. In other embodiments, an acetylated cysteine residue is added to the N-terminus of the agents, and the thiol group of the cysteine is derivatized with N-ethylmaleimide, PEG group, cholesterol group, or palmitoyl group. In certain embodiments, the agent of the present invention is a conjugate. In certain embodiments, the agent of the present invention (e.g., agonists or antagonists) is a polypeptide consisting of an amino acid sequence which is bound with a methoxypolyethylene glycol(s) via a linker.

Substitutions of amino acids may be used to modify an agent of the present invention. The phrase "substitution of amino acids" as used herein encompasses substitution of amino acids that are the result of both conservative and non-conservative substitutions. Conservative substitutions are the replacement of an amino acid residue by another similar residue in a polypeptide. Typical but not limiting conservative substitutions are the replacements, for one another, among the aliphatic amino acids Ala, Val, Leu and Ile; interchange of Ser and Thr containing hydroxy residues, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met, and Gly. Non-conservative substitutions are the replacement, in a polypeptide, of an amino acid residue by another residue which is not biologically similar. For example, the replacement of an amino acid residue with another residue that has a substantially different charge, a substantially different hydrophobicity, or a substantially different spatial configuration.

Small Molecule

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking a binding site or activating a receptor by binding to a ligand binding site).

One type of small molecule applicable to the present invention is a degrader molecule. Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57: 107-123; and Lai et al., Modular PROTAC Design for the Degradation of Oncogenic BCR-ABL Angew Chem Int Ed Engl. 2016 Jan. 11; 55(2): 807-810).

In certain embodiments, combinations of targets are modulated (e.g., one or more targets in a gene signature). In certain embodiments, an agent against one of the targets in a combination may already be known or used clinically. In certain embodiments, targeting the combination may require less of the agent as compared to the current standard of care and provide for less toxicity and improved treatment.

Antibodies

The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')$_2$, Fabc, Fd, dAb, V$_{HH}$ and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, lgM antibodies exist in pentameric form, and IgA antibodies exist in monomeric, dimeric or multimeric form.

The term "IgG subclass" refers to the four subclasses of immunoglobulin class IgG—IgG1, IgG2, IgG3, and IgG4 that have been identified in humans and higher mammals by the heavy chains of the immunoglobulins, VI-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by p pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (1° F.n3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins—harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1 \times 10^7$ $M^{-1}$ (or a dissociation coefficient of 1 µM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$—$C_h1$-$V_H$-$C_h1$) which, together with complementary light chain polypeptides, form a pair of antigen binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. For example, an antagonist antibody may bind glucocorticoid receptor, glucocorticoid, IL-27 receptor, or IL-27 and inhibit the ability to suppress an immune response. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Aptamers

In certain embodiments, the one or more agents is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colorado). In certain embodiments, the present invention may utilize any aptamer containing any modification as described herein.

The disclosure also encompasses nucleic acid molecules. Exemplary nucleic acid molecules include aptamers, siRNA, artificial microRNA, interfering RNA or RNAi, dsRNA, ribozymes, antisense oligonucleotides, and DNA expression cassettes encoding said nucleic acid molecules. Preferably, the nucleic acid molecule is an antisense oligonucleotide. Antisense oligonucleotides (ASO) generally inhibit their target by binding target mRNA and sterically blocking expression by obstructing the ribosome. ASOs can also inhibit their target by binding target mRNA thus forming a DNA-RNA hybrid that can be a substance for RNase H. Preferred ASOs include Locked Nucleic Acid (LNA), Peptide Nucleic Acid (PNA), and morpholinos Preferably, the nucleic acid molecule is an RNAi molecule, i.e., RNA interference molecule. Preferred RNAi molecules include siRNA, shRNA, and artificial miRNA. The design and production of siRNA molecules is well known to one of skill in the art (e.g., Hajeri P B, Singh S K. Drug Discov Today. 2009 14(17-18):851-8). The nucleic acid molecule inhibitors may be chemically synthesized and provided directly to cells of interest. The nucleic acid compound may be provided to a cell as part of a gene delivery vehicle. Such a vehicle is preferably a liposome or a viral gene delivery vehicle.

Genetic Modifying Agents

In certain embodiments, the one or more modulating agents may be a genetic modifying agent. The genetic modulating agent can be used to up- or downregulate expression of a gene either by targeting a nuclease or functional domain to a DNA or RNA sequence. The genetic modifying agent may comprise a CRISPR system, a zinc finger nuclease system, a TALEN, a meganuclease or RNAi system.

CRISPR Systems

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the 3-actin promoter, the phosphoglycerol kinase (PGK) promoter, and the EF11a promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromouridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, PNAS, E7110-E7111; Allerson et al., J. Med. Chem. 2005, 48:901-904; Bramsen et al., Front. Genet., 2012, 3:154; Deng et al., PNAS, 2015, 112:11870-11875; Sharma et al., Med Chem Comm., 2014, 5:1454-1471; Hendel et al., Nat. Biotechnol. (2015) 33(9): 985-989; Li et al., Nature Biomedical Engineering, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, J. Biotech. 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., Nature Biomedical Engineering, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine ($\Psi$), N1-methylpseudouridine (mel$\Psi$), 5-methoxyuridine (5moU), inosine, 7-methylguanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI: 10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023, which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprise one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application 62/484,786, entitled "Novel Type VI CRISPR Orthologs and Systems," filed on Apr. 12, 2017.

In certain other example embodiments, the CRISPR system effector protein is a C2c2 nuclease (also referred to as Cas13a). The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional 62/432,240, entitled "Novel Crispr Enzymes and Systems" filed Dec. 9, 2016. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: *Leptotrichia, Listeria,* Corynebacter, *Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter,* and *Lachnospira,* or the C2c2 effector protein is an organism selected from the group consisting of: *Leptotrichia shahii, Leptotrichia. wadei, Listeria seeligeri, Clostridium amino-philum, Carnobacterium gallinarum, Paludibacter propionicigenes, Listeria weihenstephanensis,* or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and *Ruminococcus*. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYL1. WYL1 is a single WYL-domain protein associated primarily with *Ruminococcus*.

In other example embodiments, the Type VI RNA-targeting Cas enzyme is Cas13d. In certain embodiments, Cas13d is *Eubacterium* siraeum DSM 15702 (EsCas13d) or *Ruminococcus* sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g., Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of. Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present invention may also use a Cas12 CRISPR enzyme. Cas12 enzymes include Cas12a (Cpf1), Cas12b (C2c1), and Cas12c (C2c3), described further herein.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. *Nat Biotechnol* March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. *Nat Biotechnol* doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol*. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) *Nat Biotechnol*. Dec; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) *Nat Biotechnol*. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) *Nat Biotechnol*. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91(2015).

Shalem et al., "High-throughput functional genomics using CRISPR-Cas9," *Nature Reviews Genetics* 16, 299-311 (May 2015).

Xu et al., "Sequence determinants of improved CRISPR sgRNA design," *Genome Research* 25, 1147-1157 (August 2015).

Parnas et al., "A Genome-wide CRISPR Screen in Primary Immune Cells to Dissect Regulatory Networks," *Cell* 162, 675-686 (Jul. 30, 2015).

Ramanan et al., CRISPR-Cas9 cleavage of viral DNA efficiently suppresses hepatitis B virus," *Scientific Reports* 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., *Nature* 527(7577): 192-7 (Nov. 12, 2015) doi: 10.1038/nature15521. Epub 2015 Sep. 16.

Cpf1 Is a Single RNA-Guided Endonuclease of a Class 2 CRISPR-Cas System, Zetsche et al., *Cell* 163, 759-71 (Sep. 25, 2015).

Discovery and Functional Characterization of Diverse Class 2 CRISPR-Cas Systems, Shmakov et al., *Molecular Cell*, 60(3), 385-397 doi: 10.1016/j.molcel.2015.10.008 Epub Oct. 22, 2015.

Rationally engineered Cas9 nucleases with improved specificity, Slaymaker et al., *Science* 2016 Jan. 1 351(6268): 84-88 doi: 10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. doi: 10.1126/science.aaq0180. Epub 2017 Oct. 25.

Gaudelli et al. "Programmable base editing of A-T to G-C in genomic DNA without DNA cleavage" Nature 464(551); 464-471 (2017).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 Å resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Strepto-*

*coccus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353(6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

Also, Harrington et al. "Programmed DNA destruction by miniature CRISPR-Cas14 enzymes" Science 2018 doi:10/1126/science.aav4293, relates to Cas14.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US 2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 15, PROTECTED GUIDE RNAS (PGRNAS); U.S. application 62/091,455, filed, 12 Dec. 14, PROTECTED GUIDE RNAS (PGRNAS); U.S. application 62/096,708, 24 Dec. 14, PROTECTED GUIDE RNAS (PGRNAS); U.S. applications 62/091,462, 12 Dec. 14, 62/096,324, 23 Dec. 14, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 14 and 62/180,692, 17 Jun. 2015, ESCORTED AND FUNCTIONALIZED GUIDES FOR CRISPR-CAS SYSTEMS; U.S. application 62/091,461, 12 Dec. 14, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 14, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 14, 62/181,641, 18 Jun. 2015, and 62/181,667, 18 Jun. 2015, RNA-TARGETING SYSTEM; U.S. application 62/096,656, 24 Dec. 14 and 62/181,151, 17 Jun. 2015, CRISPR HAVING OR ASSOCIATED WITH DESTABILIZATION DOMAINS; U.S. application 62/096,697, 24 Dec. 14, CRISPR HAVING OR ASSOCIATED WITH AAV; U.S. application 62/098,158, 30 Dec. 14, ENGINEERED CRISPR COMPLEX INSERTIONAL TARGETING SYSTEMS; U.S. application 62/151,052, 22 Apr. 15, CELLULAR TARGETING FOR EXTRACELLULAR EXOSOMAL REPORTING; U.S. application 62/054,490, 24 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 14 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 14, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 14 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 14, FUNCTIONAL SCREENING WITH OPTIMIZED FUNCTIONAL CRISPR-CAS SYSTEMS; U.S. application 62/087,546, 4 Dec. 14 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 14, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X1\text{-}11\text{-}(X12X13)\text{-}X14\text{-}33$ or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as $(X1\text{-}11\text{-}(X12X13)\text{-}X14\text{-}33 \text{ or } 34 \text{ or } 35)z$, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer, which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ. I.D. No. 1)
MDPIRSRTPSPARELLSGPQPDGVQ
PTADRGVSPPAGGPLDGLPARRTMS
RTRLPSPPAPSPAFSADSFSDLLRQ
FDPSLFNTSLFDSLPPFGAHHTEAA
TGEWDEVQSGLRAADAPPPTMRVAV
TAARPPRAKPAPRRRAAQPSDASPA
AQVDLRTLGYSQQQQEKIKPKVRST
VAQHHEALVGHGFTHAHIVALSQHP
AALGTVAVKYQDMIAALPEATHEAI
VGVGKQWSGARALEALLTVAGELRG
PPLQLDTGQLLKIAKRGGVTAVEAV
HAWRNALTGAPLN

An exemplary amino acid sequence of a C-terminal capping region is:

(SEQ. I.D. No. 2)
RPALESIVAQLSRPDPALAALTNDH
LVALACLGGRPALDAVKKGLPHAPA
LIKRTNRRIPERTSHRVADHAQVVR
VLGFFQCHSHPAQAFDDAMTQFGMS
RHGLLQLFRRVGVTELEARSGTLPP
ASQRWDRILQASGMKRAKPSPTSTQ
TPDQASLHAFADSLERDLDAPSPMH
EGDQTRAS

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

ZN-Finger Nucleases

Other preferred tools for genome editing for use in the context of this invention include zinc finger systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme Fok I. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

RNAi

In certain embodiments, the genetic modifying agent is RNAi (e.g., shRNA). As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Chromatin Modifying Agents

In certain embodiments, agents capable of modifying the chromatin structure of one or more genes described herein are used. Chromatin modifying agents, such as histone modifying enzymes, may be targeted to specific genomic loci using a genetic modifying agent described herein. Chromatin modifying agents may modulate contact domains or chromatin looping (see e.g., WO2016/089920; WO 2017/031370; and WO2017106290A1).

Adoptive Cell Transfer

In certain embodiments, T cells or populations of cells comprising T cells modified according to the present invention (e.g., altered glucocorticoid signaling or altered glucocorticoid and IL-27 signaling) are used in adoptive cell transfer. The transferred cells may be used to treat a subject in need thereof (e.g., cancer or autoimmune diseases). Specific diseases are described further herein. As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., 2018) Nat Med. 2018 June; 24(6):724-730; Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, immune cells to be transferred are differentiated in culture conditions to modify the immune cell state. In certain embodiments, immune cells are differentiated to have an enhanced (e.g., activated immune response). In certain embodiments, immune cells are differentiated to have a suppressive immune state (e.g., dysfunctional). Previous studies showed that bone marrow cells differentiated with dexamethasone (Dex) combined with granulocyte macrophage colony stimulating factor (GM-CSF) generated Myeloid derived suppressor cells (MDSCs) in vitro and adoptive transfer of these MDSCs significantly prolonged heart allograft survival and also favored the expansion of regulatory T cells in vivo (Zhao et al., Dexamethasone-Induced Myeloid-Derived Suppressor Cells Prolong Allo Cardiac Graft Survival through iNOS- and Glucocorticoid Receptor-Dependent Mechanism, Front. Immunol., 15 Feb. 2018). In certain embodiments, suppressive immune cells are obtained by differentiating the immune cells according to the present invention with combined glucocorticoid and IL-27 treatment.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gplOO; BCR-ABL (breakpoint cluster region-Abelson); tyrosinase; New York esophageal squamous cell carcinoma 1 (NY-ESO-1); κ-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyltransferase V (NA17); paired box protein Pax-3 (PAX3); Androgen receptor; Cyclin B1; Cyclin Di; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triosephosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088, 379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004, 811; 6,284,240; 6,392,013; 6,410,014; 6,753,162; 8,211, 422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; U.S. Pat. No. 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916, 381; 8,975,071; 9,101,584; 9,102,760; 9,102,761). Third-generation CARs include a combination of costimulatory endodomains, such a CD3ζ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3):

```
                                  (SEQ. ID. No. 3)
IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAYRS)).
```

Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY (SEQ. I.D. No. 4) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY and continuing all the way to the carboxy-terminus of the protein. The sequence is reproduced herein:

(SEQ ID NO: 5)
IEVMYPPPYLDNEKSNGTIIHVKGKHLCPSPLFPGPSKPFWVLVVVGGVL ACYSLLVTVAFIIFWVRSKRSRLLHSDYMNMTPRRPGPTRKHYQPYAPPR DFAAYRS.

Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signalling domains (CD28-CD3ζ; 4-1BB-CD3ζ; CD27-CD3ζ; CD28-CD27-CD3ζ; 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B-cell and follicular lymphoma and also by the malignant cells of Hodgkins lymphoma, Waldenstrom's macroglobulinemia and multiple myeloma, and by HTLV-1- and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+Th1 cells and CD8+ CTLs to induce a synergistic antitumour response (see, e.g., Li et al., Adoptive cell therapy with CD4+T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent (e.g., Nr3C1, IL-27 receptor). In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional $CD8^+$ T-cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts.

Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, $\alpha$ and $\beta$, which assemble to form a heterodimer and associates with the CD3-transducing subunits to form the T cell receptor complex present on the cell surface. Each $\alpha$ and $\beta$ chain of the TCR consists of an immunoglobulin-like N-terminal variable (V) and constant (C) region, a hydrophobic transmembrane domain, and a short cytoplasmic region. As for immunoglobulin molecules, the variable region of the $\alpha$ and $\beta$ chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCR$\alpha$ or TCR$\beta$ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor $\alpha$-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, editing of cells may include editing T cells for modulating expression, preferably decrease or knockout expression, of the glucocorticoid receptor and IL-27 receptor. In certain embodiments, editing of cells may include editing T cells for modulating expression, preferably decrease or knockout expression, of downstream targets of glucocorticoid and IL-27 combined signaling as described herein. In certain embodiments, editing these targets can generate T cells resistant to immunosuppressive treatments, such as glucocorticoid treatment. In certain embodiments, the T cells can provide enhanced immune responses.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Sigmoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of $CD8^+$ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8$^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8$^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome.

Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

Diagnosis, Prognosis and Monitoring

In a further embodiment, the present invention provides for a method for determining the T cell status of a subject, or for diagnosing, prognosing or monitoring a disease comprising an immune component in a subject by detecting or quantifying CD8$^+$ T cells as defined in any embodiment herein in a biological sample of the subject. In certain embodiments, T cells expressing a glucocorticoid+IL-27 signature are detected. In certain embodiments, enzymes of steroid biogenesis are detected in a population of immune cells obtained from a subject (e.g., Cyp11a1 in macrophages). In certain embodiments, expression of IL-27 is detected in a population of immune cells obtained from a subject (e.g., in dendritic cells). In certain embodiments, the frequency of cells expressing a gene signature, Cyp11a1 and/or IL-27 are determined. In certain embodiments, a subject having a high frequency of macrophages expressing Cyp11a1 and/or dendritic cells expressing IL-27 indicates a suppressed immune response (e.g., against a tumor). In certain embodiments, a treatment is monitored, such as a treatment as described herein, by monitoring a biomarker or signature gene as described herein. For example, treatment with an agonist of glucocorticoid signaling or agonists glucocorticoid and IL-27 signaling can decrease the expression of the glucocorticoid+IL-27 signature. Specific markers in the signature may be detected (e.g., checkpoint proteins).

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Diseases

In certain example embodiments, the methods, pharmaceutical compositions and adoptive cell transfer strategies described herein may be used to treat various cancers. The cancer may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

The cancer may include, without limitation, solid tumors such as sarcomas and carcinomas. Examples of solid tumors include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumour including serous tumour, endometrioid tumor and mucinous cystadenocarcinoma, sex-cord-stromal tumor), prostate cancer, liver and bile duct carcinoma (e.g., hepatocellular carcinoma, cholangiocarcinoma, hemangioma), choriocarcinoma, seminoma, embryonal carcinoma, kidney cancer (e.g., renal cell carcinoma, clear cell carcinoma, Wilm's tumor, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, medulloblastoma, astrocytoma, medulloblastoma, craniopharyngioma, ependymoma, pinealoma, hemangioblastoma, acoustic neuroma, oligodendroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

In certain example embodiments, the methods, pharmaceutical compositions and adoptive cell transfer strategies may be used to treat various autoimmune diseases. As used throughout the present specification, the terms "autoimmune disease" or "autoimmune disorder" are used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

Examples of inflammatory diseases or disorders include, but are not limited to, asthma, allergy, allergic rhinitis, allergic airway inflammation, atopic dermatitis (AD), chronic obstructive pulmonary disease (COPD), inflammatory bowel disease (IBD), multiple sclerosis, arthritis, psoriasis, eosinophilic esophagitis, eosinophilic pneumonia, eosinophilic psoriasis, hypereosinophilic syndrome, graft-versus-host disease, uveitis, cardiovascular disease, pain, multiple sclerosis, lupus, vasculitis, chronic idiopathic urticaria and Eosinophilic Granulomatosis with Polyangiitis (Churg-Strauss Syndrome).

The asthma may be allergic asthma, non-allergic asthma, severe refractory asthma, asthma exacerbations, viral-induced asthma or viral-induced asthma exacerbations, steroid resistant asthma, steroid sensitive asthma, eosinophilic asthma or non-eosinophilic asthma and other related disorders characterized by airway inflammation or airway hyperresponsiveness (AHR).

The COPD may be a disease or disorder associated in part with, or caused by, cigarette smoke, air pollution, occupational chemicals, allergy or airway hyperresponsiveness.

The allergy may be associated with foods, pollen, mold, dust mites, animals, or animal dander.

The IBD may be ulcerative colitis (UC), Crohn's Disease, collagenous colitis, lymphocytic colitis, ischemic colitis, diversion colitis, Behcet's syndrome, infective colitis, indeterminate colitis, and other disorders characterized by inflammation of the mucosal layer of the large intestine or colon.

It will be understood by the skilled person that treating as referred to herein encompasses enhancing treatment, or improving treatment efficacy. Treatment may include inhibition of an inflammatory response, tumor regression as well as inhibition of tumor growth, metastasis or tumor cell proliferation, or inhibition or reduction of otherwise deleterious effects associated with the tumor.

Efficaciousness of treatment is determined in association with any known method for diagnosing or treating the particular disease. The invention comprehends a treatment method comprising any one of the methods or uses herein discussed.

The phrase "therapeutically effective amount" as used herein refers to a sufficient amount of a drug, agent, or compound to provide a desired therapeutic effect.

As used herein "patient" refers to any human being receiving or who may receive medical treatment and is used interchangeably herein with the term "subject".

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of the cancer, and how the patient responds to the treatment. Additionally, a person having a greater risk of developing an inflammatory response (e.g., a person who is genetically predisposed or predisposed to allergies or a person having a disease characterized by episodes of inflammation) may receive prophylactic treatment to inhibit or delay symptoms of the disease.

Standard of Care

Aspects of the invention involve modifying the therapy within a standard of care. In one embodiment, therapy comprising an agent is administered within a standard of care where addition of the agent is synergistic within the steps of the standard of care. In one embodiment, the agent targets glucocorticoid and IL27 signaling. In one embodiment, the agent inhibits expression or activity of a gene or polypeptide selected from the downstream targets of glucocorticoid and IL-27 described herein. The term "standard of care" as used herein refers to the current treatment that is accepted by medical experts as a proper treatment for a certain type of disease and that is widely used by healthcare professionals. Standard of care is also called best practice, standard medical care, and standard therapy. Standards of care for cancer generally include surgery, lymph node removal, radiation, chemotherapy, targeted therapies, antibodies targeting the tumor, and immunotherapy. Immunotherapy can include checkpoint blockers (CBP), chimeric antigen receptors (CARs), and adoptive T-cell therapy. In certain embodiments, immunotherapy leads to immune-related adverse events (irAEs) and the standard of care includes treatment with glucocorticoids (see, e.g., Kumar, V. et al. Current Diagnosis and Management of Immune Related Adverse Events (irAEs) Induced by Immune Checkpoint Inhibitor Therapy. Front Pharmacol 2017, 8, 49; and Gelao et al., Immune Checkpoint Blockade in Cancer Treatment: A Double-Edged Sword Cross-Targeting the Host as an "Innocent Bystander", Toxins 2014, 6, 914-933; doi: 10.3390/toxins6030914). In certain embodiments, glucocorticoids may inhibit adaptive immunity when administered as part of a therapeutic regimen (e.g., in cancer).

Glucocorticoids are often administered to help patients tolerate treatment, rather than as a chemotherapeutic that targets the cancer itself (see, e.g., Pufall, Glucocorticoids and Cancer, Adv Exp Med Biol. 2015; 872: 315-333. doi: 10.1007/978-1-4939-2895-8_14). In some chemotherapeutic regimens, for example those that include cisplatin, glucocorticoids are first-line antiemetics. For others, such as folate inhibitors, they are used to blunt hypersensitivity, which can result in severe skin rashes. Glucocorticoids are used for their anti-inflammatory properties to relieve bone pain other discomfort that may arise from metastatic disease and CNS compression due to metastatic disease. Though effective for these purposes, the use of glucocorticoids in patients with cancer caries some risk of protecting the tumor against chemotherapeutic or immunotherapy agents, or even increasing proliferation rates.

In certain embodiments, downstream targets of glucocorticoid and IL-27 signaling are targeted to make T cells resistant to or blocked from becoming exhausted or dysfunctional while maintaining the anti-inflammatory activity required for patients to tolerate treatment. In certain embodiments, glucocorticoid and/or IL-27 signaling is blocked.

The standards of care for the most common cancers can be found on the website of National Cancer Institute (www.cancer.gov/cancertopics). A treatment clinical trial is a research study meant to help improve current treatments or obtain information on new treatments for patients with cancer. When clinical trials show that a new treatment is better than the standard treatment, the new treatment may be considered the new standard treatment.

The term "Adjuvant therapy" as used herein refers to any treatment given after primary therapy to increase the chance of long-term disease-free survival. The term "Neoadjuvant therapy" as used herein refers to any treatment given before primary therapy. The term "Primary therapy" as used herein refers to the main treatment used to reduce or eliminate the cancer.

In certain embodiments, glucocorticoid treatment does not provide a desired anti-inflammatory response. As described further herein, treatment targeting glucocorticoid signaling and IL-27 signaling or downstream targets of the combination treatment may be used to elicit an improved anti-inflammatory response.

Administration

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothiocyanate, triethiodide, lactate, pamoate, valerate, and the like which can be used as a dosage form for modifying the solubility or hydrolysis characteristics or can be used in sustained release or pro-drug formulations. It will be understood that, as used herein, references to specific agents (e.g., neuromedin U receptor agonists or antagonists), also include the pharmaceutically acceptable salts thereof.

Methods of administrating the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents (e.g., glucocorticoid, IL-27, antagonists) which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. In certain embodiments, suitable dosage ranges for intravenous administration of the agent are generally about 5-500 micrograms (g) of active compound per kilogram (Kg) body weight. Suitable dosage ranges for intranasal administration are generally about 0.01 pg/kg body weight to 1 mg/kg body weight. In certain embodiments, a composition containing an agent of the present invention is subcutaneously injected in adult patients with dose ranges of approximately 5 to 5000 µg/human and preferably approximately 5 to 500 µg/human as a single dose. It is desirable to administer this dosage 1 to 3 times daily. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately the attending physician will decide on the appropriate duration of therapy using compositions of the present invention. Dosage will also vary according to the age, weight and response of the individual patient.

Suitable doses of IL-27 are generally in the range of between about 1 and about 250 g/kg body weight, and may be administered from once a week up to about six times daily. Treatment may continue for a period of between one day and six months, or for as long as is deemed necessary and safe in the treatment of the aforementioned disorders, as is readily ascertained by standard tests by the attending physician, depending upon the nature of the disorder being treated.

Suitable dosages for administering glucocorticoids is known in the art. Exemplary dosages are described below. In certain embodiments, based on the discovery of synergism between IL-27 and glucocorticoids, a lower dose is administered in a combination therapy.

betamethasone: For oral dosage forms (syrup, tablets, effervescent tablets): Adults and teenagers—Dose may range from 0.25 to 7.2 milligrams (mg) a day, as a single dose or divided into several doses. For long-acting oral dosage form (extended-release tablets): Adults and teenagers—Dose may range from 1.2 to 12 mg injected into a joint, lesion, muscle, or vein as often as necessary, as determined by your doctor. For injection dosage form: Adults and teenagers-2 to 6 mg a day.

budesonide: For long-acting oral dosage form (extended-release capsules): Adults—At first, the dose is 9 milligrams (mg) a day for up to eight weeks. Then your doctor may decrease the dose to 6 mg a day. Each dose should be taken in the morning before breakfast. Children—Use and dose must be determined by your doctor.

cortisone: For oral dosage form (tablets): Adults and teenagers—25 to 300 milligrams (mg) a day, as a single dose or divided into several doses. For injection dosage form: Adults and teenagers—20 to 300 mg a day, injected into a muscle.

dexamethasone: For oral dosage forms (elixir, oral solution, tablets): Adults and teenagers—0.5 to 10 milligrams (mg) taken as often as necessary, as determined by your doctor. For injection dosage form: Adults and teenagers—20.2 to 40 mg injected into a joint, lesion, muscle, or vein as often as necessary, as determined by your doctor.

hydrocortisone: For oral dosage forms (oral suspension, tablets): Adults and teenagers—20 to 800 milligrams (mg) every one or two days, as a single dose or divided into several doses. For injection dosage form: Adults and teenagers—5 to 500 mg injected into a joint, lesion, muscle, or vein, or under the skin as often as necessary, as determined by your doctor.

methylprednisolone: For oral dosage form (tablets): Adults and teenagers—4 to 160 milligrams (mg) every one or two days, as a single dose or divided into several doses. For injection dosage form: Adults and teenagers—4 to 160 mg injected into a joint, lesion, muscle, or vein as often as necessary, as determined by your doctor.

prednisolone: For oral dosage forms (oral solution, syrup, tablets): Adults and teenagers—5 to 200 milligrams (mg) taken as often as necessary, as determined by your doctor. For injection dosage form: Adults and teenagers—2 to 100 mg injected into a joint, lesion, muscle, or vein as often as necessary, as determined by your doctor.

prednisone: For oral dosage forms (oral solution, syrup, tablets): Adults and teenagers—5 to 200 milligrams (mg) every one or two days, as a single dose or divided into several doses.

triamcinolone: For oral dosage forms (syrup, tablets): Adults and teenagers—2 to 60 milligrams (mg) a day, as a single dose or divided into several doses. For injection dosage form: Adults and teenagers—0.5 to 100 mg injected into a joint, lesion, or muscle, or under the skin as often as necessary, as determined by your doctor.

In certain embodiments, dosages of IL-27 and glucocorticoid can be decreased because of the synergistic effect of the combination treatment. In certain embodiments, a combination treatment can be tolerated by a subject for a longer period of time and have less side effects. In certain embodiments, dosages are decreased 2-fold, 10-fold, or more than 100-fold.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In preferred embodiments, antibodies are used as agonists to depress inflammatory diseases or allergen-induced asthmatic responses. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In certain embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa. In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of antibodies to the respiratory tract mucosa may be a) carbohydrates, e.g., monosaccharides such as fructose, galactose, glucose. D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like: d) peptides and proteins, such as aspartame, human serum albumin, gelatin, and the like; e) alditols, such mannitol, xylitol, and the like, and f) polycationic polymers, such as chitosan or a chitosan salt or derivative.

For dermal application, the antibodies of the present invention may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and benzylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives: wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol alginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmellose, sodium carmellose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetanyl glucoside, collagen, carrageenan, hyaluronates and alginates and chitosans.

The dose of antibody required in humans to be effective in the treatment or prevention of allergic inflammation differs with the type and severity of the allergic condition to be treated, the type of allergen, the age and condition of the patient, etc. Typical doses of antibody to be administered are in the range of 1 µg to 1 g, preferably 1-1000 µg, more preferably 2-500, even more preferably 5-50, most preferably 10-20 µg per unit dosage form. In certain embodiments, infusion of antibodies of the present invention may range from 10-500 mg/m$^2$.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

In another aspect, provided is a pharmaceutical pack or kit, comprising one or more containers filled with one or more of the ingredients of the pharmaceutical compositions described herein.

Methods of Screening

A further aspect of the invention relates to a method for identifying an agent capable of modulating one or more phenotypic aspects of a cell or cell population as disclosed herein, comprising: a) applying a candidate agent to the cell or cell population; b) detecting modulation of one or more phenotypic aspects of the cell or cell population by the candidate agent, thereby identifying the agent. The phenotypic aspects of the cell or cell population that is modulated may be a gene signature or biological program specific to a cell type or cell phenotype or phenotype specific to a population of cells (e.g., an inflammatory phenotype or suppressive immune phenotype). In certain embodiments, steps can include administering candidate modulating agents to cells, detecting identified cell (sub)populations for changes in signatures, or identifying relative changes in cell (sub) populations which may comprise detecting relative abundance of particular gene signatures.

The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof, as described herein.

The methods of phenotypic analysis can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

Aspects of the present disclosure relate to the correlation of an agent with the spatial proximity and/or epigenetic profile of the nucleic acids in a sample of cells. In some embodiments, the disclosed methods can be used to screen chemical libraries for agents that modulate chromatin architecture, epigenetic profiles, and/or relationships thereof.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures or biological programs of the present invention may be used to screen for drugs that reduce the signature or biological program in cells as described herein. The signature or biological program may be used for GE-HTS. In certain embodiments, pharmacological screens may be used to identify drugs that are selectively toxic to cells having a signature.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature or biological program of the present invention in silico.

Identifying Immunomodulators

A further aspect of the invention relates to a method for identifying an immunomodulant capable of modulating one or more phenotypic aspects of an immune cell or immune cell population as disclosed herein, comprising: a) applying a candidate immunomodulant to the immune cell or immune cell population; b) detecting modulation of one or more phenotypic aspects of the immune cell or immune cell population by the candidate immunomodulant, thereby identifying the immunomodulant.

The term "immunomodulant" broadly encompasses any condition, substance or agent capable of modulating one or more phenotypic aspects of an immune cell or immune cell population as disclosed herein. Such conditions, substances or agents may be of physical, chemical, biochemical and/or biological nature. The term "candidate immunomodulant" refers to any condition, substance or agent that is being examined for the ability to modulate one or more phenotypic aspects of an immune cell or immune cell population as disclosed herein in a method comprising applying the candidate immunomodulant to the immune cell or immune cell population (e.g., exposing the immune cell or immune cell population to the candidate immunomodulant or contacting the immune cell or immune cell population with the candidate immunomodulant) and observing whether the desired modulation takes place (e.g. using functional assays, detecting biomarkers and/or gene signatures).

Immunomodulants may include any potential class of biologically active conditions, substances or agents, such as for instance antibodies, proteins, peptides, nucleic acids, oligonucleotides, small molecules, or combinations thereof.

In Vitro Cell-Based Systems

In certain embodiments, modulation of glucocorticoid and IL-27 signaling and/or downstream targets are used to generate dysfunctional cells that recapitulate in vivo dysfunctional cells. Embodiments disclosed herein provide for in vitro cell-based systems that faithfully recapitulate an in vivo dysfunctional phenotype and methods of generating and using the cell-based systems. In certain embodiments, in vitro dysfunctional T cells can be used to screen for immunomodulators.

In certain embodiments, T cells are obtained from a biological sample subject (e.g., from a mouse or human subject). The terms "sample" or "biological sample" as used throughout this specification include any biological specimen obtained from a subject. Particularly useful samples are those known to comprise, or expected or predicted to comprise immune cells as taught herein. Preferably, a sample may be readily obtainable by minimally invasive methods, such as blood collection or tissue biopsy, allowing the removal/isolation/provision of the sample from the subject. Examples of particularly useful samples include without limitation whole blood or a cell-containing fraction of whole blood, such as serum, white blood cells, or peripheral blood mononuclear cells (PBMC), lymph, lymphatic tissue, inflammation fluid, tissue specimens, or tissue biopsies. The term "tissue" as used throughout this specification refers to any animal tissue types including, but not limited to, bone, bone marrow, neural tissue, fibrous connective tissue, cartilage, muscle, vasculature, skin, adipose tissue, blood and glandular tissue or other non-bone tissue. The tissue may be healthy or affected by pathological alterations, e.g., tumor tissue or tissue affected by a disease comprising an immune component. The tissue may be from a living subject or may be cadaveric tissue. The tissue may be autologous tissue or syngeneic tissue or may be allograft or xenograft tissue. A biological sample may also include cells grown in tissue culture, such as cells used for screening drugs or primary cells grown in culture for expansion.

In certain embodiments, T cells are obtained from peripheral blood mononuclear cells (PBMC) (e.g., using Dynabeads® described further herein). In certain embodiments, the T cells are treated with Glucocorticoid (dexamethasone) and IL-27 in combination. In certain embodiments, the T cells are treated with an agent that modulates a downstream target of combined glucocorticoid and IL-27 signaling. In certain embodiments, dysfunctional cells are characterized by assaying dysfunctional markers as described herein.

The invention is further described in the following examples, which do not limit the scope of the invention described in the claims.

EXAMPLES

Example 1—Glucocorticoid and IL-27 Synergize to Promote Dysfunction or Suppressive Immune States in Both CD8+ and CD4+ T Cells FIG. 1 shows that the Glucocorticoid signature is highest in $CD8^+$ Tils also expressing the highest level of the dysfunction signature in from B16F10 melanoma tumors.

Figure 2A:
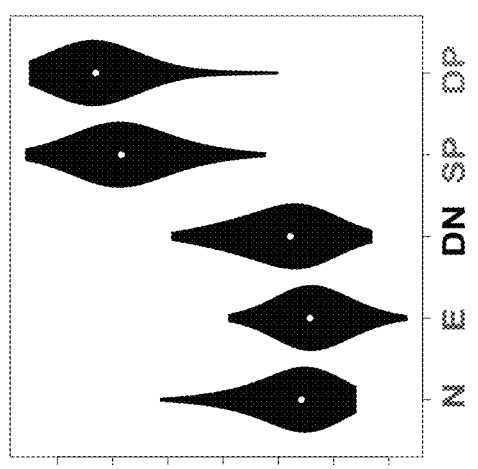
Figure 6A:
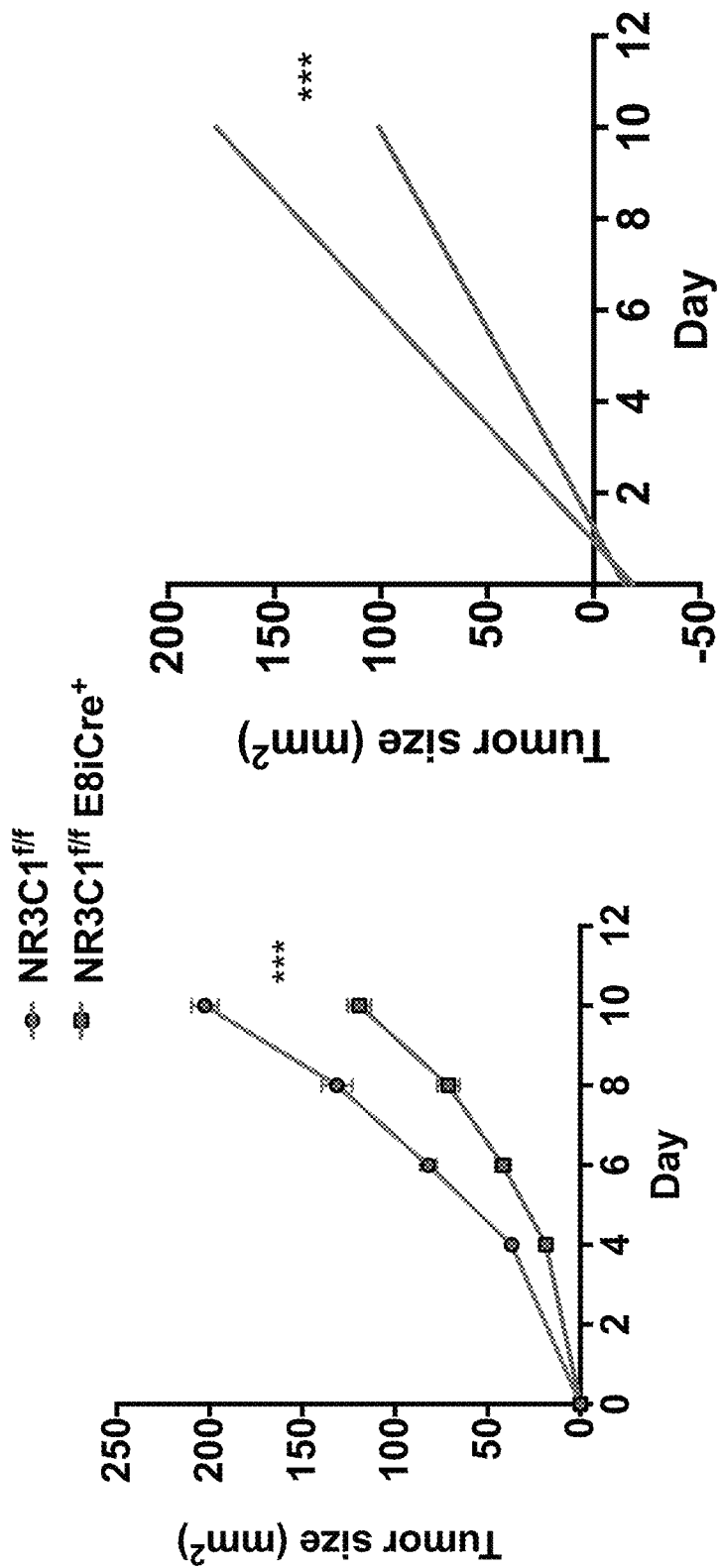
FIG. 6A-6D—a. Plot showing tumor control in control floxed mice and floxed mice expressing Cre to knockout Nr3c1, b. FACS experiment detecting the indicated co-inhibitory receptor and CD8 in WT and Nr3c1 KO cells, c. plots showing expression of the indicated co-inhibitory receptor and CD8 in WT and Nr3c1 KO cells, d. Plot showing expression of the indicated cytokines in WT and Nr3c1 KO cells.
Figure 6B:
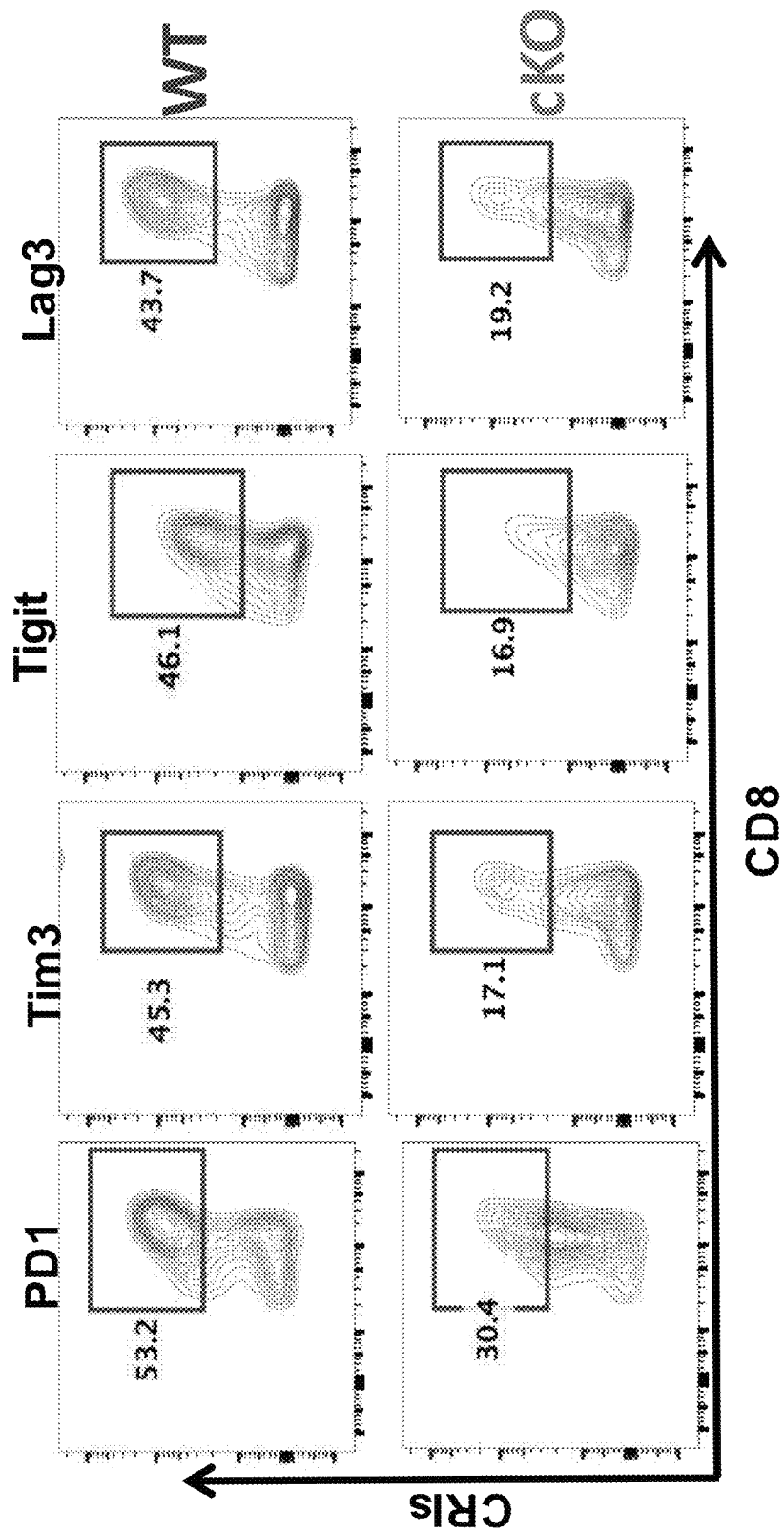
Figure 6C:
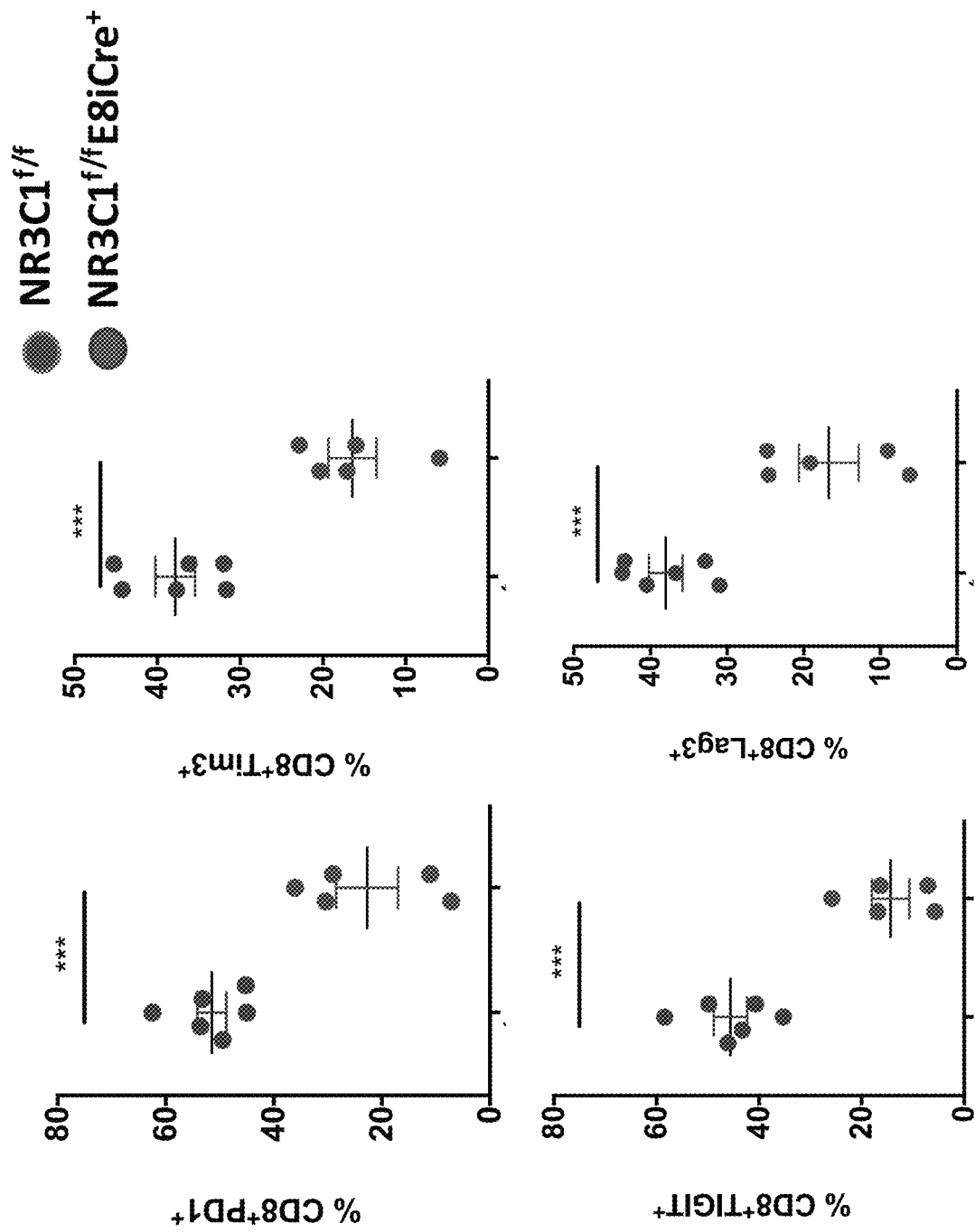
Figure 6D:
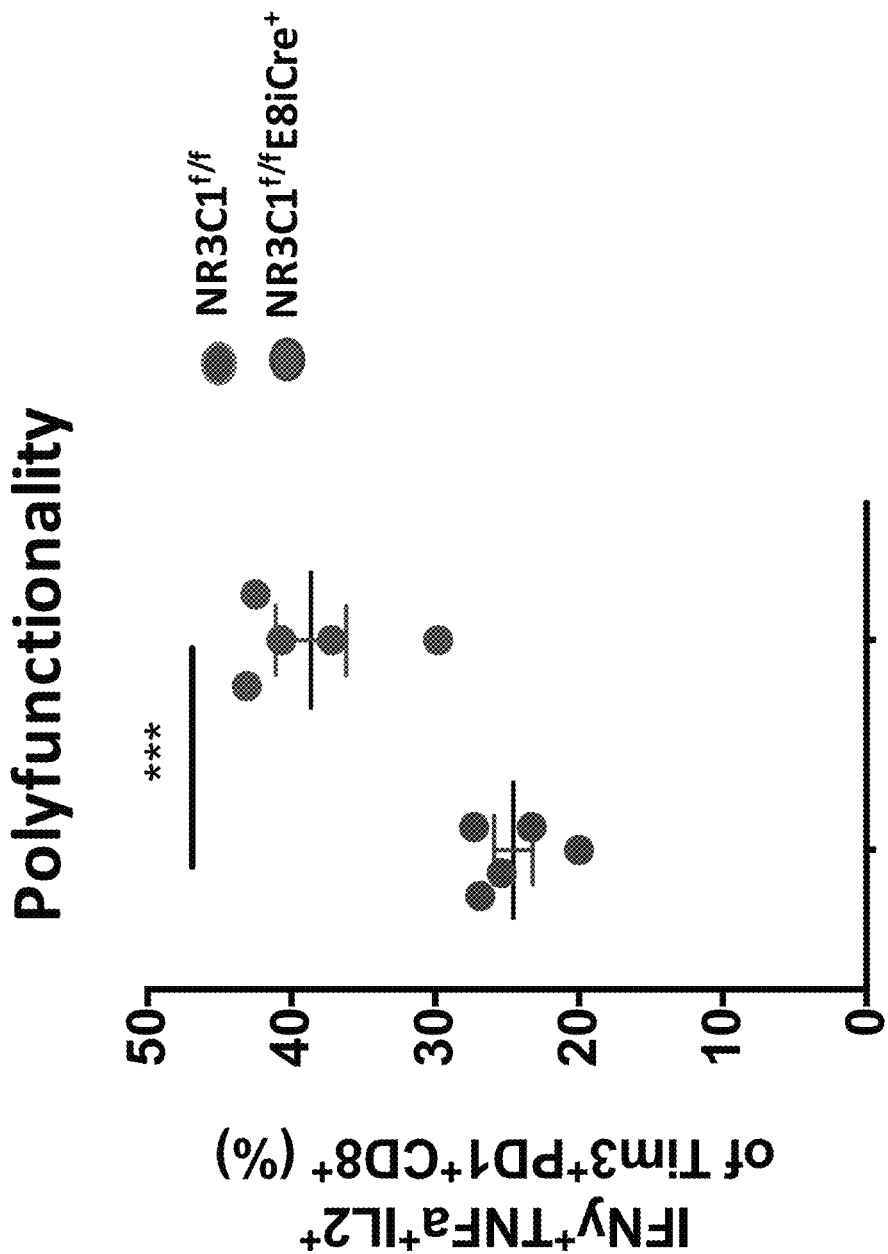

FIG. 2 shows an analysis of Nr3c1 expression in the clusters of $CD8^+$ T cells performed in Singer et al., 2016. Nr3c1 is within cluster 1 (C1). The genes in this cluster are progressively up-regulated across Tim-3−PD-1− (DN), Tim-3−PD-1+(SP), and Tim-3+PD-1+(DP) CD8+ TILs. DP TILs exhibit the most severe dysfunctional phenotype.

FIG. 3 shows that treatment of cells with glucocorticoid promotes expression of co-inhibitory receptors (Tim-3 and PD-1) and dampens proinflammatory effector functions (IFNg, Granzyme B, IL-2, TNFa) but augments suppressive cytokine, IL10.

FIG. 4 shows that Nr3C1 is dynamically regulated with TCR activation, i.e. downregulated with TCR activation and re-expressed when T cells return to resting state.

FIG. 5 shows that glucocorticoid (dexamethasone) induces expression of metallothionein 1 (MT1) and MT2 and that the effects of glucocorticoid on T cells are dampened in absence of MT1/MT2. Moreover, these data are consistent with the previous work on metallothioneins reported in Singer et al., 2016.

FIG. 6 shows that the lack of glucocorticoid signaling in vivo improves tumor control (MC38-Ova), reduces co-inhibitory receptor expression and improves functionality of CD8+ TILs.

Figure 7A:
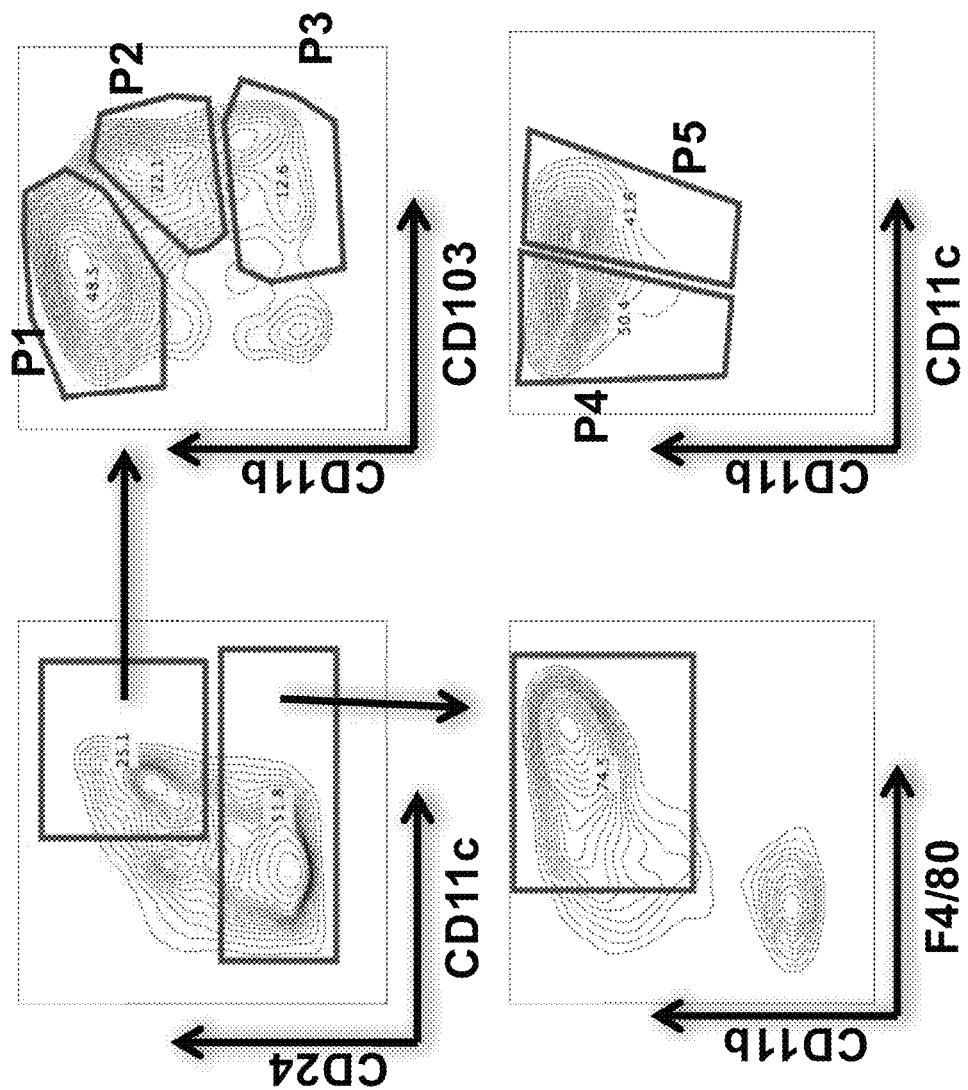
FIG. 7A-7C—a. FACS with the indicated cell markers to sort macrophages, b. plots showing expression of Cholesterol side-chain cleavage enzyme (Cyp11a1) in macrophages, c. bar graph showing Cyp11a1 expression in macrophages.
Figure 7B:
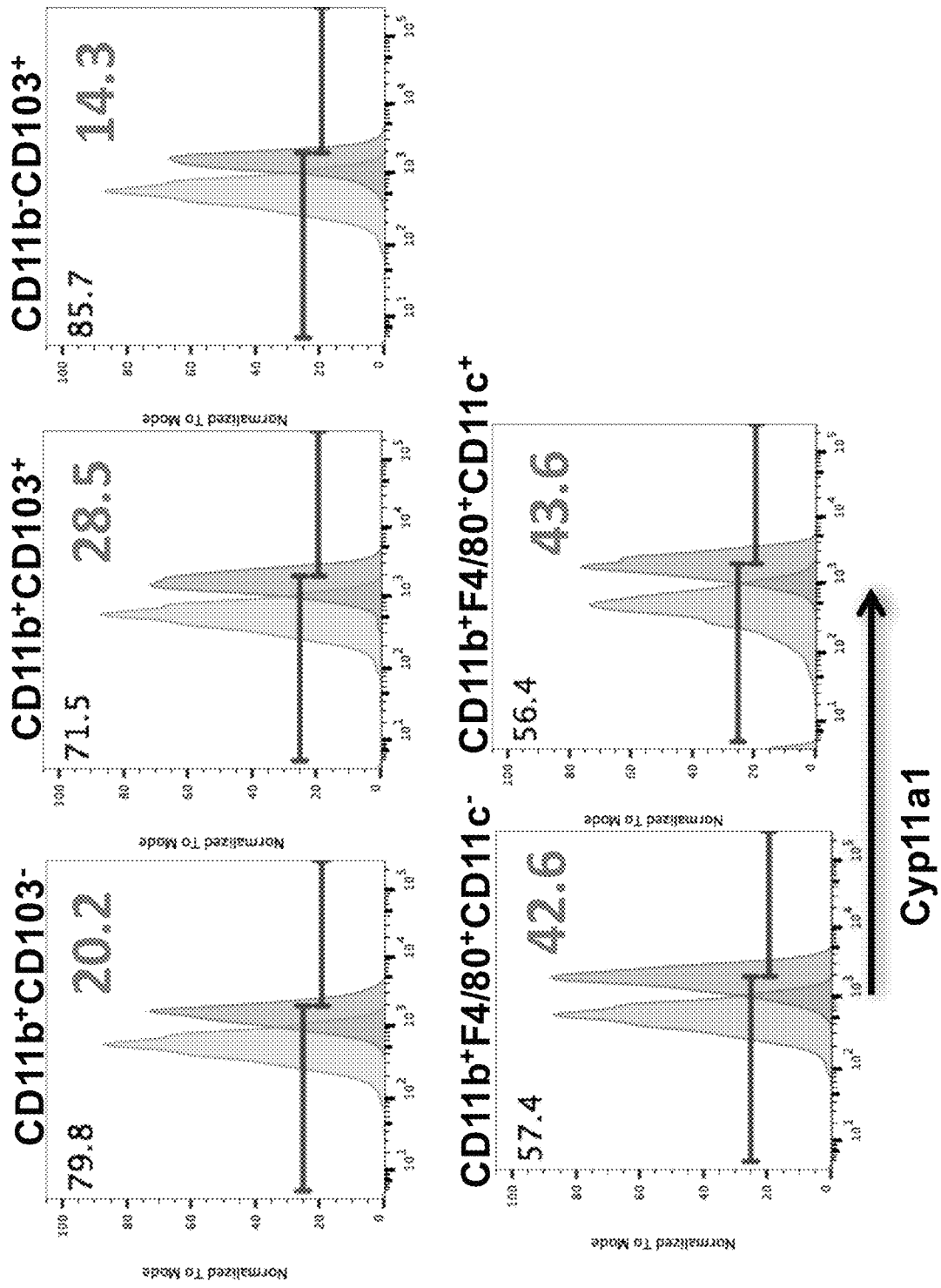
Figure 7C:
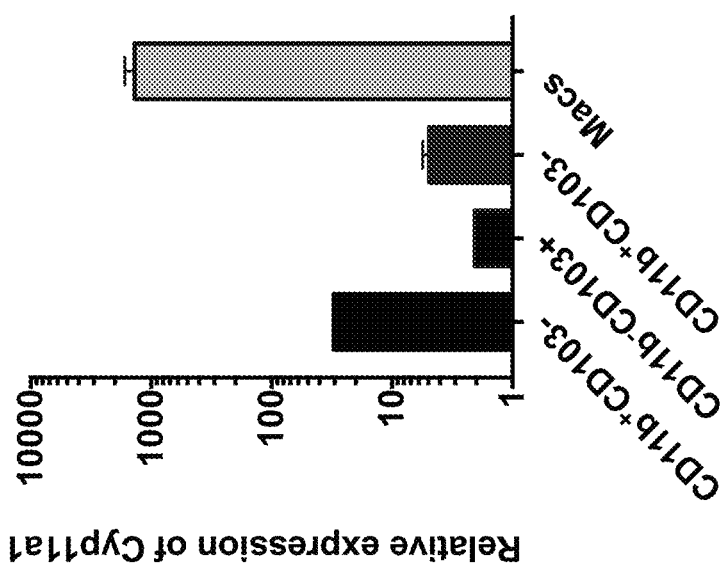
Figure 8:
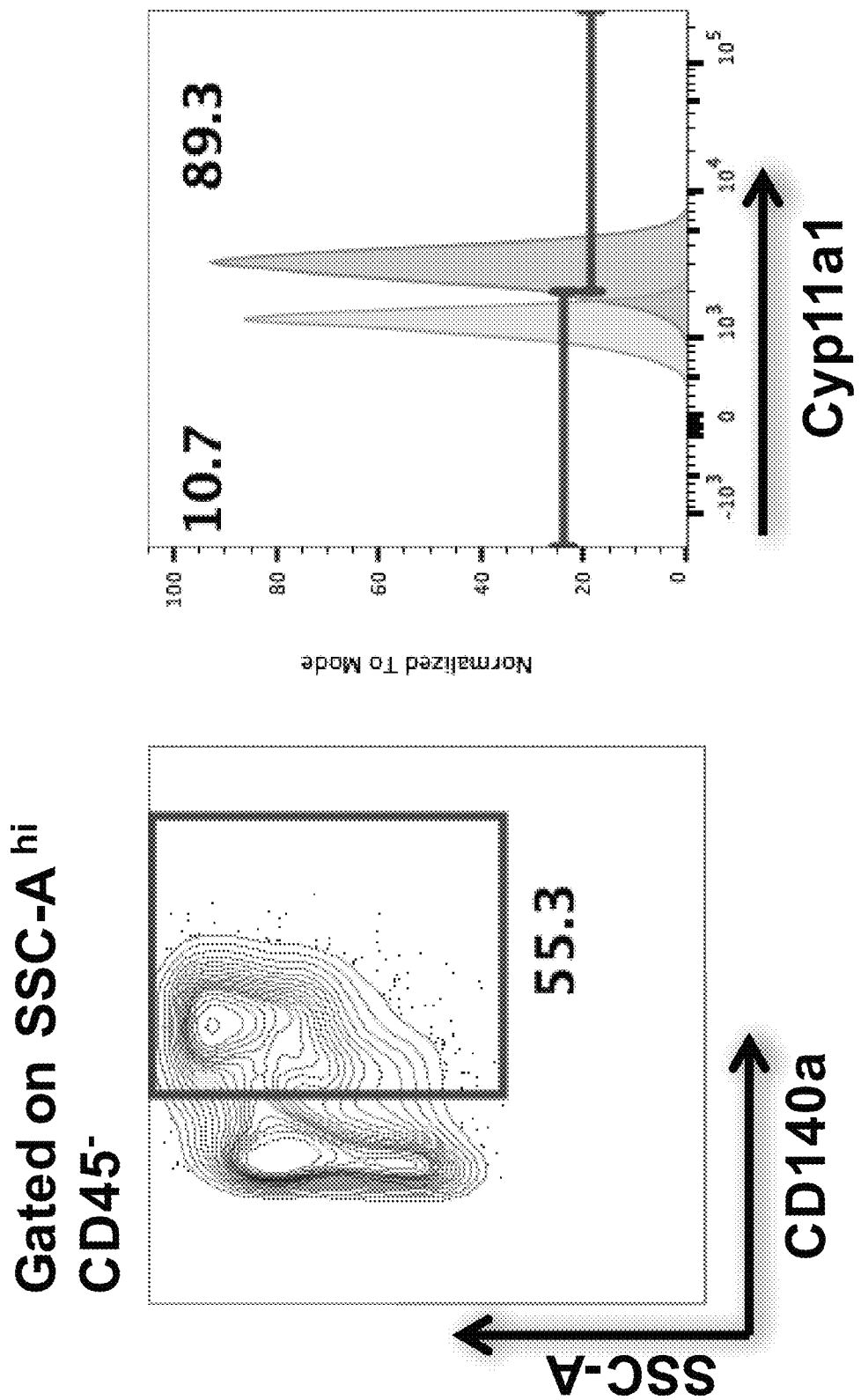
FIG. 8—FACS with the indicated cell markers to sort PDGRa+ cells, b. plots showing expression of Cholesterol side-chain cleavage enzyme (Cyp11a1) in PDGRa+ cells.

FIG. 7 shows that steroid biosynthesis is primarily active in tumor associated macrophages in the tumor microenvironment (TME). FIG. 8 shows that steroid biosynthesis is also high in PDGRa+ cells.

Figure 9:
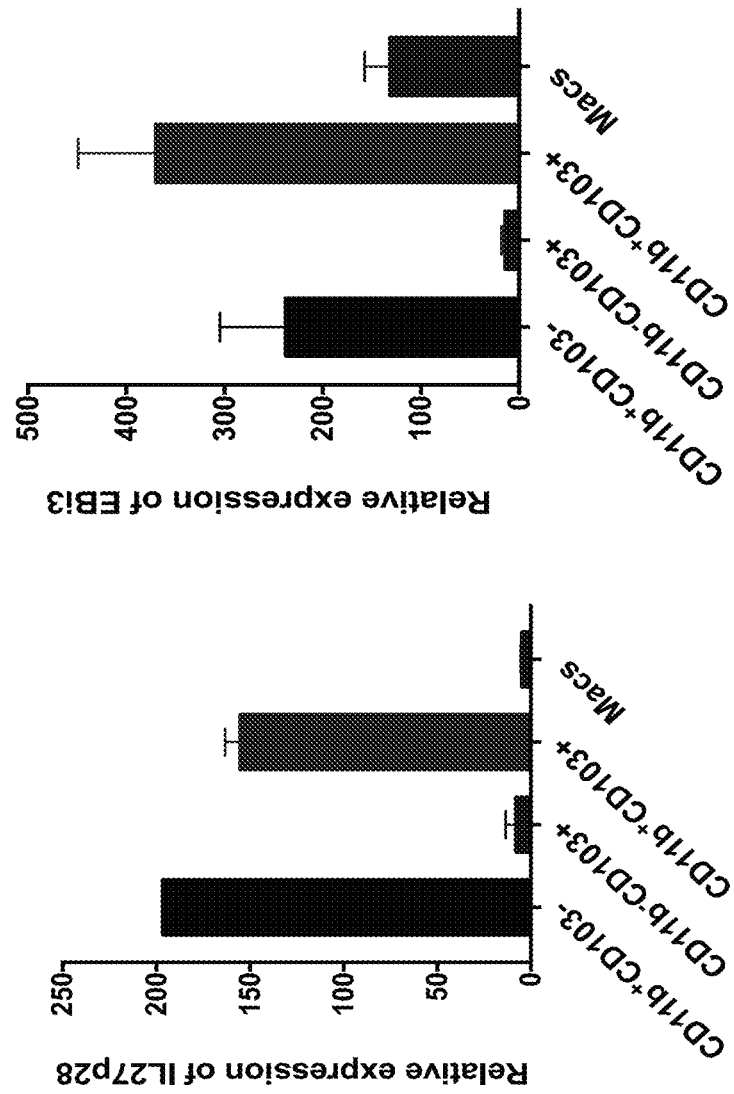
FIG. 9—Bar graphs showing IL27p28 expression in dendritic cells.

FIG. 9 shows that IL-27 is made by dendritic cell populations in tumors (CD11b+CD103− and CD11b+CD103+).

FIG. 10 shows that glucocorticoid (Dexamethasone) and IL-27 synergize to promote co-inhibitory receptor expression and IL-10 production while dampening pro-inflammatory cytokine production in CD8+ T cells.

Figure 11A:
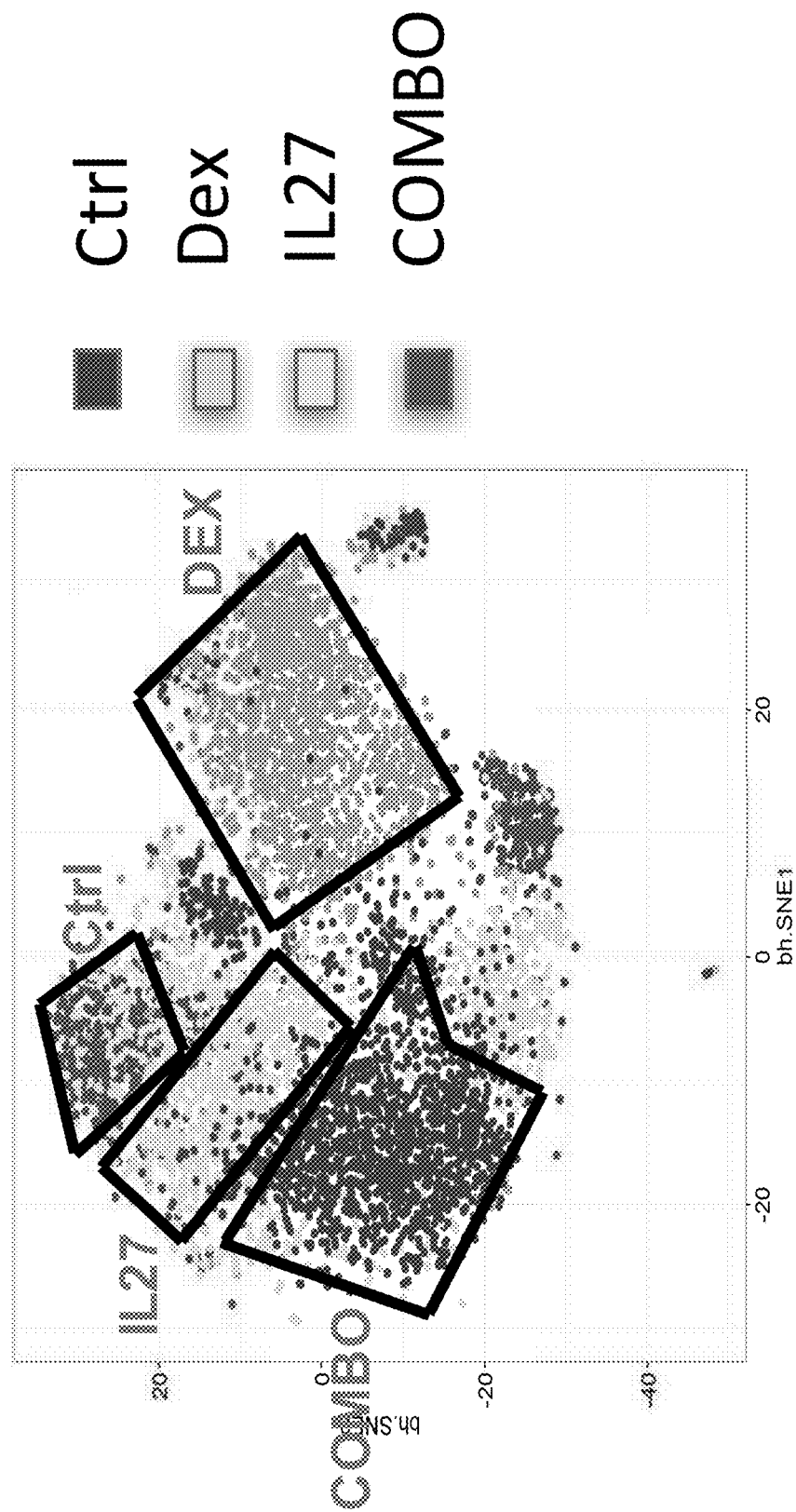
FIG. 11A-11B—a. tSNE clustering of cells treated with control, Dex, IL27 and Dex+IL27 and measured by CyTOF, b. Expression of indicated targets in the different clusters (boxed area indicates the Dex+IL27 combination).
Figure 11B:
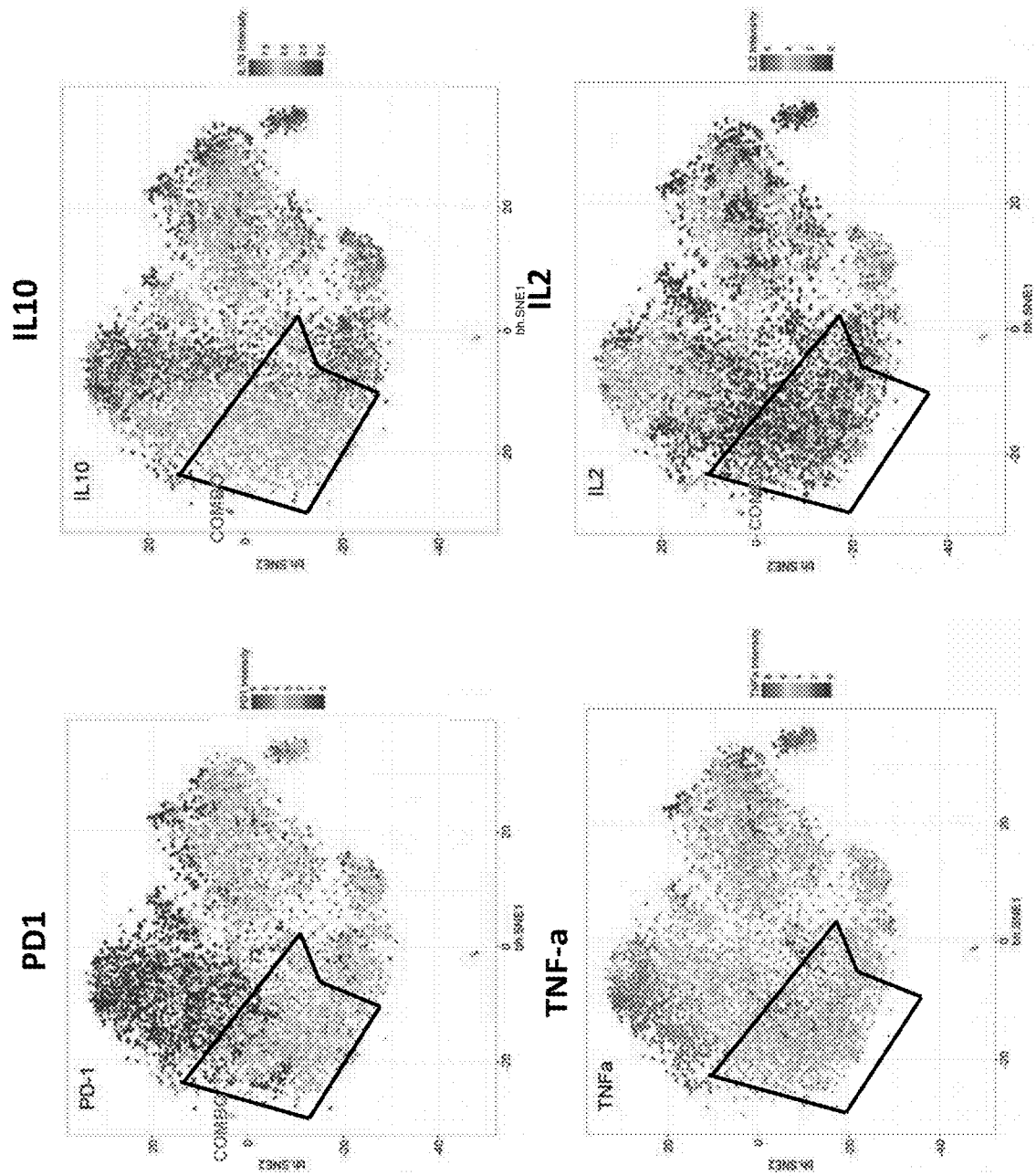

FIG. 11 shows the synergy of glucocorticoid and IL-27 on CD8+ T cells shown by CyTOF.

Figure 12:
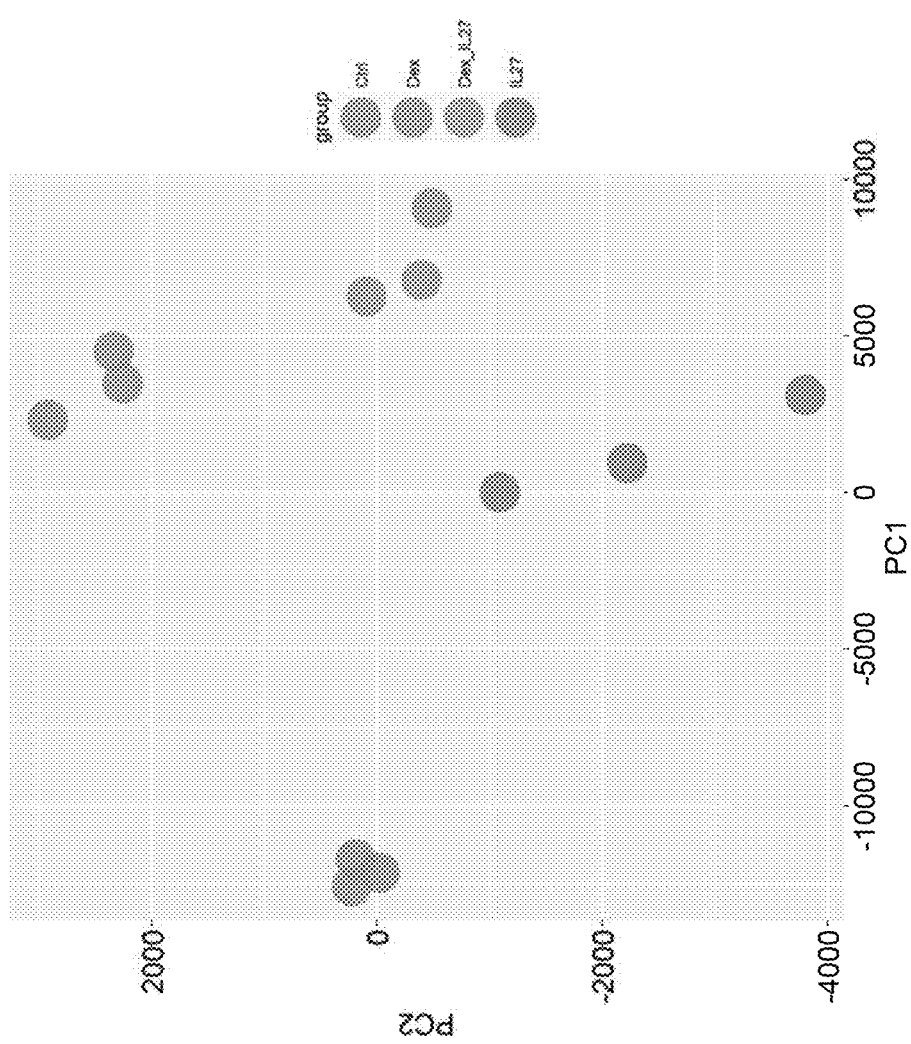
FIG. 12—Plot showing transcriptionally distinct CD8+ T cells after treatment with control, Dex, IL27 and Dex+IL27.

FIG. 12 shows that CD8+ T cells stimulated in the presence of IL-27, dexamethasone, or IL-27+Dex are transcriptionally distinct. Thus, the downstream targets are specific to the combination treatment and were not previously discovered in experiments treating cells with either glucocorticoid or IL-27 alone.

Figure 13:
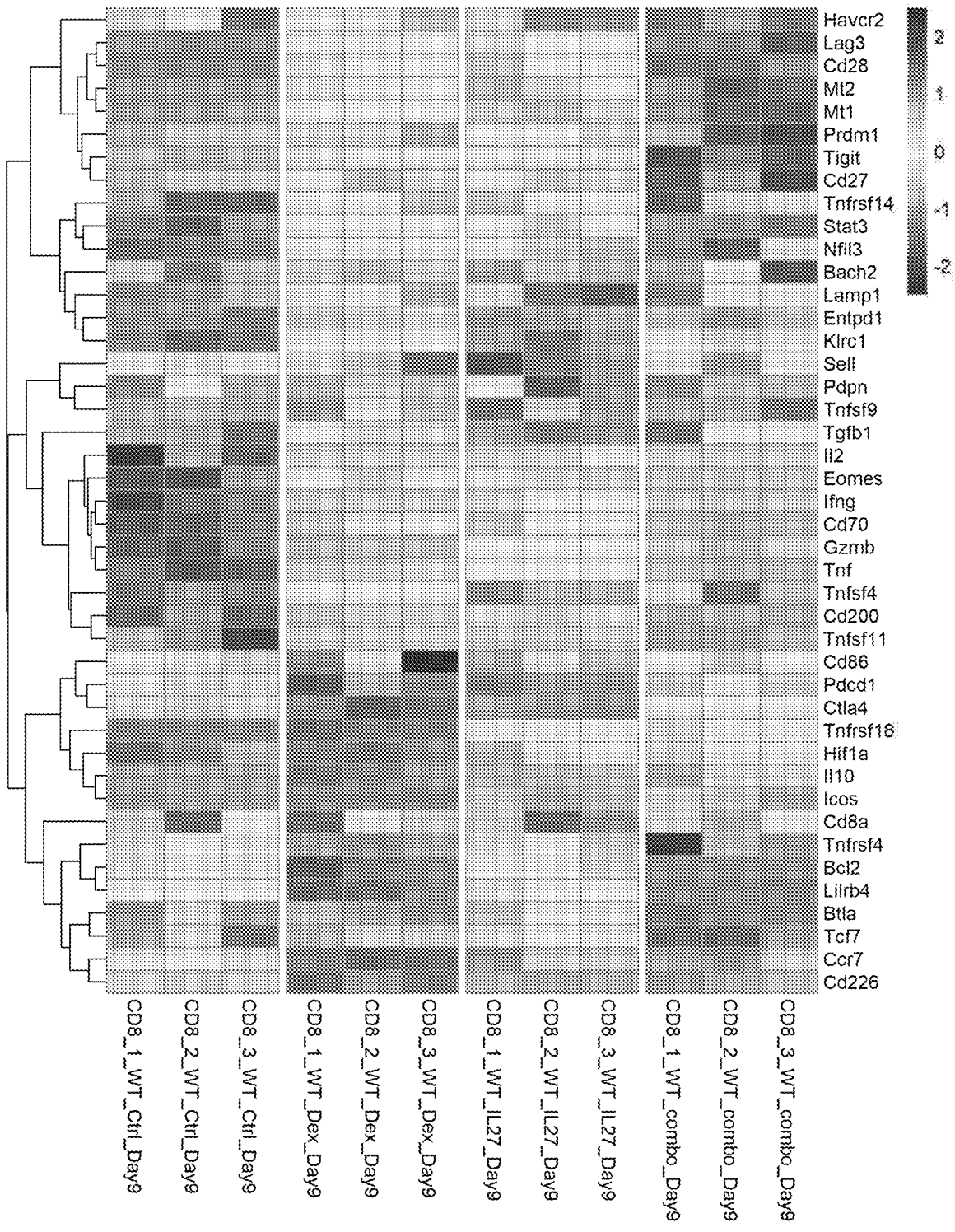
FIG. 13—Heat map showing differentially expressed genes in CD8+ T cells after treatment with control, Dex, IL27 and Dex+IL27.

FIG. 13 shows a heat map showing differentially expressed genes in CD8+ T cells after treatment with control, Dex, IL27 and Dex+IL27. Thus, these are downstream targets for modulating T cell immune states.

Figure 14:
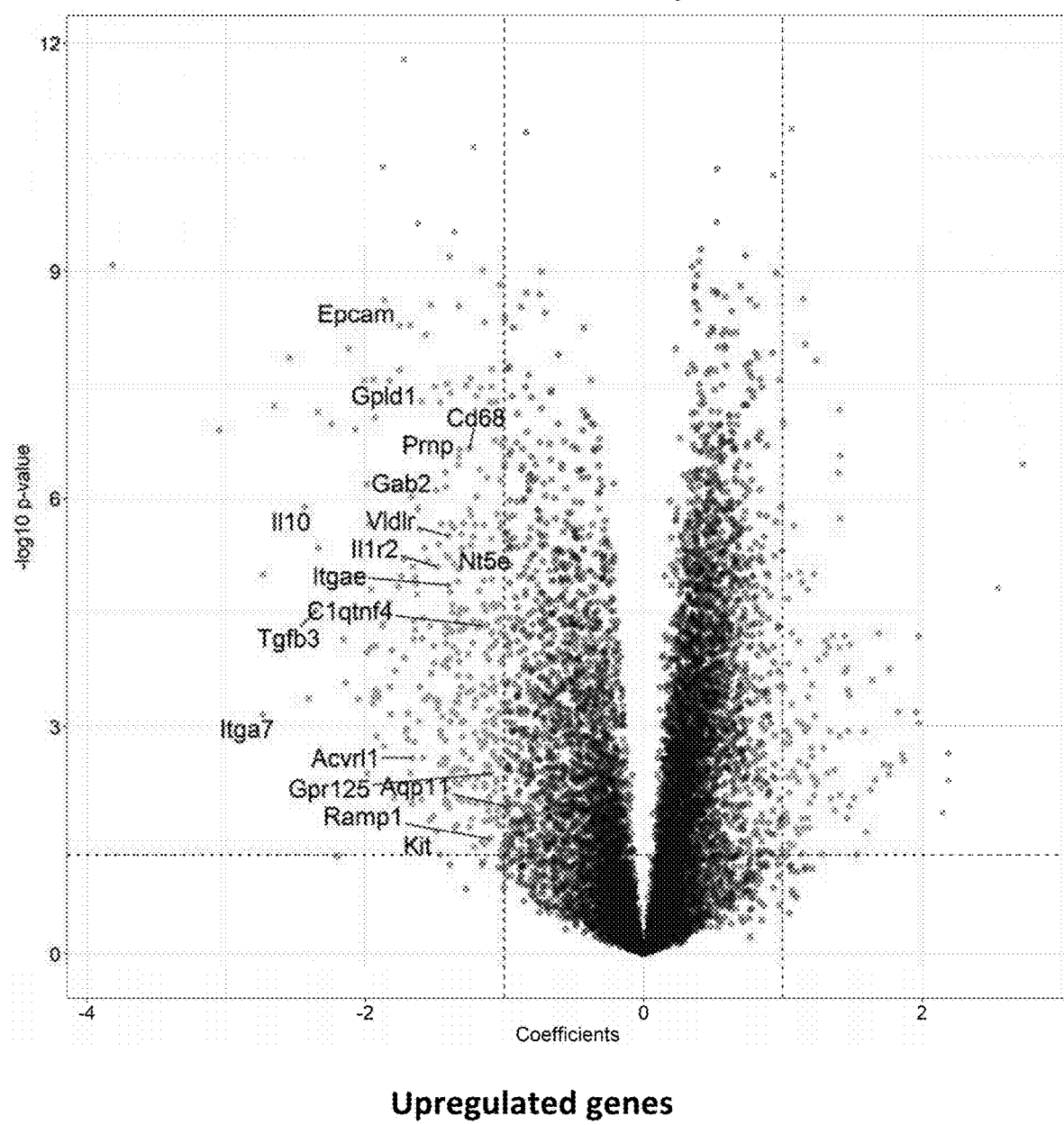
FIG. 14—Plots showing upregulated and downregulated transcription factors, cell surface proteins and cytokines in CD8+ T cells after treatment with Dex+IL27.
Figure 14:
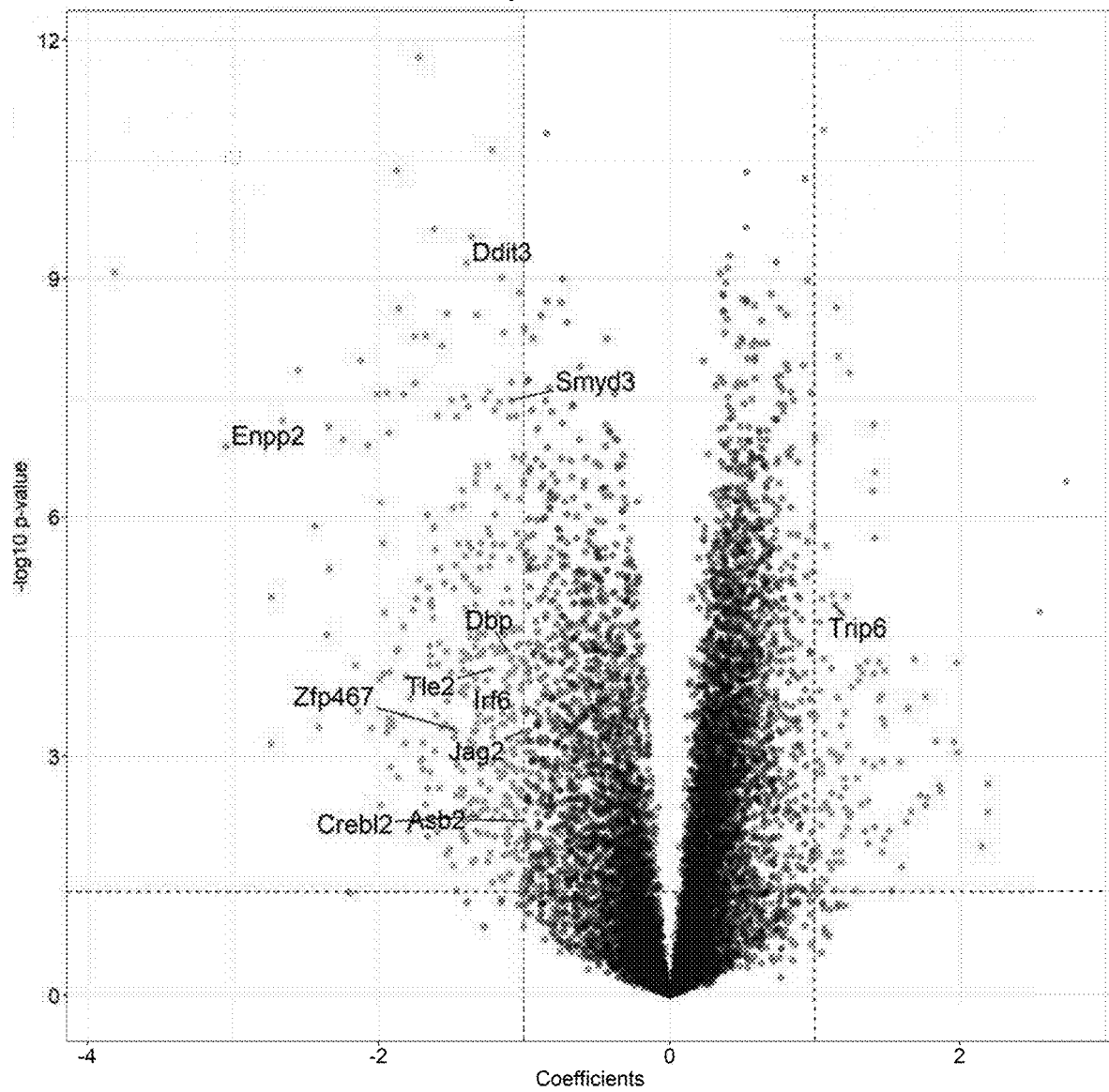
Figure 14:
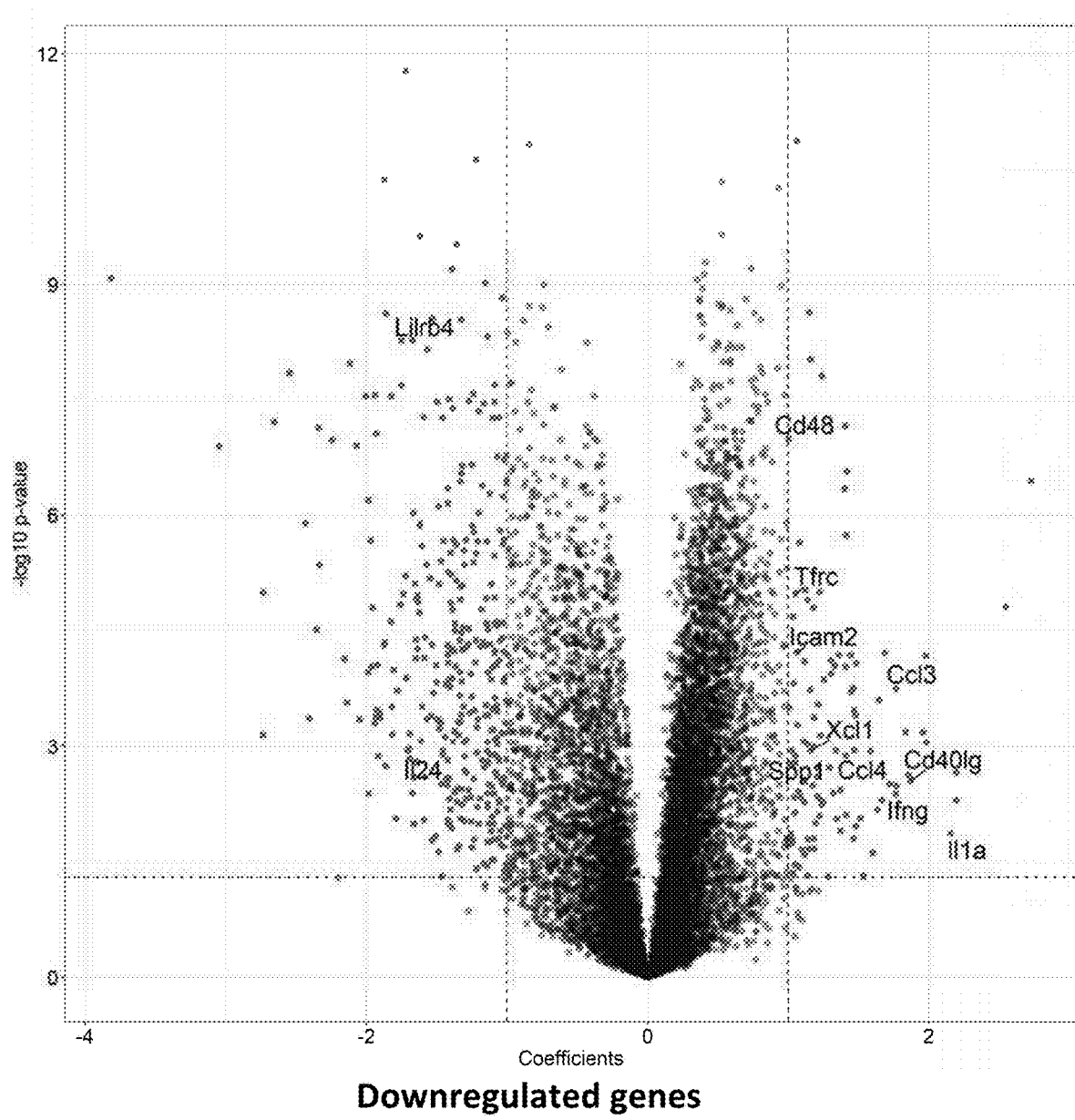
Figure 14:
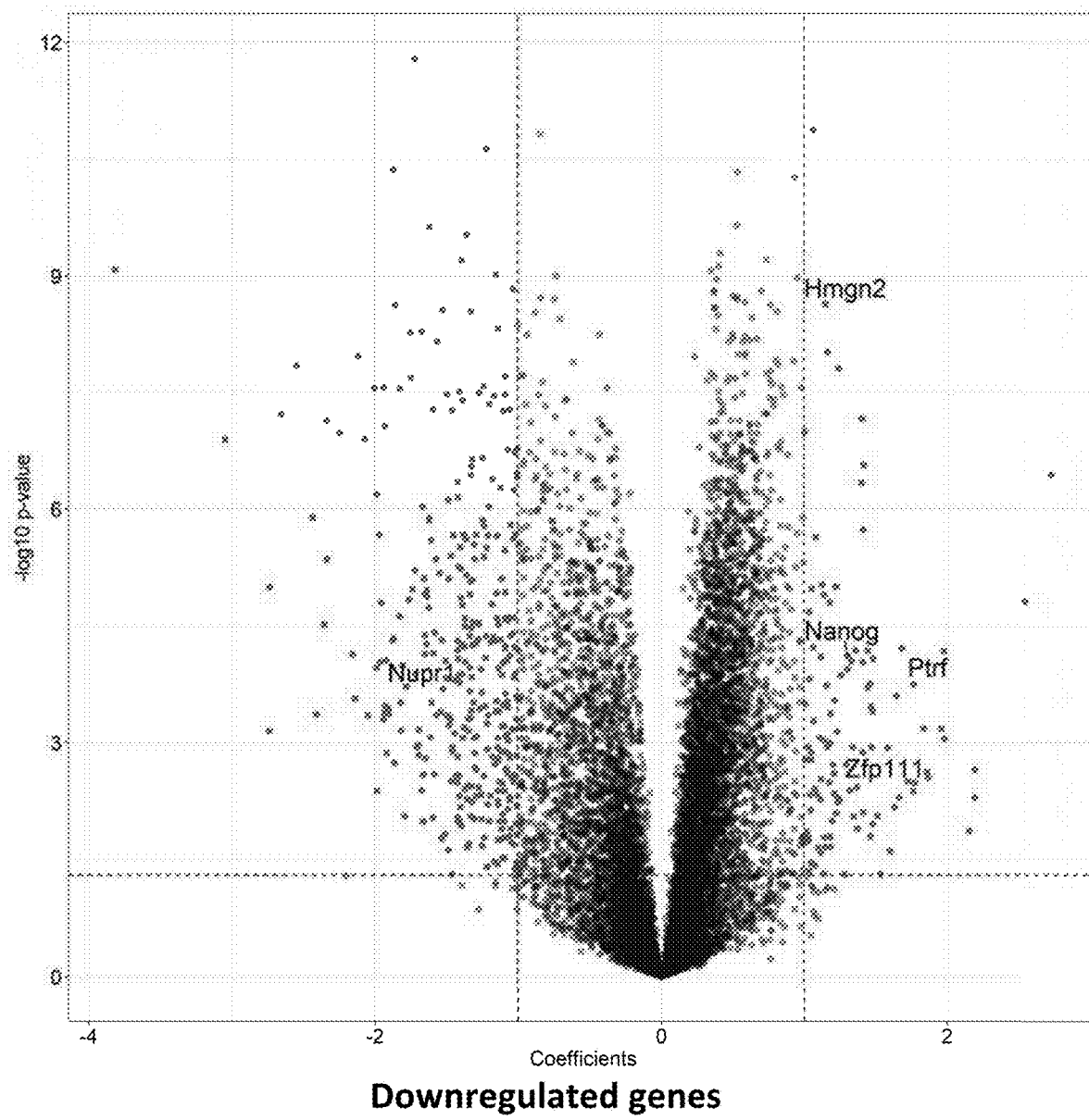

FIG. 14 shows the upregulated and downregulated transcription factors, cell surface protein and cytokines in CD8+ T cells after treatment with Dex+IL27. Thus, these are downstream targets for modulating T cell immune states. The upregulated genes include Epcam, Gpld1, Cd68, Prnp, Gab2, Vldlr, Il10, Il1r2, Nt5e, Itgae, C1qtnf4, Tgfb3, Itga7, Acvrl1, Gpr125, Aqp11, Ramp1, Kit, Trip6, Ddit3, Smyd3, Enpp2, Dbp, Tle2, Irf6, Zfp467, Jag2, Crebl2 and Asb2. The downregulated genes include Lilrb4, Il24, Cd48, Tfrc, Icam2, Ccl3, Xcl1, Spp1, Ccl4, Cd40lg, Ifng, Il1a, Nupr1, Hmgn2, Nanog, Ptrf and Zfp111.

Figure 15:
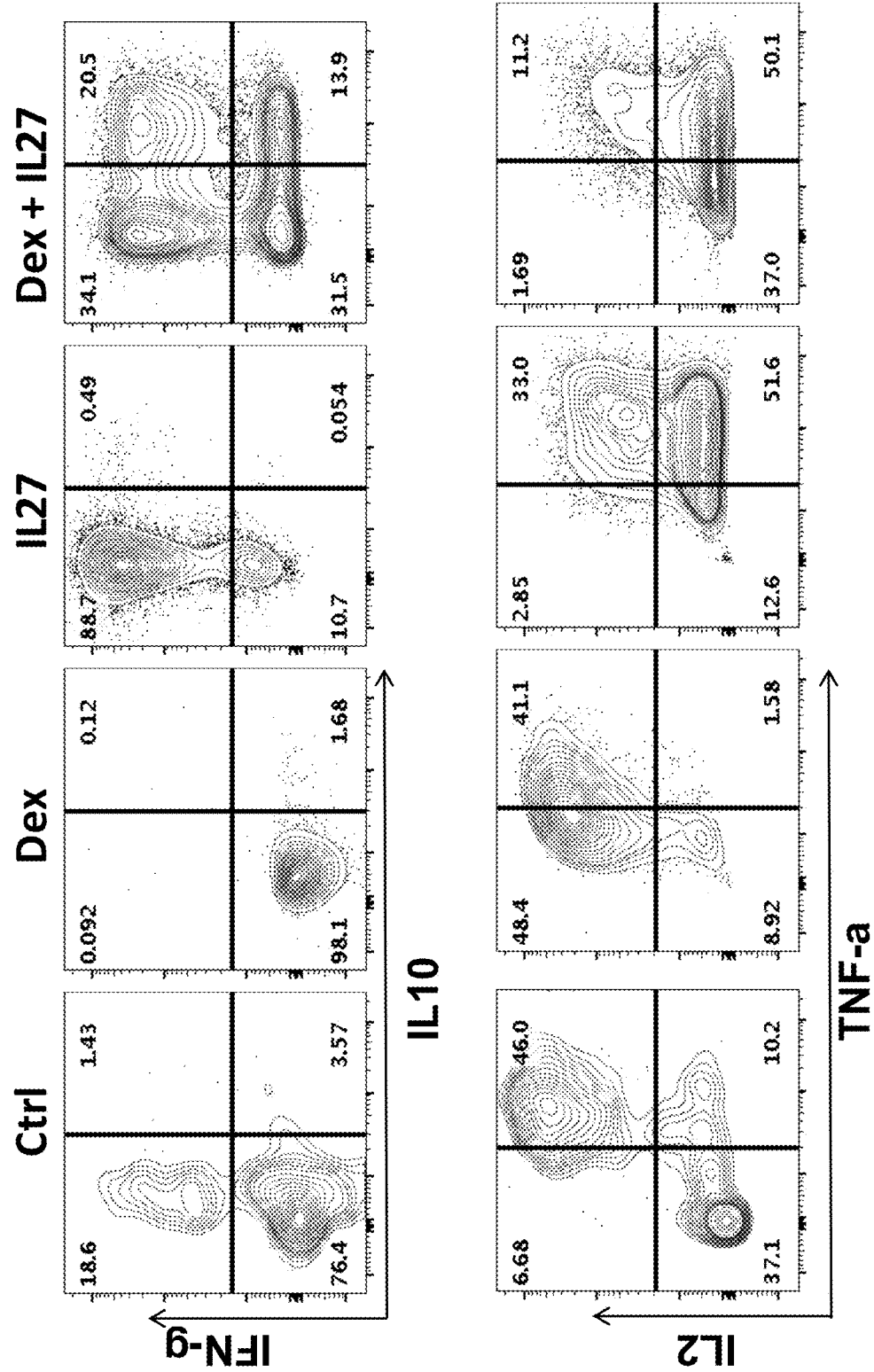
FIG. 15—FACS experiments detecting the indicated cytokine after treatment of CD4+ T cells with control, Dex, IL27 and Dex+IL27.

FIG. 15 shows that the synergy of glucocorticoid and IL-27 is also detected in CD4+ T cells.

Figure 16:
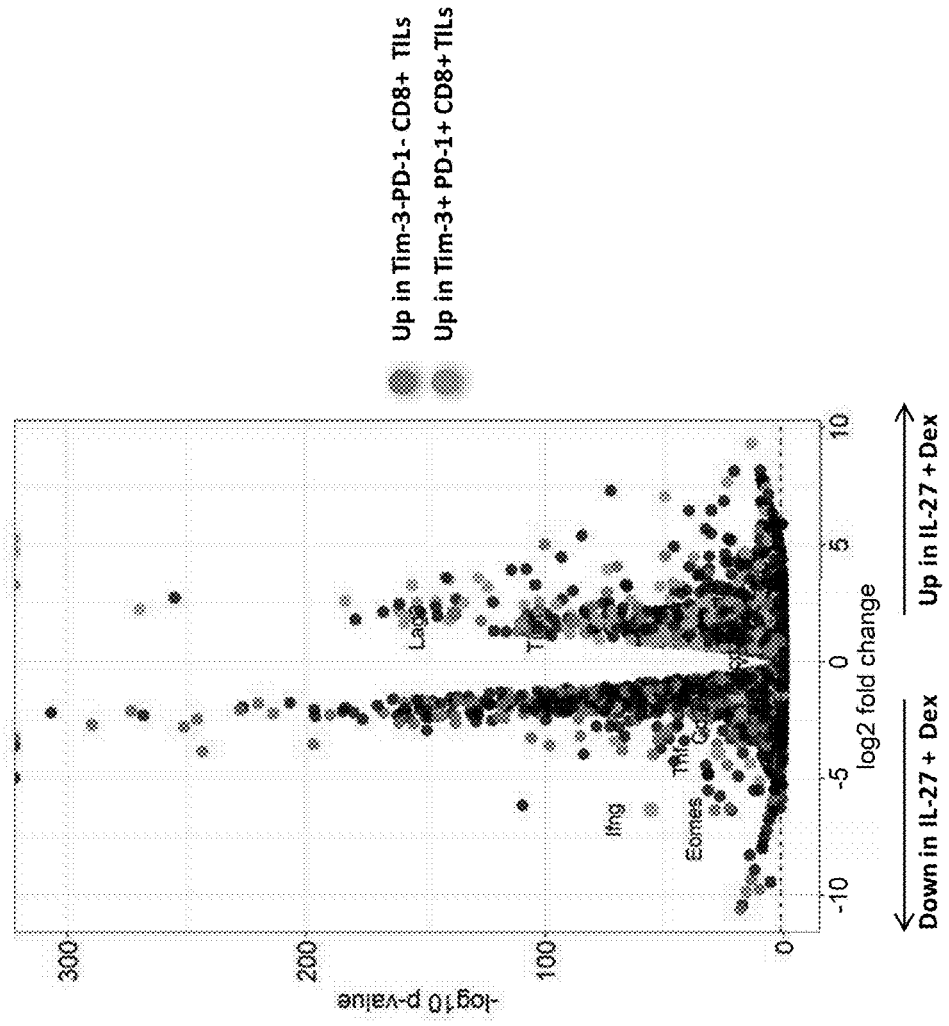
FIG. 16—Plot comparing expression of genes upregulated in Tim-3−PD-1− TILs and genes upregulated in Tim-3+PD-1+ TILs to genes upregulated in CD8+ T cells after treatment with Dex+IL27.

FIG. 16 shows that glucocorticoid and IL-27 induce gene programs that overlap with T cell dysfunction in CD8+ T cells. Genes upregulated in Tim-3−PD-1− TILs are downregulated in CD8+ T cells after treatment with Dex+IL27 and genes upregulated in Tim-3+PD-1+TILs (i.e., dysfunction T cells) are upregulated in CD8+ T cells after treatment with Dex+IL27.

Figure 17:
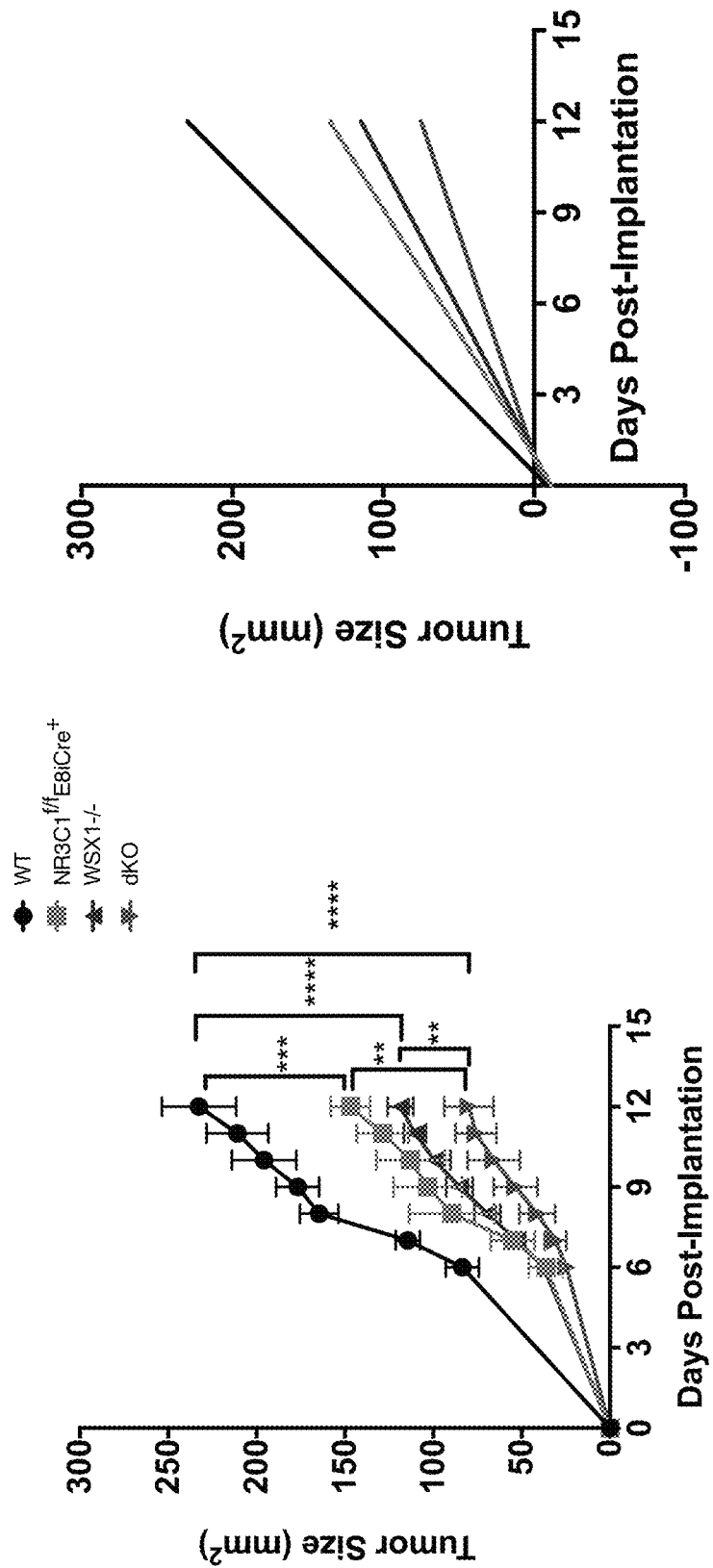
FIG. 17—Plots showing tumor control in WT mice, Nr3c1 conditional knockout mice (CD8+ T cells), IL-27 receptor knockout mice, and double knockout mice.

FIG. 17 shows an enhanced tumor control phenotype in a conditional knockout mouse where the glucocorticoid receptor (Nr3c1) is knocked out in CD8+ T cells. Also shown is an enhanced tumor control phenotype in an Il-27 receptor (Wsx1) knockout mouse. Finally, the double knockout mouse demonstrated a further enhanced tumor control phenotype. Therefore, glucocorticoid-glucocorticoidreceptor and IL27 signaling pathways synergize in CD8+ T cells in vivo. Thus, Applicants show that CD8+ T cells lacking both glucocorticoid-glucocorticoid receptor and IL27 signaling pathways have enhanced tumor control activity.

Example 2—Glucocorticoid Signaling is Active in Dysfunctional CD8+ TILs

Figure 18A:
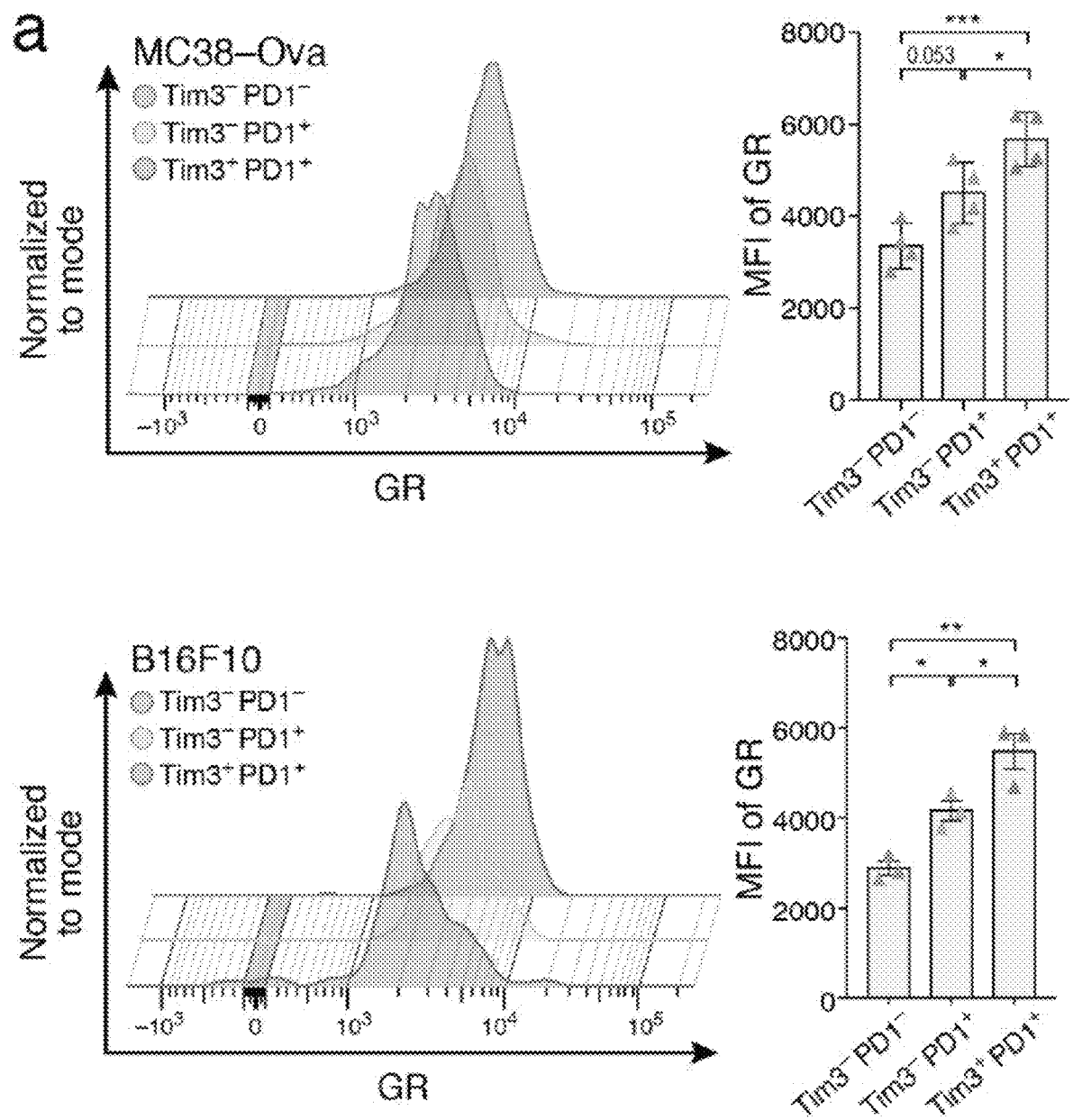
FIG. 18A-18C—Glucocorticoid signaling is active in dysfunctional CD8$^+$ TILs. TILs were harvested from (a) mice bearing MC38-Ova colon carcinoma (n=4) or B16F10 melanoma (n=3) or (b) from human colorectal carcinomas (n=7) for the examination of glucocorticoid receptor (GR) expression by intracellular staining. Representative histograms show GR expression in the indicated CD8+ TILs populations. Summary plots show the mean fluorescence intensity (MFI) of GR expression in the indicated populations. For human colorectal carcinoma TILs, data are normalized to the expression level in Tim-3−PD-1− CD8+ TILs. *p<0.05, p<0.01, *p<0.001, Ordinary one-way ANOVA (Tukey's multiple comparisons test). Mean±SEM is shown. c) tSNE plot showing projection of a glucocorticoid signature (top left), a CD8+ T cell dysfunction signature (top right), and Mt1 (bottom left) and Nfil3 (bottom right) gene expression onto the single-cell RNA profiles of CD8+ TILs3. The contour marks cells showing highest expression and the color scale indicates low (dark blue) to high (red) expressing cells.
Figure 18B:
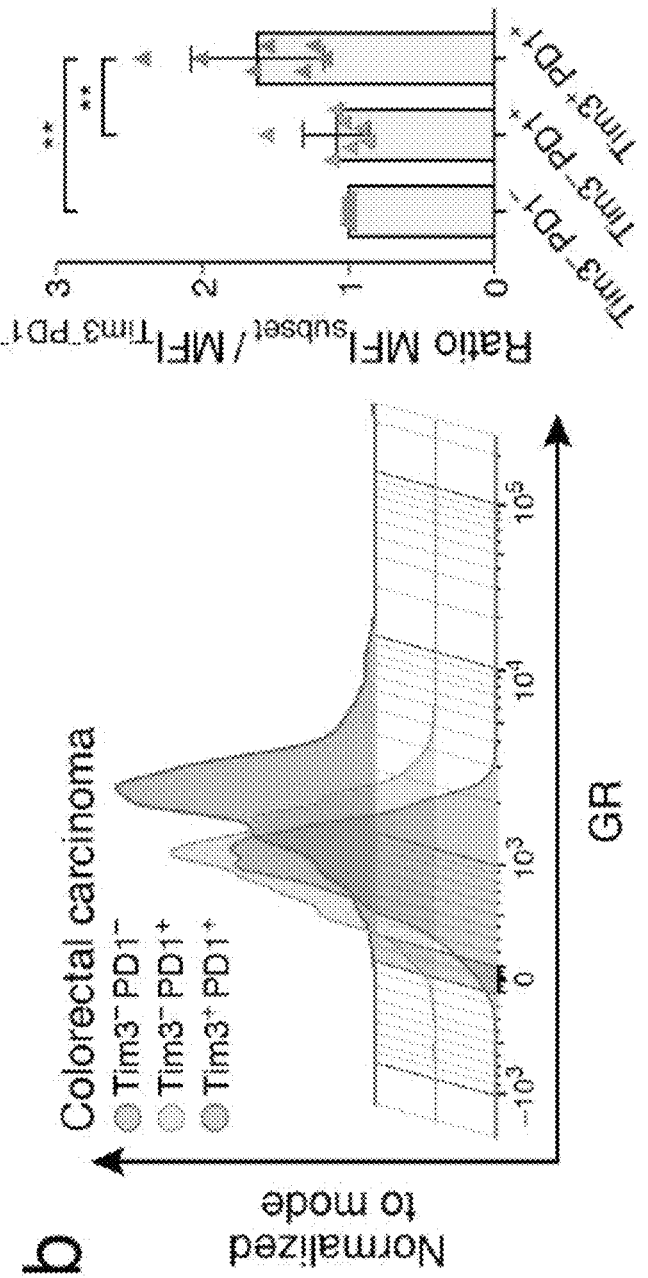
Figure 24:
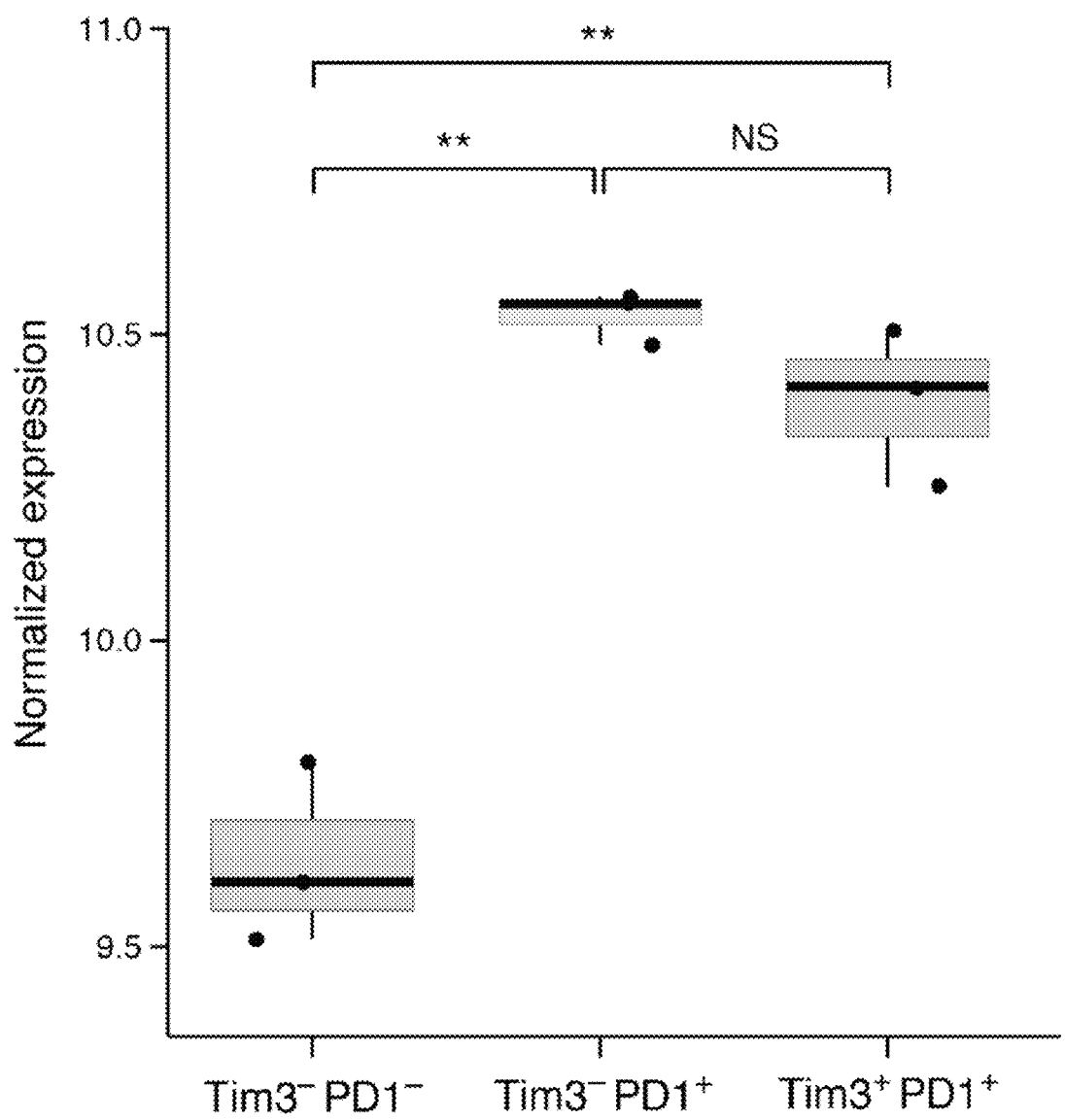
FIG. 24—Glucocorticoid receptor expression in CD8+ TILs populations. Gene expression value of Nr3c1 on Tim3−PD1−, Tim3−PD1+, and Tim3+PD1+CD8+ TILs from CT26 colon carcinoma3. **p<0.01. One way ANOVA.

Analysis of transcriptional profiles[3], showed that Nr3c1, the gene encoding the glucocorticoid receptor (GR) is highly expressed in the PD-1+CD8+ and Tim-3+PD-1+CD8+ TIL subsets that exhibit intermediate and severe dysfunctional phenotype, respectively (FIG. 24). Examination of GR protein showed that it is most highly expressed in severely dysfunctional Tim3+PD1+ CD8+ TILs in two different tumor models, MC38-Ova colon carcinoma and B16F10 melanoma (FIG. 18a), indicating that dysfunctional CD8+ T cells may have increased sensitivity to glucocorticoid signaling. Consistent with the expression pattern on murine CD8+ TILs subsets, the GR was also most highly expressed in Tim-3+ PD-1+CD8+ TILs from human colon carcinoma tumors (FIG. 18b). Thus, Applicants hypothesized that glucocorticoid signaling may be associated with the dysfunctional CD8+ T cell state in both murine and human tumors.

Figure 18C:
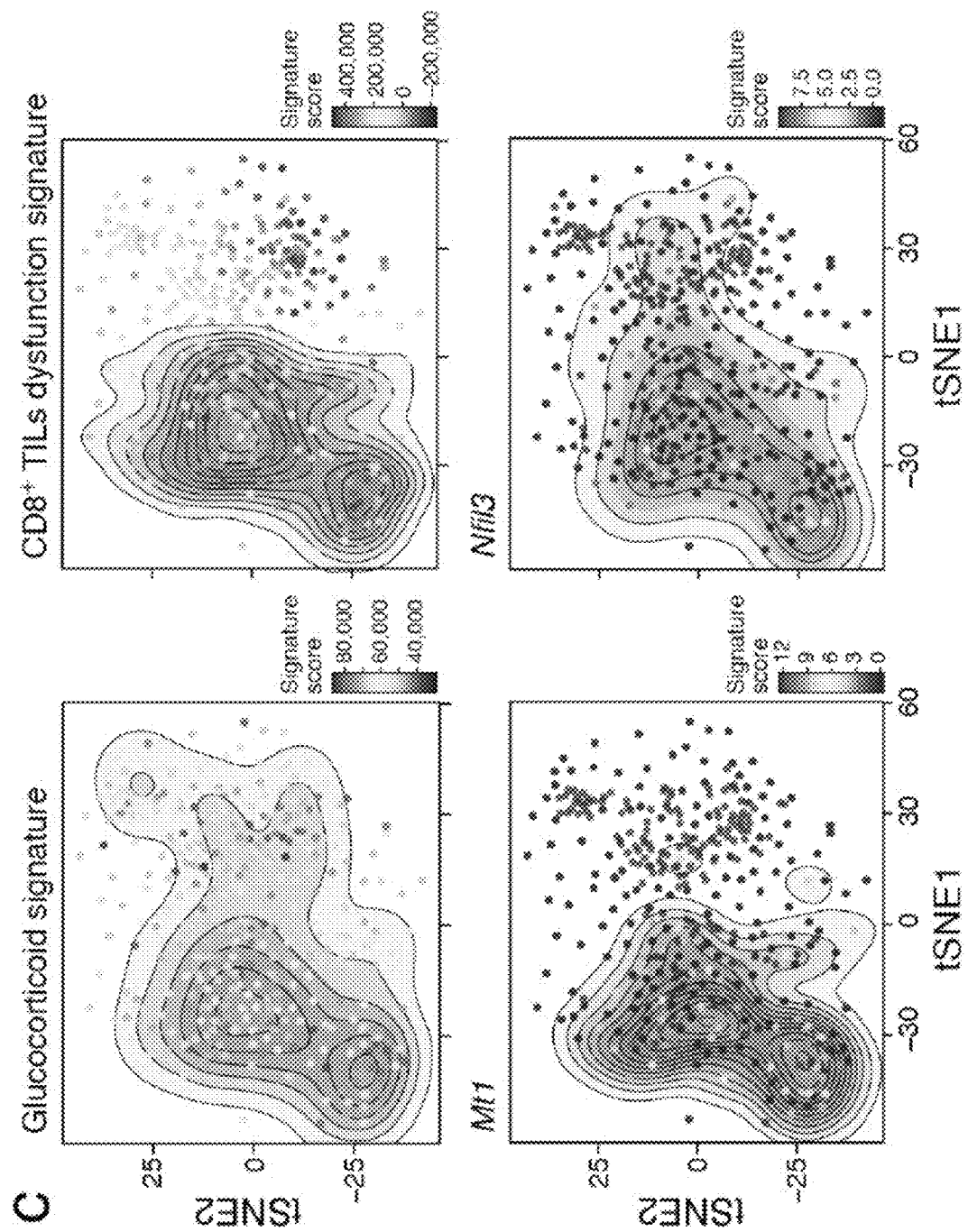

To further test the possible association of glucocorticoid signaling with CD8+ T cell dysfunction, Applicants scored the expression of a previously established glucocorticoid signature[17] (Methods) in the single-cell RNA-Seq (scRNA-Seq) profiles of CD8+ TILs[18] from B16F10 melanoma (FIG. 18c). Cells expressing the glucocorticoid signature and known GR target genes, such as Mt1[19] and Nfil3[20], also scored highly for expression of the T cell dysfunction or "exhaustion" signature (Methods), indicating that glucocorticoid signaling was active in CD8+ TILs that exhibit dysfunctional phenotype.

Figure 19A:
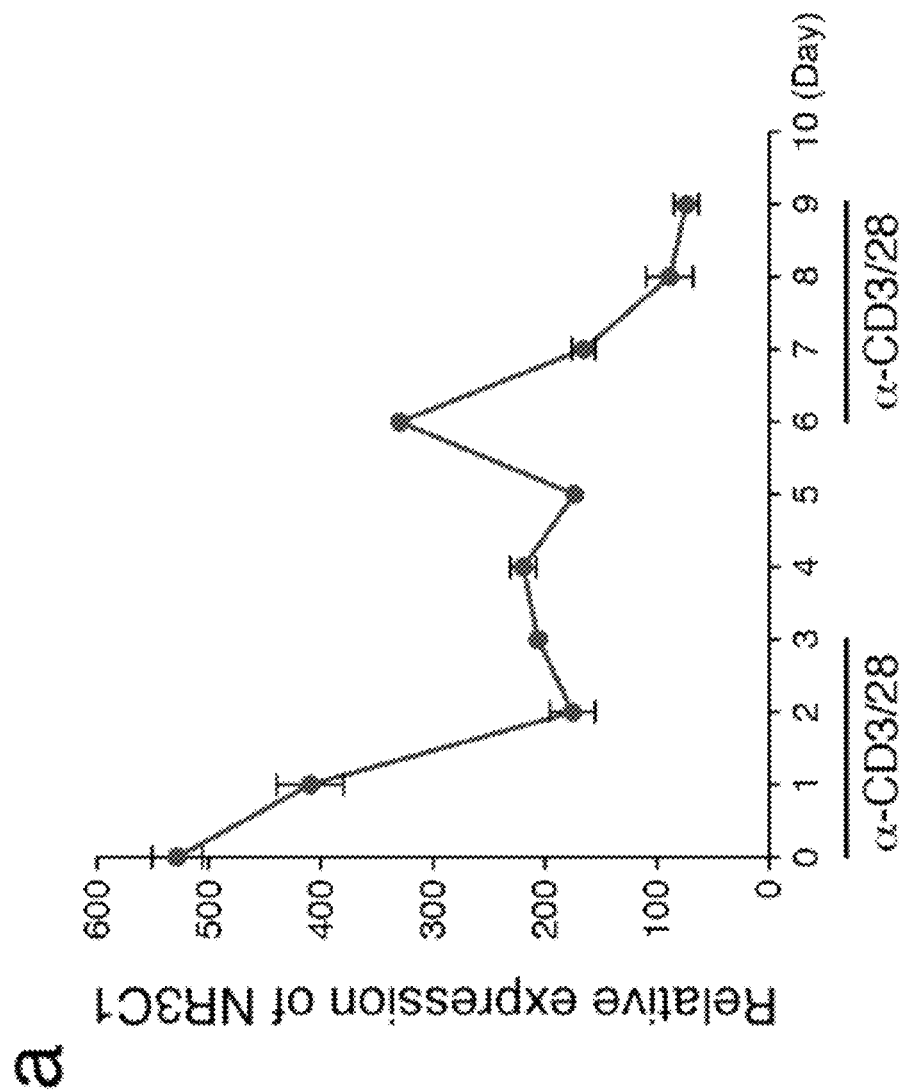
FIG. 19A-19D—Glucocorticoid signaling promotes checkpoint receptor expression and dampens CD8+ T cell effector functions. a) Naïve CD8+ T cells from wild type mice were activated with anti CD3/28 (1 µg/ml) on days 0 and 6. On days 3-6, cells were rested in the presence of IL-2 (5 ng/ml). RNA was extracted at the indicated time points for examination of Nr3c1 expression by qPCR. Data shown are representative of 2 independent experiments. b,c) Naïve CD8+ T cells from wild type mice (n=5) were activated in the presence or absence of Dex (GC) as in FIG. 19a and harvested on Day 9. b) Cells were stimulated with PMA/ionomycin for 4 hrs followed by intracellular staining for IL-2, TNF-α, and IFN-γ. c) Expression of Tim-3, PD-1, Lag3, and Tigit was examined by flow cytometry. Data shown are representative of 3 independent experiments. d) Human CD8+ T cells were activated in the presence or absence of Dex (GC) as in FIG. 19a and expression of Tim-3, PD-1, Lag-3, and Tigit was examined by flow cytometry on Day 9. Data shown are representative of 2 independent experiments. *p<0.05, p<0.01, *p<0.001, ****p<0.0001, Student's t test. Mean±SEM is shown.
Figure 19B:
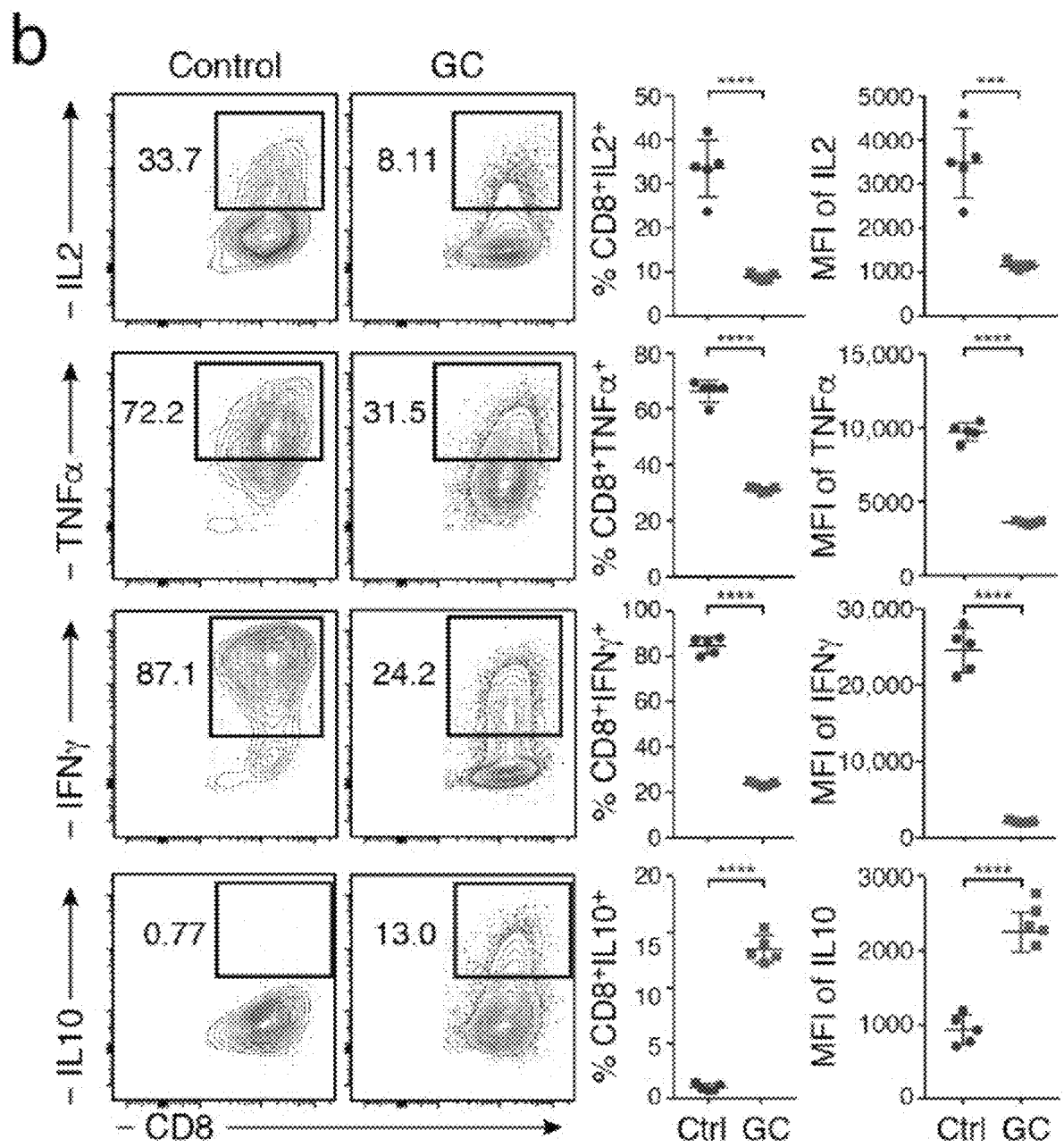
Figure 19C:
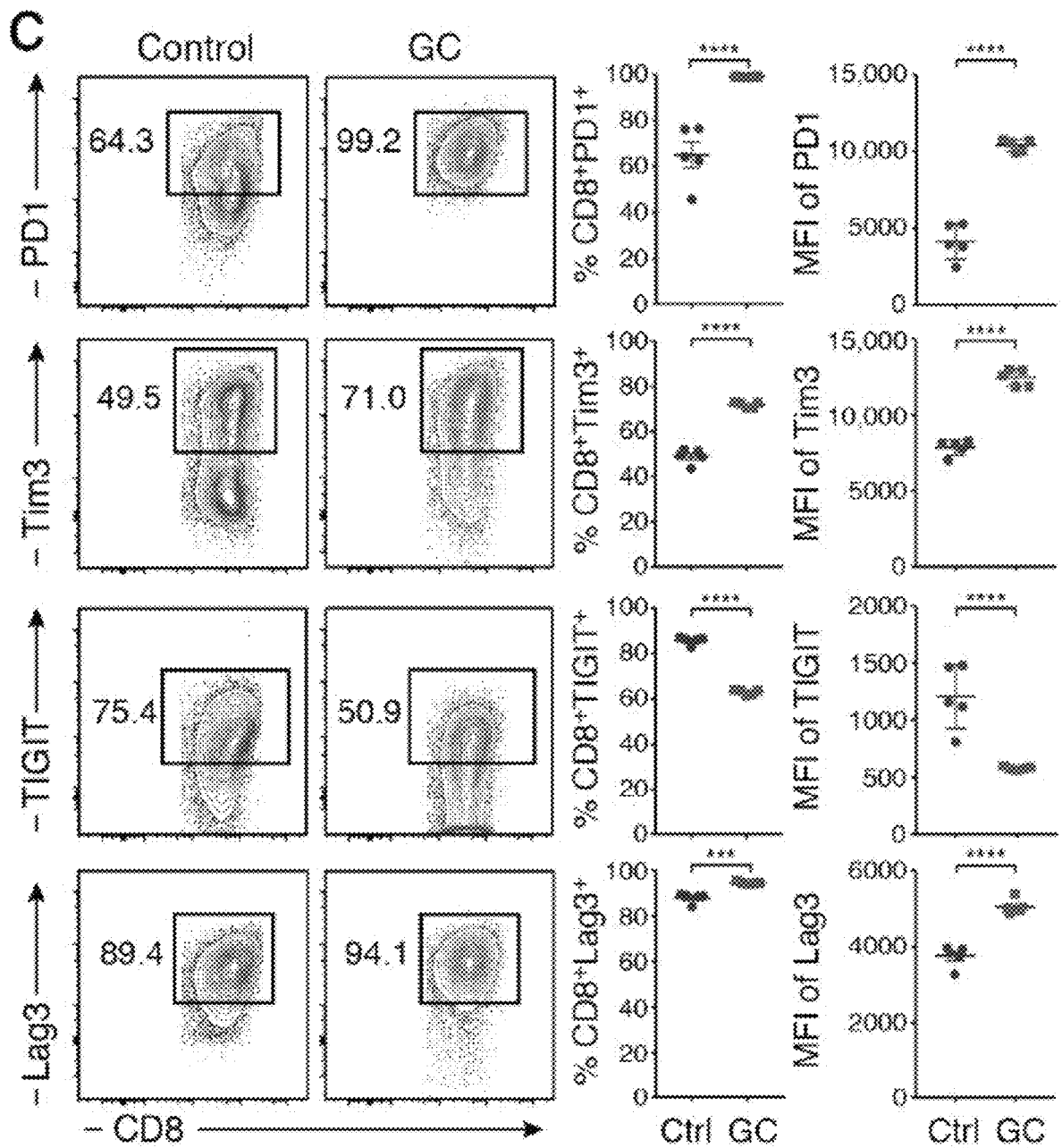
Figure 19D:
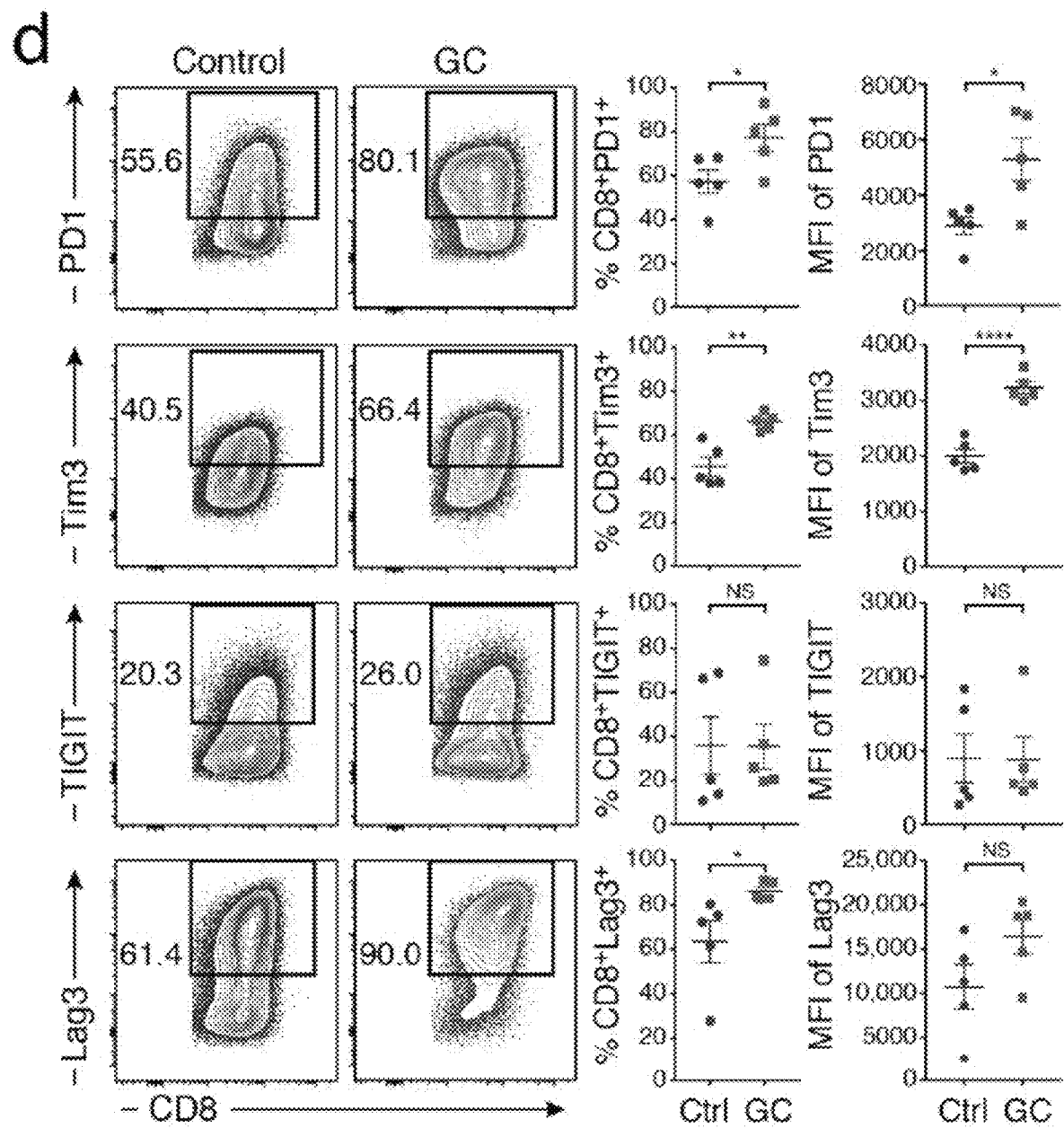

Example 3—Glucocorticoid Signaling Promotes Features of Dysfunctional Phenotype in CD8+ T Cells Accordingly, Applicants hypothesized that glucocorticoid signaling might promote T cell dysfunction in mouse and human cells. Applicants, therefore, examined Nr3c1 expression during repeated T cell activation. Applicants found that Nr3c1 was expressed at high levels in naïve CD8+ T cells, rapidly down-regulated by 48 hours after activation, and restored to half of the starting level as cells returned to the resting state (FIG. 19a). Upon re-activation, Nr3c1 was down-regulated to an even lower level than observed after primary activation (FIG. 19a). These data suggested that the GR may play a role in maintaining T cells in a quiescent state and its downregulation being requisite for T cell activation to ensue. Furthermore, in line with observations in primary activated cells[11, 15, 21], repeated activation of CD8+ T cells in the presence of exogenous glucocorticoid (dexamethasone; Dex) profoundly suppressed the production of the pro-inflammatory cytokines IFN-γ, IL-2, and TNF-α, and up-regulated the immune-suppressive cytokine IL-10 (FIG. 19b), a phenotype consistent with dysfunctional T cells. Indeed, Applicants found that glucocorticoid treatment dramatically upregulated checkpoint receptors associated with dysfunctional phenotype including PD-1, Tim-3, and Lag-3, but not Tigit (FIG. 19c). Notably, the glucocorticoid-mediated induction of checkpoint receptor expression was conserved in human CD8+ T cells (FIG. 19d and FIG. 25b). Additionally, Applicants observed that glucocorticoid increased the frequency of Tim-3+PD-1+CD8+ T cells in both murine and human samples (FIG. 25a).

Figure 25C:
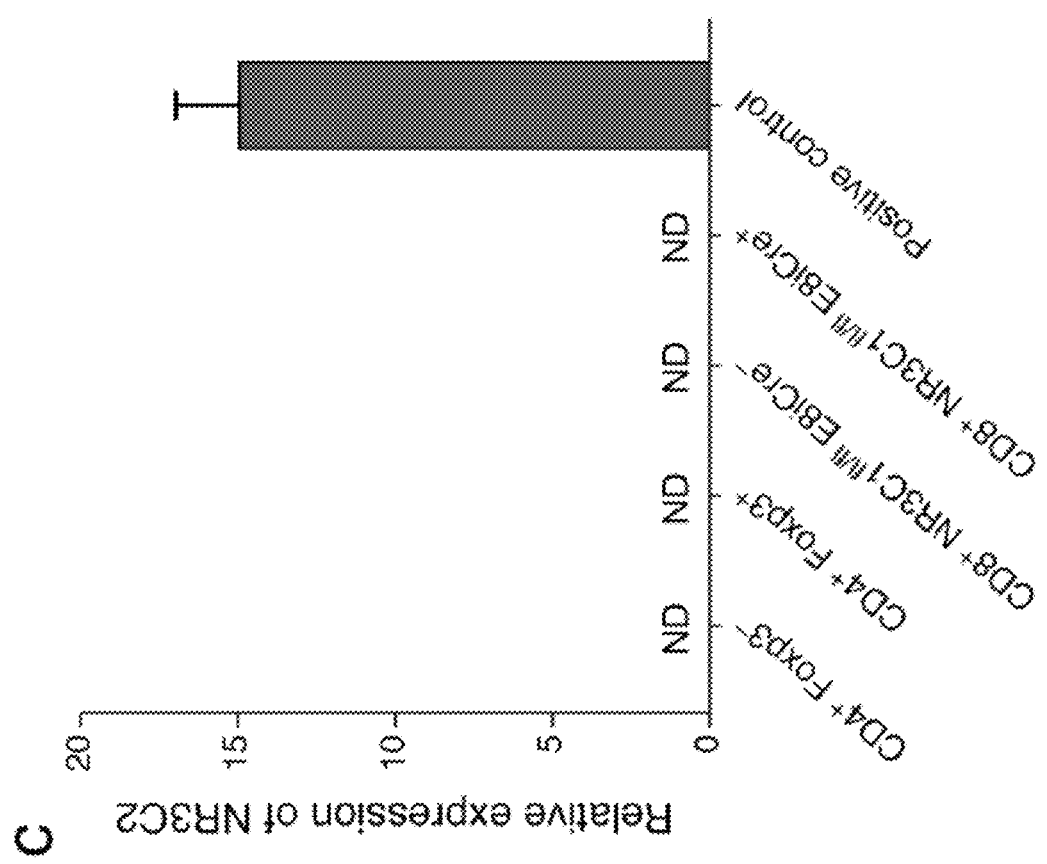
Figure 25D:
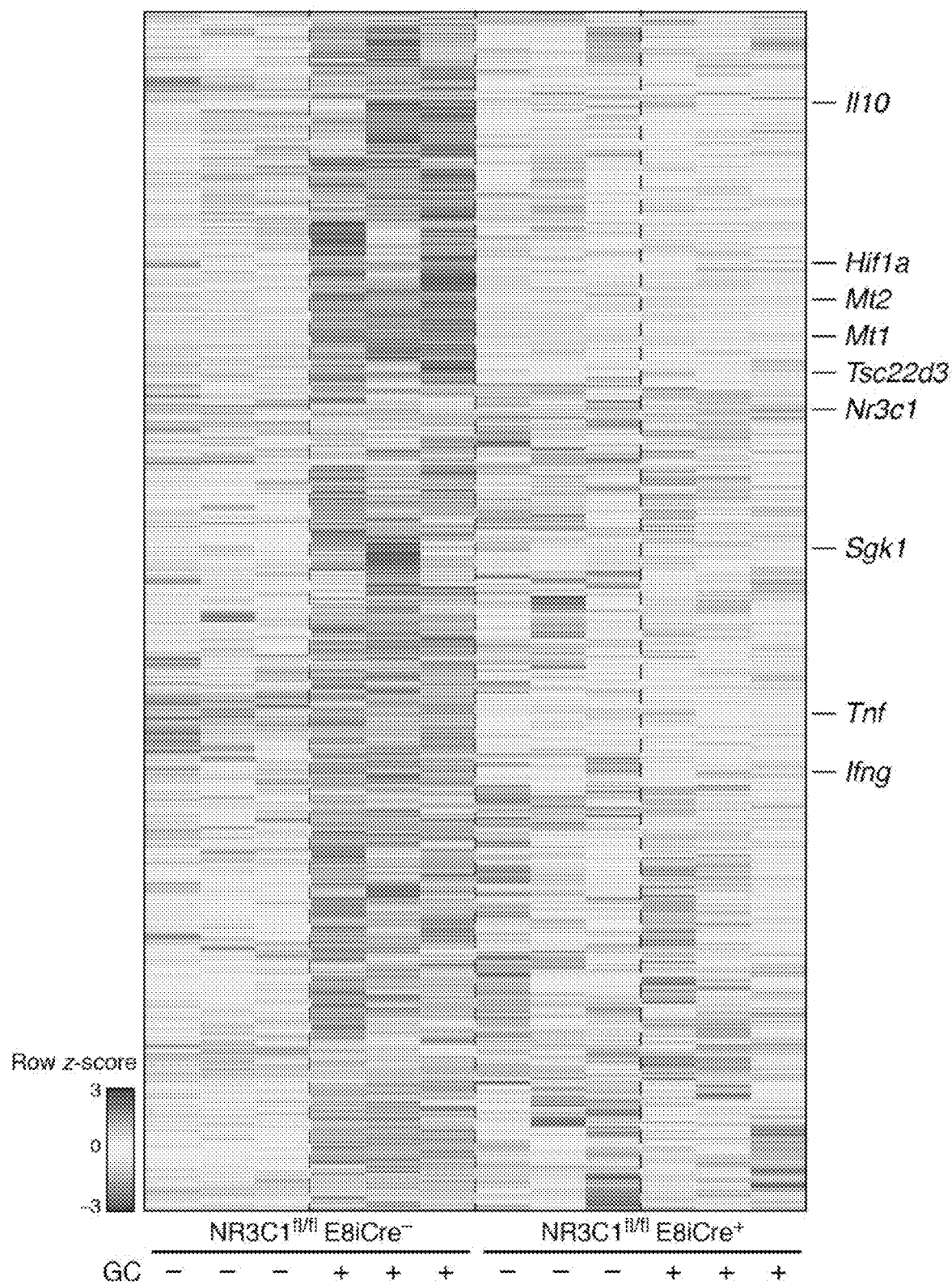

The observed effects of glucocorticoid on CD8+ T cells depended on Nr3c1. First, Applicants examined expression of Nr3c2, which encodes the mineralocorticoid receptor (MR) that shares high structural homology with GR and can bind glucocorticoids with high affinity[22]. Applicants found that Nr3c2 is not expressed by wild type CD4+ and CD8+ T cells or in CD8+ T cells from mice that lack Nr3c1 expression specifically in mature CD8+ T cells (E8i-Cre×Nr3c1$^{fl/fl}$) (FIG. 25c). Second, comparison of the RNA profiles of wild type and E8i-Cre×Nr3c1$^{fl/fl}$ CD8+ T cells stimulated with or without glucocorticoid showed distinct glucocorticoid-induced changes in wild type but not E8i-Cre×Nr3c1$^{fl/fl}$ CD8+ T cells, indicating that glucocorticoid-induced transcription in CD8+ T cells was Nr3c1 dependent (FIG. 25d). Thus, repeated stimulation in the presence of active glucocorticoid signaling dramatically influenced the effector differentiation of CD8+ T cells, resulting in cells that exhibited features shared with dysfunctional T cells, including up-regulation of multiple checkpoint receptors, dampened pro-inflammatory cytokine production, and increased IL-10 production.

Example 4—Glucocorticoid Signaling in CD8+ TILs Promotes Tumor Progression

Figure 20A:
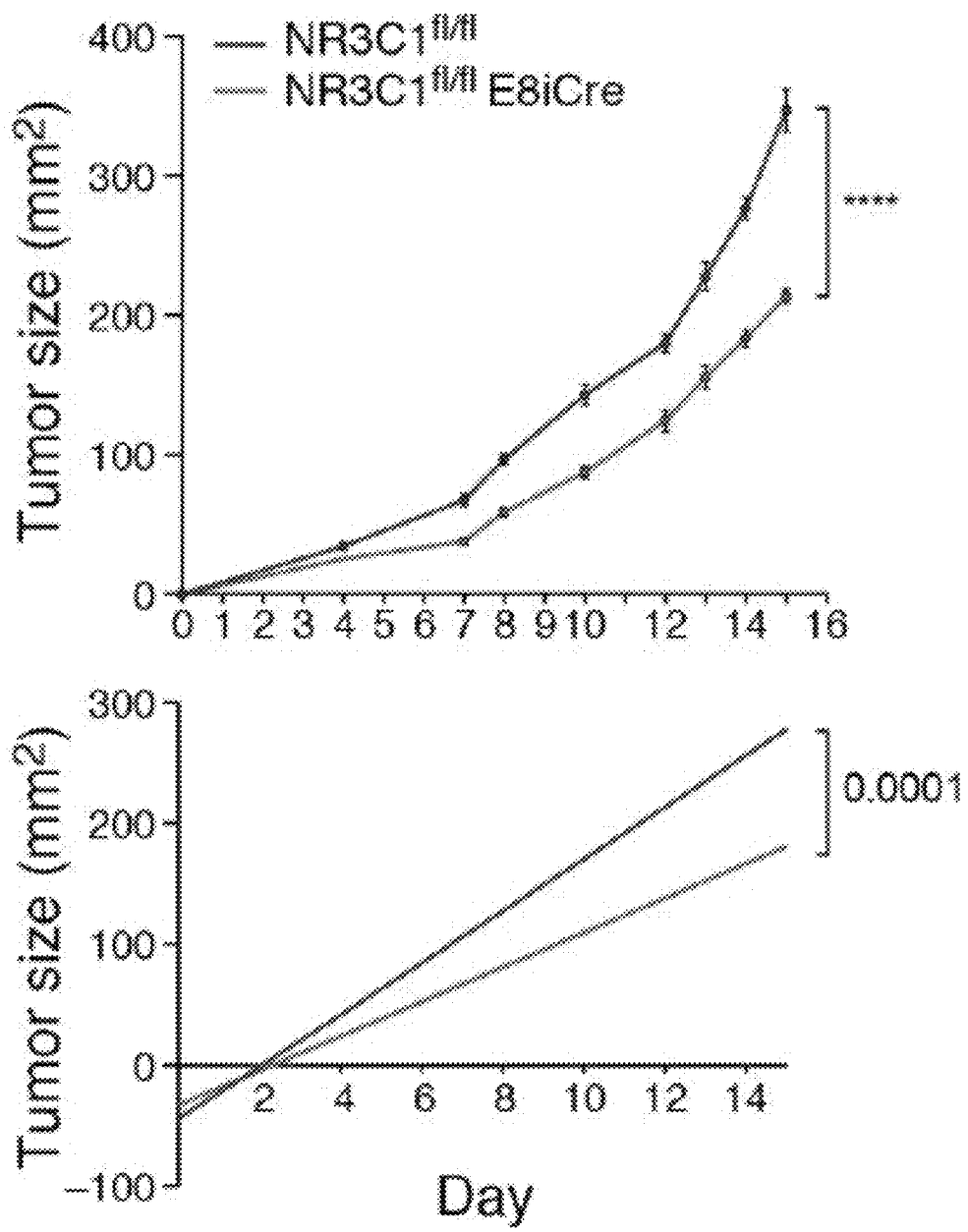
FIG. 20A-20F—Glucocorticoid signaling dampens CD8+ TILs effector functions. a) MC38-Ova was implanted into wild type (E8i-Cre−Nr3c1$^{fl/fl}$) and E8i-Cre+Nr3c1$^{fl/fl}$ mice (n=8-9). Mean tumor growth is shown. ****p<0.0001, linear regression. Data are representative of 3 independent experiments. b) TILs were harvested on Day 13 post tumor implantation and the expression of checkpoint receptors was analyzed by flow cytometry. Representative flow cytometry data are shown. Scatter plots show summary data (n=6-7) from 3 independent experiments. c,d) TILs were harvested and activated with 5 µg/ml OVA$_{257-264}$ (SIINFEKL). c) Representative flow cytometry data and summary scatter plots showing the frequency of IL-2, TNF-α, and IFN-γ-producing CD8+ T cells (n=9-10). Data are pooled from 2 independent experiments. d) Representative flow and summary scatter plots show the frequency of CD107a and Granzyme B expression (n=6). Data are pooled from 2 independent experiments. e) TILs were stained with H-2Kb/OVA257-264 dextramer, scatter plot shows the frequency of tumor antigen-specific CD8+ T cells (n=8-9). Data are pooled from 2 independent experiments. *p<0.05, P<0.01, *p<0.001, ****p<0.0001, Student's t-test. Mean±SEM are shown. f) Correlation of NR3C1 mRNA with checkpoint receptor mRNA in colon adenocarcinoma patients using TIMER.
Figure 26A:
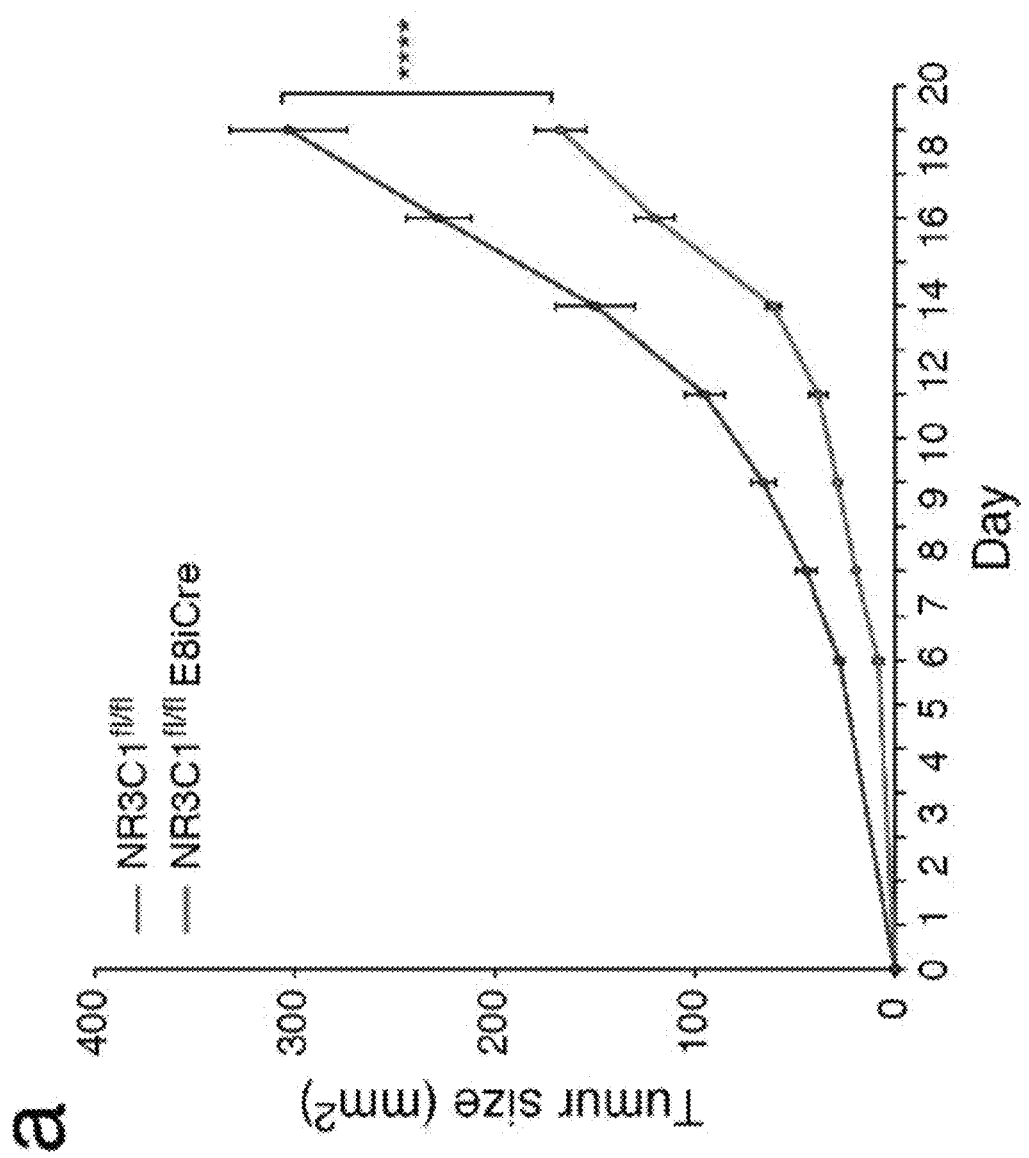

Applicants next tested whether glucocorticoid signaling impacts the functional state of CD8+ TILs in vivo. Applicants implanted either ovalbumin expressing MC38 colon carcinoma (MC38-Ova) or B16F10 melanoma cells into wild type and E8i-Cre×Nr3c1$^{fl/fl}$ mice and found that E8i-Cre×Nr3c1$^{fl/fl}$ mice exhibited improved tumor growth control in both models (FIG. 20a and FIG. 26a), indicating that the effect of glucocorticoid signaling in CD8$^+$ T cells is conserved across tumor types.

Figure 20B:
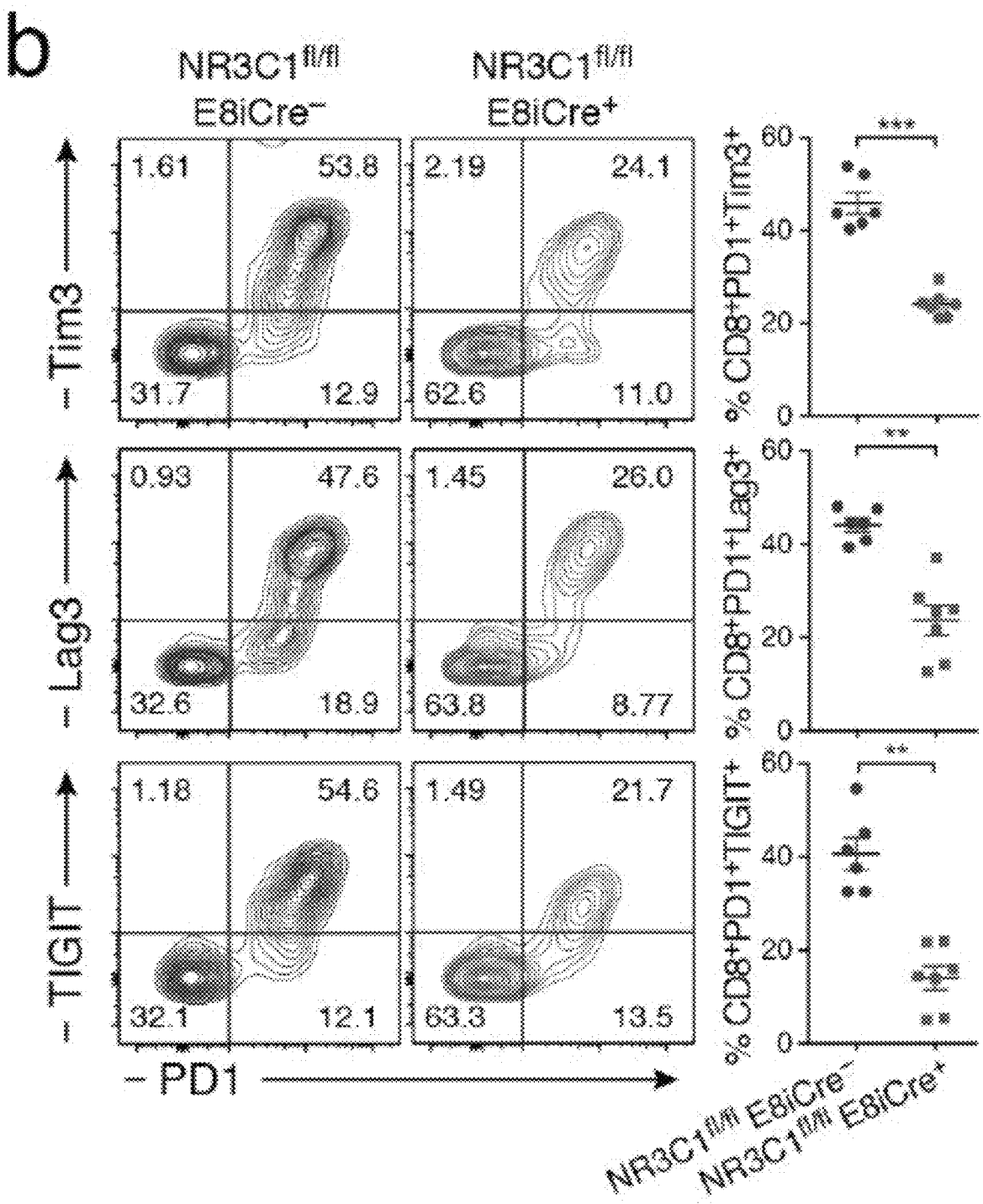
Figure 20C:
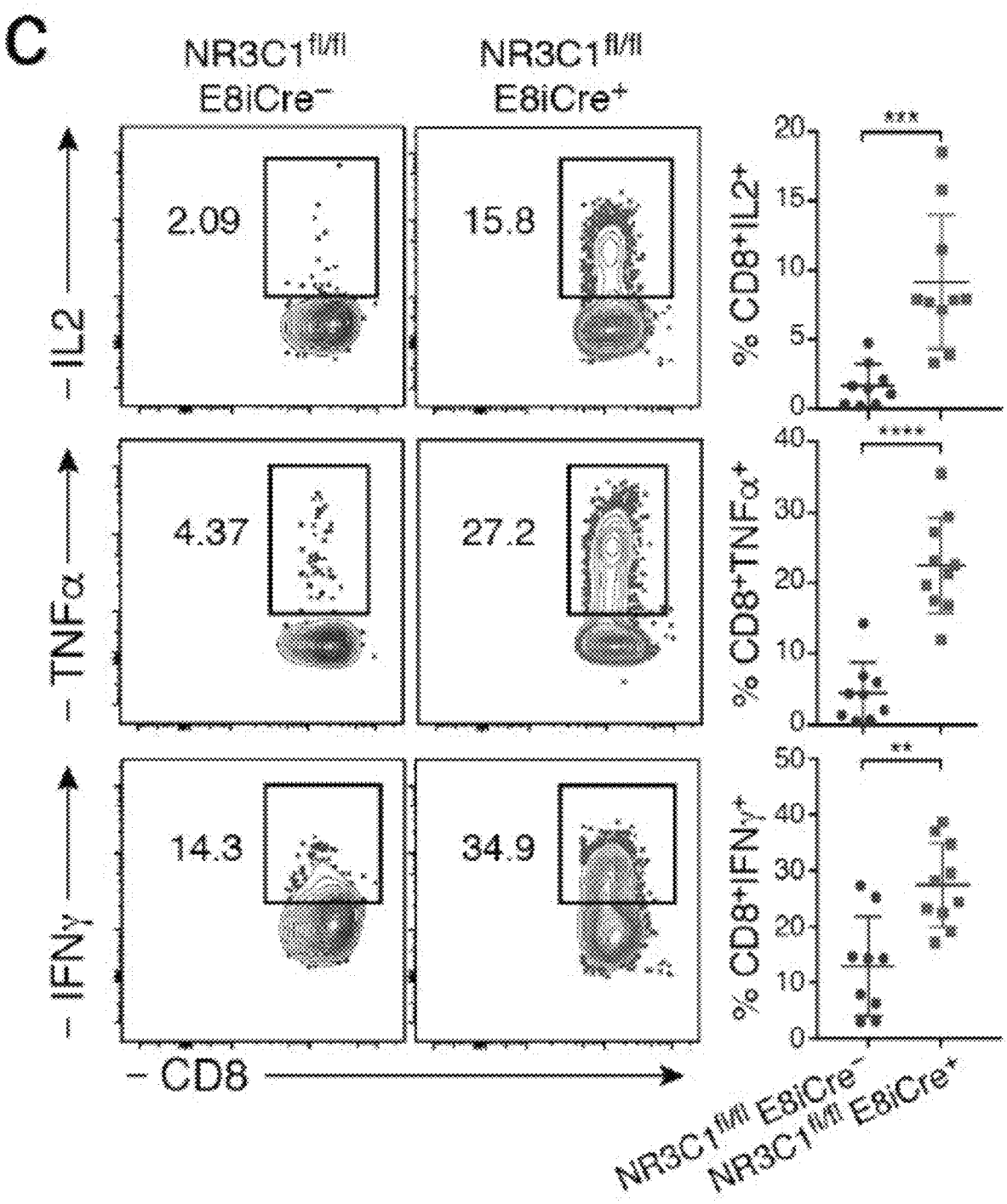
Figure 20D:
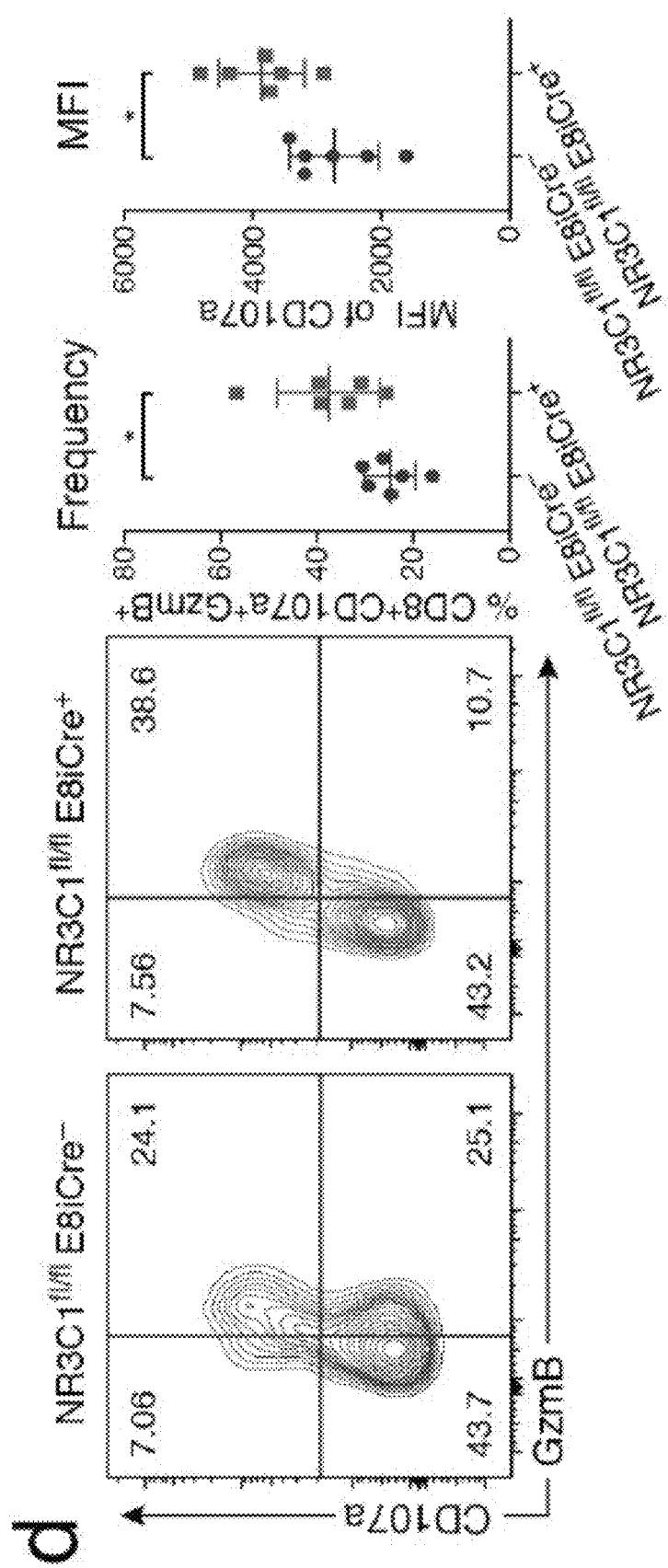
Figure 20E:
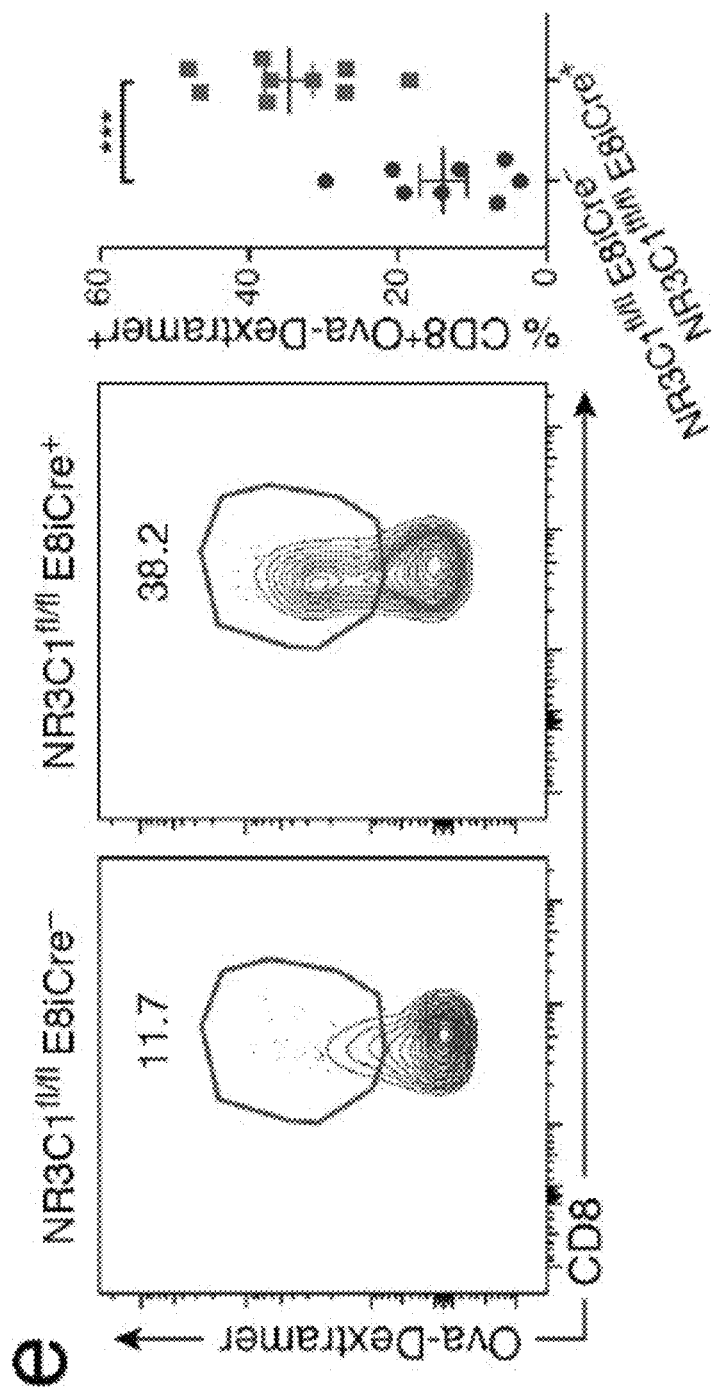
Figure 20F:
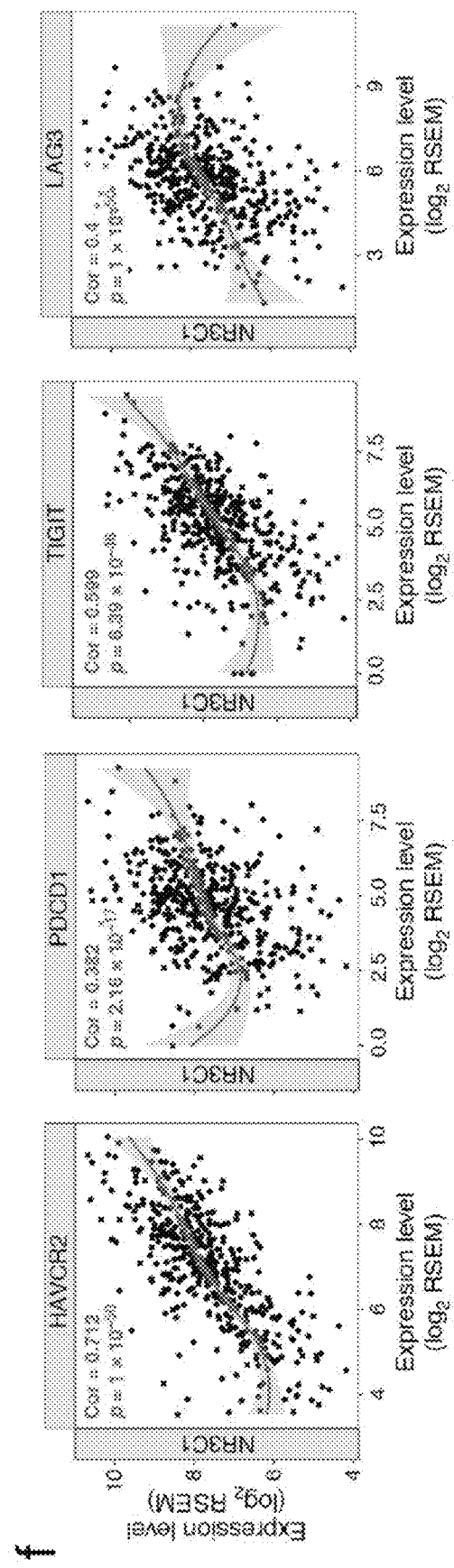
Figure 26D:
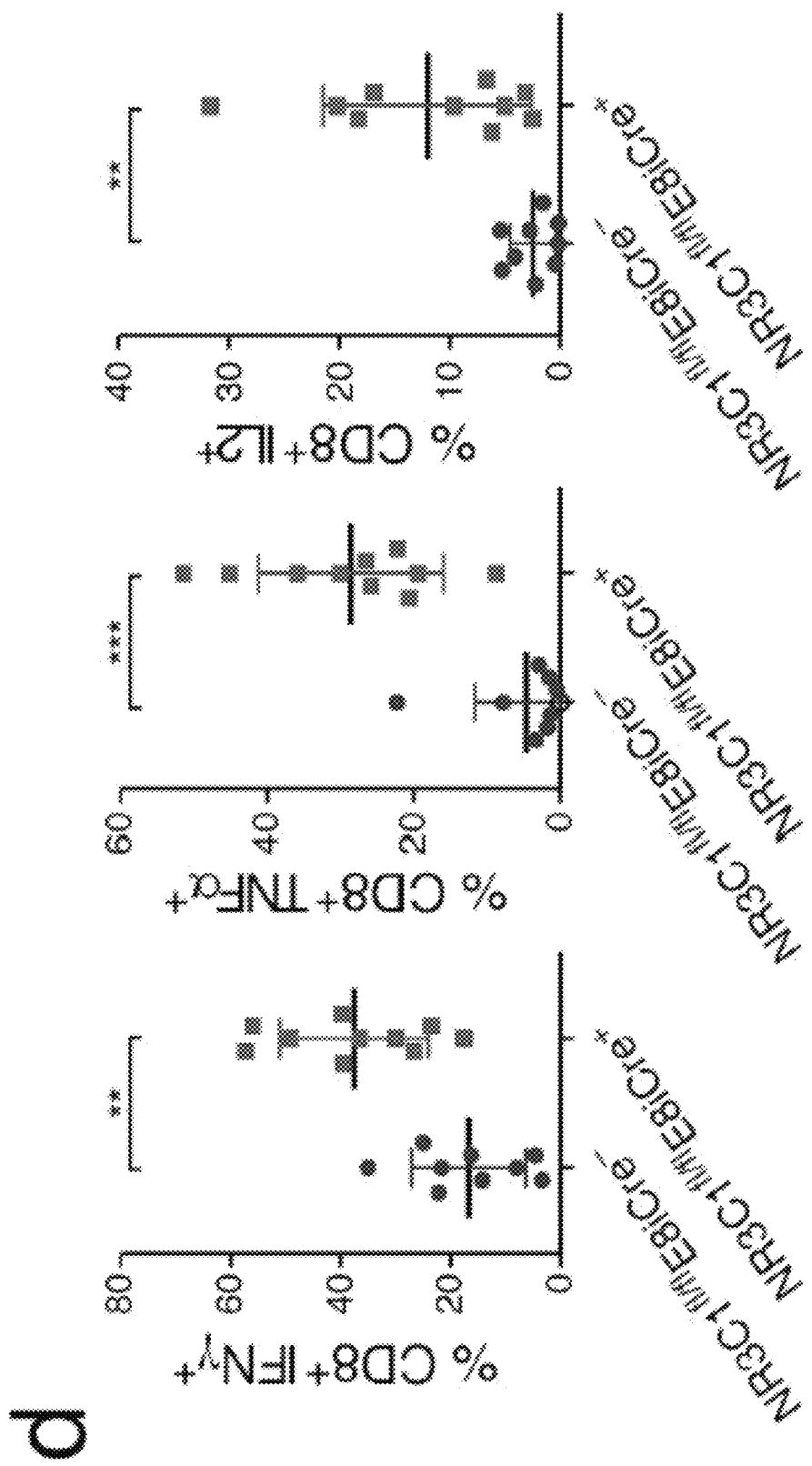
Figure 26E:
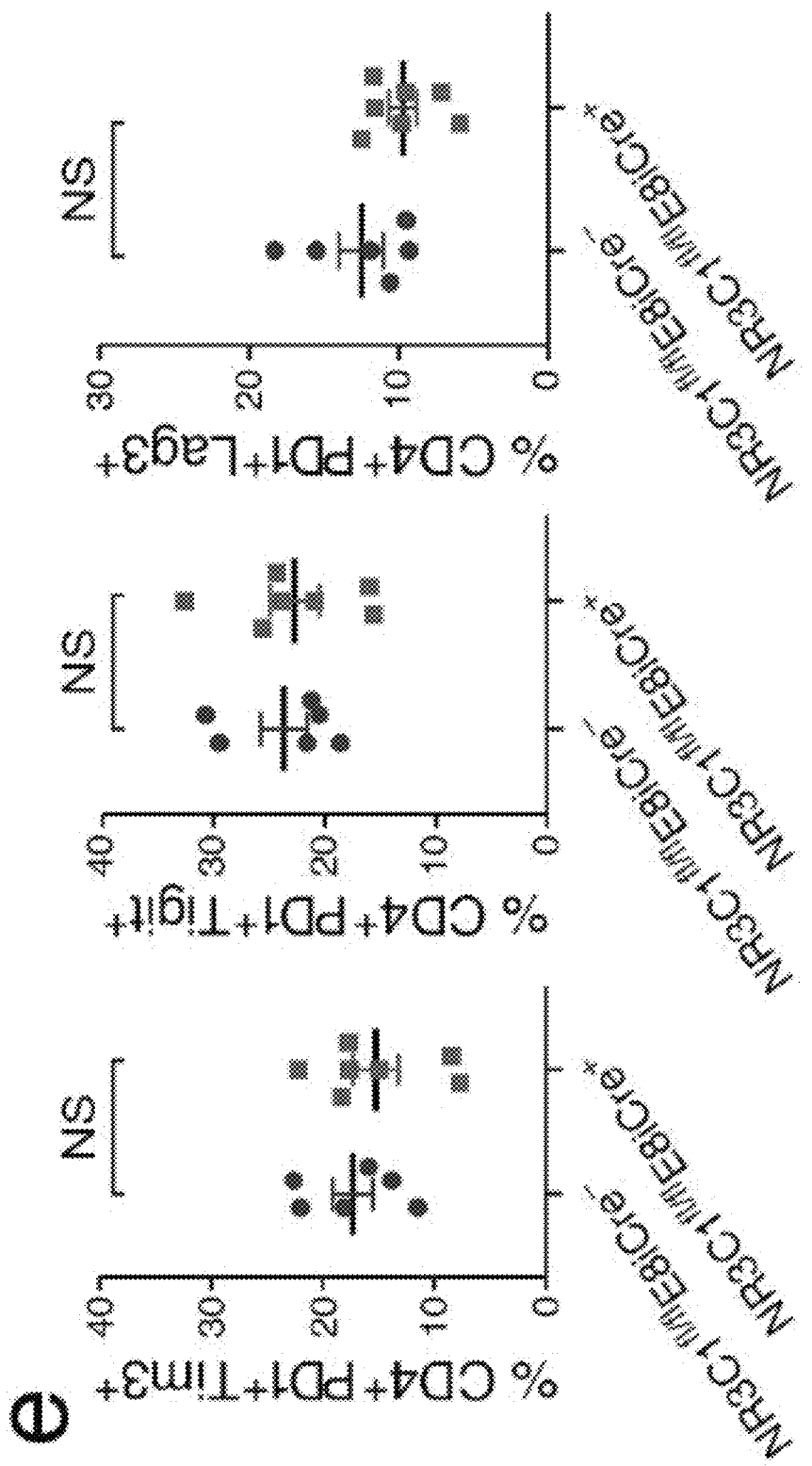
Figure 26F:
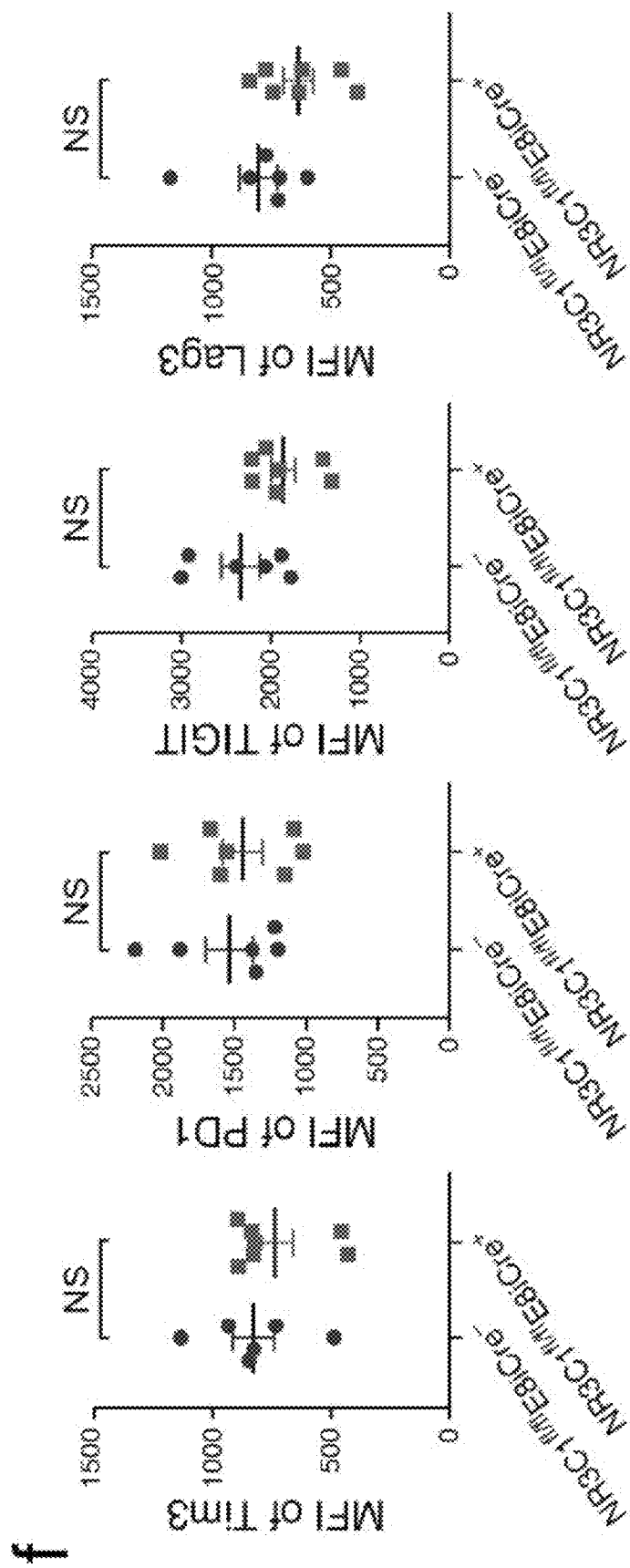

Glucocorticoid signaling impacted the functional state of CD8$^+$ TILs in vivo, based on the difference in several key parameters between E8i-Cre×Nr3c1$^{fl/fl}$ and wild type (Nr3c1$^{fl/fl}$) MC38-Ova-bearing mice. First, not only was there a dramatic reduction in the frequency of CD8$^+$ TILs co-expressing PD-1, Tim-3, Lag-3, and Tigit in CD8$^+$ TILs from E8i-Cre×Nr3c1$^{fl/fl}$ mice (FIG. 20b), but even the expression level of each of these checkpoint receptors was also significantly reduced (FIG. 26b). Of note, Tigit expression was down-regulated in CD8$^+$ TILs from E8i-Cre×Nr3c1$^{fl/fl}$ mice (FIG. 20b and FIG. 26b), in contrast to the in vitro observations where Tigit expression was not induced by GR stimulation (FIG. 19c). Second, CD8$^+$ TILs from E8i-Cre×Nr3c1$^{fl/fl}$ mice had enhanced tumor-antigen (OVA$_{257-264}$)-specific responses, producing more IL-2, TNF-α, and IFN-γ (FIG. 20c). Indeed, the CD8$^+$ TILs from E8i-Cre×Nr3c1$^{fl/fl}$ mice were more polyfunctional in terms of pro-inflammatory cytokine production (FIG. 26c). Furthermore, the few Tim-3$^+$PD-1$^+$CD8$^+$ TILs in E8i-Cre× Nr3c1$^{fl/fl}$ mice exhibited increased pro-inflammatory cytokine production in response to OVA$_{257-264}$ stimulation (FIG. 26d), in contrast to their typical severe dysfunctional phenotype observed in wild type mice. Third, CD8$^+$ TILs from E8i-Cre×Nr3c1$^{fl/fl}$ mice had higher cytotoxic capacity, as shown by the increased frequency of Granzyme B$^+$CD107a$^+$ cells upon OVA$_{257-264}$ stimulation (FIG. 20d). Fourth, E8i-Cre×Nr3c1$^{fl/fl}$ mice harbored more H-2K$^b$/OVA$_{257-264}$ dextramer$^+$ CD8$^+$ TILs (FIG. 20e). Notably, checkpoint receptor expression on CD4$^+$ TILs in E8i-Cre×Nr3c1$^{fl/fl}$ mice was not significantly different from that of wild type CD4$^+$ TILs, indicating that the regulation of checkpoint receptors in CD8$^+$ TILs was cell-intrinsic and not due to a secondary effect of loss of GR in CD8$^+$ TILs (FIG. 26e,f). Finally, in human colon adenocarcinoma from TCGA (http://cancergenome.nih.gov/), Applicants found (using TIEWR[23], Methods) that NR3C1 mRNA levels positively correlated with HAVCR2 (Tim-3), PDCD1 (PD-1), LAG3, and TIGIT mRNA levels (FIG. 20f). Collectively, these data supported that glucocorticoid signaling is active in the TME of both murine and human tumors and functions to promote checkpoint receptor expression and dampen the effector function of CD8$^+$ TILs.

Example 5—the Glucocorticoid Receptor Transactivates the Expression of Checkpoint Receptors and IL-10

Figure 27E:
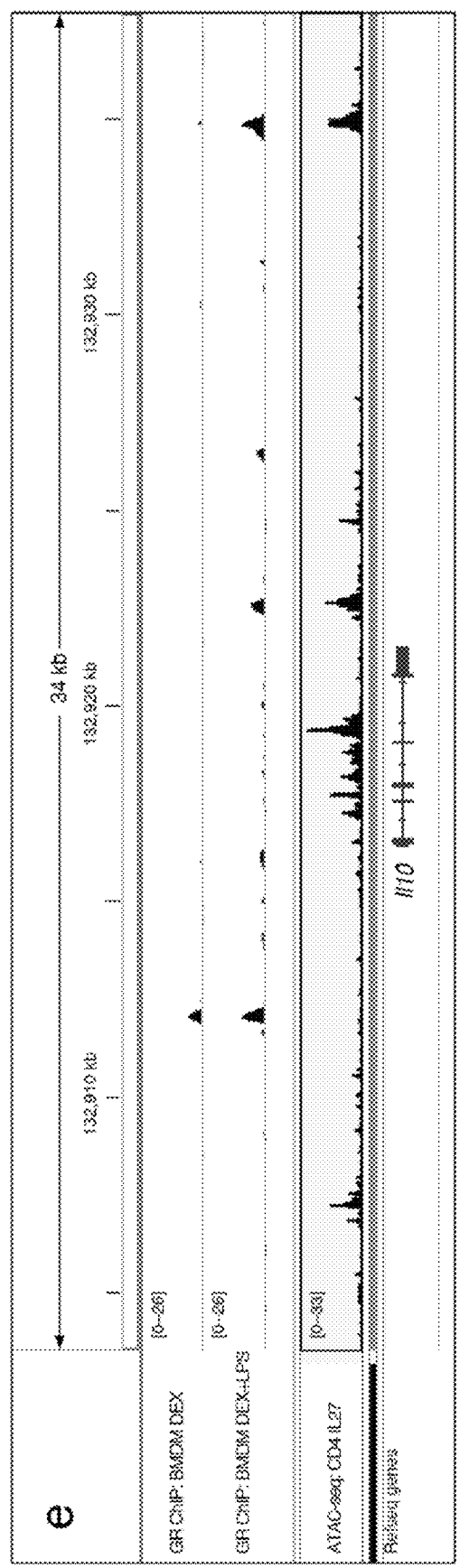

Applicants next tested if the GR directly regulates the expression of checkpoint receptor genes and IL-10. First, Applicants analyzed GR-binding peaks in the loci of Havcr2 (Tim-3), Pdcd1 (PD-1), Lag3, Tigit, and IL10 in publicly available ChIP-seq data[24] from bone marrow-derived macrophages (BMDMs) (FIG. 27). Applicants found GR-binding peaks in the loci of Havcr2, Lag3, and IL10 but not Pdcd1 or Tigit, likely reflecting the lack of PD-1 and Tigit expression in BMDMs. Applicants further found that some of the GR binding peaks in the Havcr2, Lag3, and IL10 loci overlapped regions of accessible chromatin (based on ATAC-seq) in IL-27 stimulated T cells[25], which are known to express high levels of these molecules[26]. Applicants therefore tested the effect of GR binding to the cis-regulatory elements in the Havcr2, Pdcd1, Lag3, and Tigit loci identified by the ATAC-seq peaks in IL-27-treated T cells using luciferase reporter assays. For IL10, Applicants utilized luciferase reporters of a previously established enhancer element of Il10—HSS$^+$2.98 as well as the proximal promoter (−1.5 kb)[25]. Applicants transfected the different luciferase reporter constructs along with a Nr3c1 expressing vector or empty vector into 293T cells and treated the cells with glucocorticoid to assay the transactivation capability of the GR. In line with the observations in glucocorticoid treated CD8$^+$ T cells (FIG. 19), the GR potently transactivated Tim-3, PD-1, Lag-3, and IL-10 expression (FIG. 21). Tigit was also induced but to a much lower degree (FIG. 21d).

Figure 22C:
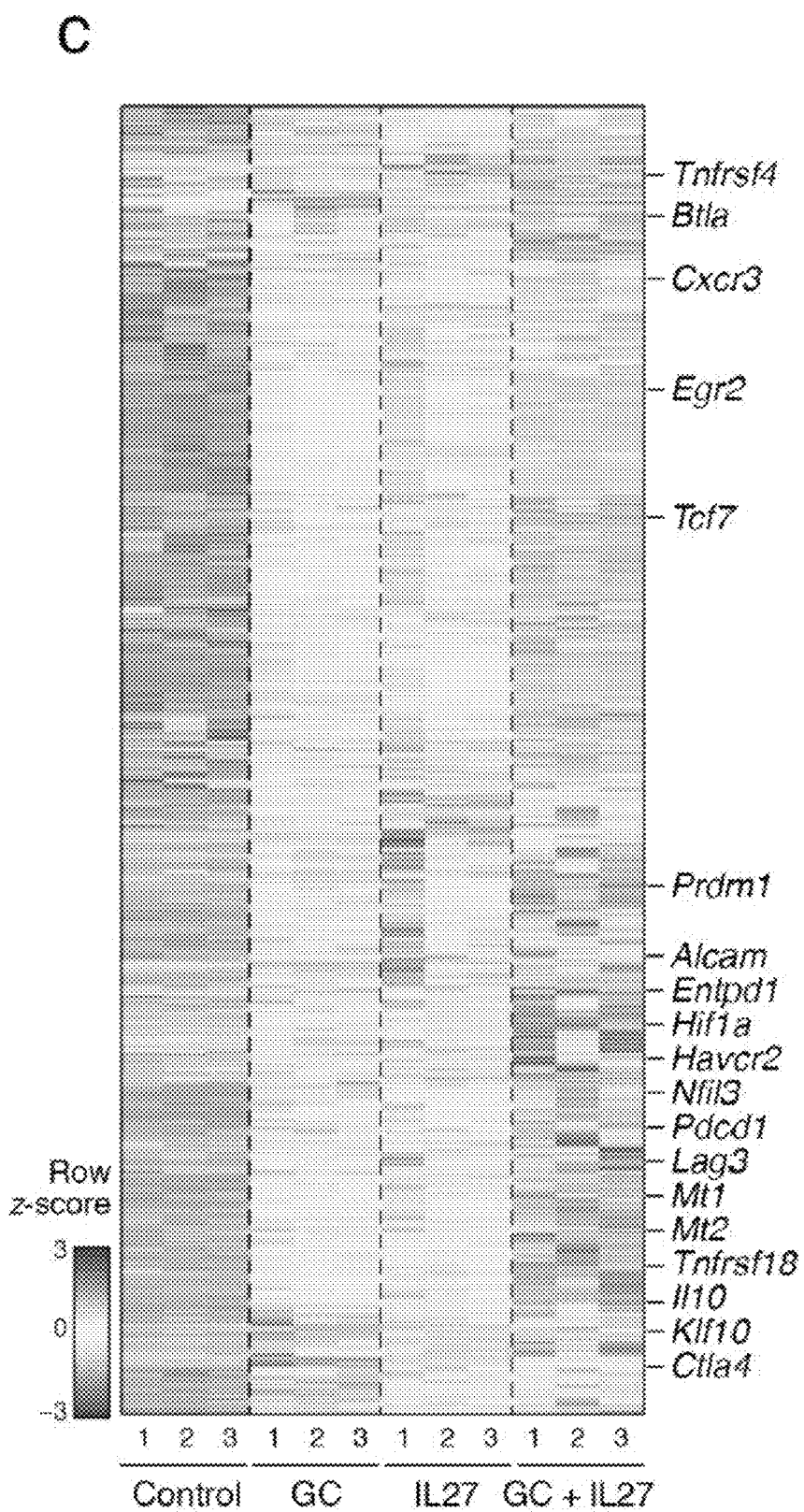
Figure 28A:
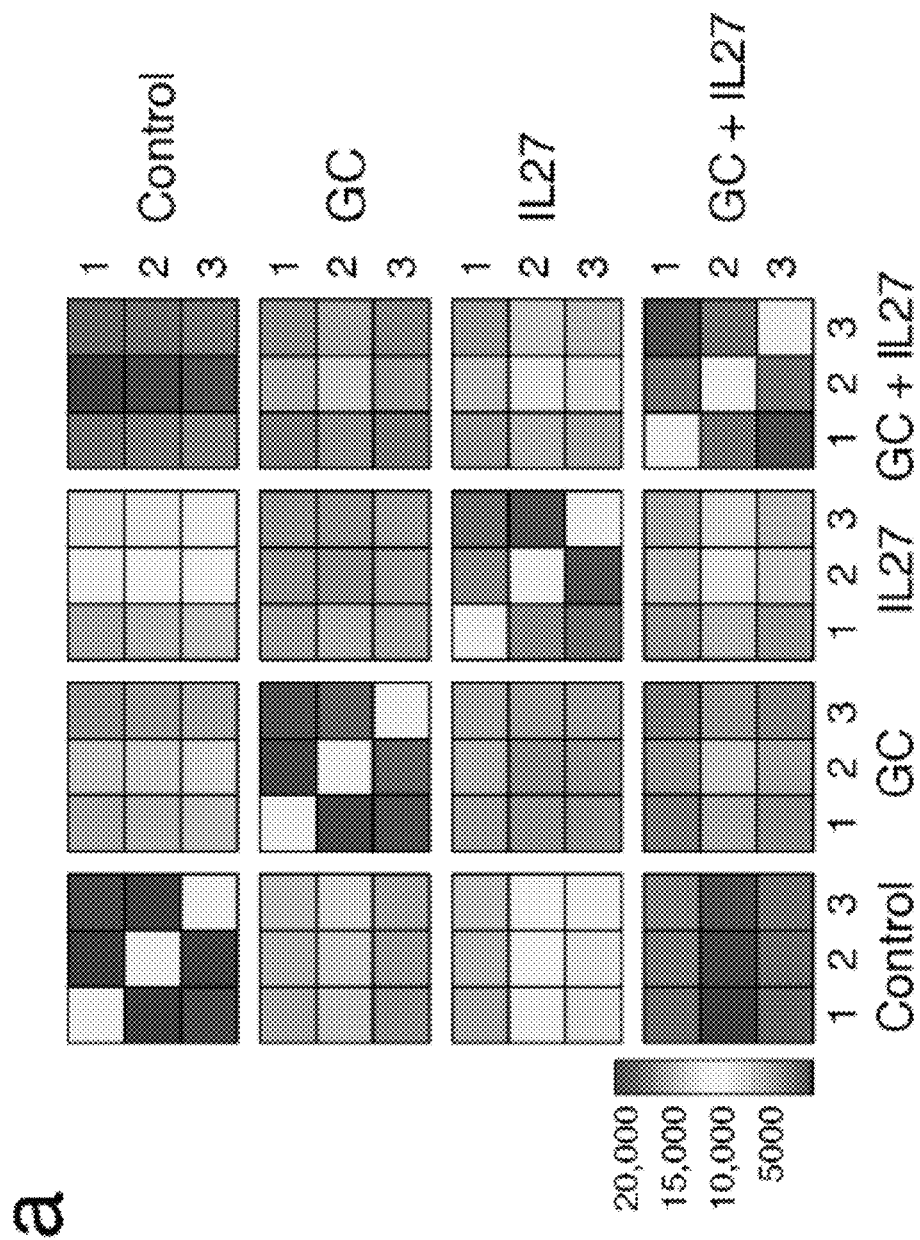

Example 6—Glucocorticoid and IL-27 Signaling Co-Operate to Promote CD8$^+$ T Cell Dysfunction The transactivation of multiple checkpoint receptors and IL-10 by GR and the effect of glucocorticoid signaling on the effector responses of CD8$^+$ TILs were reminiscent of the recent observation that IL-27 regulates a gene module that includes checkpoint receptors (Tim-3, Lag3, Tigit) and IL-10 and suppresses the responses of CD8$^+$ TILs[26,27]. Interestingly, glucocorticoids have been shown to work in concert with TFs such as the STAT family[28] and STAT1 and STAT3 are downstream of IL-27. This prompted us to ask whether the glucocorticoid and IL-27 pathways are redundant. To address this, Applicants collected and analyzed the RNA-Seq profiles from cells treated with glucocorticoid, IL-27, or both. Unsupervised principle component analysis (PCA) showed that glucocorticoid and IL-27 treatment are not redundant as they each induced a distinct transcriptional profile with glucocorticoid+IL-27 treatment inducing the largest transcriptional change relative to control (FIGS. 22a and b and FIG. 28a). 6,812 genes were differentially expressed (DE) between glucocorticoid+IL-27 compared to control out of which 3,417 (50%) showed non-additive regulation (FIG. 22c and Table 1). Among the genes that were highly up-regulated by glucocorticoid+IL-27 compared to glucocorticoid or IL-27 alone were Prdm1 and Nfil3, which encode TFs with known roles in promoting/maintaining T cell dysfunction[26, 27, 29, 30]. In contrast, Tcf7, which encodes TCF-1, a TF important for maintaining stem-like T cells and sustaining response to checkpoint blockades[31, 32], was down-regulated by glucocorticoid+IL-27. Using qPCR, Applicants confirmed that Prdm1 and Nfil3 expression was most highly up-regulated by treatment with glucocorticoid+IL-27 compared to glucocorticoid or IL-27 alone. Tcf7 was dramatically reduced by glucocorticoid or IL27 alone and treatment with glucocorticoid+IL-27 showed a trend of further reduction (FIG. 28b). These observations indicated that glucocorticoid+IL-27 signaling may co-operate to promote gene programs associated with T cell dysfunction in CD8$^+$ T cells. Accordingly, Applicants tested all of the differentially expressed genes induced by glucocorticoid+IL-27 for overlap with the T cell dysfunction signature. 1,022 out of 6,812 DE genes overlapped with the dysfunction signature (Table 2). The genes down-regulated by glucocorticoid+IL-27 significantly overlapped with genes expressed in CD8$^+$ TIM-3$^-$PD-1$^-$ TILs (p=2.1×10$^{-10}$, Mean-rank Gene Set Test) and the genes up-regulated by glucocorticoid+IL-27 showed significant overlap with the genes expressed in dysfunctional CD8$^+$Tim-3$^+$PD-1$^+$ TILs (p=4.3×10$^{-05}$ Mean-rank Gene Set Test) (FIG. 22d and FIG. 28c).

To determine the functional consequences of the glucocorticoid+IL-27 signaling pathways on T cell dysfunction in vivo, Applicants crossed E8i-Cre⁺Nr3c1$^{fl/fl}$ mice with WSX1$^{-/-}$ (IL27ra$^{-/-}$) mice to generate mice that can be used as a source of double knock-out (DKO) CD8⁺ T cells, lacking both the glucocorticoid and IL-27 signaling pathways. Applicants isolated CD8⁺ T cells from wild type, E8i-Cre⁺Nr3c1$^{fl/fl}$, WSX-1$^{-/-}$, or DKO mice and transferred them along with wild type CD4⁺ T cells into Rag-1$^{-/-}$ mice followed by implant of MC38-Ova colon carcinoma cells. In line with previous findings (FIG. 20a)[27], absence of either glucocorticoid or IL-27 signaling alone individually conferred tumor growth control; however, absence of both of pathways together led to significantly greater tumor growth inhibition (FIG. 22e).

Figure 22F:
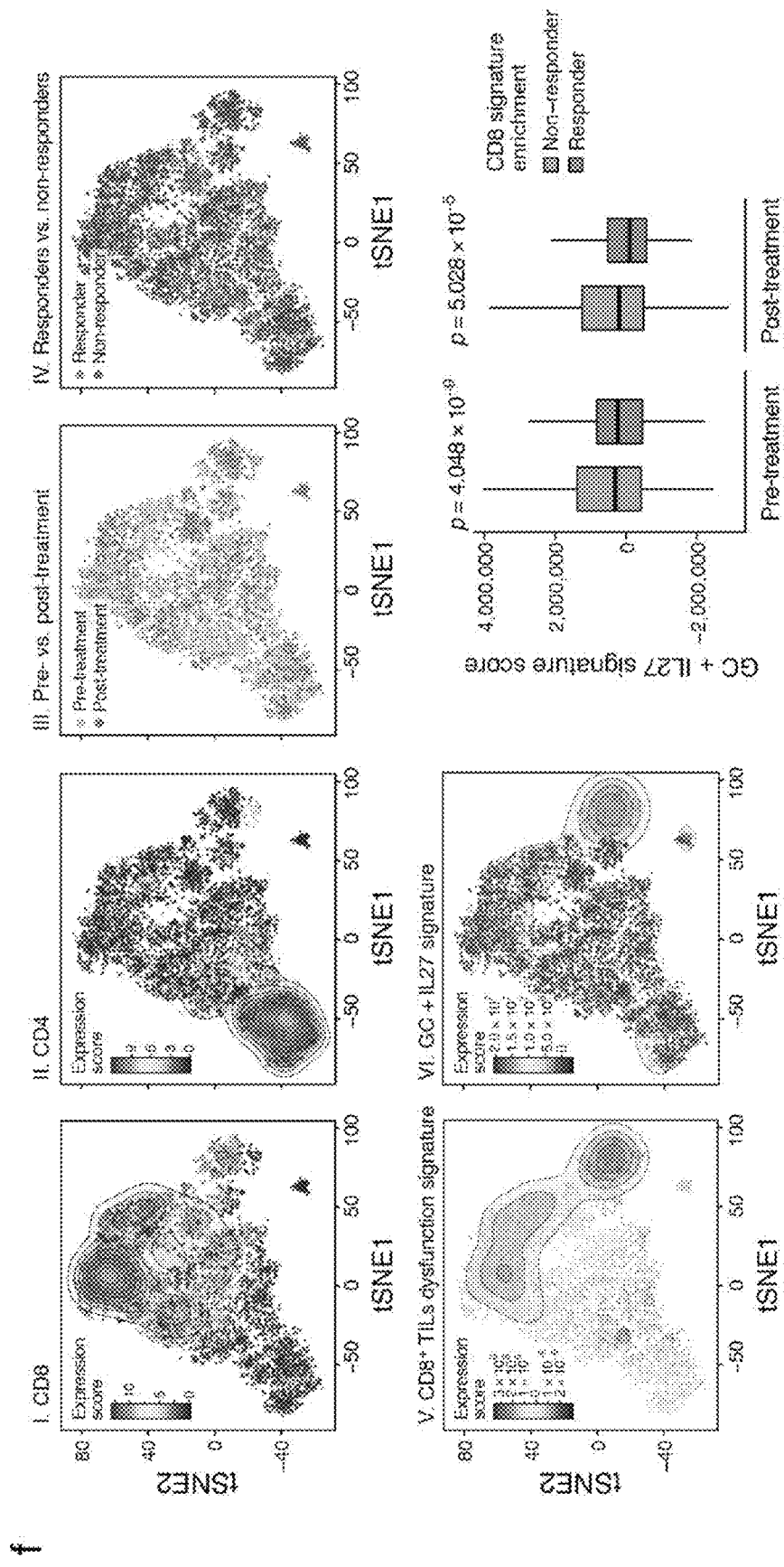

To examine the relevance of glucocorticoid+IL-27 signaling in human disease, Applicants scored the glucocorticoid+IL-27 signature in the single-cell data of TILs from melanoma patients pre- and post-treatment with checkpoint blockade[33]. Applicants found that the glucocorticoid+IL-27 signature scored highly in CD8⁺ TILs that also scored highly for the T cell dysfunction signature (FIG. 22f). Most importantly, Applicants found that high expression of the glucocorticoid+IL-27 signature correlated with non-responsiveness to checkpoint inhibitor in pre-(p=4.048×10⁻⁹) and post-(p=5.028×10⁻⁰⁵) treatment samples (FIG. 22f). Altogether, the data indicated that glucocorticoid and IL-27 signaling combined in the TME to promote CD8⁺ T cell dysfunction and dampen anti-tumor immunity.

Figure 23A:
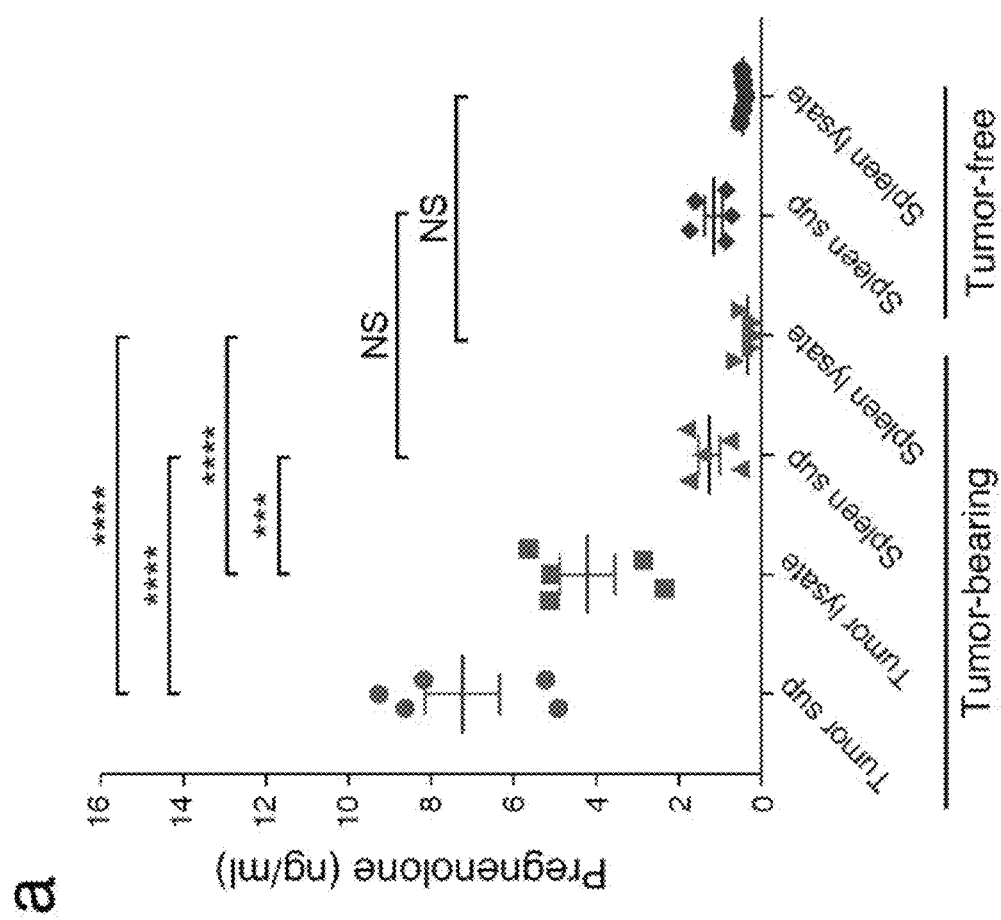
FIG. 23A-23E—Glucocorticoid and IL-27 are synthesized by different cells in the TME. a) Pregnenolone and b) Corticosterone levels in the indicated tissues were quantified by ELISA. (n=5). Quantitative RT-PCR analysis of Cyp11a1 (c) and (d) IL-27 (p28 and Ebi3) mRNA expression in the indicated cells. Data are pooled from 2 independent experiments. e) Correlation of Cyp11a1 expression level with survival in patients with colon adenocarcinoma (COAD) and stomach adenocarcinoma (STAD) using TIMER. P<0.01, *p<0.001, ****p<0.0001. Ordinary-one way ANOVA (Tukey's multiple comparisons test). Data are mean S.E.M.
Figure 23B:
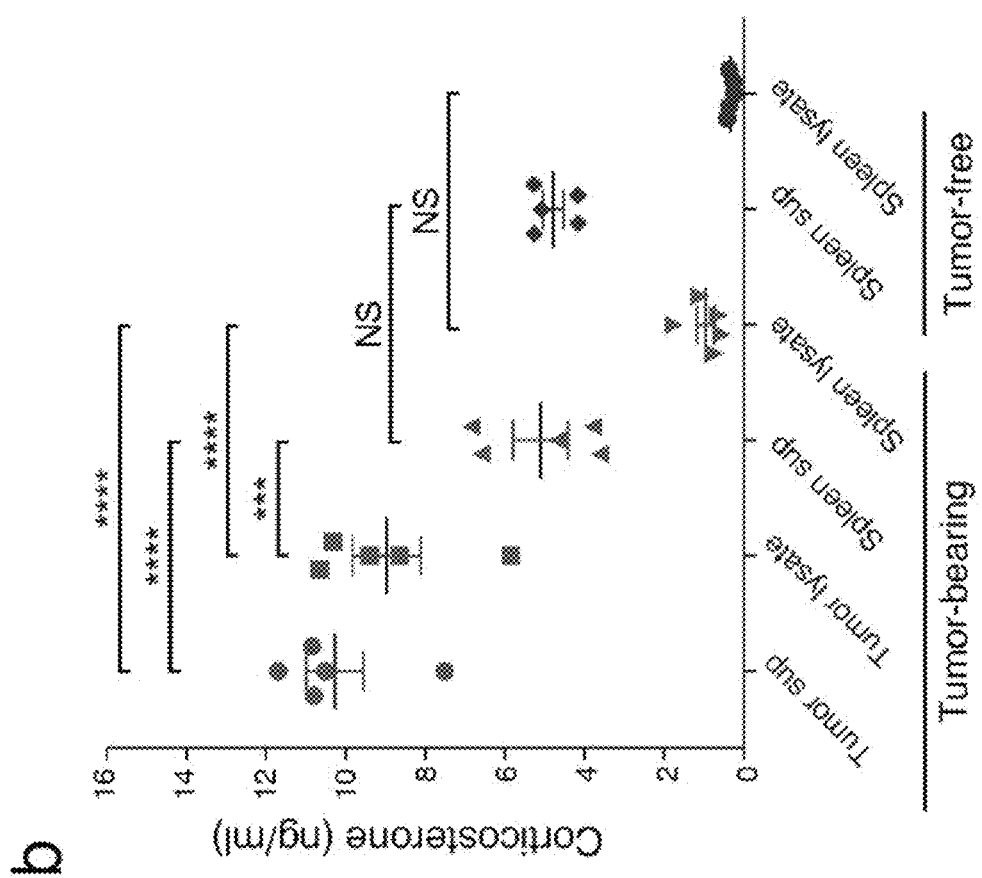

Example 7—Myeloid Cells are the Primary Sources of Glucocorticoid and IL-27 in the TME Applicants next asked whether local sources in the TME provided endogenous glucocorticoid and IL-27 signals. Although steroids are mainly synthesized in the adrenal cortex, it has been suggested that tumor cells are also capable of steroidogenesis[34]. Steroids are produced by the breakdown of cholesterol by a series of enzymatic reactions, where cytochrome P450 cholesterol side-chain cleavage enzyme (Cyp11a1 or P450scc) catalyzes the first and the rate-limiting step in the breakdown of cholesterol to pregnenolone, the steroid precursor[35]. Applicants measured pregnenolone and found that it was much more highly expressed in the tumor tissue compared to the spleen of MC38-Ova tumor-bearing mice (FIG. 23a). Indeed, the levels of pregnenolone in the spleen of tumor-bearing mice were similar to those in non-tumor bearing mice. Moreover, corticosterone levels showed a similar pattern of production in the TME with similar levels in the spleen of tumor-bearing and non-tumor bearing mice (FIG. 23b). Together these data indicated local steroid production in the TME.

Figure 23C:
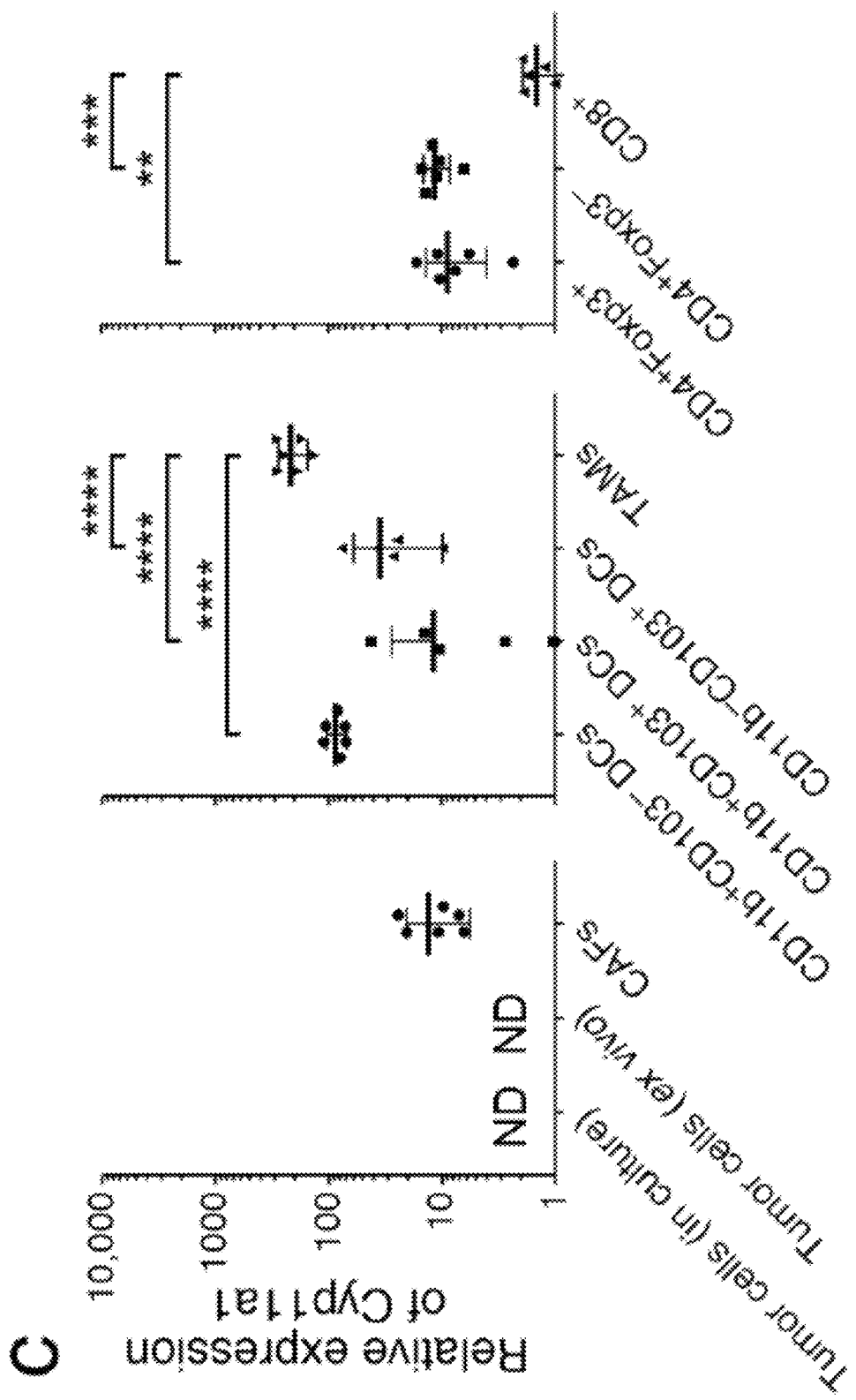
Figure 23D:
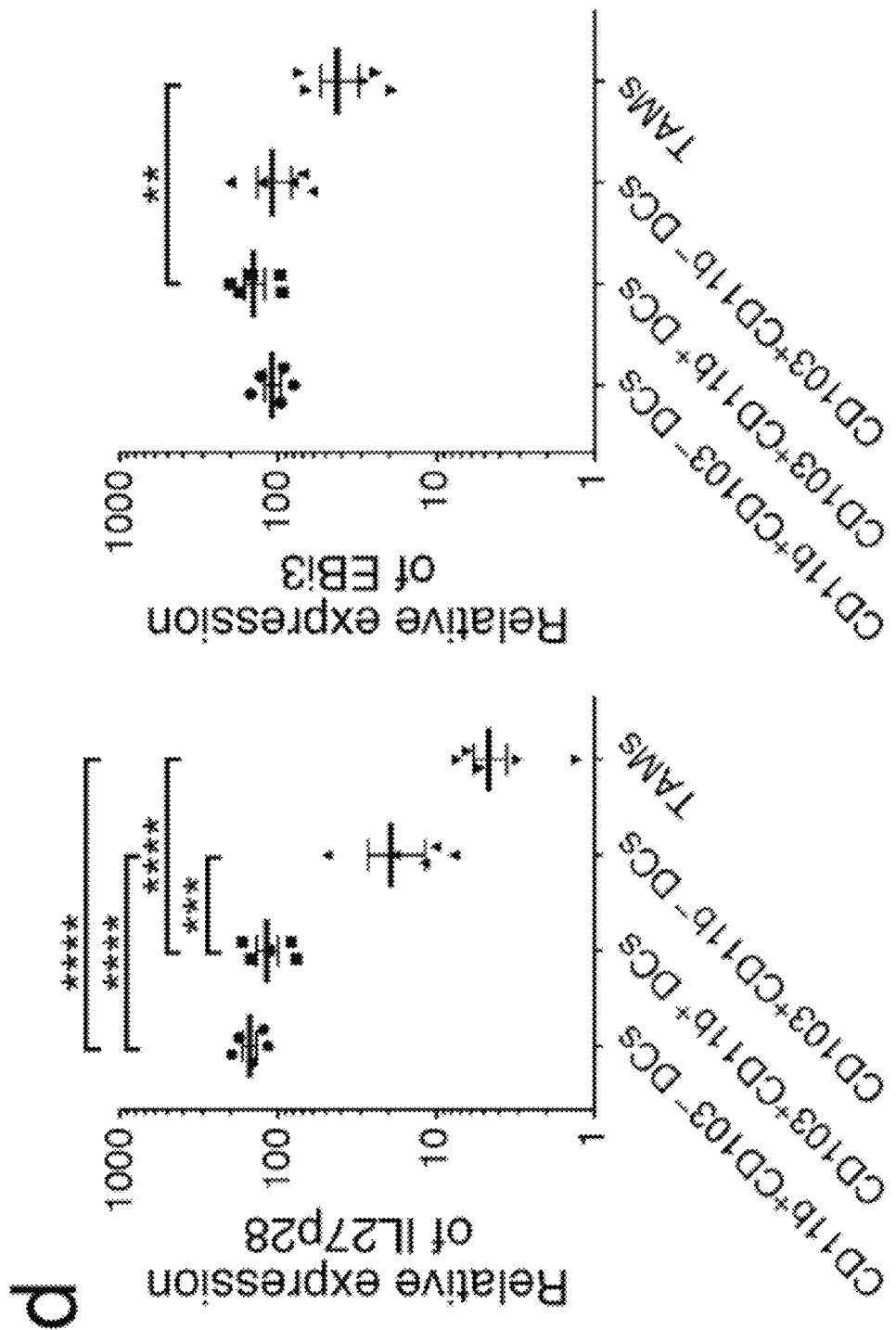
Figure 23E:
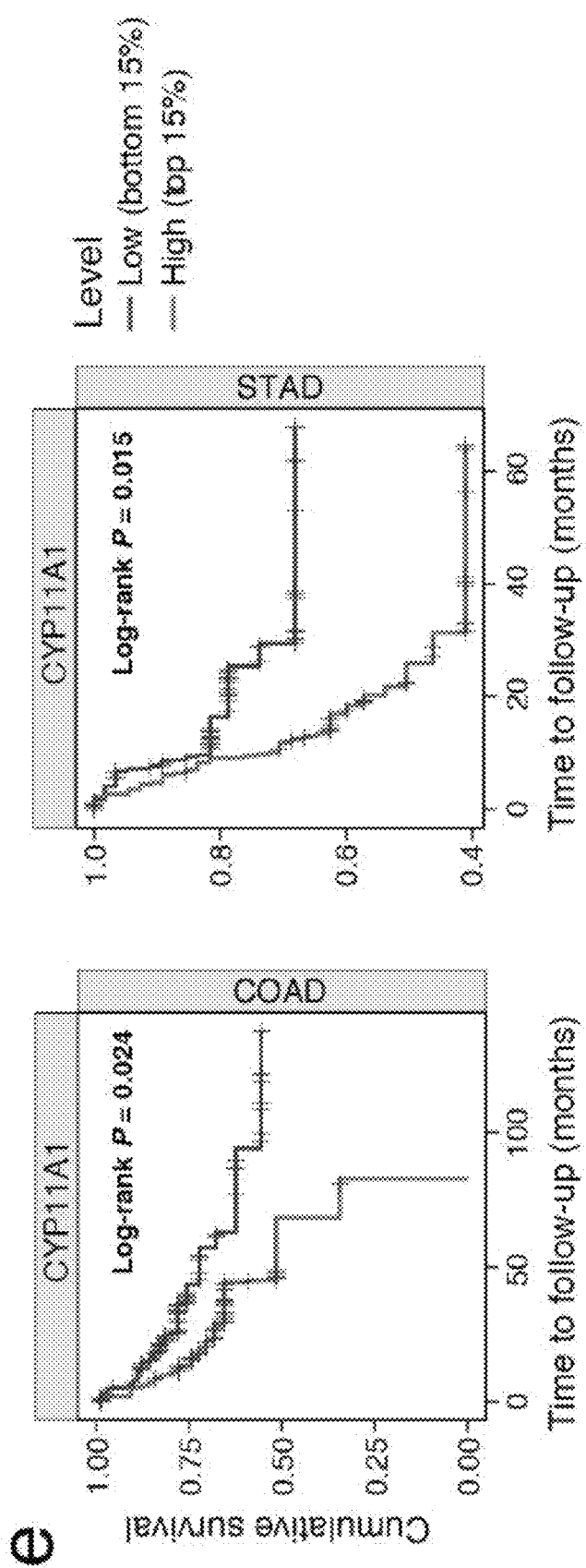

To identify which cell types were responsible for steroid production in the TME, Applicants examined the expression of Cyp11a1 in the MC38-Ova tumor cell line both in vitro and ex vivo, as well as in cells isolated from the TME. In vitro cultured MC38-Ova cells did not express Cyp11a1 (FIG. 23c). To test if factors present in the TME could induce expression of Cyp11a1 in MC38-Ova tumor cells, Applicants implanted MC38-Ova-GFP cells in mice and examined Cyp11a1 expression in tumor cells (CD45⁻GFP⁺). Applicants did not detect Cyp11a1 expression in isolated tumor cells (FIG. 23c). However, examination of other cells in the TME showed that tumor-associated macrophages (TAMs, CD11b⁺F4/80⁺) expressed the highest levels of Cyp11a1 among the cell types analyzed. Cancer-associated fibroblasts (CAFs) (CD45⁻GFP⁻ PDGFRa⁺) (FIG. 29a and FIG. 23c), and tumor-associated dendritic cells (TADCs) and T cells (mostly CD4⁺ T cells) also expressed Cyp11a1 but at much lower levels (FIG. 29b). Since macrophages comprise more than 50% of total CD45⁺ cells in MC38-Ova colon tumors, they are likely the chief source of steroid in the TME. Conversely, TADCs were the main source of IL-27, as they expressed both p28 and EBi3 (FIG. 23d). Thus, different cell types within the TME produced glucocorticoid and IL-27. Lastly, Applicants examined the relevance of steroid abundance in the TME in human cancers. Using TIMER, Applicants found that low Cyp11a1 mRNA levels were associated with a substantial survival benefit in patients with colon adenocarcinoma and stomach adenocarcinoma (FIG. 23e). Collectively, the data demonstrate that glucocorticoid signaling co-operates with IL-27 signaling to form an immunoregulatory circuit that dampens effective anti-tumor immunity by promoting T cell dysfunction in the TME.

Example 8—Discussion

Glucocorticoids, steroid hormones, have been shown to suppress immune responses by interfering with AP-1- and NF-κB-mediated induction of pro-inflammatory cytokines[9, 10, 11, 12, 13, 14]. Here, Applicants identify a novel molecular mechanism by which glucocorticoids suppress effector T cell responses through the transactivation of multiple checkpoint receptors (Tim-3, PD-1, and Lag3) together with IL-10. Glucocorticoids combine with the immune suppressive cytokine IL-27 within the TME to promote gene programs associated with CD8⁺ T cell dysfunction in a non-redundant manner. Dysfunctional CD8⁺ T cells in turn contribute to immune suppression within the TME via their high production of IL-10. Thus, glucocorticoid and IL-27 signaling together form a feed forward circuit that suppresses anti-tumor effector T cell responses in the TME. The relevance of glucocorticoid signaling pathways to human disease is supported by the observation that increased steroidogenic capacity in the TME correlated with decreased survival of cancer patients and that high expression of the glucocorticoid+IL-27 signature in the CD8⁺ TILs of melanoma patients correlated with failure to respond to checkpoint blockade therapy[33].

The RNA profile induced by glucocorticoid+IL-27 showed significant overlap with genes associated with T cell dysfunction. The observation that Prdm1 and Nfil3, TFs known to be involved in T cell dysfunction[26, 27, 29, 30], are most highly induced by the combination of glucocorticoid and IL-27 provides a potential mechanism for the promotion of T cell dysfunction by these two pathways. Moreover, glucocorticoid+IL-27 reduced the expression of Tcf7, which encodes TCF-1, a TF involved in maintenance of stem-like memory precursor CD8⁺ TILs that are required for the success of checkpoint blockade therapy[31, 32, 36]. Thus, glucocorticoid+IL-27 signaling may subvert anti-tumor immunity by two mechanisms, promoting T cell dysfunction and decreasing stemness and memory potential in CD8⁺ TILs. Given that the GR has also been shown to act via chromatin remodeling[24], it possible that glucocorticoid signaling may drive epigenetic changes that together with IL-27 set the stage for CD8⁺ T cell dysfunction. The contributions of glucocorticoid and IL-27 signaling to the distinct epigenetic changes that have been described in dysfunctional CD8⁺ T cells remains to be determined[37, 38, 39].

This data demonstrates that activation of glucocorticoid and IL-27 signaling promotes the dysfunction gene program in CD8⁺ TILs. However, a previous study implicated the GR in the maintenance of memory-precursor CD8+ T cells in the context of bacterial infection[40]. Thus, the effect of glucocorticoid signaling favoring differentiation into memory or dysfunctional CD8+ T cells may be context dependent. It is possible that the GR may interact with other pathways signaling pathways depending on the tissue environment to achieve different effects. Further molecular investigation will help delineate the mechanisms operative in different contexts.

Using conditional knockout mice and in vitro studies Applicants provide insight into the CD8+ T cell intrinsic effects of glucocorticoid signaling. However, glucocorticoid signaling may also act intrinsically in other immune and non-immune cell populations in the TME. Indeed, glucocorticoids have been implicated in increasing the frequency of $T_{reg}$ cells in both humans and mice[41, 42, 43, 44]. In myeloid cells, glucocorticoids have been implicated in modulating both antigen presentation and inflammatory cytokine production by DCs[45]. Further, in line with the data, a recent study suggested that endogenous glucocorticoids regulate the expression of PD-1 on NK cells in the context of viral infection[46]. Whether these effects of glucocorticoid are due to cell intrinsic or extrinsic effects will require detailed molecular dissection using cell type specific knockouts.

The observation that Cyp11a1, the rate limiting enzyme in steroid production, inversely correlated with survival in human cancers underscores the need to identify the signals that determine the steroidogenic capacity of different cells in the TME. Inhibitors of enzymes of steroid biogenesis are used in the clinical management of cancers that are predominantly driven by steroid hormone signaling, such as breast and prostate cancer. This data indicates the potential of such drugs in a broader spectrum of cancer types.

Checkpoint blockade immunotherapy is now a standard of care for certain advanced cancers such as melanoma and non-small cell lung carcinoma. However, in many cases patients develop immune-related adverse events (IRAEs)[7]. Glucocorticoids are first-line agents for managing IRAEs. This data has important implications for cancer patients receiving immune checkpoint blockade as they indicate that glucocorticoids would oppose the therapy by promoting increased checkpoint receptor expression and acquisition of dysfunction gene programs. Moreover, Applicants have observed that patients who fail to respond to checkpoint blockade[33] have higher expression of the glucocorticoid+ IL-27 signature. Thus, having a better understanding of the mechanisms downstream of glucocorticoids and IL-27 could inform the clinical development of more precise therapies for suppressing immune responses in the clinic, the relevance of which extends beyond cancer.

Example 9—Methods and Material

Experimental Methods

Mice. 6-8 week old C57BL/6, Nr3c1$^{fl/fl}$, Rag1$^{-/-}$, E8iCre and WSX1$^{-/-}$ transgenic mice were purchased from the Jackson Laboratory. NR3C1$^{f/f}$ was crossed to E8iCre and/or E8iCre×WSX1$^{-/-}$. All mice were housed under SPF conditions. All experiments involving laboratory animals were performed under protocols approved by the Harvard Medical Area Standing Committee on Animals (Boston, MA).

Collection of colorectal carcinoma patient specimens. Primary colorectal carcinoma specimens were obtained from untreated patients undergoing surgical resection at the Brigham and Women's/Dana Farber Cancer Center and Massachusetts General Hospital (IRB protocol 03-189 and 02-240). Freshly resected CRC tumors and adjacent normal colon were recovered in Medium 199 (Thermo Fisher) supplemented with 2% heat-inactivated FCS (Sigma Aldrich) and stored briefly on ice.

Cell culture and treatment with glucocorticoid. CD8+ T cells from splenocytes and lymph nodes were isolated using CD8 microbeads (Miltenyi). Cells were further stained with antibodies against CD8, CD62L and CD44, and CD8+ CD62L$^{hi}$CD44$^{lo}$ naive cells were sorted by BD FacsAria (BD Biosciences). Sorted cells were cultured for 9 days as described below in DMEM supplemented with 10% (vol/vol) FCS, 50 mM mercaptoethanol, 1 mM sodium pyruvate, nonessential amino acids, L-glutamine, and 100 U/ml penicillin and 100 g/ml streptomycin. Specifically, naive CD8+ CD62L$^{hi}$CD44$^{lo}$ cells were stimulated with plate bound anti-CD3 (145-2C11, 1 µg/ml) and anti-CD28 (PV-1, 1 µg/ml) in the presence of either 10 nM dexamethasone (Sigma), 25 ng/ml IL-27 (R&D), or both for 3 days. Cells were then rested in the presence of 5 ng/ml IL2 (Miltenyi) for 3 days followed by restimulation with plate bound anti-CD3 (145-2C11, 1 µg/ml) and anti-CD28 (PV-1, 1 µg/ml) in the presence of either 10 nM dexamethasone (Sigma), 25 ng/ml IL-27 (R&D), or both for an additional 3 days.

Human CD8+ T cell culture. Peripheral blood was procured from healthy volunteers. Mononuclear cells were enriched by density gradient centrifugation on Ficoll-Paque PLUS (GE Healthcare) in SepMate-50 tubes (Stem Cell Technologies). CD8+ T cells were isolated from PBMCs using CD8 microbeads (Miltenyi) according to manufacturer protocol. Isolated CD8+ T cells were cultured for 9 days in RPMI supplemented with 10% (vol/vol) autologous heat-inactivated serum, 1 mM sodium pyruvate, 1× nonessential amino acids, 2 mM L-glutamine, 100 U/ml penicillin, and 100 g/ml streptomycin. CD8+cells were stimulated with plate-bound anti-CD3 (Biolegend, clone UCHT1, 1 µg/ml) and anti-CD28 (Biolegend, clone CD28.2, 1 µg/ml) in the presence of 10 nM dexamethasone (Sigma) or vehicle control for 3 days. Cells were then rested in the presence of 100 U/ml IL2 (R&D Systems) for 3 days. Next, the cells were re-stimulated with plate-bound anti-CD3 (1 µg/ml) and anti-CD28 (1 µg/ml) in the presence of either 10 nM dexamethasone (Sigma) or vehicle control for 3 days.

Tumor experiments. MC38-Ova was generously provided. B16F10 was purchased from ATCC. MC38-Ova-GFP was generated in the lab as follows, HEK293T cells were transfected with pLenti PGK GFP Puro plasmid. The resulting Lenti virus was then used to infect Mc38Ova cell line to generate GFP expressing cell line. MC38-Ova (0.5×10$^6$) or B16F10 (0.25×10$^6$), MC38-Ova-GFP (0.5×10$^6$) cells were implanted subcutaneously into the right flank of mice. Tumor size was measured in two dimensions by caliper and is expressed as the product of two perpendicular diameters.

Isolation of TILs. TILs were isolated by dissociating tumor tissue in the presence of collagenase D (2.5 mg/ml) for 20 minutes prior to centrifugation on a discontinuous Percoll gradient (GE Healthcare). Isolated cells were then used in various assays of T cell function.

Flow cytometry. Single cell suspensions were stained with antibodies against surface molecules. For murine samples, antibodies against CD4 (RM4-5), CD8 (53-6.7), CD107a (1D4B) and PD-1 (RMP1-30) were purchased from BioLegend. Antibodies against LAG-3 (clone C9B7W), Gzmb (NGZB) and Tigit (clone GIGD7) were purchased from eBioscience. Anti-Tim-3 (5D12) antibody was generated in house. Antibody against GR (G5) was purchased from Santa Cruz. For human samples, antibodies against CD8a (RPA-T8), Tim3 (F38-2E2), PD1 (EH12.2H7) and Lag3 (11C3C65) were purchased from Biolegend and antibody against TIGIT (MBSA43) was purchased from Thermo Fisher. Fixable viability dye eF506 (eBioscience) or Zombie UV dye (Biolegend) were used to exclude dead cells. For GR staining, eBioscience Foxp3/transcription factor staining buffer set was used as per manufacturer's protocol. For intra-cellular cytokine (ICC) staining of $CD8^+$ T cells in culture in vitro, cells were stimulated with 12-myristate 13-acetate (PMA) (50 ng/ml, Sigma-Aldrich, MO) and ionomycin (1 mg/ml, Sigma-Aldrich, MO) in the presence of Golgiplug (BD Biosciences) and Golgi Stop (BD Biosciences) for four hours prior to cell surface and ICC staining. For intra-cytoplasmic cytokine staining of TILs, cells were stimulated in vitro with 5 µg/ml OVA257-264 peptide for 4 hrs in the presence of Golgi stop (BD Biosciences) and Golgi Plug (BD Biosciences) prior to cell surface and ICC staining. Following fixation and permeabilization, staining with antibodies against the following was performed for murine samples: IL-2 (JES6-5H4), TNF-α (MP6-XT22), IFN-g (XMG-1.2), CD107a (1D4B) and Granzyme B (GB11) were purchased from Biolegend. Antigen specific T cells were determined by H-2Kb/OVA257-264 dextramer staining following the manufacturer's protocol (Immudex). All data were collected on a BD LsrII (BD Biosciences) or Fortessa (BD Biosciences) and analyzed with FlowJo software (TreeStar).

Adoptive transfers. For adoptive transfer experiments, $CD4^+$ ($FOXP3^+$ and $FOXP3^-$) and $CD8^+$ T cells from either WT, $Nr3c1^{fl/fl}$ E8iCre, $WSX1^{-/-}$ or $Nr3c1^{fl/fl}$ $E8iCre^+$ $WSX1^{-/-}$ (dKO) mice were isolated by cell sorting using a BD FACSAria. A total of $1.5 \times 10^6$ cells at a ratio of 1:0.5 (CD4/CD8) was mixed in PBS and injected i.v. into $Rag^{-/-}$ mice. Two days later, mice were implanted with MC38-Ova Colon carcinoma cells and followed for tumor growth.

Quantitative ELISA. Tumor and spleen were subjected to repeated freeze and thaw cycles to lyse the tissues. The resultant lysate and supernatant were analyzed following manufacturer's protocol (Pregnenolone ELISA kit, Abnova and Corticosterone ELISA kit, Arbor Assay). Absorbance was measured at 450 nm.

Luciferase assays. HEK293T cells were transfected with firefly luciferase reporter constructs for IL-10, PD1, Tim3, Lag3 or Tigit, together with *Renilla* luciferase reporter as internal control and plasmids expressing Nr3c1 or empty control vector. Dex or vehicle control was added to the culture 24 hrs after transfection. Cells were analyzed at 48 hrs with the dual luciferase assay kit (Promega). Fragments containing the proximal Il10 promoter (−1.5 kb including the $HSS^-0.12$ site), and the $HSS^+2.98$ region followed by of the Il10 minimal promoter were cloned into pGL4.10 Luciferase reporter plasmid (Promega). Fragments containing the cis-regulatory elements for the Havcr2, Pdcd1 and Lag3 loci were cloned into pGL4.23 Luciferase reporter plasmid (Promega).

Quantitative PCR. Total RNA was extracted using RNeasy columns (Qiagen). Reverse transcription of mRNA was performed in a thermal cycler (Bio-Rad) using iScript cDNA Synthesis Kit (Bio-Rad). qPCR was performed in the Vii7 Real-Time PCR system (Applied Biosystems) using the primers for Taqman gene expression (Applied Biosystems). Data were normalized to the expression of Actb.

RNA-Seq. 1,000 cells were sorted into 5 µL of Buffer TCL (Qiagen) supplemented with 1% 2 mercaptoethanol. Plates were thawed on ice for one minute and spun down at 2,000 rpm for one minute. Immediately following, RNA lysate was purified using a 2.2×RNAClean SPRI bead ratio (Beckman Coulter Genomics). The RNA captured beads were processed using a modified SMART-Seq2 protocol[48] entailing RNA secondary structure denaturation (72° C. for three minutes), reverse transcription with Maxima Reverse Transcriptase (Life Technologies), and whole-transcription amplification (WTA) with KAPA HiFi HotStart ReadyMix 2× (Kapa Biosystems) for 11 cycles. WTA products were purified with Ampure XP beads (Beckman Coulter), quantified with a Qubit dsDNA HS Assay Kit (ThermoFisher), and quality accessed with a high-sensitivity DNA chip (Agilent). 0.2 ng of purified WTA product was used as input for the Nextera XT DNA Library Preparation Kit (Illumina). Uniquely barcoded libraries were pooled and sequenced with a NextSeq 500 high output V2 75 cycle kit (Illumina) using 38 and 38 paired end reads[48].

Computational Analyses

Signature scoring in single cells. $CD8^+$ TILs single-cell data were obtained and processed as previously described[3]. Briefly, Briefly, paired reads were mapped to mouse annotation mm10 using Bowtie[49] (allowing a maximum of one mismatch in seed alignment, and suppressing reads that had more than 10 valid alignments) and TPMs were computed using RSEM[50], and log 2(TPM+1) values were used for subsequent analyses. Next, Applicants filtered out low quality cells and cell doublets, maintaining for subsequent analysis the 588 cells that had (1) 1,000-4,000 detected genes (defined by at least one mapped read), (2) at least 200,000 reads mapped to the transcriptome, and (3) at least 50% of the reads mapped to the transcriptome. Here, Applicants restricted the genes considered in subsequent analyses to be the 7,790 genes expressed at log 2(TPM+1) R 2 in at least ten percent of the cells. After removal of low quality cells/genes, the data were normalized using quantile normalization followed by PCA. PCs 1-8 were chosen for subsequent analysis due to a drop in the proportion of variance explained following PC8. Applicants used to visualize single cells in a two-dimensional non-linear embedding. To score each cell for a gene signature, expression data was initially scaled by calculating the z-score across each gene. For each gene signature, a cell-specific signature score was computed by first sorting the normalized scaled gene expression values for each cell followed by summing up the indices (ranks) of the signature genes. For signatures consisting of an upregulated and downregulated set of genes, two ranking scores were obtained separately, and the down-regulated associated signature score was subtracted from the up-regulated generated signature score. A contour plot was added on top of the tSNE space, which takes into account only those cells that have a signature score above the indicated threshold to further emphasize the region of highly scored cells.

RNA-Seq data pre-processing. RNA-seq reads were aligned using Tophat[51] (to mouse genome version mm9), and expression levels were calculated using RSEM[50] using annotated transcripts (mm9), followed by further processing using the Bioconductor package DESeq in $R^{52}$. The data was normalized using TMM normalization, and differentially expressed genes were defined using the differential expression pipeline on the raw counts with a single call to the function DESeq (FDR-adjusted P value<0.05). Heatmap figures were generated using pheatmap package[53].

Analysis of additive and non-additive effects. To test whether the glucocorticoid and IL-27 signaling pathways had additive or non-additive effects on gene expression, Applicants stimulated naïve $CD8^+$ T cells in the presence of Dex, IL-27, or Dex+IL-27 in vitro. Applicants tested for non-additive effects between IL-27 and glucocorticoid signaling using a negative binomial generalized linear model in order to account for both estimations of the mean and the dispersion across conditions, where dispersion describes the relationship between the mean and variance. The model was applied to the expression data using ANOVA between a model that takes into account the interaction between IL27 and Dex versus no interaction. Applicants found that 1,675 out of 3,496 differentially expressed genes (adjusted P<0.05, likelihood ratio test and false discovery rate (FDR) correction) between control and Dex+IL-2 stimulated CD8+ cells have non-additive effects.

Analysis of human TILs for GC+IL27 signature. Data was downloaded from[33] in a in log 2(TPM+1) format. PCA was performed after removal of non-expressed genes. PCs 1-8 were chosen for subsequent analysis due to a drop in the proportion of variance explained following PC8. Applicants used tSNE[54] to visualize single cells in a two-dimensional non-linear embedding. GC+IL27 signature was projected onto single cell RNA profiles of TILs from 48 melanoma patients treated with checkpoint blockade (with 35 anti-PD-1, 11 anti-CTLA4+PD-1, and 2 anti-CTLA4 samples)[33].

REFERENCES

1. Wherry, E. J. & Kurachi, M. Molecular and cellular insights into T cell exhaustion. Nat Rev Immunol 15, 486-499 (2015).
2. Jin, H. T. et al. Cooperation of Tim-3 and PD-1 in CD8 T-cell exhaustion during chronic viral infection. Proc Natl Acad Sci USA 107, 14733-14738 (2010).
3. Singer, M. et al. A Distinct Gene Module for Dysfunction Uncoupled from Activation in Tumor-Infiltrating T Cells. Cell 166, 1500-1511 e1509 (2016).
4. Sakuishi, K. et al. Targeting Tim-3 and PD-1 pathways to reverse T cell exhaustion and restore anti-tumor immunity. J Exp Med 207, 2187-2194 (2010).
5. Fourcade, J. et al. Upregulation of Tim-3 and PD-1 expression is associated with tumor antigen-specific CD8+ T cell dysfunction in melanoma patients. The Journal of experimental medicine 207, 2175-2186 (2010).
6. Oakley, R. H. & Cidlowski, J. A. The biology of the glucocorticoid receptor: new signaling mechanisms in health and disease. J Allergy Clin Immunol 132, 1033-1044 (2013).
7. Kumar, V. et al. Current Diagnosis and Management of Immune Related Adverse Events (irAEs) Induced by Immune Checkpoint Inhibitor Therapy. Front Pharmacol 8, 49 (2017).
8. Munck, A., Guyre, P. M. & Holbrook, N.J. Physiological functions of glucocorticoids in stress and their relation to pharmacological actions. Endocr Rev 5, 25-44 (1984).
9. Jonat, C. et al. Antitumor promotion and antiinflammation: down-modulation of AP-1 (Fos/Jun) activity by glucocorticoid hormone. Cell 62, 1189-1204 (1990).
10. Yang-Yen, H. F. et al. Transcriptional interference between c-Jun and the glucocorticoid receptor: mutual inhibition of DNA binding due to direct protein-protein interaction. Cell 62, 1205-1215 (1990).
11. Rhen, T. & Cidlowski, J. A. Antiinflammatory action of glucocorticoids—new mechanisms for old drugs. N Engl J Med 353, 1711-1723 (2005).
12. Smoak, K. A. & Cidlowski, J. A. Mechanisms of glucocorticoid receptor signaling during inflammation. Mech Ageing Dev 125, 697-706 (2004).
13. Scheinman, R. I., Cogswell, P. C., Lofquist, A. K. & Baldwin, A. S., Jr. Role of transcriptional activation of I kappa B alpha in mediation of immunosuppression by glucocorticoids. Science 270, 283-286 (1995).
14. Auphan, N., DiDonato, J. A., Rosette, C., Helmberg, A. & Karin, M. Immunosuppression by glucocorticoids: inhibition of NF-kappa B activity through induction of I kappa B synthesis. Science 270, 286-290 (1995).
15. Barrat, F. J. et al. In vitro generation of interleukin 10-producing regulatory CD4(+) T cells is induced by immunosuppressive drugs and inhibited by T helper type 1 (Th1)- and Th2-inducing cytokines. J Exp Med 195, 603-616 (2002).
16. Fourcade, J. et al. Human tumor antigen-specific helper and regulatory T cells share common epitope specificity but exhibit distinct T cell repertoire. J Immunol 184, 6709-6718 (2010).
17. Phuc Le, P. et al. Glucocorticoid receptor-dependent gene regulatory networks. PLoS Genet 1, e16 (2005).
18. Singer, M. et al. A Distinct Gene Module for Dysfunction Uncoupled from Activation in Tumor-Infiltrating T Cells. Cell 171, 1221-1223 (2017).
19. Karin, M. & Herschman, H. R. Dexamethasone stimulation of metallothionein synthesis in HeLa cell cultures. Science 204, 176-177 (1979).
20. Carey, K. T. et al. Nfil3 is a glucocorticoid-regulated gene required for glucocorticoid-induced apoptosis in male murine T cells. Endocrinology 154, 1540-1552 (2013).
21. Brattsand, R. & Linden, M. Cytokine modulation by glucocorticoids: mechanisms and actions in cellular studies. Aliment Pharmacol Ther 10 Suppl 2, 81-90; discussion 91-82 (1996).
22. Arriza, J. L. et al. Cloning of human mineralocorticoid receptor complementary DNA: structural and functional kinship with the glucocorticoid receptor. Science 237, 268-275 (1987).
23. Li, B. et al. Comprehensive analyses of tumor immunity: implications for cancer immunotherapy. Genome Biol 17, 174 (2016).
24. Jubb, A. W., Boyle, S., Hume, D. A. & Bickmore, W. A. Glucocorticoid Receptor Binding Induces Rapid and Prolonged Large-Scale Chromatin Decompaction at Multiple Target Loci. Cell Rep 21, 3022-3031 (2017).
25. Karwacz, K. et al. Critical role of IRF1 and BATF in forming chromatin landscape during type 1 regulatory cell differentiation. Nat Immunol 18, 412-421 (2017).
26. Chihara, N. et al. Induction and transcriptional regulation of the co-inhibitory gene module in T cells. Nature 558, 454-459 (2018).
27. Zhu, C. et al. An IL-27/NFIL3 signalling axis drives Tim-3 and IL-10 expression and T-cell dysfunction. Nat Commun 6, 6072 (2015).
28. Petta, I. et al. The Interactome of the Glucocorticoid Receptor and Its Influence on the Actions of Glucocorticoids in Combatting Inflammatory and Infectious Diseases. Microbiol Mol Biol Rev 80, 495-522 (2016).
29. Shin, H. et al. A role for the transcriptional repressor Blimp-1 in CD8(+) T cell exhaustion during chronic viral infection. Immunity 31, 309-320 (2009).
30. Rutishauser, R. L. et al. Transcriptional repressor Blimp-1 promotes CD8(+) T cell terminal differentiation and represses the acquisition of central memory T cell properties. Immunity 31, 296-308 (2009).
31. Im, S. J. et al. Defining CD8+ T cells that provide the proliferative burst after PD-1 therapy. Nature 537, 417-421 (2016).

32. Kurtulus, S. et al. Checkpoint Blockade Immunotherapy Induces Dynamic Changes in PD-1(−)CD8(+) Tumor-Infiltrating T Cells. *Immunity* 50, 181-194 e186 (2019).
33. Sade-Feldman, M. et al. Defining T Cell States Associated with Response to Checkpoint Immunotherapy in Melanoma. *Cell* 175, 998-1013 e1020 (2018).
34. Sidler, D. et al. Colon cancer cells produce immunoregulatory glucocorticoids. *Oncogene* 30, 2411-2419 (2011).
35. Payne, A. H. & Hales, D. B. Overview of steroidogenic enzymes in the pathway from cholesterol to active steroid hormones. *Endocr Rev* 25, 947-970 (2004).
36. Siddiqui, I. et al. Intratumoral Tcf1(+)PD-1(+)CD8(+) T Cells with Stem-like Properties Promote Tumor Control in Response to Vaccination and Checkpoint Blockade Immunotherapy. *Immunity* 50, 195-211 e110 (2019).
37. Pauken, K. E. et al. Epigenetic stability of exhausted T cells limits durability of reinvigoration by PD-1 blockade. *Science* 354, 1160-1165 (2016).
38. Philip, M. et al. Chromatin states define tumour-specific T cell dysfunction and reprogramming. *Nature* 545, 452-456 (2017).
39. Sen, D. R. et al. The epigenetic landscape of T cell exhaustion. *Science* 354, 1165-1169 (2016).
40. Yu, B. et al. Epigenetic landscapes reveal transcription factors that regulate CD8(+) T cell differentiation. *Nat Immunol* 18, 573-582 (2017).
41. Suarez, A., Lopez, P., Gomez, J. & Gutierrez, C. Enrichment of CD4+CD25high T cell population in patients with systemic lupus erythematosus treated with glucocorticoids. *Ann Rheum Dis* 65, 1512-1517 (2006).
42. Chen, X., Oppenheim, J. J., Winkler-Pickett, R. T., Ortaldo, J. R. & Howard, O. M. Glucocorticoid amplifies IL-2-dependent expansion of functional FoxP3(+)CD4(+)CD25(+) T regulatory cells in vivo and enhances their capacity to suppress EAE. *Eur J Immunol* 36, 2139-2149 (2006).
43. Hu, Y. et al. Function of regulatory T-cells improved by dexamethasone in Graves' disease. *Eur J Endocrinol* 166, 641-646 (2012).
44. Ling, Y., Cao, X., Yu, Z. & Ruan, C. Circulating dendritic cells subsets and CD4+Foxp3+ regulatory T cells in adult patients with chronic ITP before and after treatment with high-dose dexamethasone. *Eur J Haematol* 79, 310-316 (2007).
45. Piemonti, L. et al. Glucocorticoids affect human dendritic cell differentiation and maturation. *J Immunol* 162, 6473-6481 (1999).
46. Quatrini, L. et al. Endogenous glucocorticoids control host resistance to viral infection through the tissue-specific regulation of PD-1 expression on NK cells. *Nat Immunol* 19, 954-962 (2018).
47. Tingey, Z. W.B.a.F.H. One-sided confidence contours for probability distribution functions. *The Annals of Mathematical Statistics* 592-596 (1951).
48. Picelli, S. et al. Smart-seq2 for sensitive full-length transcriptome profiling in single cells. *Nat Methods* 10, 1096-1098 (2013).
49. Langmead, B., Trapnell, C., Pop, M. & Salzberg, S. L. Ultrafast and memory-efficient alignment of short DNA sequences to the human genome. *Genome Biol* 10, R25 (2009).
50. Li, B. & Dewey, C. N. RSEM: accurate transcript quantification from RNA-Seq data with or without a reference genome. *BMC Bioinformatics* 12, 323 (2011).
51. Trapnell, C., Pachter, L. & Salzberg, S. L. TopHat: discovering splice junctions with RNA-Seq. *Bioinformatics* 25, 1105-1111 (2009).
52. Anders, S. & Huber, W. Differential expression analysis for sequence count data. *Genome biology* 11, R106 (2010).
53. Kolde, R. & Vilo, J. GOsummaries: an R Package for Visual Functional Annotation of Experimental Data. *F1000Research* 4, 574 (2015).
54. Maaten, L. v. d., and Hinton, G. Visualizing Data using t-SNE. *J Machine Learning Research* 9, 2579-2605 (2008).

Tables:

TABLE 2A

| | Downregulated genes after GC + IL27 (1558 in ranked order) |
|---|---|
| 1 | Ccl1 |
| 2 | Il2 |
| 3 | Kmo |
| 4 | Il3 |
| 5 | Gzme |
| 6 | Il22 |
| 7 | Ugt1a9 |
| 8 | Il13 |
| 9 | Ugt1a6b |
| 10 | Il17a |
| 11 | Il6 |
| 12 | Lama3 |
| 13 | Zfp458 |
| 14 | Lrp11 |
| 15 | Sema6d |
| 16 | Csf2 |
| 17 | Tnni1 |
| 18 | Eomes |
| 19 | Lad1 |
| 20 | Ifng |
| 21 | Pcsk1 |
| 22 | Psg17 |
| 23 | Lmo2 |
| 24 | Ugt1a10 |
| 25 | Il1a |
| 26 | Galnt14 |
| 27 | Igfbp2 |
| 28 | Fcer1g |
| 29 | Fbln5 |
| 30 | Ptgs2 |
| 31 | Mrvi1 |
| 32 | Tm4sf19 |
| 33 | Lif |
| 34 | Gzmd |
| 35 | Nkd2 |
| 36 | Pcdhgb2 |
| 37 | Vrtn |
| 38 | Actbl2 |
| 39 | Hist1h1a |
| 40 | Olr1 |
| 41 | Slc1a2 |
| 42 | Scin |
| 43 | Ispd |
| 44 | Cx3cl1 |
| 45 | BC016579 |
| 46 | 4930525D18Rik |
| 47 | Plch1 |
| 48 | Mcoln3 |
| 49 | D130043K22Rik |
| 50 | Ramp2 |
| 51 | P2ry1 |
| 52 | Otx1 |
| 53 | Myh11 |
| 54 | Duoxa1 |
| 55 | Dapl1 |
| 56 | Tagln3 |
| 57 | Xcl1 |
| 58 | Cd36 |
| 59 | Pdzk1ip1 |
| 60 | Hemgn |

TABLE 2A-continued

Downregulated genes after GC + IL27 (1558 in ranked order)

| | |
|---|---|
| 61 | Ugt1a5 |
| 62 | Stra6 |
| 63 | Scn9a |
| 64 | Egr3 |
| 65 | Prokr1 |
| 66 | Alpl |
| 67 | Col6a2 |
| 68 | Actr3b |
| 69 | Cd40lg |
| 70 | 4930506M07Rik |
| 71 | Il23a |
| 72 | Ntrk3 |
| 73 | Wdfy4 |
| 74 | Enam |
| 75 | Pcdh19 |
| 76 | Acsl6 |
| 77 | Chl1 |
| 78 | Pde1a |
| 79 | Ffar4 |
| 80 | Hist1h3d |
| 81 | Gm14718 |
| 82 | Tnip3 |
| 83 | Crabp2 |
| 84 | Cyr61 |
| 85 | Nov |
| 86 | Ugt1a6a |
| 87 | Tnf |
| 88 | Lta |
| 89 | Amotl1 |
| 90 | Spry4 |
| 91 | Ccl3 |
| 92 | Nlrp6 |
| 93 | Hdac9 |
| 94 | Smoc1 |
| 95 | Egr2 |
| 96 | Rnf180 |
| 97 | Tgfb2 |
| 98 | Gm4858 |
| 99 | Camkv |
| 100 | Rgs18 |
| 101 | Tfrc |
| 102 | Ttc39c |
| 103 | Il20rb |
| 104 | Il24 |
| 105 | Cnrip1 |
| 106 | Cdc6 |
| 107 | Gmpr |
| 108 | Tnfcfl1 |
| 109 | Ica1 |
| 110 | Slc2a6 |
| 111 | Tnfsf8 |
| 112 | Rai14 |
| 113 | Ttc30a1 |
| 114 | Tuba8 |
| 115 | Rpph1 |
| 116 | Idi2 |
| 117 | Klhl23 |
| 118 | Hbegf |
| 119 | Hist1h2bk |
| 120 | Zfp711 |
| 121 | Cxcl10 |
| 122 | Hist1h3a |
| 123 | Exo1 |
| 124 | Rrm2 |
| 125 | Ptprn |
| 126 | Ctnnal1 |
| 127 | Gpr55 |
| 128 | Tcam1 |
| 129 | Fam46a |
| 130 | Orc1 |
| 131 | Pnp2 |
| 132 | Fgd2 |
| 133 | Gata1 |
| 134 | Lrr1 |
| 135 | Aebp1 |
| 136 | Serpine1 |
| 137 | Gyltl1b |
| 138 | Egfr |
| 139 | Tom1l1 |
| 140 | Gad2 |
| 141 | Ccbl2 |
| 142 | Tdpoz4 |
| 143 | Cd70 |
| 144 | Igfbp7 |
| 145 | Nqo1 |
| 146 | Npw |
| 147 | Myh10 |
| 148 | Serpinc1 |
| 149 | Ceacam1 |
| 150 | Ms4a4c |
| 151 | Phlda1 |
| 152 | Shmt1 |
| 153 | Cdh15 |
| 154 | Zfp334 |
| 155 | Trpa1 |
| 156 | Stxbp6 |
| 157 | Dna2 |
| 158 | Anxa3 |
| 159 | Hist1h3f |
| 160 | Depdc7 |
| 161 | E2f8 |
| 162 | Exph5 |
| 163 | 3110082I17Rik |
| 164 | 2810417H13Rik |
| 165 | Cdk14 |
| 166 | Igj |
| 167 | Nefh |
| 168 | Shroom3 |
| 169 | Penk |
| 170 | Gm6460 |
| 171 | Dnph1 |
| 172 | Fosl1 |
| 173 | Bicd1 |
| 174 | Ccdc116 |
| 175 | Cyp27a1 |
| 176 | Ddx39 |
| 177 | Pdss1 |
| 178 | Hpdl |
| 179 | Osm |
| 180 | 1110002L01Rik |
| 181 | Mlf1 |
| 182 | Dscc1 |
| 183 | Hmgn2 |
| 184 | Prpf31 |
| 185 | Gm8773 |
| 186 | Lima1 |
| 187 | Dleu7 |
| 188 | Jrk |
| 189 | Lingo3 |
| 190 | Dclk1 |
| 191 | Inhba |
| 192 | Grwd1 |
| 193 | Gucy1a3 |
| 194 | Utf1 |
| 195 | Capn3 |
| 196 | Coq7 |
| 197 | Spry1 |
| 198 | Ppic |
| 199 | Per2 |
| 200 | Heatr3 |
| 201 | Hist1h2ak |
| 202 | Hist1h2ag |
| 203 | Rad54l |
| 204 | Mcm10 |
| 205 | Ddx25 |
| 206 | Apitd1 |
| 207 | Cd302 |
| 208 | Nr4a3 |
| 209 | Hnrnpab |
| 210 | Hmgn3 |
| 211 | Ercc6l |
| 212 | Pfas |
| 213 | Grtp1 |
| 214 | Ppid |
| 215 | Syn1 |
| 216 | Gzmc |

TABLE 2A-continued

Downregulated genes after GC + IL27 (1558 in ranked order)

| | |
|---|---|
| 217 | Bcl2l14 |
| 218 | Ccne2 |
| 219 | D430020J02Rik |
| 220 | Zbtbd6 |
| 221 | Tnfrsf11b |
| 222 | Cd200 |
| 223 | Creld2 |
| 224 | Thop1 |
| 225 | Coq4 |
| 226 | Tyms |
| 227 | Psmc3ip |
| 228 | Oaf |
| 229 | Fam43a |
| 230 | Nup85 |
| 231 | Ranbp1 |
| 232 | Tomm40 |
| 233 | Hist1h2bj |
| 234 | Gm4951 |
| 235 | Slc46a1 |
| 236 | Enpp4 |
| 237 | Gen1 |
| 238 | B4galt5 |
| 239 | Nolc1 |
| 240 | 1110032F04Rik |
| 241 | Hist1h3c |
| 242 | Fen1 |
| 243 | Pus7l |
| 244 | Tmem17 |
| 245 | Ctnnd1 |
| 246 | Ccr4 |
| 247 | Baat1 |
| 248 | Srrt |
| 249 | Lyar |
| 250 | Nop56 |
| 251 | Gemin6 |
| 252 | Papss2 |
| 253 | Nudt1 |
| 254 | Gpatch4 |
| 255 | Rrp9 |
| 256 | Ptpn5 |
| 257 | Tuba4a |
| 258 | Mthfd1 |
| 259 | Hist2h3b |
| 260 | Ptger3 |
| 261 | Prodh |
| 262 | Gins1 |
| 263 | Upb1 |
| 264 | Ticam2 |
| 265 | F2rl3 |
| 266 | Tk1 |
| 267 | Ccl4 |
| 268 | Bend3 |
| 269 | Sdf2l1 |
| 270 | Mcm5 |
| 271 | Tcf7 |
| 272 | Pop1 |
| 273 | Rmdn2 |
| 274 | Chtf18 |
| 275 | P2ry14 |
| 276 | Ppp1cb |
| 277 | Recql4 |
| 278 | Piwil4 |
| 279 | Qsox2 |
| 280 | Rpl30 |
| 281 | Fsd1l |
| 282 | Ppih |
| 283 | Mybbp1a |
| 284 | Pcna |
| 285 | Hsp90aa1 |
| 286 | Cdc45 |
| 287 | Prmt1 |
| 288 | Ftsj3 |
| 289 | Ugt1a7c |
| 290 | Ebna1bp2 |
| 291 | Imp4 |
| 292 | C330027C09Rik |
| 293 | Hist2h3c2 |
| 294 | Ifrd2 |
| 295 | Hspd1 |
| 296 | 4933430I17Rik |
| 297 | Ankle1 |
| 298 | Cinp |
| 299 | Mettl16 |
| 300 | Rrp15 |
| 301 | Mrto4 |
| 302 | Pin1 |
| 303 | Clgn |
| 304 | Tuba1b |
| 305 | Srm |
| 306 | Ccdc86 |
| 307 | Gtdc2 |
| 308 | Elovl4 |
| 309 | Wisp1 |
| 310 | Mcm2 |
| 311 | Gpr150 |
| 312 | Csgalnact1 |
| 313 | Gemin4 |
| 314 | Slc7a3 |
| 315 | Srsf6 |
| 316 | Mylk |
| 317 | Rps6kl1 |
| 318 | Trip13 |
| 319 | Timeless |
| 320 | Pdpn |
| 321 | Rrm1 |
| 322 | Ssx2ip |
| 323 | Gspt2 |
| 324 | Spin4 |
| 325 | Tmem48 |
| 326 | Bysl |
| 327 | 9630033F20Rik |
| 328 | Trmt61a |
| 329 | Rad51ap1 |
| 330 | Mat2a |
| 331 | Gart |
| 332 | Mtfp1 |
| 333 | Trat1 |
| 334 | Dkc1 |
| 335 | Fancb |
| 336 | St6gal1 |
| 337 | Kbtbd8 |
| 338 | Nomo1 |
| 339 | Zcchc10 |
| 340 | Dnajc11 |
| 341 | Ruvbl1 |
| 342 | Etv5 |
| 343 | Rad51 |
| 344 | Lum |
| 345 | Dhodh |
| 346 | Mtbp |
| 347 | Rcc1 |
| 348 | Pola1 |
| 349 | Ppa1 |
| 350 | Wdr4 |
| 351 | Polr1b |
| 352 | Iigp1 |
| 353 | 4930509E16Rik |
| 354 | Clhc1 |
| 355 | Rfc5 |
| 356 | Fancd2 |
| 357 | Slc7a11 |
| 358 | Chek1 |
| 359 | C230052I12Rik |
| 360 | 9930014A18Rik |
| 361 | Prrx1 |
| 362 | Pim3 |
| 363 | Emc8 |
| 364 | Wdr89 |
| 365 | Tln2 |
| 366 | Gpx7 |
| 367 | Hist1h2ae |
| 368 | Ruvbl2 |
| 369 | Etv4 |
| 370 | Alyref |
| 371 | Orc6 |
| 372 | Gcat |

TABLE 2A-continued

Downregulated genes after GC + IL27 (1558 in ranked order)

| | |
|---|---|
| 373 | Fkbp11 |
| 374 | Wdr18 |
| 375 | Chaf1b |
| 376 | C77080 |
| 377 | Srsf3 |
| 378 | Ufsp1 |
| 379 | Asf1b |
| 380 | Lpin3 |
| 381 | Fabp5 |
| 382 | Grhl1 |
| 383 | Trmt12 |
| 384 | Traip |
| 385 | Pbk |
| 386 | 2310014L17Rik |
| 387 | Dennd5a |
| 388 | Fastkd2 |
| 389 | Hk2 |
| 390 | Cldn25 |
| 391 | Timm8a1 |
| 392 | Shcbp1 |
| 393 | S1pr3 |
| 394 | Vmn2r-ps129 |
| 395 | Icam2 |
| 396 | Gm17296 |
| 397 | Ikzf4 |
| 398 | Clspn |
| 399 | Nop16 |
| 400 | Cd44 |
| 401 | Mybl2 |
| 402 | Cpne2 |
| 403 | Cd83 |
| 404 | Hrc |
| 405 | Car12 |
| 406 | Polr3h |
| 407 | Cth |
| 408 | Ung |
| 409 | Haus5 |
| 410 | Psmd1 |
| 411 | Polq |
| 412 | Dhfr |
| 413 | Srsf7 |
| 414 | Fads2 |
| 415 | Slc25a32 |
| 416 | Lacc1 |
| 417 | Oas1a |
| 418 | Shq1 |
| 419 | Hist2h4 |
| 420 | Nudc |
| 421 | Chchd4 |
| 422 | Tra2a |
| 423 | Arxes2 |
| 424 | Tuba1c |
| 425 | Tubb4b |
| 426 | Adsl |
| 427 | Kntc1 |
| 428 | Opn3 |
| 429 | Nek6 |
| 430 | Ivd |
| 431 | Hspbp1 |
| 432 | 2310008H09Rik |
| 433 | Nup155 |
| 434 | Sept8 |
| 435 | Stmn1 |
| 436 | Alg8 |
| 437 | Coro2a |
| 438 | Timp1 |
| 439 | Pwp2 |
| 440 | Tra2b |
| 441 | Il1rl1 |
| 442 | Tm4sf5 |
| 443 | Cad |
| 444 | Idh3a |
| 445 | A930004D18Rik |
| 446 | B3galt6 |
| 447 | Hars |
| 448 | Ptcd3 |
| 449 | Ptrf |
| 450 | Abcf2 |
| 451 | Eme1 |
| 452 | Nasp |
| 453 | Tnp2 |
| 454 | Nup107 |
| 455 | Ptgir |
| 456 | Exosc6 |
| 457 | Pitrm1 |
| 458 | Hsph1 |
| 459 | Hn1l |
| 460 | Cyb5rl |
| 461 | Plscr1 |
| 462 | Ppap2a |
| 463 | Trdmt1 |
| 464 | Lipg |
| 465 | Cacybp |
| 466 | Idi1 |
| 467 | Nkain1 |
| 468 | Ppan |
| 469 | Ubiad1 |
| 470 | Btla |
| 471 | Rpf2 |
| 472 | Fignl1 |
| 473 | Nop2 |
| 474 | Ran |
| 475 | Zfp229 |
| 476 | Cd48 |
| 477 | Siah1b |
| 478 | Timm17a |
| 479 | Rnmtl1 |
| 480 | Mtap |
| 481 | Nup160 |
| 482 | Tubg1 |
| 483 | Tuba1a |
| 484 | Utp20 |
| 485 | Noc4l |
| 486 | Lrpprc |
| 487 | Cct3 |
| 488 | Hirip3 |
| 489 | Hist1h2ab |
| 490 | Trmt6 |
| 491 | Smyd5 |
| 492 | Tjp2 |
| 493 | Eme2 |
| 494 | E2f7 |
| 495 | Pla1a |
| 496 | Nop58 |
| 497 | Rpl7l1 |
| 498 | 2610318N02Rik |
| 499 | Hnrnpm |
| 500 | Spp1 |
| 501 | Egr1 |
| 502 | Fam136a |
| 503 | Ms4a4b |
| 504 | Cd74 |
| 505 | Erh |
| 506 | Col5a3 |
| 507 | Ppif |
| 508 | Cenpi |
| 509 | Tipin |
| 510 | Bop1 |
| 511 | Rbm19 |
| 512 | Nfyc |
| 513 | Eef1e1 |
| 514 | N6amt2 |
| 515 | Pdcd11 |
| 516 | Dnajc22 |
| 517 | Notch2 |
| 518 | Syncrip |
| 519 | Gmppb |
| 520 | Fkbp4 |
| 521 | Mcm8 |
| 522 | Chaf1a |
| 523 | Lsm7 |
| 524 | Ctps |
| 525 | St3gal2 |
| 526 | Tbl3 |
| 527 | Xpo5 |
| 528 | Jam2 |

TABLE 2A-continued

Downregulated genes after GC + IL27 (1558 in ranked order)

| | |
|---|---|
| 529 | Ahsa1 |
| 530 | Nutf2-ps1 |
| 531 | Dtl |
| 532 | Wdr77 |
| 533 | Armc6 |
| 534 | Ppat |
| 535 | Rad54b |
| 536 | Nhp2 |
| 537 | Psmd6 |
| 538 | Klri2 |
| 539 | Calr |
| 540 | Dis3 |
| 541 | Slc43a3 |
| 542 | Exosc2 |
| 543 | Mgat5 |
| 544 | Slc35b1 |
| 545 | Glrp1 |
| 546 | Pole2 |
| 547 | Ift27 |
| 548 | Hmgb2 |
| 549 | Cks1b |
| 550 | Ywhab |
| 551 | Tmem97 |
| 552 | Rrp12 |
| 553 | Gcsh |
| 554 | Slc43a1 |
| 555 | Slc25a25 |
| 556 | Myo19 |
| 557 | Slc19a1 |
| 558 | Set |
| 559 | Dynll1 |
| 560 | Mcm3 |
| 561 | Pter |
| 562 | Phtf2 |
| 563 | Umps |
| 564 | Nup93 |
| 565 | 4930427A07Rik |
| 566 | Gadd45g |
| 567 | Tex30 |
| 568 | Gusb |
| 569 | Plk2 |
| 570 | Mrps2 |
| 571 | Eftud2 |
| 572 | Uchl3 |
| 573 | Myo1e |
| 574 | Utp6 |
| 575 | Cycs |
| 576 | Gm9855 |
| 577 | Lilrb4 |
| 578 | Taf6l |
| 579 | Hnrnpa2b1 |
| 580 | Mrps10 |
| 581 | Wdhd1 |
| 582 | Ddx56 |
| 583 | Cct6a |
| 584 | Uhrf1 |
| 585 | Unc5cl |
| 586 | Yy2 |
| 587 | Tespa1 |
| 588 | Lgmn |
| 589 | Bola3 |
| 590 | Cpd |
| 591 | Ehd3 |
| 592 | Uqcr11 |
| 593 | Manf |
| 594 | Ttll4 |
| 595 | Gins2 |
| 596 | Hnrpll |
| 597 | Ankrd32 |
| 598 | Tomm5 |
| 599 | Slc16a13 |
| 600 | Snrpd3 |
| 601 | Psmd7 |
| 602 | Exoc3l |
| 603 | Galnt7 |
| 604 | Pbld1 |
| 605 | Gltpd1 |
| 606 | Il1rl2 |
| 607 | Ube2v2 |
| 608 | Cdca7 |
| 609 | Nup37 |
| 610 | Socs2 |
| 611 | Nme1 |
| 612 | Gyk |
| 613 | AA414768 |
| 614 | Cman |
| 615 | Sf3b4 |
| 616 | Mcm4 |
| 617 | Pdia6 |
| 618 | Poc1a |
| 619 | Lrrc32 |
| 620 | Dhx9 |
| 621 | Gar1 |
| 622 | Fastkd3 |
| 623 | Fh1 |
| 624 | Zfp239 |
| 625 | Ndufa4 |
| 626 | Nip7 |
| 627 | Hat1 |
| 628 | Rtel1 |
| 629 | Hapln4 |
| 630 | Rbks |
| 631 | Ifitm3 |
| 632 | Nup35 |
| 633 | Ska1 |
| 634 | Lcmt2 |
| 635 | Cdk1 |
| 636 | Spc24 |
| 637 | Ipo4 |
| 638 | Esco2 |
| 639 | Lsm3 |
| 640 | Nme6 |
| 641 | Dgcr8 |
| 642 | Phf19 |
| 643 | Cse1l |
| 644 | Ptger4 |
| 645 | Fam64a |
| 646 | Timm10 |
| 647 | Nabp1 |
| 648 | Pomgnt1 |
| 649 | Mcm7 |
| 650 | Fanca |
| 651 | Gm15645 |
| 652 | Zwilch |
| 653 | Pole |
| 654 | D030028A08Rik |
| 655 | Nudt5 |
| 656 | Tmtc4 |
| 657 | Ncbp2 |
| 658 | Stip1 |
| 659 | Wdr74 |
| 660 | Srsf10 |
| 661 | Ddx3x |
| 662 | Cbwd1 |
| 663 | Psmc5 |
| 664 | Cenpn |
| 665 | Nrp1 |
| 666 | Emc4 |
| 667 | Ube2m |
| 668 | Heatr1 |
| 669 | Cdh23 |
| 670 | Mrpl20 |
| 671 | Hist1h2ao |
| 672 | Pno1 |
| 673 | Ndufaf4 |
| 674 | Lsm2 |
| 675 | Lars |
| 676 | Pole3 |
| 677 | Nid1 |
| 678 | Fam111a |
| 679 | Ipo11 |
| 680 | Dnajc27 |
| 681 | Loxl2 |
| 682 | Sigmar1 |
| 683 | Abcd3 |
| 684 | 0610010F05Rik |

TABLE 2A-continued

Downregulated genes after GC + IL27 (1558 in ranked order)

| | |
|---|---|
| 685 | Adpgk |
| 686 | Plk1 |
| 687 | Atad3a |
| 688 | Sfxn2 |
| 689 | Uros |
| 690 | Pa2g4 |
| 691 | C1qbp |
| 692 | Rbmx2 |
| 693 | Acy1 |
| 694 | Brix1 |
| 695 | Armcx4 |
| 696 | Casc4 |
| 697 | Dcun1d2 |
| 698 | Cd226 |
| 699 | Naa50 |
| 700 | Cenph |
| 701 | Hist1h1b |
| 702 | Enthd1 |
| 703 | Wdr46 |
| 704 | Mlh1 |
| 705 | Mlf1ip |
| 706 | Polr2f |
| 707 | Nhp2l1 |
| 708 | Ncapg2 |
| 709 | Magoh |
| 710 | Psmc4 |
| 711 | Omd |
| 712 | Wdr3 |
| 713 | Polr1e |
| 714 | Znhit3 |
| 715 | Amd2 |
| 716 | Car13 |
| 717 | Ncln |
| 718 | Aff3 |
| 719 | Cysltr1 |
| 720 | Srl |
| 721 | Polr2l |
| 722 | Pmpca |
| 723 | Mki67ip |
| 724 | Spint1 |
| 725 | Slc7a5 |
| 726 | Xrcc5 |
| 727 | Slc17a6 |
| 728 | Npl |
| 729 | Shmt2 |
| 730 | Mpv17l |
| 731 | Cdc34 |
| 732 | Palb2 |
| 733 | Itgb1 |
| 734 | Atp2a2 |
| 735 | Prdx1 |
| 736 | Nr4a1 |
| 737 | Fitm2 |
| 738 | Dbi |
| 739 | Ikbkap |
| 740 | Hspa5 |
| 741 | Ttc27 |
| 742 | Kctd17 |
| 743 | Nupr1 |
| 744 | Espl1 |
| 745 | Mphosph6 |
| 746 | Dus4l |
| 747 | Alg6 |
| 748 | Acsf3 |
| 749 | Mad1l1 |
| 750 | Tfdp1 |
| 751 | Phb |
| 752 | Spred1 |
| 753 | Rars |
| 754 | Tubb6 |
| 755 | Abcb6 |
| 756 | Snrpb |
| 757 | Ltv1 |
| 758 | Pilra |
| 759 | Orc2 |
| 760 | Rpp40 |
| 761 | Wrb |
| 762 | Tmem144 |
| 763 | Fubp1 |
| 764 | Kif15 |
| 765 | Tmem69 |
| 766 | BC030867 |
| 767 | Jmjd4 |
| 768 | Procr |
| 769 | Aurka |
| 770 | Lyrm7 |
| 771 | Pet112 |
| 772 | Wdr90 |
| 773 | Ddx27 |
| 774 | Bag2 |
| 775 | Ccnb1 |
| 776 | Polr3d |
| 777 | Wdr75 |
| 778 | Cltb |
| 779 | Ppp2r1b |
| 780 | Psat1 |
| 781 | Psme3 |
| 782 | Psmb7 |
| 783 | 2310057M21Rik |
| 784 | Hist1h3i |
| 785 | Rrs1 |
| 786 | Otud6b |
| 787 | Mrpl3 |
| 788 | Spdl1 |
| 789 | Pmf1 |
| 790 | Igfbp4 |
| 791 | Pkib |
| 792 | Sf3b3 |
| 793 | Eif1ad |
| 794 | Crtam |
| 795 | Rbm8a |
| 796 | Mansc1 |
| 797 | Anp32e |
| 798 | Bard1 |
| 799 | Nol6 |
| 800 | Bub1 |
| 801 | Klhdc4 |
| 802 | Mov10 |
| 803 | Birc5 |
| 804 | Abcb1b |
| 805 | Rpa3 |
| 806 | Lap3 |
| 807 | Pfkfb1 |
| 808 | E2f3 |
| 809 | Mboat1 |
| 810 | Ippk |
| 811 | Pphln1 |
| 812 | Gnl3 |
| 813 | Zbtb8os |
| 814 | Ntmt1 |
| 815 | 4930579G24Rik |
| 816 | Slc25a33 |
| 817 | 2700029M09Rik |
| 818 | Dynll2 |
| 819 | Tdrkh |
| 820 | Cops7a |
| 821 | Tlr1 |
| 822 | Dek |
| 823 | Rgsl6 |
| 824 | Cttn |
| 825 | Dhrs4 |
| 826 | Pfdn4 |
| 827 | Dclre1a |
| 828 | Gmnn |
| 829 | Psph |
| 830 | Abcb1a |
| 831 | Ccna2 |
| 832 | Kpna2 |
| 833 | Actb |
| 834 | Clpp |
| 835 | Pdhx |
| 836 | Dhx37 |
| 837 | Melk |
| 838 | Gca |
| 839 | Dnaja1 |
| 840 | Gcnt2 |

TABLE 2A-continued

Downregulated genes after GC + IL27 (1558 in ranked order)

| | |
|---|---|
| 841 | Anapc15 |
| 842 | Coq10b |
| 843 | Esf1 |
| 844 | Scap |
| 845 | Siglec5 |
| 846 | Slc25a10 |
| 847 | Mrps22 |
| 848 | Ttc32 |
| 849 | Zranb3 |
| 850 | Rpp38 |
| 851 | Skp2 |
| 852 | Gpt2 |
| 853 | Pask |
| 854 | Chac2 |
| 855 | Wars |
| 856 | Smc2 |
| 857 | Atf3 |
| 858 | Hmgn1 |
| 859 | Tmem132a |
| 860 | Tnfrsf21 |
| 861 | Rbm12 |
| 862 | Pus11 |
| 863 | Cluh |
| 864 | A230046K03Rik |
| 865 | Rpp14 |
| 866 | Fam174b |
| 867 | Cxcr2 |
| 868 | Rhot2 |
| 869 | Psma4 |
| 870 | Noc3l |
| 871 | Exosc7 |
| 872 | Ccdc14 |
| 873 | Polr2k |
| 874 | Slco4a1 |
| 875 | F2rl2 |
| 876 | Gm5531 |
| 877 | Rapsn |
| 878 | Eno3 |
| 879 | Pkd1l3 |
| 880 | D630039A03Rik |
| 881 | Fbxo5 |
| 882 | Nol11 |
| 883 | Adk |
| 884 | Timm50 |
| 885 | Galnt3 |
| 886 | L2hgdh |
| 887 | Srsf9 |
| 888 | 5430427O19Rik |
| 889 | Slc35a4 |
| 890 | Mrpl12 |
| 891 | Phgdh |
| 892 | Snrpc |
| 893 | Psmc1 |
| 894 | Bcat1 |
| 895 | Atp8b4 |
| 896 | Banf1 |
| 897 | Etfb |
| 898 | Polr1a |
| 899 | Spc25 |
| 900 | Pold2 |
| 901 | 2810004N23Rik |
| 902 | Cirh1a |
| 903 | Kdm8 |
| 904 | Ddx51 |
| 905 | Dse |
| 906 | Rras2 |
| 907 | Ncbp1 |
| 908 | Smyd2 |
| 909 | Ddx18 |
| 910 | Mrps18a |
| 911 | Pros1 |
| 912 | Fasl |
| 913 | Cdc20 |
| 914 | Mfsd2a |
| 915 | Dctd |
| 916 | Atp6v1a |
| 917 | Prps1l3 |
| 918 | Ak2 |
| 919 | Cox10 |
| 920 | 2210016F16Rik |
| 921 | Kti12 |
| 922 | Cct8 |
| 923 | Mrpl28 |
| 924 | Cstf2 |
| 925 | Hnrnph1 |
| 926 | Skp1a |
| 927 | Tyw3 |
| 928 | Ifngr2 |
| 929 | Psmg3 |
| 930 | Zfp446 |
| 931 | Gps1 |
| 932 | Tmem199 |
| 933 | Nanog |
| 934 | Mrpl42 |
| 935 | Doc2a |
| 936 | Mir17hg |
| 937 | Slc35g1 |
| 938 | Al836003 |
| 939 | Diablo |
| 940 | Alg3 |
| 941 | Nle1 |
| 942 | Prps1 |
| 943 | Ubtf |
| 944 | Mogs |
| 945 | Pnpt1 |
| 946 | Snrpd1 |
| 947 | Kif20a |
| 948 | Ttk |
| 949 | Ssca1 |
| 950 | Eif5a |
| 951 | Slfn5 |
| 952 | Prim1 |
| 953 | Igsf8 |
| 954 | Tmem109 |
| 955 | Yars2 |
| 956 | Med27 |
| 957 | Nudt15 |
| 958 | Ier5 |
| 959 | Rbmxl1 |
| 960 | Odc1 |
| 961 | Mrpl55 |
| 962 | Fasn |
| 963 | Rbpms2 |
| 964 | Pbdc1 |
| 965 | Ydjc |
| 966 | Mecr |
| 967 | Yrdc |
| 968 | Fanci |
| 969 | Zfp783 |
| 970 | Atpbd4 |
| 971 | Sapcd2 |
| 972 | Fkbp2 |
| 973 | Myef2 |
| 974 | Naf1 |
| 975 | Ppil1 |
| 976 | Dclre1b |
| 977 | Eif6 |
| 978 | Hdac1 |
| 979 | Slmo2 |
| 980 | Ptgfrn |
| 981 | Hsd17b7 |
| 982 | Mycbp |
| 983 | Actl6a |
| 984 | U2af2 |
| 985 | Exosc3 |
| 986 | Larp4 |
| 987 | Exosc1 |
| 988 | Ino80e |
| 989 | Pelp1 |
| 990 | Sfxn1 |
| 991 | Arhgdig |
| 992 | Cyp4f16 |
| 993 | Dsn1 |
| 994 | Rfc4 |
| 995 | Psma5 |
| 996 | Mettl13 |

TABLE 2A-continued

Downregulated genes after GC + IL27 (1558 in ranked order)

| | |
|---|---|
| 997 | Cenpk |
| 998 | Hsp90b1 |
| 999 | Dpp3 |
| 1000 | Uchl5 |
| 1001 | Irf4 |
| 1002 | Lig1 |
| 1003 | 0610007P14Rik |
| 1004 | Eif2s1 |
| 1005 | Tacc3 |
| 1006 | Dus1l |
| 1007 | Prmt5 |
| 1008 | Pdss2 |
| 1009 | U2af1 |
| 1010 | Calm1 |
| 1011 | Gpn2 |
| 1012 | Wdr61 |
| 1013 | Rpn1 |
| 1014 | Hspa14 |
| 1015 | Rbm14 |
| 1016 | Ercc8 |
| 1017 | Yae1d1 |
| 1018 | Ccdc50 |
| 1019 | Ndufs6 |
| 1020 | Aco2 |
| 1021 | Hmgb1 |
| 1022 | Txnrd1 |
| 1023 | Trim16 |
| 1024 | Gfpt2 |
| 1025 | Dimt1 |
| 1026 | Fpgs |
| 1027 | Tbrg4 |
| 1028 | Rnd1 |
| 1029 | Fam203a |
| 1030 | G6pdx |
| 1031 | Slc29a1 |
| 1032 | Psmb5 |
| 1033 | Dars2 |
| 1034 | Hnrnpu |
| 1035 | Farsa |
| 1036 | Txn1 |
| 1037 | Mettl25 |
| 1038 | Slc2a1 |
| 1039 | Lepr |
| 1040 | 2210408I21Rik |
| 1041 | Snrnp40 |
| 1042 | Spin2 |
| 1043 | Eif4g2 |
| 1044 | Pfn1 |
| 1045 | Sgol1 |
| 1046 | Nuf2 |
| 1047 | Gtf2h1 |
| 1048 | Gp49a |
| 1049 | Ccnd3 |
| 1050 | Fam118b |
| 1051 | Ube2s |
| 1052 | Elp5 |
| 1053 | Slc25a26 |
| 1054 | Dusp4 |
| 1055 | Arhgap19 |
| 1056 | Ppp5c |
| 1057 | Timm9 |
| 1058 | Usp10 |
| 1059 | Lrrc8d |
| 1060 | Aven |
| 1061 | Fus |
| 1062 | Hus1 |
| 1063 | Bms1 |
| 1064 | Leo1 |
| 1065 | Thoc3 |
| 1066 | Gzmb |
| 1067 | Mdn1 |
| 1068 | Apoo |
| 1069 | Rps27l |
| 1070 | Ssr2 |
| 1071 | Trmt2a |
| 1072 | Inpp5b |
| 1073 | Cpsf3 |
| 1074 | Zswim7 |
| 1075 | Nup205 |
| 1076 | Zfp324 |
| 1077 | Mrpl17 |
| 1078 | Vac14 |
| 1079 | Ap1s1 |
| 1080 | Cish |
| 1081 | Mbd3 |
| 1082 | Ndufa5 |
| 1083 | Slc25a13 |
| 1084 | Rrn3 |
| 1085 | Mettl1 |
| 1086 | Dlat |
| 1087 | Psmg1 |
| 1088 | Mrpl11 |
| 1089 | Elac2 |
| 1090 | Sgk3 |
| 1091 | Bzw2 |
| 1092 | Eif4a3 |
| 1093 | Rbbp7 |
| 1094 | D19Bwg1357e |
| 1095 | Eif1a |
| 1096 | Smn1 |
| 1097 | Tomm6 |
| 1098 | Hist1h4i |
| 1099 | Prmt7 |
| 1100 | Ddx39b |
| 1101 | Htra2 |
| 1102 | Slc16a1 |
| 1103 | Fastkd5 |
| 1104 | Sf3a3 |
| 1105 | Psmd12 |
| 1106 | Ndufa12 |
| 1107 | Lyrm1 |
| 1108 | Vrk1 |
| 1109 | Bdh1 |
| 1110 | Enoph1 |
| 1111 | Pcyox1l |
| 1112 | Ddx1 |
| 1113 | Mrpl36 |
| 1114 | Vma21 |
| 1115 | Zmynd8 |
| 1116 | Sfn |
| 1117 | Wbscr22 |
| 1118 | Neil3 |
| 1119 | Bccip |
| 1120 | Bckdk |
| 1121 | Nup43 |
| 1122 | Bckdhb |
| 1123 | Eif5a2 |
| 1124 | Senp3 |
| 1125 | Ccnb2 |
| 1126 | Pgd |
| 1127 | Atp5g3 |
| 1128 | Farsb |
| 1129 | Comt |
| 1130 | Wdr43 |
| 1131 | Atp5g1 |
| 1132 | Pfdn2 |
| 1133 | Dbt |
| 1134 | Magohb |
| 1135 | Syce2 |
| 1136 | Ptcra |
| 1137 | Metap2 |
| 1138 | Ccnd2 |
| 1139 | Ggct |
| 1140 | Aifm1 |
| 1141 | Drg2 |
| 1142 | Rars2 |
| 1143 | Gm12504 |
| 1144 | C330018D20Rik |
| 1145 | Ccne1 |
| 1146 | Timm23 |
| 1147 | Pcyt1a |
| 1148 | 3110001I22Rik |
| 1149 | Ssrp1 |
| 1150 | Usp46 |
| 1151 | Bzw1 |
| 1152 | Myc |

TABLE 2A-continued

Downregulated genes after GC + IL27 (1558 in ranked order)

| | |
|---|---|
| 1153 | Gfm1 |
| 1154 | Ppia |
| 1155 | Ctu2 |
| 1156 | Prmt6 |
| 1157 | Sec23b |
| 1158 | Nif3l1 |
| 1159 | Eif3b |
| 1160 | Jagn1 |
| 1161 | Suv39h2 |
| 1162 | Slc7a14 |
| 1163 | Samm50 |
| 1164 | Sgsm3 |
| 1165 | Cd3eap |
| 1166 | Dnmt1 |
| 1167 | Nupl2 |
| 1168 | Ecd |
| 1169 | Urb1 |
| 1170 | Cyb5b |
| 1171 | Mrpl37 |
| 1172 | Haus7 |
| 1173 | Xrcc2 |
| 1174 | Enkd1 |
| 1175 | Chml |
| 1176 | Mrps18b |
| 1177 | Psmb3 |
| 1178 | Mthfsd |
| 1179 | Ccnf |
| 1180 | Papd7 |
| 1181 | Cep78 |
| 1182 | Moap1 |
| 1183 | Gm6793 |
| 1184 | Lmnb2 |
| 1185 | Taf9 |
| 1186 | Mrps5 |
| 1187 | Uba2 |
| 1188 | Egfl7 |
| 1189 | Denr |
| 1190 | Sppl2b |
| 1191 | Mtr |
| 1192 | Haus6 |
| 1193 | Fancm |
| 1194 | Pus7 |
| 1195 | Snhg3 |
| 1196 | Ulbp1 |
| 1197 | Thoc6 |
| 1198 | Ptma |
| 1199 | Bclaf1 |
| 1200 | Gtpbp4 |
| 1201 | Toe1 |
| 1202 | Zdhhc6 |
| 1203 | Scoc |
| 1204 | BC003965 |
| 1205 | Mrpl49 |
| 1206 | Galnt1 |
| 1207 | Nek2 |
| 1208 | Wdr55 |
| 1209 | Larp7 |
| 1210 | Hyou1 |
| 1211 | Apex1 |
| 1212 | Mtg1 |
| 1213 | Ywhaq |
| 1214 | Mmd |
| 1215 | Dtymk |
| 1216 | Cops3 |
| 1217 | Rcl1 |
| 1218 | St6galnac4 |
| 1219 | Bcap29 |
| 1220 | Ect2 |
| 1221 | Utp15 |
| 1222 | Tox |
| 1223 | Echdc2 |
| 1224 | Lrdd |
| 1225 | Zfp286 |
| 1226 | Anapc5 |
| 1227 | Slc39a6 |
| 1228 | Aimp2 |
| 1229 | Camkk2 |
| 1230 | Nubp2 |
| 1231 | Dhps |
| 1232 | Atp5b |
| 1233 | Fbxo17 |
| 1234 | Atic |
| 1235 | Dph5 |
| 1236 | Sh2b3 |
| 1237 | Ptpla |
| 1238 | Pkmyt1 |
| 1239 | Dut |
| 1240 | Rtn4ip1 |
| 1241 | Lancl2 |
| 1242 | Larp1 |
| 1243 | Skiv2l2 |
| 1244 | Mrpl16 |
| 1245 | Impa1 |
| 1246 | Sfpq |
| 1247 | Zscan22 |
| 1248 | Strap |
| 1249 | 2410016O06Rik |
| 1250 | Rexo2 |
| 1251 | Cpsf6 |
| 1252 | Tnfsf14 |
| 1253 | Cdt1 |
| 1254 | Psmd14 |
| 1255 | 1810009A15Rik |
| 1256 | Glrx5 |
| 1257 | Fem1a |
| 1258 | Psmc2 |
| 1259 | Psmd13 |
| 1260 | Lsg1 |
| 1261 | Ptges3 |
| 1262 | Nt5c2 |
| 1263 | Psmc3 |
| 1264 | Gpn1 |
| 1265 | Prkrip1 |
| 1266 | Pola2 |
| 1267 | Cep128 |
| 1268 | Dgkh |
| 1269 | Dpy30 |
| 1270 | Ndufb6 |
| 1271 | Ddc |
| 1272 | Pinx1 |
| 1273 | 1810055G02Rik |
| 1274 | Prpf3 |
| 1275 | Tmem185b |
| 1276 | Cyc1 |
| 1277 | Ppa2 |
| 1278 | Polr2c |
| 1279 | Clptm1l |
| 1280 | Wdr12 |
| 1281 | Ilkap |
| 1282 | Cmss1 |
| 1283 | Gtf3c6 |
| 1284 | Bud31 |
| 1285 | Selrc1 |
| 1286 | Itga5 |
| 1287 | Mtx1 |
| 1288 | Mrps28 |
| 1289 | Yif1a |
| 1290 | Lyrm4 |
| 1291 | Asns |
| 1292 | Snhg11 |
| 1293 | H2afz |
| 1294 | Ppp1r8 |
| 1295 | 1190007I07Rik |
| 1296 | Stk3 |
| 1297 | Edem2 |
| 1298 | Nsun5 |
| 1299 | Timd2 |
| 1300 | Ddx21 |
| 1301 | Hmbs |
| 1302 | Susd1 |
| 1303 | Paox |
| 1304 | Rfc2 |
| 1305 | Cenpb |
| 1306 | Zbtb45 |
| 1307 | Cd9 |
| 1308 | Mrps12 |

TABLE 2A-continued

Downregulated genes after GC + IL27 (1558 in ranked order)

| | |
|---|---|
| 1309 | Siva1 |
| 1310 | Efcab7 |
| 1311 | Dynlt1a |
| 1312 | Asna1 |
| 1313 | Acsl4 |
| 1314 | Mrpl46 |
| 1315 | Hypk |
| 1316 | Tpx2 |
| 1317 | Cdca5 |
| 1318 | Zfp828 |
| 1319 | Sf3a2 |
| 1320 | Trnt1 |
| 1321 | Dctpp1 |
| 1322 | Tsr2 |
| 1323 | Dennd5b |
| 1324 | Dohh |
| 1325 | Ndufc1 |
| 1326 | Pcca |
| 1327 | BC055324 |
| 1328 | Eif2b1 |
| 1329 | Top1mt |
| 1330 | Isyna1 |
| 1331 | Top1 |
| 1332 | Gpr155 |
| 1333 | Slbp |
| 1334 | Adap1 |
| 1335 | Mrps7 |
| 1336 | Wdr36 |
| 1337 | Serpine2 |
| 1338 | Entpd7 |
| 1339 | Cetn3 |
| 1340 | Galm |
| 1341 | Cdk4 |
| 1342 | Srsf1 |
| 1343 | Aacs |
| 1344 | Slc10a3 |
| 1345 | Timm13 |
| 1346 | Osbpl3 |
| 1347 | Dph3 |
| 1348 | Qtrtd1 |
| 1349 | Chd1l |
| 1350 | Ada |
| 1351 | Ncoa7 |
| 1352 | Pnp |
| 1353 | Casc5 |
| 1354 | Ttc7b |
| 1355 | Furin |
| 1356 | Ftsj2 |
| 1357 | Atf6b |
| 1358 | Kcnk5 |
| 1359 | Psmb4 |
| 1360 | Tnfsf4 |
| 1361 | Cct7 |
| 1362 | Pycr2 |
| 1363 | Riok2 |
| 1364 | Dlgap5 |
| 1365 | Brca2 |
| 1366 | Elp4 |
| 1367 | Abcf1 |
| 1368 | Sco2 |
| 1369 | Znhit6 |
| 1370 | Eif4e |
| 1371 | Ddost |
| 1372 | Dbr1 |
| 1373 | Elmo1 |
| 1374 | Clns1a |
| 1375 | Tob2 |
| 1376 | Cyb561d2 |
| 1377 | Hspa9 |
| 1378 | Lrrc59 |
| 1379 | Osgin2 |
| 1380 | Ampd2 |
| 1381 | Ftsjd1 |
| 1382 | Pafah1b2 |
| 1383 | Pitpnb |
| 1384 | Fam98a |
| 1385 | Cdkn3 |
| 1386 | Atp5j |
| 1387 | Hras1 |
| 1388 | Atpif1 |
| 1389 | Apex2 |
| 1390 | Ctsz |
| 1391 | Gramd1b |
| 1392 | Msto1 |
| 1393 | Oip5 |
| 1394 | Slc29a2 |
| 1395 | Nucks1 |
| 1396 | Ccp110 |
| 1397 | Ier3 |
| 1398 | BC035044 |
| 1399 | G3bp1 |
| 1400 | Psmd9 |
| 1401 | Arpp19 |
| 1402 | Gfpt1 |
| 1403 | Depdc1a |
| 1404 | Wdr73 |
| 1405 | Fam73b |
| 1406 | D2Wsu81e |
| 1407 | Hax1 |
| 1408 | Psma3 |
| 1409 | Rwdd4a |
| 1410 | Kif22 |
| 1411 | Cd63 |
| 1412 | Pabpc4 |
| 1413 | Las1l |
| 1414 | Smarca4 |
| 1415 | Diap3 |
| 1416 | 9130401M01Rik |
| 1417 | Rpa2 |
| 1418 | Lrp8 |
| 1419 | Eaf1 |
| 1420 | Prpf38a |
| 1421 | Rrp8 |
| 1422 | Trappc13 |
| 1423 | Megf8 |
| 1424 | Msrb2 |
| 1425 | Pcnxl4 |
| 1426 | Supt16 |
| 1427 | Med29 |
| 1428 | Pwp1 |
| 1429 | Kif2c |
| 1430 | Bid |
| 1431 | Blm |
| 1432 | Ints2 |
| 1433 | Spink2 |
| 1434 | Gle1 |
| 1435 | Rpgr |
| 1436 | Rnf19b |
| 1437 | Pacsin2 |
| 1438 | 2310033P09Rik |
| 1439 | Drosha |
| 1440 | Pdzd11 |
| 1441 | Lipt2 |
| 1442 | Nnt |
| 1443 | Stoml2 |
| 1444 | Rpp30 |
| 1445 | Rnaseh2b |
| 1446 | Senp5 |
| 1447 | Mul1 |
| 1448 | Nars |
| 1449 | Inpp4b |
| 1450 | Arl6ip6 |
| 1451 | Srd5a3 |
| 1452 | Tsr1 |
| 1453 | Coq6 |
| 1454 | Dusp6 |
| 1455 | Pomt2 |
| 1456 | Wdr35 |
| 1457 | L3mbtl2 |
| 1458 | Tcf19 |
| 1459 | Slc35a1 |
| 1460 | Dclre1c |
| 1461 | 6720489N17Rik |
| 1462 | Rab23 |
| 1463 | Dhx33 |
| 1464 | Atad5 |

TABLE 2A-continued

Downregulated genes after GC + IL27 (1558 in ranked order)

| | |
|---|---|
| 1465 | Tmem70 |
| 1466 | Ttll12 |
| 1467 | Urb2 |
| 1468 | Slc39a10 |
| 1469 | Zranb2 |
| 1470 | Twistnb |
| 1471 | Polr2j |
| 1472 | Sec13 |
| 1473 | Nup88 |
| 1474 | Psma6 |
| 1475 | Camsap2 |
| 1476 | Eif4g1 |
| 1477 | Pes1 |
| 1478 | Fbxo30 |
| 1479 | Pccb |
| 1480 | Ube2n |
| 1481 | Cdca3 |
| 1482 | Recql |
| 1483 | Usp14 |
| 1484 | Prdm16 |
| 1485 | Xrcc6 |
| 1486 | Rbm34 |
| 1487 | Synj2 |
| 1488 | Ggh |
| 1489 | Thoc1 |
| 1490 | Dcaf13 |
| 1491 | Slc37a2 |
| 1492 | Sephs1 |
| 1493 | Atpaf2 |
| 1494 | Cenpm |
| 1495 | Tsfm |
| 1496 | Uqcrq |
| 1497 | Nutf2 |
| 1498 | Dpp9 |
| 1499 | Far1 |
| 1500 | Ptprk |
| 1501 | Lcp2 |
| 1502 | Psmb6 |
| 1503 | Prkar2a |
| 1504 | Tcof1 |
| 1505 | Apip |
| 1506 | Gnpnat1 |
| 1507 | Abcc4 |
| 1508 | Gtf2h4 |
| 1509 | Apoe |
| 1510 | Hsd17b12 |
| 1511 | Rwdd2b |
| 1512 | Trmu |
| 1513 | Mrpl1 |
| 1514 | Tube1 |
| 1515 | Slc7a1 |
| 1516 | Ddx20 |
| 1517 | C2cd5 |
| 1518 | Eif4a1 |
| 1519 | Rttn |
| 1520 | Ecsit |
| 1521 | Ndufab1 |
| 1522 | Crim1 |
| 1523 | Nadk |
| 1524 | Gemin5 |
| 1525 | Ndufs1 |
| 1526 | Hemk1 |
| 1527 | Neu3 |
| 1528 | Xpo1 |
| 1529 | Zcchc17 |
| 1530 | Kif4 |
| 1531 | Mthfd2 |
| 1532 | Mrps27 |
| 1533 | Pdap1 |
| 1534 | Nkiras1 |
| 1535 | Kctd14 |
| 1536 | Chrna1 |
| 1537 | Nol10 |
| 1538 | Mrpl51 |
| 1539 | Bub1b |
| 1540 | Smarcb1 |
| 1541 | Zmynd19 |
| 1542 | Ilf2 |

TABLE 2A-continued

Downregulated genes after GC + IL27 (1558 in ranked order)

| | |
|---|---|
| 1543 | Phldb1 |
| 1544 | Prr5l |
| 1545 | Gsg2 |
| 1546 | Slc16a6 |
| 1547 | Mrps11 |
| 1548 | Wls |
| 1549 | Pms1 |
| 1550 | Nsfl1c |
| 1551 | Sco1 |
| 1552 | Gas8 |
| 1553 | Sgcb |
| 1554 | Nup133 |
| 1555 | Fkbp3 |
| 1556 | Mmachc |
| 1557 | Nfkbib |
| 1558 | Pop7 |

TABLE 2B

Upregulated genes after GC + IL27 (1592 in ranked order)

| | |
|---|---|
| 1 | Baz2a |
| 2 | Rpl22l1 |
| 3 | B4galt7 |
| 4 | Asap1 |
| 5 | Srr |
| 6 | Paip2 |
| 7 | Hsdl1 |
| 8 | Reep1 |
| 9 | Pex13 |
| 10 | Mapk14 |
| 11 | Hmg20a |
| 12 | Zcchc11 |
| 13 | Zfp592 |
| 14 | Zkscan17 |
| 15 | Adam8 |
| 16 | Tmem108 |
| 17 | Lyst |
| 18 | Ppp1r12b |
| 19 | Tmem43 |
| 20 | Slc7a4 |
| 21 | Rnf38 |
| 22 | Slc25a36 |
| 23 | Arl14ep |
| 24 | Gm14308 |
| 25 | Zbtb38 |
| 26 | Klf13 |
| 27 | B3gntl1 |
| 28 | Acp6 |
| 29 | Csnk1d |
| 30 | Nxpe3 |
| 31 | Rbl2 |
| 32 | Plekha5 |
| 33 | Itgb3 |
| 34 | Tgfbr3 |
| 35 | Smim14 |
| 36 | Sec24a |
| 37 | Nit2 |
| 38 | Arhgap9 |
| 39 | Gtf2ird2 |
| 40 | A630007B06Rik |
| 41 | Zfp839 |
| 42 | Acot11 |
| 43 | Gid4 |
| 44 | Tmub2 |
| 45 | Itgav |
| 46 | S1pr4 |
| 47 | Pcnx |
| 48 | Whsc1l1 |
| 49 | Tpd52 |
| 50 | Arhgef12 |
| 51 | Cmip |
| 52 | Prkab2 |
| 53 | H2-DMb1 |
| 54 | Cers4 |

TABLE 2B-continued

Upregulated genes after GC + IL27 (1592 in ranked order)

| | |
|---|---|
| 55 | Sh2b1 |
| 56 | Bace1 |
| 57 | Acsbg1 |
| 58 | Fmnl1 |
| 59 | Cyhr1 |
| 60 | Rere |
| 61 | Afap1 |
| 62 | Cgl2 |
| 63 | Ipcef1 |
| 64 | Zyx |
| 65 | Cdk19 |
| 66 | Pex26 |
| 67 | Gm6313 |
| 68 | Plin3 |
| 69 | Crtc3 |
| 70 | Phf8 |
| 71 | Zfp956 |
| 72 | Coq10a |
| 73 | Rps2 |
| 74 | Afg3l2 |
| 75 | Gpsm1 |
| 76 | Evi5l |
| 77 | Galc |
| 78 | Rftn1 |
| 79 | Entpd4 |
| 80 | BC022687 |
| 81 | Tnfrsf14 |
| 82 | AB124611 |
| 83 | Mms19 |
| 84 | Snx14 |
| 85 | Tmem219 |
| 86 | Rpl37a |
| 87 | Zdhhc17 |
| 88 | Rps6ka3 |
| 89 | Slc2a4rg-ps |
| 90 | Gbp10 |
| 91 | Usp11 |
| 92 | Gabarap |
| 93 | Prkd2 |
| 94 | Ppox |
| 95 | Pgap1 |
| 96 | Smg6 |
| 97 | Mndal |
| 98 | C2cd2 |
| 99 | Ctss |
| 100 | Hopx |
| 101 | Acsl3 |
| 102 | Limk1 |
| 103 | Kif13b |
| 104 | Cnn2 |
| 105 | Atat1 |
| 106 | Klhdc1 |
| 107 | Slc17a5 |
| 108 | Il6st |
| 109 | Bcas3 |
| 110 | Rcor3 |
| 111 | Tmx4 |
| 112 | Itga4 |
| 113 | Zmym5 |
| 114 | Plcb3 |
| 115 | Acox3 |
| 116 | Atp7a |
| 117 | Irf6 |
| 118 | Wash |
| 119 | Mif4gd |
| 120 | Marf1 |
| 121 | Xist |
| 122 | 4930486L24Rik |
| 123 | Smyd3 |
| 124 | Dopey2 |
| 125 | Cyp4v3 |
| 126 | Sfi1 |
| 127 | Tmem141 |
| 128 | Pou2f1 |
| 129 | Efemp2 |
| 130 | Gns |
| 131 | Map1lc3b |
| 132 | Gpbp1l1 |
| 133 | Heatr2 |
| 134 | H2afv |
| 135 | Nanos1 |
| 136 | Tnrc6b |
| 137 | Sirt3 |
| 138 | Helb |
| 139 | Gbp3 |
| 140 | Rsph3b |
| 141 | 1700011J10Rik |
| 142 | Lst1 |
| 143 | Sp100 |
| 144 | Arntl |
| 145 | 4632428N05Rik |
| 146 | Ccng2 |
| 147 | Zmynd11 |
| 148 | Zeb1 |
| 149 | P2rx4 |
| 150 | BC017643 |
| 151 | Rrad |
| 152 | Flcn |
| 153 | Lsm11 |
| 154 | Lrrfip2 |
| 155 | Utrn |
| 156 | Abcg3 |
| 157 | Sqstm1 |
| 158 | Trpm4 |
| 159 | BC021614 |
| 160 | Ltb4r1 |
| 161 | Fam65a |
| 162 | Zfp688 |
| 163 | 0610030E20Rik |
| 164 | Car9 |
| 165 | Gm12942 |
| 166 | Trafd1 |
| 167 | Pfkfb3 |
| 168 | Mir703 |
| 169 | Lrig2 |
| 170 | Rnf215 |
| 171 | Rps15a-ps4 |
| 172 | Pcsk4 |
| 173 | Rreb1 |
| 174 | Slc24a6 |
| 175 | Rnf31 |
| 176 | Enah |
| 177 | Tcta |
| 178 | Tnrc6c |
| 179 | Gm4827 |
| 180 | Tk2 |
| 181 | Eno2 |
| 182 | 1700113A16Rik |
| 183 | Gm2382 |
| 184 | Zbtb25 |
| 185 | Prss16 |
| 186 | Mllt4 |
| 187 | Pisd-ps2 |
| 188 | St3gal6 |
| 189 | Sipa1l1 |
| 190 | Zfp317 |
| 191 | Mcl1 |
| 192 | Rab9 |
| 193 | Trim41 |
| 194 | Chp1 |
| 195 | Taz |
| 196 | Grap |
| 197 | Fam168a |
| 198 | Ahnak |
| 199 | Trappc6a |
| 200 | Polg2 |
| 201 | Suv420h2 |
| 202 | Trp53i11 |
| 203 | Pddc1 |
| 204 | Zrsr1 |
| 205 | Slc25a30 |
| 206 | Myadm |
| 207 | Kansl1l |
| 208 | 4833420G17Rik |
| 209 | H2-DMa |
| 210 | Fam214a |

TABLE 2B-continued

Upregulated genes after GC + IL27 (1592 in ranked order)

| | |
|---|---|
| 211 | Tmem194b |
| 212 | Osbpl1a |
| 213 | St3gal1 |
| 214 | Pcf11 |
| 215 | Idua |
| 216 | Zfp867 |
| 217 | Lmbr1l |
| 218 | 5730507C01Rik |
| 219 | Ndufa6 |
| 220 | Tspan14 |
| 221 | Ssh1 |
| 222 | Ormdl3 |
| 223 | Gbp8 |
| 224 | Gpsm3 |
| 225 | Kctd11 |
| 226 | Phxr4 |
| 227 | Slfn1 |
| 228 | Sox5 |
| 229 | Wdr91 |
| 230 | Plk1s1 |
| 231 | Bbx |
| 232 | Zfp874a |
| 233 | Gpr114 |
| 234 | Hif3a |
| 235 | Oas1b |
| 236 | Apaf1 |
| 237 | Tubg2 |
| 238 | Vamp5 |
| 239 | Lamc1 |
| 240 | Itpk1 |
| 241 | Mll5 |
| 242 | Btbd16 |
| 243 | Rps15a |
| 244 | Tmem218 |
| 245 | Rab12 |
| 246 | Hist2h2be |
| 247 | Lpin1 |
| 248 | Plekhg5 |
| 249 | Tmem123 |
| 250 | 2310067B10Rik |
| 251 | Il18 |
| 252 | Ankrd13d |
| 253 | Lamp1 |
| 254 | Kif9 |
| 255 | Ptk2b |
| 256 | 2810468N07Rik |
| 257 | Zfp580 |
| 258 | Sdf2 |
| 259 | Atf7 |
| 260 | Nol3 |
| 261 | Lancl1 |
| 262 | Chd2 |
| 263 | Zbtb7a |
| 264 | Thap4 |
| 265 | Pqlc1 |
| 266 | 1810026B05Rik |
| 267 | Zbed6 |
| 268 | Inpp4a |
| 269 | Wdr13 |
| 270 | 2900008C10Rik |
| 271 | Scand1 |
| 272 | Gramd1a |
| 273 | Prkcq |
| 274 | Acadl |
| 275 | Snrk |
| 276 | Letm2 |
| 277 | Prex1 |
| 278 | Znrf1 |
| 279 | 1700010I14Rik |
| 280 | Maf1 |
| 281 | Ptms |
| 282 | Epcam |
| 283 | Angptl6 |
| 284 | Gimap4 |
| 285 | Kdm3b |
| 286 | Ogt |
| 287 | Cdc14b |
| 288 | C920025E04Rik |
| 289 | Neurl3 |
| 290 | Tmc4 |
| 291 | Mgst3 |
| 292 | Prkacb |
| 293 | Fcho2 |
| 294 | Dennd3 |
| 295 | Gcm2 |
| 296 | Prkcz |
| 297 | Tgoln1 |
| 298 | Slc25a37 |
| 299 | Taf1d |
| 300 | Ctns |
| 301 | Dennd4c |
| 302 | Trip6 |
| 303 | Fam13b |
| 304 | Pias3 |
| 305 | H2-T10 |
| 306 | Tbc1d17 |
| 307 | Rnf149 |
| 308 | D730005E14Rik |
| 309 | Slc35f5 |
| 310 | Gm16907 |
| 311 | Sec22c |
| 312 | Flt3l |
| 313 | Tpk1 |
| 314 | Ebf1 |
| 315 | Zfp954 |
| 316 | Surf1 |
| 317 | Rfx3 |
| 318 | Cox7a2l |
| 319 | Hectd3 |
| 320 | Ccdc17 |
| 321 | Bcl3 |
| 322 | Itpr2 |
| 323 | Dock6 |
| 324 | Limk2 |
| 325 | Vstm5 |
| 326 | Eef2k |
| 327 | Rb1cc1 |
| 328 | Trpc4ap |
| 329 | Rps27 |
| 330 | Fndc3a |
| 331 | Zcchc6 |
| 332 | Crebzf |
| 333 | Ankrd50 |
| 334 | Pik3c2a |
| 335 | Wdr81 |
| 336 | Mef2a |
| 337 | Sfrs18 |
| 338 | Ifngr1 |
| 339 | Thap11 |
| 340 | Atraid |
| 341 | Rara |
| 342 | Dguok |
| 343 | Irf7 |
| 344 | Vamp4 |
| 345 | Dhx40 |
| 346 | Sipa1 |
| 347 | Prickle3 |
| 348 | Map3k1 |
| 349 | Cnppd1 |
| 350 | Lnpep |
| 351 | Casp1 |
| 352 | Golgb1 |
| 353 | Clybl |
| 354 | Chd7 |
| 355 | Optn |
| 356 | Arap2 |
| 357 | Abi3 |
| 358 | Lrrc61 |
| 359 | Fam105a |
| 360 | Casp9 |
| 361 | Ap3m2 |
| 362 | Gm4759 |
| 363 | Ankrd12 |
| 364 | Ikzf3 |
| 365 | Brwd1 |
| 366 | Ap1m2 |

TABLE 2B-continued

Upregulated genes after GC + IL27 (1592 in ranked order)

| | |
|---|---|
| 367 | Tmem159 |
| 368 | Dtx3l |
| 369 | Spata13 |
| 370 | 5830432E09Rik |
| 371 | Rps15a-ps6 |
| 372 | Rassf1 |
| 373 | Fam102b |
| 374 | E4f1 |
| 375 | Plekhb2 |
| 376 | Zfp512 |
| 377 | H2-T9 |
| 378 | BC147527 |
| 379 | Tgfbr2 |
| 380 | Snhg7 |
| 381 | Plcg1 |
| 382 | Sepw1 |
| 383 | Gm13212 |
| 384 | B3galt4 |
| 385 | Fth1 |
| 386 | Sgsm2 |
| 387 | Ctsa |
| 388 | Use1 |
| 389 | Dyrk3 |
| 390 | Eif4a2 |
| 391 | Gm11127 |
| 392 | Stx5a |
| 393 | Mplkip |
| 394 | Zfp362 |
| 395 | Snx18 |
| 396 | Msl1 |
| 397 | Nt5e |
| 398 | Plcg2 |
| 399 | Ggnbp2 |
| 400 | Rlf |
| 401 | Akap9 |
| 402 | Nr2c2 |
| 403 | Atg9a |
| 404 | 2810008D09Rik |
| 405 | Naga |
| 406 | Abhd15 |
| 407 | Rdm1 |
| 408 | Dgka |
| 409 | Usp48 |
| 410 | Usf2 |
| 411 | Pde3b |
| 412 | Vps54 |
| 413 | Capn5 |
| 414 | Fam53b |
| 415 | Oxr1 |
| 416 | Fcho1 |
| 417 | Insr |
| 418 | Parp4 |
| 419 | Igbp1 |
| 420 | Eml5 |
| 421 | 2010003O02Rik |
| 422 | Hcst |
| 423 | Maml1 |
| 424 | Atg2a |
| 425 | Ubn2 |
| 426 | Arhgef1 |
| 427 | Cux1 |
| 428 | Gpi1 |
| 429 | 1810034E14Rik |
| 430 | Wdr19 |
| 431 | Hist3h2a |
| 432 | Gm5918 |
| 433 | Itm2c |
| 434 | P2ry10 |
| 435 | Ddb2 |
| 436 | Mnt |
| 437 | Sp140 |
| 438 | Mll3 |
| 439 | Sigirr |
| 440 | Tnks1bp1 |
| 441 | Efcab4b |
| 442 | Camk2d |
| 443 | Hexdc |
| 444 | Fchsd2 |
| 445 | Ltbp4 |
| 446 | Smtn |
| 447 | Itpr3 |
| 448 | Usp53 |
| 449 | Fxyd5 |
| 450 | Dzip1 |
| 451 | Sh3yl1 |
| 452 | Kat2b |
| 453 | Rala |
| 454 | Fam98c |
| 455 | Ptpn13 |
| 456 | Srgap3 |
| 457 | F8a |
| 458 | Ccpg1 |
| 459 | Rab11fip4 |
| 460 | Pfdn5 |
| 461 | Atxn7l1 |
| 462 | Tmem66 |
| 463 | Ercc5 |
| 464 | Il33 |
| 465 | Slc12a6 |
| 466 | Fhod1 |
| 467 | Gtf2i |
| 468 | Zfp768 |
| 469 | Dusp7 |
| 470 | Cst7 |
| 471 | Ubald1 |
| 472 | Lbh |
| 473 | Zfp354c |
| 474 | Pan2 |
| 475 | Glcci1 |
| 476 | Ttc38 |
| 477 | Kif7 |
| 478 | Rasgrp2 |
| 479 | Mctp2 |
| 480 | Tanc1 |
| 481 | 2310001H17Rik |
| 482 | Yes1 |
| 483 | Kxd1 |
| 484 | Fam210b |
| 485 | Irgq |
| 486 | Zfp358 |
| 487 | Airn |
| 488 | 4932415G12Rik |
| 489 | Stab1 |
| 490 | C030039L03Rik |
| 491 | Arl5c |
| 492 | Peli1 |
| 493 | Fbxo32 |
| 494 | Cd97 |
| 495 | Rbm33 |
| 496 | Zbtb2 |
| 497 | Lgr4 |
| 498 | Rab11fip1 |
| 499 | Gdpd5 |
| 500 | Ing2 |
| 501 | Psrc1 |
| 502 | Inpp1 |
| 503 | A930015D03Rik |
| 504 | Fchsd1 |
| 505 | Nudt18 |
| 506 | Sytl1 |
| 507 | Zfp97 |
| 508 | Gpt |
| 509 | Irs2 |
| 510 | Rapgef4 |
| 511 | Pycard |
| 512 | Pkn1 |
| 513 | Mettl20 |
| 514 | Trim14 |
| 515 | Amz2 |
| 516 | Satb1 |
| 517 | Tbcel |
| 518 | Ar |
| 519 | Patz1 |
| 520 | Thap3 |
| 521 | Laptm5 |
| 522 | Myo6 |

TABLE 2B-continued

Upregulated genes after GC + IL27 (1592 in ranked order)

| # | Gene |
|---|---|
| 523 | Cd1d1 |
| 524 | Jak3 |
| 525 | Glul |
| 526 | Rec8 |
| 527 | Rgp1 |
| 528 | Zfp429 |
| 529 | Gltscr2 |
| 530 | Cblb |
| 531 | Susd3 |
| 532 | Abca7 |
| 533 | Tnip2 |
| 534 | Inpp5k |
| 535 | Smarca2 |
| 536 | Aldoa |
| 537 | Zyg11b |
| 538 | Gm2a |
| 539 | Egln3 |
| 540 | Tpra1 |
| 541 | Pld2 |
| 542 | 2810013P06Rik |
| 543 | Sesn3 |
| 544 | Pde4d |
| 545 | Gna13 |
| 546 | Ddx50 |
| 547 | Atp5sl |
| 548 | Ypel5 |
| 549 | Mlxip |
| 550 | Slc22a15 |
| 551 | BC068157 |
| 552 | Kbtbd3 |
| 553 | Dip2a |
| 554 | Ccdc92 |
| 555 | Gja1 |
| 556 | Oxld1 |
| 557 | Tmem167b |
| 558 | Ccdc88c |
| 559 | Whamm |
| 560 | Fau |
| 561 | Sdf4 |
| 562 | Panx1 |
| 563 | Smpd1 |
| 564 | Rasa3 |
| 565 | Acp5 |
| 566 | Hip1r |
| 567 | Zfp260 |
| 568 | Fam102a |
| 569 | Gltscr1l |
| 570 | Scpep1 |
| 571 | Tnfaip3 |
| 572 | Zmym6 |
| 573 | Mnda |
| 574 | I730030J21Rik |
| 575 | Wdtc1 |
| 576 | Gpr146 |
| 577 | Rictor |
| 578 | Rnf138 |
| 579 | Zfp622 |
| 580 | 1600014C10Rik |
| 581 | D4Wsu53e |
| 582 | Kcnk7 |
| 583 | Mt1 |
| 584 | Arrdc2 |
| 585 | Atf7ip |
| 586 | Mfge8 |
| 587 | Pde1b |
| 588 | Megf9 |
| 589 | Phf21a |
| 590 | Pstpip1 |
| 591 | Fam149b |
| 592 | E330033B04Rik |
| 593 | Uhrf2 |
| 594 | Tctex1d1 |
| 595 | Cd200r4 |
| 596 | 9030624G23Rik |
| 597 | Ropn1l |
| 598 | Cyp4f13 |
| 599 | Uvrag |
| 600 | Carf |
| 601 | Sgpl1 |
| 602 | Fkbp7 |
| 603 | Dym |
| 604 | Smad1 |
| 605 | Sord |
| 606 | Irf1 |
| 607 | Sdc3 |
| 608 | Leng8 |
| 609 | Serinc5 |
| 610 | Cela1 |
| 611 | Mgarp |
| 612 | Crbn |
| 613 | Aaed1 |
| 614 | Ccdc28a |
| 615 | Apbb1 |
| 616 | Pak1 |
| 617 | Gm16845 |
| 618 | Dyx1c1 |
| 619 | E130317F20Rik |
| 620 | Nfatc3 |
| 621 | Spsb2 |
| 622 | Mob2 |
| 623 | 4931428F04Rik |
| 624 | Rhog |
| 625 | Ccser2 |
| 626 | Zkscan14 |
| 627 | Ctsl |
| 628 | 9130221F21Rik |
| 629 | Sepp1 |
| 630 | Lrrk2 |
| 631 | Arhgap27 |
| 632 | Zfp821 |
| 633 | Srpk2 |
| 634 | Nat2 |
| 635 | Vopp1 |
| 636 | Btg2 |
| 637 | 4921511C10Rik |
| 638 | Nbeal1 |
| 639 | 4932438A13Rik |
| 640 | Acpl2 |
| 641 | Birc2 |
| 642 | Wdr45 |
| 643 | Adora2a |
| 644 | Il17ra |
| 645 | Emb |
| 646 | Pxk |
| 647 | Lsp1 |
| 648 | Mapk8ip3 |
| 649 | Eif3f |
| 650 | Lat2 |
| 651 | Bcar1 |
| 652 | Arhgef25 |
| 653 | Cd151 |
| 654 | Gm10845 |
| 655 | Tm6sf1 |
| 656 | Nipbl |
| 657 | Slc48a1 |
| 658 | A930013F10Rik |
| 659 | Pacs1 |
| 660 | Kdelr1 |
| 661 | B630005N14Rik |
| 662 | Tbc1d23 |
| 663 | Sp4 |
| 664 | E130112N10Rik |
| 665 | 4933409K07Rik |
| 666 | Xlr3a |
| 667 | Trim46 |
| 668 | Ttyh2 |
| 669 | Smad7 |
| 670 | Lcorl |
| 671 | Cd37 |
| 672 | Prkra |
| 673 | Arhgef9 |
| 674 | 4931406C07Rik |
| 675 | Rftn2 |
| 676 | Vamp1 |
| 677 | Trim7 |
| 678 | Cercam |

TABLE 2B-continued

Upregulated genes after GC + IL27 (1592 in ranked order)

| | |
|---|---|
| 679 | BC029214 |
| 680 | Snhg10 |
| 681 | Fam78a |
| 682 | Pear1 |
| 683 | 1110038B12Rik |
| 684 | Ccl27a |
| 685 | Arhgap25 |
| 686 | B130006D01Rik |
| 687 | Qsox1 |
| 688 | Gimap1 |
| 689 | Slc39a13 |
| 690 | Ankzf1 |
| 691 | 1600016N20Rik |
| 692 | Zfp395 |
| 693 | Bmpr1a |
| 694 | Tfdp2 |
| 695 | Pik3ap1 |
| 696 | Pld3 |
| 697 | Rnf19a |
| 698 | Tmem59 |
| 699 | Tmem221 |
| 700 | Sgms1 |
| 701 | Atp1a3 |
| 702 | Camkk1 |
| 703 | Gm9846 |
| 704 | 2410004N09Rik |
| 705 | Slc9a9 |
| 706 | Snx29 |
| 707 | H2-Ke6 |
| 708 | Hdac5 |
| 709 | Insrr |
| 710 | Cbx7 |
| 711 | Gyg |
| 712 | Akap8l |
| 713 | Bckdha |
| 714 | Sertad3 |
| 715 | Glrx |
| 716 | Ttc17 |
| 717 | Smpdl3a |
| 718 | Wbp1 |
| 719 | Tlr6 |
| 720 | Cnnm2 |
| 721 | Mrgpre |
| 722 | Dusp22 |
| 723 | Hscb |
| 724 | Rcn3 |
| 725 | Ptpn22 |
| 726 | Fyco1 |
| 727 | 2210039B01Rik |
| 728 | Dcaf15 |
| 729 | Hpse |
| 730 | Frat1 |
| 731 | Runx3 |
| 732 | H2-Q4 |
| 733 | Rell1 |
| 734 | Polr3gl |
| 735 | Synpo |
| 736 | Atp2b4 |
| 737 | Armcx6 |
| 738 | Slc37a4 |
| 739 | Fgd3 |
| 740 | Pgap3 |
| 741 | Guca1a |
| 742 | Narf |
| 743 | H2-Ob |
| 744 | Fbxo36 |
| 745 | Mettl7a1 |
| 746 | Kctd2 |
| 747 | Brdt |
| 748 | Wasl |
| 749 | Zfp963 |
| 750 | Ubac2 |
| 751 | 9930111J21Rik1 |
| 752 | H2-Q5 |
| 753 | Zfp120 |
| 754 | Agbl5 |
| 755 | 4930581F22Rik |
| 756 | Accs |
| 757 | Dcaf6 |
| 758 | Gm16515 |
| 759 | Rabac1 |
| 760 | Dock9 |
| 761 | Ccdc111 |
| 762 | Gm19757 |
| 763 | Dgat1 |
| 764 | Igflr1 |
| 765 | Ppp6r2 |
| 766 | Doc2g |
| 767 | Atg12 |
| 768 | Irf2 |
| 769 | Med12l |
| 770 | Syt5 |
| 771 | 1600020E01Rik |
| 772 | Crispld2 |
| 773 | Galnt6 |
| 774 | Clcf1 |
| 775 | Rac3 |
| 776 | Cul9 |
| 777 | Slc2a8 |
| 778 | Ssh2 |
| 779 | Adamts10 |
| 780 | 2810403D21Rik |
| 781 | Lrp5 |
| 782 | Cass4 |
| 783 | Adam9 |
| 784 | Rusc1 |
| 785 | Tpst2 |
| 786 | Obsl1 |
| 787 | Zfp292 |
| 788 | Lgals8 |
| 789 | Per1 |
| 790 | Cpne8 |
| 791 | Bach1 |
| 792 | Zc3h6 |
| 793 | 2900076A07Rik |
| 794 | Snhg5 |
| 795 | Sh3glb1 |
| 796 | Lyn |
| 797 | Gab3 |
| 798 | Zfp831 |
| 799 | Zfp516 |
| 800 | Stard10 |
| 801 | Gltscr1 |
| 802 | Pde4c |
| 803 | Fam195b |
| 804 | Cacnb3 |
| 805 | Prdm1 |
| 806 | Syngr3 |
| 807 | Ndrg4 |
| 808 | Gm3414 |
| 809 | Gnaq |
| 810 | Dand5 |
| 811 | Arhgap15 |
| 812 | Rasa4 |
| 813 | Nfkbil1 |
| 814 | Tax1bp3 |
| 815 | Kdm5b |
| 816 | Pfn2 |
| 817 | Usp3 |
| 818 | Mthfs |
| 819 | Camk2n1 |
| 820 | Abr |
| 821 | Tanc2 |
| 822 | Tbc1d14 |
| 823 | Fas |
| 824 | Slc38a9 |
| 825 | Foxn3 |
| 826 | Tmem163 |
| 827 | Unc119b |
| 828 | Cdc42ep4 |
| 829 | Mllt3 |
| 830 | Gatsl2 |
| 831 | Fscn1 |
| 832 | Gimap3 |
| 833 | Snrnp48 |
| 834 | Zfp949 |

TABLE 2B-continued

Upregulated genes after GC + IL27 (1592 in ranked order)

| | |
|---|---|
| 835 | Lemd2 |
| 836 | Zfp341 |
| 837 | Zfp874b |
| 838 | Slc31a2 |
| 839 | 2900026A02Rik |
| 840 | Nicn1 |
| 841 | Dhrs3 |
| 842 | Sgk1 |
| 843 | Npc2 |
| 844 | Gm15800 |
| 845 | Slc25a45 |
| 846 | 1810032O08Rik |
| 847 | Arhgef4 |
| 848 | Tmem171 |
| 849 | 4931406H21Rik |
| 850 | Sun2 |
| 851 | Zfp652 |
| 852 | Gpr18 |
| 853 | Hdac7 |
| 854 | Ssh3 |
| 855 | Il11ra1 |
| 856 | Rab37 |
| 857 | 2210417K05Rik |
| 858 | Xpa |
| 859 | Pnpla7 |
| 860 | Ly6c1 |
| 861 | 9430091E24Rik |
| 862 | Dixdc1 |
| 863 | Rdh12 |
| 864 | Zfp85-rs1 |
| 865 | Osbpl5 |
| 866 | Tmem63a |
| 867 | Ccnl2 |
| 868 | Podnl1 |
| 869 | Sft2d3 |
| 870 | A430078G23Rik |
| 871 | Slc2a9 |
| 872 | Zfp36 |
| 873 | Rnf114 |
| 874 | H2-Eb1 |
| 875 | Rnase4 |
| 876 | Zfp784 |
| 877 | Cd28 |
| 878 | Kbtbd11 |
| 879 | Hist2h2aa1 |
| 880 | Styk1 |
| 881 | Tle6 |
| 882 | Arl4c |
| 883 | Arsg |
| 884 | Shisa2 |
| 885 | Cml1 |
| 886 | Mast1 |
| 887 | Amica1 |
| 888 | Zbtb4 |
| 889 | Akap5 |
| 890 | Impa2 |
| 891 | Zfyve1 |
| 892 | Hpcal1 |
| 893 | Aqp11 |
| 894 | Arfgap3 |
| 895 | Kcnq2 |
| 896 | Vmac |
| 897 | Tulp4 |
| 898 | Tcf4 |
| 899 | Tfr2 |
| 900 | A530072M11Rik |
| 901 | Zfp383 |
| 902 | Filip1 |
| 903 | Hdac4 |
| 904 | Gm17762 |
| 905 | Lsr |
| 906 | Kif21b |
| 907 | Dkkl1 |
| 908 | N4bp1 |
| 909 | Smurf2 |
| 910 | A930024E05Rik |
| 911 | Slc25a23 |
| 912 | Ralgapa2 |
| 913 | Ndst1 |
| 914 | Eva1b |
| 915 | Fam193b |
| 916 | Clk1 |
| 917 | Tigit |
| 918 | Folr4 |
| 919 | Cd109 |
| 920 | Jag2 |
| 921 | Jakmip1 |
| 922 | Atg16l2 |
| 923 | 2310047M10Rik |
| 924 | Qprt |
| 925 | Rad52 |
| 926 | Zfp787 |
| 927 | Gramd4 |
| 928 | Neb |
| 929 | Gbp2 |
| 930 | Trim62 |
| 931 | Dexi |
| 932 | Sqrdl |
| 933 | Themis2 |
| 934 | Appl2 |
| 935 | Eif2ak3 |
| 936 | Vdr |
| 937 | Slc26a11 |
| 938 | Cir1 |
| 939 | Blvrb |
| 940 | Hmha1 |
| 941 | Ttyh3 |
| 942 | Dap |
| 943 | Ltbp3 |
| 944 | Pacsin3 |
| 945 | Ube2h |
| 946 | Isoc2b |
| 947 | Malat1 |
| 948 | Kcnip2 |
| 949 | Prnp |
| 950 | Gm10658 |
| 951 | Rasgrp4 |
| 952 | Slc27a1 |
| 953 | Gm12216 |
| 954 | Pcmtd2 |
| 955 | Apol7b |
| 956 | Apol7e |
| 957 | Nipal3 |
| 958 | Tmem220 |
| 959 | Itgae |
| 960 | Foxo3 |
| 961 | Gpc1 |
| 962 | Gpr160 |
| 963 | Cox7a1 |
| 964 | 5430416N02Rik |
| 965 | B3gnt9 |
| 966 | Serpinb6b |
| 967 | Plekhg2 |
| 968 | Itgb7 |
| 969 | Mt2 |
| 970 | Tmsb15l |
| 971 | Cage1 |
| 972 | Sfrp2 |
| 973 | Acap1 |
| 974 | Fyb |
| 975 | Fkbp5 |
| 976 | H2-Q1 |
| 977 | Sorl1 |
| 978 | 1700001O22Rik |
| 979 | Ss18l1 |
| 980 | Pbxip1 |
| 981 | Eaf2 |
| 982 | 2610204G22Rik |
| 983 | 2010016I18Rik |
| 984 | Klc4 |
| 985 | 3110056K07Rik |
| 986 | Izumo4 |
| 987 | Fam132a |
| 988 | Icos |
| 989 | Ston2 |
| 990 | Gabbr1 |

TABLE 2B-continued

Upregulated genes after GC + IL27 (1592 in ranked order)

| | |
|---|---|
| 991 | Tead2 |
| 992 | Rhod |
| 993 | Tmem140 |
| 994 | Vill |
| 995 | Tsix |
| 996 | Gm19557 |
| 997 | Rgs11 |
| 998 | Ddit3 |
| 999 | Zfp524 |
| 1000 | Ccni |
| 1001 | Gm20098 |
| 1002 | Kremen2 |
| 1003 | Syt12 |
| 1004 | a |
| 1005 | 9330151L19Rik |
| 1006 | Thra |
| 1007 | Gm4285 |
| 1008 | Zfp945 |
| 1009 | Apc2 |
| 1010 | Pacs2 |
| 1011 | Jmy |
| 1012 | Tcn2 |
| 1013 | Ulk1 |
| 1014 | Col11a2 |
| 1015 | Cdnf |
| 1016 | Il7r |
| 1017 | Pram1 |
| 1018 | Rarg |
| 1019 | 6330403M23Rik |
| 1020 | Rwdd2a |
| 1021 | Gpr137b-ps |
| 1022 | Rnf128 |
| 1023 | Zfp30 |
| 1024 | Fam171b |
| 1025 | Usp35 |
| 1026 | Cysltr2 |
| 1027 | Ston1 |
| 1028 | Gm14305 |
| 1029 | Itfg3 |
| 1030 | Entpd1 |
| 1031 | 4933439C10Rik |
| 1032 | Rab6b |
| 1033 | Vgll4 |
| 1034 | Zfp69 |
| 1035 | Irak3 |
| 1036 | Pion |
| 1037 | Arhgef10 |
| 1038 | Hhat |
| 1039 | Ccr2 |
| 1040 | Dtx3 |
| 1041 | Lypd6b |
| 1042 | Adrb2 |
| 1043 | Pdcd4 |
| 1044 | Jhdm1d |
| 1045 | Nnat |
| 1046 | Tiparp |
| 1047 | Lynx1 |
| 1048 | Heca |
| 1049 | Pnrc1 |
| 1050 | Aldh6a1 |
| 1051 | Usp28 |
| 1052 | Bnip3l |
| 1053 | Atg14 |
| 1054 | Gm16973 |
| 1055 | Oit3 |
| 1056 | Sipa1l2 |
| 1057 | Dlg4 |
| 1058 | Sfxn3 |
| 1059 | Gzf1 |
| 1060 | Prss41 |
| 1061 | Stom |
| 1062 | Abcg1 |
| 1063 | Rras |
| 1064 | Aldh1l1 |
| 1065 | Mpp2 |
| 1066 | Col7a1 |
| 1067 | Dach2 |
| 1068 | Pgm2l1 |
| 1069 | Gimap6 |
| 1070 | 9330179D12Rik |
| 1071 | Ifit1 |
| 1072 | Maml3 |
| 1073 | Dab2 |
| 1074 | Osgin1 |
| 1075 | Tmem176a |
| 1076 | Haao |
| 1077 | Pitpnc1 |
| 1078 | Sult2b1 |
| 1079 | Snhg1 |
| 1080 | Tecpr1 |
| 1081 | Tjp3 |
| 1082 | Ttc12 |
| 1083 | Mapre3 |
| 1084 | Il1r2 |
| 1085 | Nrbp2 |
| 1086 | Ddx60 |
| 1087 | Card6 |
| 1088 | Mapk8ip1 |
| 1089 | Amigo1 |
| 1090 | Napb |
| 1091 | Fam65b |
| 1092 | Lgals6 |
| 1093 | R74862 |
| 1094 | Ddit4 |
| 1095 | Tmem176b |
| 1096 | Fbxl12 |
| 1097 | Kdm4b |
| 1098 | Rnf130 |
| 1099 | Ntng2 |
| 1100 | Abhd14b |
| 1101 | Tet2 |
| 1102 | Kazald1 |
| 1103 | Ezh1 |
| 1104 | Metrnl |
| 1105 | Bend6 |
| 1106 | H2-Q2 |
| 1107 | Tet1 |
| 1108 | Gm9199 |
| 1109 | Gigyf1 |
| 1110 | 5830418P13Rik |
| 1111 | Plag1 |
| 1112 | Asb2 |
| 1113 | Rnf167 |
| 1114 | Ctdsp2 |
| 1115 | Kiss1r |
| 1116 | B3gnt8 |
| 1117 | Lag3 |
| 1118 | Ppp1r13l |
| 1119 | Paqr7 |
| 1120 | Zfp467 |
| 1121 | Rab31 |
| 1122 | H2-K2 |
| 1123 | Gngt2 |
| 1124 | Irak2 |
| 1125 | Khnyn |
| 1126 | Rnf166 |
| 1127 | Tmem91 |
| 1128 | Ing4 |
| 1129 | Trerf1 |
| 1130 | Mss51 |
| 1131 | Fbxl20 |
| 1132 | Noxo1 |
| 1133 | A930016O22Rik |
| 1134 | Arid5b |
| 1135 | Fam161a |
| 1136 | Klhl6 |
| 1137 | Arhgap26 |
| 1138 | A630072M18Rik |
| 1139 | Gimap7 |
| 1140 | Prss30 |
| 1141 | Nfil3 |
| 1142 | Acer2 |
| 1143 | Bmf |
| 1144 | Snx21 |
| 1145 | 2810408A11Rik |
| 1146 | Wnt4 |

TABLE 2B-continued

Upregulated genes after GC + IL27 (1592 in ranked order)

| | |
|---|---|
| 1147 | Map1lc3a |
| 1148 | H2-Q9 |
| 1149 | Ccdc117 |
| 1150 | Disp1 |
| 1151 | Zpbp2 |
| 1152 | P4ha2 |
| 1153 | 2210408F21Rik |
| 1154 | Msantd1 |
| 1155 | Ppp4r1l-ps |
| 1156 | Parp6 |
| 1157 | Macrod1 |
| 1158 | Adck3 |
| 1159 | Zfp629 |
| 1160 | Fam117b |
| 1161 | Dirc2 |
| 1162 | Cdkn1b |
| 1163 | Sap25 |
| 1164 | Zer1 |
| 1165 | Cxcr6 |
| 1166 | Fbxl8 |
| 1167 | Emp1 |
| 1168 | Tenc1 |
| 1169 | Prtn3 |
| 1170 | 1110007C09Rik |
| 1171 | Gpr125 |
| 1172 | Trp53inp1 |
| 1173 | Ntf5 |
| 1174 | Plcxd1 |
| 1175 | 4930402H24Rik |
| 1176 | Map3k15 |
| 1177 | Aldoc |
| 1178 | 4930579K19Rik |
| 1179 | Gm11110 |
| 1180 | Kdelr3 |
| 1181 | Klf9 |
| 1182 | Gbe1 |
| 1183 | Pold4 |
| 1184 | Sorcs2 |
| 1185 | Mpzl2 |
| 1186 | Samhd1 |
| 1187 | 2810029C07Rik |
| 1188 | C1qtnf4 |
| 1189 | Serpinb1b |
| 1190 | Lgi4 |
| 1191 | Camk2b |
| 1192 | Plekha4 |
| 1193 | Ctla2b |
| 1194 | Pbx4 |
| 1195 | Apln |
| 1196 | 1500012F01Rik |
| 1197 | Ctla2a |
| 1198 | Igf1r |
| 1199 | Ovgp1 |
| 1200 | Ccno |
| 1201 | Gprc5a |
| 1202 | Apbb2 |
| 1203 | Tmie |
| 1204 | Arrb1 |
| 1205 | Plekha7 |
| 1206 | Cd93 |
| 1207 | Nod2 |
| 1208 | Hyi |
| 1209 | Tmem71 |
| 1210 | Mmp11 |
| 1211 | Cpeb2 |
| 1212 | Wdr96 |
| 1213 | Klrc3 |
| 1214 | Ctsw |
| 1215 | Insl3 |
| 1216 | Kcnab3 |
| 1217 | Btg1 |
| 1218 | Copz2 |
| 1219 | Spata2l |
| 1220 | Rsad2 |
| 1221 | Vldlr |
| 1222 | Zfp36l2 |
| 1223 | Gab2 |
| 1224 | BC028528 |
| 1225 | Phf1 |
| 1226 | Klf10 |
| 1227 | Dnm3 |
| 1228 | Pygl |
| 1229 | Sdc4 |
| 1230 | Atp10d |
| 1231 | Aplp1 |
| 1232 | Ddr1 |
| 1233 | Asap3 |
| 1234 | Bzrap1 |
| 1235 | Arhgef18 |
| 1236 | Zbtb20 |
| 1237 | Cxcr4 |
| 1238 | Rbm47 |
| 1239 | Scel |
| 1240 | Crebl2 |
| 1241 | Gstm1 |
| 1242 | 5830454E08Rik |
| 1243 | Mylip |
| 1244 | Thada |
| 1245 | Acpp |
| 1246 | Sytl2 |
| 1247 | Rhov |
| 1248 | Tmem8b |
| 1249 | E130102H24Rik |
| 1250 | Dok4 |
| 1251 | Lonrf3 |
| 1252 | Gramd3 |
| 1253 | Ceacam15 |
| 1254 | Tha1 |
| 1255 | 4921525B02Rik |
| 1256 | Grina |
| 1257 | Chit1 |
| 1258 | Gm4013 |
| 1259 | Lmtk3 |
| 1260 | Shpk |
| 1261 | Frmd4b |
| 1262 | Kit |
| 1263 | Tbkbp1 |
| 1264 | Dbp |
| 1265 | Cnbd2 |
| 1266 | Pink1 |
| 1267 | Kifc2 |
| 1268 | Scml4 |
| 1269 | Plekhf1 |
| 1270 | Cxcr1 |
| 1271 | Dapk1 |
| 1272 | Tmem191c |
| 1273 | Adamtsl5 |
| 1274 | Runx1 |
| 1275 | Dyrk1b |
| 1276 | Dusp2 |
| 1277 | Abtb1 |
| 1278 | Parp16 |
| 1279 | Man1c1 |
| 1280 | B3galt5 |
| 1281 | Myo1h |
| 1282 | Carns1 |
| 1283 | Plaur |
| 1284 | Fbxo10 |
| 1285 | Pde4b |
| 1286 | Zbtb42 |
| 1287 | Abcd2 |
| 1288 | 2410066E13Rik |
| 1289 | Naprt1 |
| 1290 | Sgip1 |
| 1291 | Tesc |
| 1292 | Kank2 |
| 1293 | Ip6k1 |
| 1294 | Gpld1 |
| 1295 | Hbp1 |
| 1296 | Klra18 |
| 1297 | Spred3 |
| 1298 | Rnf122 |
| 1299 | Sept4 |
| 1300 | Snhg12 |
| 1301 | Tmem51 |
| 1302 | Esm1 |

TABLE 2B-continued

Upregulated genes after GC + IL27 (1592 in ranked order)

| | |
|---|---|
| 1303 | Dpf1 |
| 1304 | Tmem45a |
| 1305 | H2-Ab1 |
| 1306 | Cd68 |
| 1307 | Slc38a8 |
| 1308 | Lcn4 |
| 1309 | Bend5 |
| 1310 | 5730508B09Rik |
| 1311 | Zcchc24 |
| 1312 | Cacnb4 |
| 1313 | 4831440E17Rik |
| 1314 | Sema4f |
| 1315 | Malt1 |
| 1316 | Lgals4 |
| 1317 | Pla2g4e |
| 1318 | Calcoco1 |
| 1319 | Gm2011 |
| 1320 | Myh7b |
| 1321 | 5830416P10Rik |
| 1322 | Bcl2l15 |
| 1323 | Lrrc25 |
| 1324 | Mex3b |
| 1325 | Kctd12 |
| 1326 | Got1l1 |
| 1327 | Fam46c |
| 1328 | 2410006H16Rik |
| 1329 | Aqp3 |
| 1330 | Aif1l |
| 1331 | Rasgef1a |
| 1332 | Hdac11 |
| 1333 | Fmo5 |
| 1334 | Gpx8 |
| 1335 | Bhlhe41 |
| 1336 | Btn1a1 |
| 1337 | Tceal1 |
| 1338 | 2210404O07Rik |
| 1339 | Nfia |
| 1340 | Akap7 |
| 1341 | 1700084E18Rik |
| 1342 | Slc41a3 |
| 1343 | 6430531B16Rik |
| 1344 | Ccdc114 |
| 1345 | Inha |
| 1346 | 4930565N06Rik |
| 1347 | Acrbp |
| 1348 | 4930429F24Rik |
| 1349 | Slc15a2 |
| 1350 | Tubb4a |
| 1351 | Ctsf |
| 1352 | Serpinb1a |
| 1353 | Bbc3 |
| 1354 | 5033411D12Rik |
| 1355 | Fam184b |
| 1356 | Tceal3 |
| 1357 | Eml1 |
| 1358 | Pdk2 |
| 1359 | D630029K05Rik |
| 1360 | Sv2c |
| 1361 | Gfra1 |
| 1362 | Chst15 |
| 1363 | Cd163l1 |
| 1364 | Id1 |
| 1365 | 2310015A10Rik |
| 1366 | Fam114a1 |
| 1367 | Fry |
| 1368 | Ablim2 |
| 1369 | 2610035D17Rik |
| 1370 | 1700012B09Rik |
| 1371 | Deptor |
| 1372 | Col18a1 |
| 1373 | Ddah2 |
| 1374 | A330023F24Rik |
| 1375 | Tle2 |
| 1376 | Ypel3 |
| 1377 | LOC100503496 |
| 1378 | 9430083A17Rik |
| 1379 | 4933406I18Rik |
| 1380 | B430306N03Rik |
| 1381 | Bahcc1 |
| 1382 | Fam71f2 |
| 1383 | Rdh9 |
| 1384 | Zcchc18 |
| 1385 | Adssl1 |
| 1386 | Selm |
| 1387 | 1810011H11Rik |
| 1388 | Ypel4 |
| 1389 | Mboat2 |
| 1390 | Wipi1 |
| 1391 | Mxd1 |
| 1392 | Tspan9 |
| 1393 | Cyp2s1 |
| 1394 | Gck |
| 1395 | Ramp3 |
| 1396 | Gnaz |
| 1397 | Acss1 |
| 1398 | Spsb1 |
| 1399 | Ica1l |
| 1400 | Ramp1 |
| 1401 | Pls1 |
| 1402 | Klrb1f |
| 1403 | Gpc2 |
| 1404 | N4bp2l1 |
| 1405 | Fam217b |
| 1406 | Txnip |
| 1407 | Ndrg1 |
| 1408 | Matk |
| 1409 | Zscan2 |
| 1410 | Capn11 |
| 1411 | Lhx6 |
| 1412 | B930003M22Rik |
| 1413 | Crebrf |
| 1414 | Casz1 |
| 1415 | Rgs9 |
| 1416 | Mxd4 |
| 1417 | Tmcc3 |
| 1418 | Dok7 |
| 1419 | Cntnap1 |
| 1420 | Dntt |
| 1421 | Abca1 |
| 1422 | Alpk2 |
| 1423 | Slc41a2 |
| 1424 | Optc |
| 1425 | Stbd1 |
| 1426 | Col20a1 |
| 1427 | Cd33 |
| 1428 | Axin2 |
| 1429 | Tcp11l2 |
| 1430 | Ffar2 |
| 1431 | Cdc42ep2 |
| 1432 | Selenbp2 |
| 1433 | Ccl5 |
| 1434 | Klhl24 |
| 1435 | Mas1 |
| 1436 | Selenbp1 |
| 1437 | Dsg2 |
| 1438 | A730043L09Rik |
| 1439 | Klf4 |
| 1440 | Krt18 |
| 1441 | Atp7b |
| 1442 | Cstad |
| 1443 | Pglyrp1 |
| 1444 | Wdr95 |
| 1445 | Leprel4 |
| 1446 | Cacna1s |
| 1447 | Sema3f |
| 1448 | Dlgap1 |
| 1449 | Pkp2 |
| 1450 | Pyroxd2 |
| 1451 | Arrdc4 |
| 1452 | Smtnl2 |
| 1453 | Itga1 |
| 1454 | Thsd7b |
| 1455 | Gpr56 |
| 1456 | Glis1 |
| 1457 | Jup |
| 1458 | Dnahc10 |

TABLE 2B-continued

Upregulated genes after GC + IL27 (1592 in ranked order)

| | |
|---|---|
| 1459 | Gzmk |
| 1460 | Ptges |
| 1461 | Atp2a1 |
| 1462 | Dtx1 |
| 1463 | Cd24a |
| 1464 | Dgkg |
| 1465 | Serpinf1 |
| 1466 | Efhc1 |
| 1467 | Lamc2 |
| 1468 | Tbx6 |
| 1469 | Bcl2l11 |
| 1470 | Sema3a |
| 1471 | Otud1 |
| 1472 | Gm20139 |
| 1473 | Tnfsf13b |
| 1474 | Ust |
| 1475 | Fgfr1 |
| 1476 | Afap1l1 |
| 1477 | Acvrl1 |
| 1478 | Snx20 |
| 1479 | Cyp46a1 |
| 1480 | Shd |
| 1481 | Dapk2 |
| 1482 | Kcna4 |
| 1483 | Chn2 |
| 1484 | Card10 |
| 1485 | Gm19705 |
| 1486 | Adamtsl4 |
| 1487 | Map3k9 |
| 1488 | Gzma |
| 1489 | Dnm1 |
| 1490 | Rassf6 |
| 1491 | Agap1 |
| 1492 | Zfp13 |
| 1493 | Gm5122 |
| 1494 | Ier5l |
| 1495 | AF529169 |
| 1496 | Rapgef3 |
| 1497 | Nxpe4 |
| 1498 | Ssc5d |
| 1499 | Zfr2 |
| 1500 | Ecm1 |
| 1501 | Ypel2 |
| 1502 | Trib2 |
| 1503 | Npcd |
| 1504 | C3 |
| 1505 | Enpp2 |
| 1506 | Irgc1 |
| 1507 | Pde2a |
| 1508 | Fam183b |
| 1509 | Pou6f1 |
| 1510 | Igsf5 |
| 1511 | Hlx |
| 1512 | Cyp2d22 |
| 1513 | Frat2 |
| 1514 | Endou |
| 1515 | Lin7b |
| 1516 | Pik3ip1 |
| 1517 | Itga11 |
| 1518 | Ovol2 |
| 1519 | Hs3st6 |
| 1520 | Nrep |
| 1521 | Bcl6 |
| 1522 | Plcd1 |
| 1523 | Spns2 |
| 1524 | Efna1 |
| 1525 | Baiap3 |
| 1526 | Rbm20 |
| 1527 | 5930412G12Rik |
| 1528 | E230016M11Rik |
| 1529 | Mmp15 |
| 1530 | Rassf4 |
| 1531 | Ace |
| 1532 | Gjc2 |
| 1533 | Matn1 |
| 1534 | Mfi2 |
| 1535 | Gipr |
| 1536 | Gpnmb |
| 1537 | Col24a1 |
| 1538 | 5031434O11Rik |
| 1539 | Tsc22d3 |
| 1540 | Sbsn |
| 1541 | BC021767 |
| 1542 | Mcin |
| 1543 | Prss55 |
| 1544 | Sertad4 |
| 1545 | Srms |
| 1546 | Muc2 |
| 1547 | Hey1 |
| 1548 | P2ry4 |
| 1549 | Sult5a1 |
| 1550 | Flt4 |
| 1551 | Adamtsl3 |
| 1552 | Bmp2 |
| 1553 | Kif1a |
| 1554 | Itgam |
| 1555 | Tnnt3 |
| 1556 | Ghr |
| 1557 | Slc30a3 |
| 1558 | Itga7 |
| 1559 | Porcn |
| 1560 | Epha7 |
| 1561 | Grin1 |
| 1562 | Ret |
| 1563 | Gm4926 |
| 1564 | D630041G03Rik |
| 1565 | 1700023L04Rik |
| 1566 | Fam5c |
| 1567 | Miat |
| 1568 | Mpped2 |
| 1569 | 4933433H22Rik |
| 1570 | Gm11435 |
| 1571 | Atp8a2 |
| 1572 | Il10 |
| 1573 | Mef2b |
| 1574 | Stac2 |
| 1575 | Fn3k |
| 1576 | Htra3 |
| 1577 | Ndst3 |
| 1578 | Dysf |
| 1579 | Kctd8 |
| 1580 | Fxyd7 |
| 1581 | Klra7 |
| 1582 | Serpinb5 |
| 1583 | Tgfb3 |
| 1584 | Cd7 |
| 1585 | Acaa1b |
| 1586 | Zan |
| 1587 | 5031414D18Rik |
| 1588 | Lrrc3b |
| 1589 | Rasgrf1 |
| 1590 | Maf |
| 1591 | Arhgef28 |
| 1592 | Klra6 |

TABLE 3

Shared genes between the glucocorticoid + IL-27 and T cell dysfunction signatures.

| Exhaustion_up | | Exhaustion_down | |
|---|---|---|---|
| Chst12 | Pros1 | Dnajc7 | Tm4sf5 |
| Timp1 | Alcam | Fas | Vrk1 |
| Cysltr2 | Fars2 | Samhd1 | Pus3 |
| Alg8 | Elmo2 | Map4k2 | Frat2 |
| Gsg2 | Mt2 | Urb1 | Acp5 |
| Aplp1 | Fcer1g | Pus7l | Ldhb |
| Kif22 | Spin4 | Man1c1 | Commd8 |
| Ccdc109b | Rpgr | Amz2 | Pou6f1 |
| Nup107 | Usp40 | Lrp12 | Fam53b |
| Crat | Styk1 | Rftn1 | Gpr132 |
| Ifng | Ccdc6 | Il4ra | Dhx58 |

TABLE 3-continued

Shared genes between the glucocorticoid + IL-27 and T cell dysfunction signatures.

| Exhaustion_up | | Exhaustion_down | |
|---|---|---|---|
| Trib3 | Bend6 | Klf9 | Card11 |
| Rabgef1 | AF529169 | Idua | Kctd12 |
| 5330426P16Rik | Ppme1 | Clasp1 | Acpp |
| Ccl4 | Mrgpre | Snhg7 | Cxcr4 |
| Gpr160 | Mtbp | Psap | Dus21 |
| Serpine2 | Exph5 | Bcl3 | Dntt |
| Rpa2 | Slc17a6 | Zscan12 | Hpcal1 |
| Arsb | Ankle1 | Pcca | 2810013P06Rik |
| Enpp2 | Cd38 | Gpd1l | Tpst2 |
| Nsmaf | Vamp8 | Tmem50b | Aff3 |
| Cdca3 | Nipa2 | Tcp11l2 | Dapl1 |
| Cenpn | Gpt2 | Dhcr24 | Aqp9 |
| Cdc27 | Fhl2 | Rarg | Wdr59 |
| Slc35b1 | Gatm | Zer1 | Mll3 |
| Il1r2 | Id2 | Idh2 | Ado |
| Shcbp1 | Nr3c1 | Atp2a1 | Slc9a9 |
| Dclk1 | Cenpi | Nfia | Pja1 |
| Kpna2 | Gzme | Vdr | Hmgn1 |
| Esco2 | Itga5 | Mtap | Eif2ak3 |
| Ppp1r3b | Csf2 | Gramd1a | Etnk1 |
| Eno3 | Slc22a15 | Cmah | Abtb2 |
| Ero1l | Sema6d | Npc1 | 2900076A07Rik |
| Demd4a | Slc2a8 | Gpr18 | Srpk1 |
| Sepn1 | Mettl7a1 | Nefh | D1Ertd622e |
| Mtmr1 | Cd200 | Rbm38 | Glcci1 |
| Abcb1b | Tjp2 | Macrod1 | Ceacam1 |
| Birc5 | Tox | Zc3h12d | Heatr1 |
| Magohb | Suv39h2 | Gimap6 | Itpr3 |
| Samsn1 | Mlkl | Cd24a | Gucy1a3 |
| Zfp692 | 2900026A02Rik | Slfn5 | Usp53 |
| Gcsh | Il1rl1 | Slco3a1 | Zfp1 |
| Ccl9 | Higd1a | Bdh1 | Phf17 |
| Zwilch | Car13 | Noc4l | Brap |
| Spp1 | Ica1 | Ddr1 | BC026590 |
| Zc3h12a | Kazald1 | Ctsl | Pqlc1 |
| Tmbim4 | Kif20b | Btla | Pprc1 |
| Tmem171 | Nfatc1 | Epcam | Arntl |
| Casp4 | Cd200r4 | Gramd4 | Tlr6 |
| Tnfrsf18 | Rab31 | Cryll | Kcnn4 |
| Ube2i | Rad54b | Mboat1 | Net1 |
| Mthfs | Dusp6 | Igfbp4 | Foxp1 |
| Plekhb2 | Arl6 | Bphl | Tha1 |
| Sdf4 | Bcl2l1 | Atp10d | Kif21b |
| Ccl3 | Mt1 | Rere | Vrk3 |
| Serpinb6a | Camk2n1 | Afap1 | Irgm2 |
| Anapc4 | Fam5c | Hs3st3b1 | Herc1 |
| Ifitm3 | Sat1 | St6gal1 | Unc5c1 |
| Ndfip2 | Rbpj | Ppa1 | Cd302 |
| Sec23a | Lamc1 | Ung | Usp28 |
| Stard4 | Agtrap | Mbp | Pgap3 |
| Fasl | Itga1 | Rpp40 | Gpr114 |
| Ccnb1 | Cxcr6 | Arhgef3 | Dedd2 |
| Nek8 | Galc | Satb1 | Sgms1 |
| Myadm | 1190002F15Rik | Cxcr3 | Mrpl30 |
| Tmem48 | Bst1 | Exosc1 | Btbd6 |
| Cenpt | L2hgdh | Sf3a2 | Fam65b |
| Gm11110 | Lyrm1 | Acss2 | Rasa3 |
| Ttk | Carhsp1 | ligp1 | Bzw2 |
| Arhgap18 | Tpi1 | 2610035D17Rik | Dirc2 |
| Slc7a3 | Mthfd2 | Als2cl | Nudt15 |
| Chac1 | Pik3cg | Rnf157 | Dnajc27 |
| Armc1 | Fcho2 | Jhdm1d | Parp3 |
| Cars | Chn2 | Tpd52 | Mylip |
| Mlf1 | Ncapg2 | Kti12 | Gbp2 |
| Gab2 | Apobec3 | Ralgps2 | Alpl |
| Cenpa | Jam2 | Prnp | Ssh2 |
| Tmem218 | Dtl | Itgae | Phc2 |
| Nrp1 | Aldoa | Atp1b3 | Furin |
| Sephs1 | Tnf | Ecm1 | Eef2k |
| Prdm1 | Ulbp1 | Sema4f | Notch1 |
| Sh3bgrl | D630039A03Rik | Ddx54 | Wdr45 |
| Filip1 | Mapk6 | Pde4b | Tcf4 |
| Agl | 1500009L16Rik | Aldh6a1 | Ccr7 |
| Qsox1 | Igfbp7 | Socs1 | Ssbp2 |
| Plek | Kctd17 | Tlr1 | Axin2 |
| Adam9 | Pex11b | Camkk1 | 2310044G17Rik |
| Igf2r | Bnip3 | Tspan13 | Npc2 |
| Pkp2 | Xpot | Vmac | Laptm4b |
| Npnt | Unc119b | Med4 | Gimap9 |
| Kif20a | Rnf128 | Sorl1 | P2ry14 |
| Cep170 | Ehd4 | Taf5l | Fam43a |
| Idh3a | Rhbdf2 | Tecpr1 | Mcoln3 |
| Pmaip1 | Ptplb | Fads2 | Dclre1a |
| Wbp5 | Rab12 | Kbtbd11 | Fgfr1op |
| Prf1 | Tg | Hagh | Tnik |
| Lgals3 | Casp1 | AB124611 | Adrb2 |
| Gdpd5 | Tpk1 | Sesn3 | Evl |
| Ccdc50 | Plscr1 | Serinc5 | Pkd1 |
| Lpgat1 | Ftsjd1 | Fosl2 | 4921511C10Rik |
| Tyw1 | Slc43a3 | Vav2 | Gramd3 |
| Zbtb32 | Gpr56 | Tax1bp3 | Prickle1 |
| BC068157 | 4930422G04Rik | Map4k4 | Gpc1 |
| Arhgef9 | Trip10 | Gatsl3 | Ccbl1 |
| Nrn1 | Irf4 | Rras2 | Iqgap2 |
| 2310001H17Rik | Upp1 | 3110043O21Rik | Klrb1f |
| Tacc3 | Ctsd | Lcmt2 | Cdyl2 |
| Spry2 | Padi2 | Rgs10 | B430306N03Rik |
| Slco4a1 | Stx11 | Me2 | Rasgrp2 |
| Htatip2 | Ide | Ifnar2 | Tk2 |
| Nr4a2 | Tmem120b | Itga7 | Card6 |
| Trappc4 | Prrx1 | Clpb | Gpr146 |
| Abhd14a | Tpx2 | Mppe1 | Dph5 |
| Nupr1 | Ect2 | Rbm19 | Crim1 |
| AA467197 | Bcl2l15 | Ccpg1 | Fgfr1 |
| Polk | Fam57a | Dzip1 | Fbxo17 |
| Anxa3 | Acot7 | Pdlim5 | Ctps2 |
| Cnnm2 | Mylk | Ctdsp2 | Nbn |
| Ndrg1 | Pdpn | Prep | Dse |
| Lrp1 | Rfc3 | Cdt1 | Xpc |
| Slc16a13 | Bard1 | Zcchc11 | Add3 |
| Sh2d2a | 1810011H11Rik | Ptcra | Pex26 |
| Dnajc24 | Cisd3 | Ifngr2 | Bach1 |
| Gins1 | Cenpf | Med8 | Sfrp2 |
| Cox17 | Ccnb2 | Insr | Irf1 |
| Zfp52 | Gm14288 | Slc16a6 | Enpp4 |
| Gata3 | Ubash3b | 1810043H04Rik | Thra |
| Dynlt3 | Glis1 | Stk38 | Gab3 |
| Gtf2ird1 | Cstad | Ascc1 | Bend5 |
| Vldlr | Fkbp7 | Zdhhc13 | Tmem55b |
| Dctn4 | Stk39 | Arid5a | Dtx3l |
| Syngr3 | Ap1s2 | Ddx18 | Arhgap15 |
| Asns | Krt18 | 2610002M06Rik | Itfg3 |
| Uhrf2 | Camk4 | Tfam | Gm8369 |
| Ino80c | Spata21 | Phc1 | Acsl1 |
| Ppap2c | Trps1 | Parp9 | Faah |
| Pggt1b | Flywch1 | Sqrdl | Armcx6 |
| Cd93 | Gbe1 | Gtf2i | Smad3 |
| Ttc39c | Fam64a | Lmo4 | Zfp652 |
| Tubb6 | 1700012B09Rik | Gpx1 | Lrrc8a |
| Dab2 | Etv5 | Tmem141 | Slc11a2 |
| Zdhhc5 | Demd3 | Trim62 | Dus4l |
| Usp46 | Nt5dc2 | Icam2 | Il6st |
| Mrps6 | Sar1a | Irf7 | Hey1 |
| Kctd11 | Sult2b1 | Utrn | Atp8a2 |
| Gnb5 | Sytl3 | Cd40lg | Smpdl3a |
| B4galt5 | Cdc14a | Smc6 | 3230401D17Rik |
| Tk1 | Tmem170b | Zfp260 | Mycbp2 |
| Rhoq | Srgap3 | Dhx37 | Zfp354c |
| Gja1 | Zfp511 | Ift80 | Fbrs |
| 3110082I17Rik | Ostf1 | Klhdc1 | Klhdc5 |
| Osbpl3 | Fam72a | Nop2 | Ptpla |
| Tm9sf3 | Endod1 | Umps | Kbtbd8 |
| Smc2 | Raph1 | Pim2 | St3gal6 |
| Cenpp | Nsl1 | Igf1r | Dtx1 |
| Copz2 | Apoe | Osbpl9 | Cd2 |
| Klf10 | Hivep1 | Cdc14b | Dym |
| Degs1 | Wisp1 | Ccr4 | Shisa2 |
| Nbeal1 | Tspan6 | Tom1 | Camkk2 |
| Cdca5 | Csda | Fgr | Slc41a1 |

TABLE 3-continued

Shared genes between the glucocorticoid + IL-27 and T cell dysfunction signatures.

| Exhaustion_up | | Exhaustion_down | |
|---|---|---|---|
| 4932415G12Rik | Pglyrp1 | Slamf6 | Sepp1 |
| Adam15 | Serpinb6b | Sgip1 | Atp2a3 |
| Mpi | Ppp3cb | Sigmar1 | Mgst2 |
| Dapk2 | B3galt5 | Uvrag | Sipa1l1 |
| Plk1 | Ier3 | Sdccag3 | Chd8 |
| Hip1r | Ddx17 | Traf4 | Lef1 |
| Amigo1 | Osgin1 | Lpin1 | Tapt1 |
| Optn | Foxm1 | Ipcef1 | Il7r |
| 1700017805Rik | Calu | Rab37 | Ramp1 |
| Ctsc | Rad51 | Top1mt | Elk4 |
| Ltbp3 | Anxa2 | Chst15 | Zfp53 |
| Mrps36 | Ndc80 | Ehd3 | Csrnp1 |
| Atf4 | Kif4 | Zkscan3 | Tgfbr3 |
| Rab5b | Med12l | Rcn3 | Lypd6b |
| Acadl | Efcab7 | Tnfsf8 | Kremen1 |
| Pld2 | Havcr2 | Abcc4 | Bcl9 |
| Ptrf | Lclat1 | Ephx1 | Emb |
| Nqo2 | Atp10a | Peo1 | Arl6ip6 |
| Scyl2 | Slc2a3 | A230046K03Rik | Rnf19b |
| Myo1e | Rapsn | P2rx4 | Foxo1 |
| Tmem39a | Gpd2 | Socs3 | Fbxo32 |
| Nuf2 | Depdc1a | Zeb1 | Scml4 |
| Rnaseh2c | Calm3 | Frmd4b | Ms4a4c |
| Spag9 | Sdcbp2 | Skp1a | Jakmip1 |
| Atad5 | Fkbp1a | Egln3 | Jak2 |
| Ncaph | Rab27a | Mapk1ip1 | P4ha1 |
| 2610318N02Rik | Plekhf1 | Tcf7 | Klhl6 |
| Traip | Nid1 | Adk | Frat1 |
| Gem | Plod2 | Cyp2s1 | Hmgxb3 |
| Elk3 | E2f8 | Pepd | Sos1 |
| Egr1 | Kif24 | Rcl1 | S1pr4 |
| Adssl1 | Iqgap3 | Pde7a | Crtc3 |
| 1110007C09Rik | St14 | Tmem41a | Nisch |
| Icos | Trifsf11 | St8sia1 | Ifit1 |
| Tbc1d7 | Elovl4 | Hspb11 | Tnfaip8l2 |
| Itgav | Ifitm2 | Irf6 | Fitm2 |
| C330027C09Rik | S100a11 | Pik3ip1 | Atp1a3 |
| Anxa4 | Adam8 | Polr3a | Slfn1 |
| Entpd1 | Tnfsf9 | Lrrc33 | Jmjd1c |
| Omd | 0610010F05Rik | Nxf1 | Cpne3 |
| Pter | Dusp4 | Zbtb24 | Gcnt2 |
| Ccdc14 | Ermp1 | Itgb7 | Slc12a7 |
| Apbb1 | Hbegf | Fam117b | Abca1 |
| Gpld1 | Npl | Zfp362 | Bcl6 |
| Gabbr1 | Cyr61 | Nufip2 | Fam189b |
| Oit3 | Armc7 | Sgk3 | Il1r12 |
| Hmmr | Emilin2 | Arl6ip5 | Bach2 |
| Tmem159 | Ndufb4 | Yes1 | Mdn1 |
| Cenph | Hhat | Capn3 | Lif |
| Ndufaf2 | E2f7 | Cpne2 | Prkcb |
| Kdm2b | Slc30a9 | Dip2c | Kmo |
| Ptplad1 | Klra7 | Serp1 | Pcnxl3 |
| Aldoc | Neil3 | Jmy | Zrsr1 |
| Mmd | Abcb9 | Zfp281 | Myc |
| Atg1612 | Rab19 | Zmym2 | Scpep1 |
| Ephb6 | AI836003 | 2410066E13Rik | As3mt |
| Aqp11 | Tnfsf4 | Znrf1 | Zfp592 |
| Nedd9 | Selm | Gypc | Dopey1 |
| Dkkl1 | Siglec5 | Tanc1 | Egr3 |
| Abhd4 | Actr10 | Ikbke | Zfp87 |
| Pddc1 | Il2 | Cyth1 | Smad1 |
| Exo1 | Cldn12 | Ulk1 | Dgka |
| Slc37a2 | Il33 | Ttc32 | Arhgef18 |
| Impa2 | Tmem175 | Etv3 | Rapgef4 |
| Farp1 | Tmcc3 | Rnf122 | Zfp365 |
| Gpr174 | Piwil2 | Plaur | Pitpnc1 |
| Rps6kcl | Pear1 | Gpr155 | Gcc2 |
| Cyp20al | Nmt2 | Rsad2 | Lysmd1 |
| Tmem126a | Lat2 | Tctex1d1 | Ubac2 |
| Fam188a | Phf23 | Rnf149 | Ldlrap1 |
| Hif1a | Abi2 | Tdrkh | Hemgn |
| Mtmr7 | Gldc | Egr2 | Tubb2a |
| Casp3 | Lpxn | Cxcl10 | Ddx60 |
| Dut | Cdkn3 | Mmachc | Aqp3 |
| Stab1 | Fancd2 | Rab35 | Id3 |
| Ctla2a | Atxn1 | Cd7 | Spsb1 |
| E130112N10Rik | Cnrip1 | Rapgef6 | Itpr2 |
| 2810417H13Rik | Galnt3 | Trat1 | Grn |
| Pilra | Spag5 | Prkcq | 5730508809Rik |
| Eno2 | Brca2 | Ncf1 | |
| Tnfrsf4 | Kif18a | | |
| Ptgr1 | Sytl2 | | |
| Ptprk | Plekho2 | | |
| Kit | Tbc1d2b | | |
| Crabp2 | Mid1ip1 | | |
| Tecr | A430093F15Rik | | |
| Bcat1 | Gzmd | | |
| Tmem180 | Penk | | |
| Zfp760 | Pdcd1 | | |
| Il2ra | Litaf | | |
| Ptpn11 | Bub1 | | |
| Kcna4 | Ccng1 | | |
| Ovol2 | Ccl1 | | |
| Creb3l2 | 4930429F24Rik | | |
| Pla1a | Dusp3 | | |
| Rgs16 | Ctla4 | | |
| Lag3 | Alg6 | | |
| Rai14 | Slc35f5 | | |
| Pask | Ube2c | | |
| Sestd1 | Mpzl2 | | |
| Tulp4 | Diap3 | | |
| Utf1 | Paqr4 | | |
| Cst7 | Cep55 | | |
| Hnrpll | Cdca8 | | |
| Trifsf13b | Oaz2 | | |
| Cercam | Bub1b | | |
| Ptgs2 | Lxn | | |
| Ankra2 | Pcyt1a | | |
| Slc25a13 | Ern1 | | |
| Cyp4v3 | | | |

TABLE 4

| Dysfunction Signature | | | | |
|---|---|---|---|---|
| Cancer_Down | | | | |
| KRT10 | TGFBR1 | UBE1L | MAN1C1 | PRR5 |
| SMC6 | NARG2 | CCDC45 | RNF19B | CMBL |
| BZW2 | HMGXB3 | ACP5 | PRX | NR1D2 |
| PDLIM1 | ZNRF3 | MFSD6 | KCNN4 | 6230400D17RIK |
| ITGB7 | BRAP | RPL30 | LCMT2 | FBRS |
| PHC1 | SNHG7 | CD7 | 1700021C14R1K | 3110043O21R1K |
| UNC5CL | SRPK1 | RFTN1 | 1700025G04R1K | PTGES2 |
| ARHGAP15 | BC018507 | GRAMD1A | FRAT2 | SLFN5 |
| AB124611 | GPR114 | PUS7L | ELOVL6 | FCNA |
| NPC2 | 4930432O21RIK | PRDM15 | GM568 | NCF1 |

TABLE 4-continued

| Dysfunction Signature | | | | |
|---|---|---|---|---|
| 1110008L16RIK | DZIP1 | DAXX | 1700028N14RIK | EHHADH |
| TNFSF8 | CTSE | CYP2S1 | SMAD5 | DTX4 |
| A630057N01RIK | SLAMF6 | 2810043O03RIK | TGFBR3 | GM3626 |
| SMAD3 | TLE4 | 3230401D17RIK | ALDH6A1 | ZCCHC11 |
| CAMKK1 | A1504432 | NSG2 | AB041803 | 6720475J19R1K |
| DOPEY1 | ZFP365 | NMNAT2 | BCL6 | PRCP |
| INSR | VRK3 | DSE | FAM134B | PRNP |
| 1200003I10RIK | CEP152 | C78516 | NRARP | MPEG1 |
| 1200015M12RIK | SLC39A11 | ITGAE | DNAJC27 | TXNDC5 |
| 1200016E24RIK | TCF7 | GBP1 | ZBTB10 | SERPINI1 |
| A130040M12RIK | 2310044G17R1K | NUDT15 | D13ERTD608E | SLC40A1 |
| E430024C06R1K | 2810453I06R1K | 1110034G24R1K | AQP3 | MAP4K3 |
| FYN | GM1060 | GM8350 | IFNAR2 | CDH5 |
| RXRA | SEMA4B | NCK2 | FAS | SH3BGR |
| DHCR24 | CXCL10 | ITFG3 | ATP2A3 | NFE2L2 |
| ADO | ATP1B3 | MYC | 1810049H13RIK | KLK1B27 |
| IGTP | CAMKK2 | KLHDC2 | H2.0A | 1190005F20RIK |
| RTP4 | HRH1 | RP23.39409.3 | RNF122 | 2210020M01R1K |
| 9130004J05RIK | TNFRSF1OB | GM14446 | ARNTL | MAGED1 |
| FOSL2 | CCPG1 | ZDHHC23 | SLC16A6 | SF3A2 |
| PPRC1 | FAM109B | COMMD9 | GTF2I | CAMK1D |
| CYTH1 | HSPB11 | C730025P13RIK | 2610201A13RIK | TAF4B |
| TAGAP.TAGAP1 | ATP1B1 | CRTC3 | GGT1 | TYROBP |
| NSMCE1 | TOP1MT | AU022434 | IL4RA | OTTMUSG00000010657 |
| HEMGN | CSRNP1 | ELK4 | IFIT2 | DUS2L |
| HPCAL1 | SEMA4F | GM8369 | GLCCI1 | L0C497255 |
| RTN4RL1 | ZFP1 | JMY | MTAP1S | PITPNC1 |
| HMGN1 | 4921511C10RIK | SIPA1L1 | LMO4 | A1465300 |
| AFF3 | PIM2 | AU015680 | TRIO | ZFP407 |
| BCL3 | RARG | GPR15 | UNG | GM5785 |
| RPL31 | IFT172 | BB163080 | 1190002H23R1K | USP18 |
| ATP1OD | D19ERTD386E | CRYL1 | 9030607L20RIK | SNN |
| IL7R | TRPM1 | LPHN1 | D730040F13RIK | ELOVL7 |
| PMEPA1 | MX2 | HSPA8 | THRA | IKBKE |
| KLK1.KLK1B5 | CCM2 | GM10392 | IDH2 | GZMM |
| HAGH | YES1 | 2610002M06RIK | ASB13 | MTHFR |
| PKD1 | CCDC64 | 9130401L11R1K | DDX60 | 6720462K09R1K |
| 5730508609RIK | ENTPD5 | KLF7 | AMZ2 | CTSH |
| CHD8 | 5830468F06RIK | PARD6B | RPP40 | D130037M23RIK |
| ETNK1 | LMBR1 | KRBA1 | 9530029012RIK | 2310009A05RIK |
| ID3 | AU021025 | SMAD1 | 9630025H16R1K | L00625360 |
| EPCAM | TMEM108 | GRAMD4 | NKRF | WDR41 |
| IL1RL2 | SH3BP5 | CDC14B | FAM158A | ACPP |
| TMEM86A | TAPT1 | 2610035D17RIK | ALPL | TCF4 |
| RNF213 | UBAC2 | FOX01 | RNF149 | H2.T24 |
| MPPE1 | SGMS1 | MAP4K2 | MGAT4A | 4930535I16RIK |
| MAPK1IP1 | COMMD8 | TPD52 | CHD9 | VCAM1 |
| PHF17 | SBK1 | ITGA6 | 4930523C07RIK | RCN3 |
| FAM49A | SORL1 | MKL1 | TRIM32 | LPAR6 |
| LONRF1 | ANTXR2 | ARHGAP5 | MOBKL2B | GSN |
| NBN | AXIN2 | JAG1 | MYB | 1700023D09RIK |
| FAM26F | ACYP1 | BAMBI.PS1 | RRAS2 | CSF2RB2 |
| DNMBP | ERF | TMEM55B | SYNE2 | SYDE2 |
| RASA3 | CRIM1 | GCNT2 | D7ERTD413E | 4933407I012RIK |
| ASCC1 | DTX3L | P2RX4 | DNTT | EPHX1 |
| GALNT10 | ARL6IP5 | TAF3 | TCRG.V1 | ZFP3 |
| FOXP1 | SEPP1 | THA1. | AFAP1 | BCO26590 |
| NXF1 | SERPL | OSBPL9 | GM9958 | TRIM62 |
| KLHL6 | IN080 | POU6F1 | RAB37 | WARS2 |
| SOCS1 | RPAP3 | 2310010J17RIK | JMJD1C | ALS2CL |
| ADK | RCC2 | LY6C1 | LIN52 | WNT5B |
| KIF21B | ZBP1 | LY6C2 | D630030622RIK | GNG12 |
| FGF13 | RGS10 | ADRB2 | HIST2H3C1 | ZBTB24 |
| HMGN1 | SELL | ZFP53 | FAM109A | CCDC125 |
| SOCS3 | EIF2AK3 | GRAP2 | KLK1B22.KLK1B9 | CXCR5 |
| 4833423F13RIK | 2810454H06RIK | ABTB2 | FBX032 | NINJ1 |
| 2010107H07RIK | E230032D23RIK | SLC12A7 | PPARD | CNN3 |
| ENC1 | ZMYM2 | 4930431H11RIK | D1ERTD646E | GPR137B |
| GATSL3 | ITGA7 | INADL | PLCXD2 | LRP12 |
| HEG1 | HEATR5A | A1131651 | BACH2 | BC017158 |
| TCF12 | TRIT1 | RCSD1 | PSAP | FGFR1OP |
| PGS1 | PLAUR | TM7SF2 | LHFPL3 | ZFP608 |
| ZSCAN12 | NFIA | DLG5 | BLNK | SPSB1 |
| GRLF1 | PEPD | CDYL2 | ST8SIA1 | RGMB |
| 2810001G2ORIK | SMCHD1 | GPC1 | ZER1 | 5830443J22RIK |
| ST3GAL6 | MRPL30 | TNIK | P2RX7 | A130091K22RIK |
| DDX54 | PARP14 | PCCA | KLRB1F | BTBD11 |
| 4930445K14RIK | TSPAN13 | D18ERTD653E | GARNL4 | 2010001M09RIK |

TABLE 4-continued

| Dysfunction Signature | | | | |
|---|---|---|---|---|
| 1E147 | C230085N15RIK | ACAD10 | KCTD12 | EPHA2 |
| SSBP2 | BC067068 | MCOLN3 | 9130019022RIK | TCTEX1D1 |
| FAM65B | SHB | KLK1B4 | OGFOD1 | SLC30A1 |
| YEATS2 | CD79B | FOS | RPS20 | PEX11C |
| ARHGEF3 | ZFP362 | FAM122A | LDLRAP1 | KBTBD7 |
| CTAGE5 | CAPN3 | SGTB | 4932433NO3RIK | ENDOG |
| STIM2 | ALDH1B1 | GPX1 | GDAP10 | ATP2A1 |
| TUBB2B | A1429363 | PLEKHA1 | LYSMD1 | GRN |
| CARD6 | KREMEN1 | ABCA1 | GPR132 | A130001GO5RIK |
| UTRN | 2210010C17RIK | H2.D1.H2.T18.H2.13 | EMID1 | MCAM |
| DYNC1H1 | 2310050P2ORIK | 1200016E24RIK | EWSR1 | SIGLECH |
| 6030458A19RIK | ARMCX6 | A630023P12RIK | GM11346 | SHISA2 |
| LOC100044376 | SLC25A15 | BTF3 | CAR2 | PARP11 |
| CEP164 | ACTN2 | IGFBP4 | ECM1 | CCR4 |
| A230046K03RIK | SETDB2 | ALDH4A1 | D16H22S680E | DIP2C |
| C77651 | NOD1 | GM5817 | 5330403D14RIK | STX1A |
| 4930513N1ORIK | KLF9 | ZXDB | RASGRP2 | IGF1 |
| HS3ST3B1 | RBM4B | JAKMIP1 | KTI12 | CCNJ |
| IFIT3 | C330006K01RIK | RIC8B | DPH5 | 4921524M04RIK |
| GPR18 | PDE7A | RAMP1 | A130064L14RIK | WFS1 |
| IRF1 | STAT5A | SNTB2 | SERINC5 | 4732423E21RIK |
| UBE1L | SLCO3A1 | KCNH2 | XPC | GPR137B.PS |
| SKP1A | GRAMD3 | KTELC1 | 1500015A07RIK | 2010309G21RIK.IGL.C2.1GL.C3 |
| MBOAT1 | PTK2 | GOLM1 | ACSS2 | 2900076A13RIK |
| USP6NL | 1500011603RIK | B130065D12RIK | 50X4 | PSD |
| RNF113A2 | GM16489 | IGF1R | 4930534I15RIK | SPIB |
| IFIT1 | JAK2 | PDE2A | NCK2 | DGAT2 |
| SPON1 | LRRC8A | PPA1 | OAS3 | DAAM1 |
| PARP9 | PRKCQ | RCL1 | LDHB | EEF1G |
| HS6ST1 | KDM1 | ZRSR1 | HDGFRP3 | NUFIP2 |
| VIPR1 | GSTK1 | 9530028C05 | B230214009R1K | GM4814 |
| A430028G04RIK | IRG M2 | BB236558 | CLCN6 | LPHN2 |
| NME4 | NOC4L | C030034122RIK | BACH1 | GPR137B |
| CDC2L6 | 2310003H01RIK | RBM19 | UBTD2 | PARP3 |
| DYM | CCR7 | 6230427J02RIK | ZFP809 | KLK4 |
| DDX18 | MN1 | ZFP652 | TNFRSF19 | TM4SF5 |
| PIK3R5 | CAMSAP1L1 | BCL9 | TCP11L2 | PTPRF |
| ZDHHC8 | C77626 | 9530086P17R1K | DNAHC8 | F630110N24R1K |
| EMB | CD72 | MGST2 | CD4OLG | PARD6G |
| DMRTA1 | SMPDL3A | RALGPS2 | BPHL | SLC16A5 |
| USP53 | SATB1 | BC059842 | HP1BP3 | 1190002A17RIK |
| PPP1R13B | D8ERTD82E | SSFA2 | 2410066E13RIK | LAIR1 |
| 3110070M22RIK | MYCBP2 | F2RL1 | SIAH1A | FADS3 |
| P4HA1 | TUBB2A | 2810001A02RIK | HEY1 | PLD4 |
| IRF6 | LYSMD2 | GGT5 | TIMP2 | CPT2 |
| PDLIM5 | TMEM57 | NEFH | ZFP623 | 6530415H11RIK |
| TOM1 | SCML4 | ARHGAP29 | RSAD2 | 2810021J22RIK |
| IQGAP2 | PPARGC1B | OASL1 | GIGYF2 | SNURF |
| CD2 | MLL3 | A930005H1ORIK | 5430434G16RIK | SNRPN |
| 4932441K18R1K | 9330175E14R1K | DYRK2 | RNF157 | IL12A |
| ZNRF1 | USP12 | FBX034 | IL6ST | LRIG1 |
| CXCR4 | PVR | HOXB4 | SLAMF7 | 3110037C07RIK |
| SLC39A8 | FURIN | FAAH | TAF4A | GSTZ1 |
| CELSR1 | TPST1 | DCUN1D4 | C430010001 | CPNE3 |
| EVL | RORA | FAM82B | XKRX | RNASE6 |
| FAM69A | TLR6 | BC057079 | DNAJC7 | PLXDC1 |
| LOC100047863 | SLFN1 | SIDT1 | SH3BGRL2 | SPNS3 |
| 1810043H04RIK | NEDD4L | SQRDL | CD24A | ATP1A3 |
| TPST2 | GPR183 | C230021P08RIK | LIFR | COX6A2 |
| GBP2 | 2610019N06R1K | 5430427G11R1K | RBM38 | GM5547 |
| MS4A4C | D1ERTD622E | GYPC | TRNP1 | BTLA |
| SAMHD1 | ICAM2 | SESN3 | SLC9A9 | A1449212 |
| LPIN1 | RAB35 | MYLIP | ZFAND2A | DHX58 |
| ITPR2 | LTA4H | RAI2 | MAPK8 | SYK |
| XAB2 | SAMD9L | MDN1 | BEND5 | ZKSCAN3 |
| TGTP | WDR59 | KCNJ8 | ZFP566 | HPVC.PS |
| TGTP2 | ZFP354C | APOL7C | AKAP2 | LAPTM4B |
| ST6GAL1 | TRAT1 | ZFYVE27 | TAX1BP3 | 1700056E22RIK |
| LY9 | UVRAG | TTC28 | L3MBTL3 | TDRKH |
| CCDC52 | GGA2 | FBX017 | BEX1 | CYBASC3 |
| GM11696 | CTDSP2 | ZFP260 | TEAM | CYBB |
| GIMAP6 | PDLIM4 | PJA1 | FGFR1 | PELI2 |
| PHC2 | E430014602RIK | COR07 | DHX37 | CD302 |
| CLPB | PDE8A | CLEC2I | SESN1 | RAPGEF4 |
| MPND | NOTCH1 | CUGBP1 | EHD3 | P2RY14 |
| LPP | ASF1A | FAM53B | S1PR1 | STC2 |
| MAP4K4 | 2900064618R1K | B430306NO3R1K | 6720418601R1K | FRAT1 |
| BC002199 | TMEM5OB | ZC3H12D | ZFP87 | FADS2 |

TABLE 4-continued

| Dysfunction Signature | | | | |
|---|---|---|---|---|
| RCBTB2 | RAPGEF6 | CACNA2D4 | C130039016RIK | DDR1 |
| KLHDC1 | PIK3IP1 | FAM117A | SCPEP1 | PLAT |
| INPP5F | GAB3 | PIK3CD | MMACHC | BCL11A |
| TNFAIP8L2 | BC006779 | PGLYRP2 | IRF7 | 6330509M05RIK |
| S1PR4 | GIMAP9 | CCR9 | A130006112RIK | FCRLA |
| ARMCX2 | GPR155 | MXRA8 | RRAGD | GRIT |
| EGLN3 | FOXP3 | CHST15 | SAMD10 | CD180 |
| PRKCB | EXT1 | GALNT12 | D930015E06RIK | LEFTY1 |
| TLR1 | ETV3 | MICAL3 | CYTH3 | KLHDC5 |
| DCLRE1A | FRMD4B | E230012J19RIK | USP45 | ENTPD6 |
| C330006A16RIK | BC005561 | AS3MT | ACSL1 | MEF2C |
| CDK5RAP3 | KBTBD8 | EVL | WIZ | SDCCAG3 |
| GM10726 | CXCR3 | ZFP238 | PKN1.PTGER1 | 9630025121RIK |
| FAM108B | 2610019F03RIK | UTP14B | IFT80 | DUS4L |
| ARHGEF18 | STXBP3A | MAP4K5 | 2010004M13RIK | C80120 |
| CDK5R1 | FAM189B | TLE1 | 1MEM141 | GNAI1 |
| MED8 | SSH2 | USP28 | ZSWIM6 | CADM1 |
| LOC100046855 | ATP8A2 | JHDM1D | DUSP10 | BST2 |
| RAI1 | D530037H12RIK | ADD3 | ST8SIA4 | CMAH |
| IKBKB | ABCC4 | PANK4 | PEX26 | P2RY13 |
| UTP14A | 5830411NO6RIK | NANP | EEPD1 | CD163 |
| TSHZ3 | GALNT9 | PLTP | BC050254 | TUBB2A |
| BDH1 | 1810007M14RIK | NUDT15 | AMD1 | TUBB2B |
| RERE | EGR2 | 2810488GO3RIK | NPC1 | LIF |
| PDE4B | 5830405N20RIK | PACSIN1 | DEP1 | GCC2 |
| ARL6IP6 | GPD1L | 6330416G13RIK | SOCS6 | NUCB2 |
| DAPL1 | ART4 | 2310022605RIK | MUTED | RGS20 |
| PREI4 | AQP9 | FHIT | LYPD6B | HS3ST1 |
| SOS1 | TSPAN3 | PRICKLE1 | NET1 | SH2B3 |
| NLK | 2310035P21RIK | ZFP335 | AI451458 | GUCY1A3 |
| TGFBRAP1 | HEATR1 | ARID5A | SIN3A | D17WSU92E |
| WHRN | TMEM42 | DTX1 | PCNXL3 | FGR |
| CDT1 | SPNB2 | ACOT6 | ARHGEF11 | AMIG02 |
| NIN | BTBD6 | 6030400A10R1K | 2900093K20R1K | D930001602 |
| RP23 | STK38 | CTPS2 | PNCK | PUS3 |
| KBTBD11 | CCBL1 | BOLL | SGIP1 | ZFYVE28 |
| TNFRSF25 | OAS2 | GPR146 | CNKSR3 | CPNE2 |
| MTAP | TNFRSF13B | POLR3A | ULK1 | 1BC1D8 |
| MMP17 | CMPK2 | 3830612M24 | USP33 | HSPA12B |
| LATS2 | REV3L | ZEB1 | VDR | HAVCR1 |
| EGR3 | MBP | PTCRA | BRWD2 | D7BWG0826E |
| ZFP592 | TECPR1 | ZDHHC13 | VAV2 | GPR25 |
| RECK | WDR45 | IRGM1 | IFNGR2 | CSF2RB.CSF2RB2 |
| ZFP422 | TK2 | CDC42SE2 | 1700100M05RIK | KC1D21 |
| RHOBTB2 | IPCEF1 | TLR7 | TRIB2 | PPIFOS |
| HIST2H2BB | UMPS | EEF2K | FITM2 | AU019157 |
| C430003N24RIK | SEC11A | 8430419L09RIK | AUTS2 | CCNB1IP1 |
| IL6RA | 4930438A08RIK | ZFP281 | PQLC1 | SIGMAR1 |
| VRK1 | KIF1B | SLC41A1 | PCGF5 | KM0 |
| N4BP2 | SFRP2 | SCG5 | ANKZF1.GLB1L | LY6K |
| LEF1 | PRKAG2 | L00552906 | CREG1 | GNAT1 |
| CHD3 | KLF2 | NUAK2 | IDUA | PLEKHO1 |
| LRRC33 | TESC | MAGEF1 | ZDHHC14 | PCBP3 |
| NOB1 | ENPP4 | AFF1 | MAST4 | PRKCC |
| HERC1 | GM5617 | TANC1 | CD59A | SPIC |
| ME2 | URB1 | FAM134C | SETD6 | H2.0B |
| CLASP1 | DIRC2 | PPM1M | ADAR | PARD3 |
| MFHAS1 | CDKN1C | SPSB4 | TMEM41A | TTC32 |
| PHF2 | METAPL1 | DEDD2 | IIGP1 | L0C100040377 |
| EFCAB2 | 6330415G19RIK | D130062J21RIK | SLPI | MGL1 |
| VMAC | MBTD1 | ZBTB9 | RAMP3 | CEACAM1 |
| DLEU2 | UBE2CBP | KLK1 | 2810013P06RIK | TUBB3 |
| RASSF3 | 9130208E07RIK | SLC15A4 | GABRR2 | TIFA |
| A630038E17R1K | 2310014D11R1K | 2410002022R1K | ZBTB40 | PIR |
| ACVR1B | MACROD1 | ACTN1 | INPP5A | EMR4 |
| SLC11A2 | Sept8 | 2900076A07R1 K | FAM43A | PPFIA4 |
| NISCH | FAM117B | TXNRD3 | NIPAL1 | GRIA3 |
| DGKA | MED4 | FGFRL1 | TATDN2 | TCF7L2 |
| A130038J17RIK | TRAF4 | PTPLA | 1700124K17RIK | PGAP3 |
| ITPR3 | PEO1 | CTSL | NACC1 | AI447881 |
| MEX3A | RALY | FAM101B | TMEM64 | FES |
| NOP2 | AGAP3 | EXOSC1 | TREML2 | 5031439G07RIK |
| DUSP28 | PML | TAF5L | PDZD4 | KYNU |
| MMAA | CLEC2D | CARD11 | TSC22D1 | SGK3 |
| GM2643 | | | | |

TABLE 4-continued

Dysfunction Signature

Cancer_Up

| | | | | |
|---|---|---|---|---|
| GM11428 | HMMR | PEAR1 | CD200 | SEMA4C |
| FAM149A | NID1 | CASP1 | CALM3 | ZFP750 |
| AIF1 | MELA | 2600002607RIK | FKBP1A | CST7 |
| MUC20 | RGS16 | FAH | 5730493619RIK | MASTL |
| MS4A6C | ABHD14A | NCAM1 | USP40 | FUT7 |
| TGFBI | NUP107 | SUMF2 | CCNB2 | 2610039C10RIK |
| GATM | MORN4 | 2310046K01RIK | SEC23A | KDELC2 |
| IRAK1BP1 | ARL3 | AI747699 | CCDC6 | 2410127L17RIK |
| C1QB | MS4A6D | RHOQ | SEMA6D | PLSCR4 |
| MAFB | MTBP | DUT | 1EX15 | MRPS6 |
| COL4A4 | SLC15A3 | FCH02 | OTOA | EN03 |
| CLEC4A3 | EFCAB7 | DIAP3 | S100A4 | CHCHD8 |
| PTGER2 | PDPN | PLEKHB2 | NUDT11 | MSRB3 |
| EN02 | AW555355 | KLHL30 | POLK | CDC25C |
| APOE | D10WSU159E | HISPPD1 | 1MEM175 | HSPA13 |
| 2300004M11R1K | A930038C07R1 K | FZD5 | CHAC1 | SLC16A11 |
| FCGR2B | IL18RAP | HNRPLL | B230380D07RIK | NSL1 |
| FOXGI | D102 | 4932415G12RIK | B930095G15RIK | MDFIC |
| QS0X1 | CSTAD | FILIPI | UBASH3B | NINJ2 |
| HBEGF | COCH | ERNI. | B230354K17RIK | E2F8 |
| PDDCI | BEND6 | 9430087J23RIK | FAMI88A | 2310016C08RIK |
| CIQC | SLC7A8 | SLC35F5 | 1300014106RIK | KCTDI7 |
| GM11110 | NAIP5 | TPMT | DUSP6 | GSTT3 |
| ANPEP | EBAG9 | NDUFAF2 | ANKRD39 | SERPINB9 |
| LIPE | 2600001M11RIK | LTBP3 | IN080C | CALCB |
| MYADM | SAG | 2810039614RIK | ABCBIB | PDCDI |
| CXCLI6 | 6330412A17RIK | CKAP2 | F630043A04RIK | EHD4 |
| CALDI | ZDHHC9 | EIF2AK2 | MGAT3 | BCL2L1 |
| VPSI8 | GTPBP3 | SDCCAG10 | SPRY2 | GPRI74 |
| PCOLCE | SHCBPI | MTMR7 | NAPIL3 | PRKACA |
| CPE | SRCRB4D | PRRII | D430041D05RIK | ATP2B2 |
| EHBPI | LRRKI | 9630013D21RIK | ICOS | STX1I |
| IRGI | CCL8 | 4833442J19RIK | IFNG | FAM176B |
| RHBDF2 | 5H2D5 | TMEMI63 | 1110067D22RIK | COMMD5 |
| FST | CBR4 | MYLK | IPP | 2500002613RIK |
| RSLI | 5330433J24RIK | PON3 | GM10786 | RAPSN |
| ZFP429 | AK3LI | ERCI | ANUBLI | D830012124RIK |
| ZFP455 | WWTRI | KLRC2 | TACC3 | NMT2 |
| ZFP456 | CLDND2 | B4GALT5 | CDCA8 | ALDOA |
| S100A9 | METTL7A1 | CDC2A | VASHI | SPATS2 |
| SNXI6 | DOCK7 | JDP2 | 9230116N13RIK | CCDC99 |
| PTRF | TMEM38B | KIF18A | PIER | CDC27 |
| LPARI | CSF2 | TMEM180 | APIS2 | IRF4 |
| COL1A2 | 1200009F1ORIK | ARHGAP21 | SATI | ARHGEF5 |
| CIQA | GNG3 | CCLI | D3ERTD75IE | TMPRSS6 |
| LTBPI | DCLKI | CD80 | GM9529 | DENND3 |
| TIMPI | 1700017605RIK | TIRAP | CHN2 | C030046G05 |
| SDPR | PEXIIA | TRPTI | ZCCHCI4 | TMEMI35 |
| AQPI | 1700009P17RIK | FAM92A | CCNGI | RAP2A |
| CD34 | JAZFI | ACOT7 | ELOVL4 | FAM72A |
| 1700012609RIK | PLKI | SMC2 | PGM2 | CSFI |
| THBS2 | NUDT10 | TJP2 | MXI1 | ASPM |
| GJAI | UBE2I | MRGPRE | ALCAM | CCNBI |
| KRT20 | FZD4 | IFITM2 | CAPG | CAMK4 |
| CAVI | ALS2CR4 | GM9861.LITAF | 51K40 | KCND3 |
| 1E1204 | HIGDIC | LCLATI | MTHFS | SYTL2 |
| VLDLR | METTL7A1 | ADRBI | GPR160 | XLR4A |
| ZFHX3 | METTL7A2 | CLSTNI | DUSP3 | XLR4B |
| PRKG2 | 2900001GO8RIK | MOBKLIA | CERCAM | XLR4C |
| EREG | 4833420D23RIK | CYSLTR2 | GIPC2 | UHRF2 |
| ANXA3 | 3830408D07RIK | IFITM3 | FAM110A | MTMRI |
| HMGA2 | B830008J18RIK | 4930503L19RIK | 5730469M1ORIK | NCAPH |
| EIF2AK1 | FBX045 | KIF4 | LCMTI | PBX3 |
| SGMS2 | GPT2 | 8430429K09RIK | ANXA5 | TECR |
| GAB2 | ATF5 | 5LC25A24 | TPX2 | PLSCRI |
| FATI | CYTSB | 0610037D15RIK | KLF10 | ACTR10 |
| CXCL3 | AIFM2 | TRPS1 | 2810408111RIK | KIT |
| TM4SF1 | D1ERTD83E | SRGAP3 | DYNLT3 | A1120166 |
| MXRA7 | KAZALD1 | GDPD5 | FBX011 | 4933437NO3RIK |
| GABBR1 | BST1 | TSGA10 | CNRIP1 | TMEM126A |
| APOM | CCL9 | SYNC | PTGS1 | ANXA2 |
| DCN | IL2 | B3GALT5 | GCSH | NEDD9 |
| CD40 | CD14 | USH1C | 5330426P16RIK | OCIAD2 |
| KCNA4 | CDH17 | PHKA2 | NEIL3 | TMEM120B |
| GREM1 | RHOU | 1110035E04RIK | PDGFB | 4930595D18RIK |
| SPARC | GM14057.PPP1R14C | CENPP | PRC1 | D2ERTD750E |

TABLE 4-continued

Dysfunction Signature

| | | | | |
|---|---|---|---|---|
| 5100A8 | PLS3 | SULT2B1 | SLFN10 | ARF2 |
| L0073899 | MMP12 | MY016 | RFC3 | EXO1 |
| 50X9 | 4930551013R1K | A130009E19RIK | PTPLAD1 | C130068602R1K |
| MGP | FANCF | GSG2 | BUB1B | OAZ2 |
| CNNM3 | HHAT | DDX28 | STX17 | AF529169 |
| CPA3 | DNAJC25 | NCAPG2 | BUB1 | IGF2R |
| AGTRAP | D430033H22RIK | 1700106N22RIK | NFIL3 | D10627 |
| 1110032A03RIK | RALGDS | IL2RA | PIWIL2 | GRK5 |
| CD22 | PTPN3 | ZDHHC2 | CRYBG3 | TTBK2 |
| CLEC5A | GGTA1 | BB557941 | STARD3NL | PKP2 |
| RHOX5 | HBA.A1.HBA.A2 | TARSL2 | A1845619 | C76533 |
| LAMB1.1 | TNFSF9 | KIF2C | MAPK6 | ATXN1 |
| TPSAB1 | LPAR3 | ESCO2 | CHST12 | TMEM49 |
| SIGLEC5 | FOXM1 | KIF22 | CLDN12 | TUBB6 |
| DPYSL3 | SDC1 | FGFBP3 | GCNT1 | TFF1 |
| ENSMUSG00000043151 | SPIRE1 | ATP10A | TRIM45 | PTPLB |
| MCPT4 | March8 | RNF128 | GM10397 | RPA2 |
| CYR61 | KCNK10 | PLA1A | MTAP2 | GAPDH |
| ANKRA2 | B3GNT5 | BSPRY | 5LC37A2 | 6030487A22RIK |
| MMP14 | BCL6B | ADAM15 | 2310079F09RIK | EGR1 |
| 5ept4 | C76872 | NBEAL1 | A930012016RIK | GPR56 |
| PILRA | 5730453C05RIK | DNAJC12 | ALG6 | PGGT1B |
| C78115 | PPFIBP1 | WDR67 | 2210403K04RIK | RPGR |
| GM5188 | ECE1 | 5T14 | KLRA3.KLRA9 | STYK1 |
| CMA1 | ECT2 | REEP2 | A930012M21RIK | MSC |
| ARSK | CCDC58 | IL33 | ATF4 | RNASEH2C |
| NUPR1 | ORC1L | NSBP1 | ID2 | 1810011H11RIK |
| CAR6 | 2810433K01R1K | STAP1 | SLC2A8 | 4930520004R1K |
| ITGA5 | FPR2 | HIST1H2BC | CCDC112 | RBPJ |
| TWIST1 | CRABP2 | PPP1R16B | ZDHHC5 | CTSC |
| SFMBT1 | DKKL1 | FAM57A | RASL12 | SEPHS1 |
| HTR7 | SEPN1 | WIPF1 | GPR65 | ABI2 |
| 3110052M02RIK | DCXR | BIRC5 | TMED8 | ICA1 |
| CLEC7A | E130008017RIK | FAM54A | ANKLE1 | FASL |
| CNNM2 | TMPRSS2 | CMTM7 | IMPA2 | LAMC1 |
| STAB1 | EHD2 | CALCA | 5LC17A6 | DU5P14 |
| CLIP2 | IL1RN | BARD1 | FOXRED2 | ELK3 |
| PLAU | CCR5 | CENPT | SH2D2A | SERPINB6B |
| RENBP | CHST10 | NRGN | GTF2IRD1 | MY010 |
| HSPB9 | TMEM48 | TNFSF4 | HIP1R | PENK |
| BAIAP2L1 | ARL6 | LASS6 | 6330503K22RIK | PRDM1 |
| PTGS2 | KDM2B | D5WSU178E | CCL17 | MRPS36 |
| L0C100046401 | PAQR4 | 3110073H01R1K | EPDR1 | SLC39A14 |
| SPATA2L | PLEKHO2 | SCD2 | CD200R4 | PABPC1L |
| ZFP862 | TMEM149 | S100A1 | PERP | NDRG1 |
| THBS1 | FAM69B | GCNT7 | MMD | IDE |
| PDLIM7 | CYP4V3 | CCDC109B | FGL2 | TMEM158 |
| INTS9 | MED12L | NLRX1 | DLG2 | MID1IP1 |
| 5830456J23RIK | CCDC14 | SPAG9 | OPTN | CD244 |
| 0610009020RIK | ARMC7 | ZFP52 | ATP6V0E2 | HIVEP1 |
| SIRPB1 | C5AR1 | PRSS2 | APOBEC3 | CCNB1 |
| CCL6 | TCRG.V4 | 5830485P09RIK | PGLYRP1 | GALC |
| LRRC20 | 5430405H02R1 K | CYP20A1 | WDFY1 | SERPINA3G |
| LOH12CR1 | CENPH | DNAJC24 | EEA1 | CDK6 |
| BBS12 | AMIG01 | COBLL1 | TRPC1 | CHSY1 |
| PEX11B | TRIM72 | 5033418A18RIK | CDCA5 | NKG7 |
| LXN | PROS1 | TK1 | L00677224 | IL1R2 |
| F13A1 | FUCA2 | PHACTR4 | C920021A13 | 2610029101R1K |
| CAV2 | LGALS7 | GABARAPL1 | CCDC50 | ITGAV |
| ARL4D | RAI14 | HCFC2 | PIGN | RAB12 |
| CXCL11 | LPGAT1 | GM14288 | GBE1 | ALOX5 |
| TPSB2 | KLRB1A | NFAT5 | C1QL3 | ABCB9 |
| FN1 | TSPAN6 | B4GALNT2 | 0610010F05RIK | HTRA1 |
| ELAC1 | ADAMTS6 | WBP5 | GM2663 | CASP4 |
| PLXDC2 | 1700110K17RIK | ZWILCH | 1810009J06RIK | ARMC1 |
| A1450241 | OVOL2 | PAQR3 | CETN4 | STK38L |
| 4930429F24R1K | C77545 | TBC1D8B | A930026122R1K | E330009J07R1K |
| SLFN3 | D3ERTD246E | KLRA7 | AGL | EMILIN2 |
| TREM2 | SP011 | 4921509J17RIK | CD38 | TM9SF3 |
| ARG2 | CCL12 | TPK1 | FHL2 | TRIM36 |
| GM5113 | C330027C09RIK | DAPK2 | SLC25A40 | CTSD |
| 3110021A11RIK | MND1 | GPR97 | DEGS1 | D3ERTD740E |
| ODZ4 | SPDYA | GINS1 | NSUN3 | SAR1A |
| KIF20A | MY01E | LRRC39 | AI314976 | DUSP16 |
| RNF216 | 1190002F15RIK | RAB39B | GAS2L1 | CALU |
| L2HGDH | WISP1 | APBB1 | PHACTR2 | OSGIN1 |
| KDM4D | C130057M05RIK | GUF1 | GATA3 | CTLA4 |
| NBEAL2 | BATF2 | ENDOD1 | MORN3 | BHLHE40 |

TABLE 4-continued

| Dysfunction Signature | | | | |
|---|---|---|---|---|
| RAD51 | SLC5A3 | ANXA4 | CTLA2A | ASNS |
| TLR4 | SPAG5 | BCAT1 | CTLA2B | GLDC |
| 1110007C09RIK | ABHD4 | MARVELD2 | FAM5C | SUOX |
| RPS6KC1 | IER3 | CEP170 | UNC119B | KCNF1 |
| 1700019DO3RIK | ZC3H12A | RABGEF1 | SSBP3 | NRN1 |
| NDUFB4 | 2010107G23RIK | PLOD2 | HSPA2 | TNFRSF18 |
| BC046404 | AIM2 | FTSJD1 | WDR54 | LITAF |
| COMT1 | BAI2.LOC100048816 | TRIB3 | CENPA | CISD3 |
| OMD | IKZF2 | ATHL1 | CD244 | GOLGA7 |
| PPME1 | SESTD1 | ALAD | RAD54B | TBC1D7 |
| SPATA5L1 | UNC119 | PLAGL1 | 9230110C19RIK | STK39 |
| LRP1 | CARS | JMJD5 | PHLPP1 | PIK3CG |
| A230083N12RIK | GAN | TYW1 | FAM110C | 0113 |
| 3110048L19RIK | MEST | TNFSF10 | TWSG1 | IP08 |
| 6330416L07RIK | D330040H18RIK | UGP2 | CTLA2A | GLT8D3 |
| CCL7 | CEP55 | MAGOHB | EN01 | ITIH5 |
| ACAD11 | PXMP2 | TULP4 | PKD2 | HIGD1A |
| NPHP3 | NEBL | E030047P09RIK | PLEKHF1 | ITGA1 |
| NRP1 | TLR2 | AREG | H2.Q5 | AKTIP |
| LRRC4 | MUC1 | 4930518I15RIK | SH3BGRL | 2310001H17RIK |
| CD160 | PMAIP1 | PPAP2C | GAS2 | CCRL2 |
| PRRX1 | PAWR | ZCCHC3 | 0610010608RIK | 2700007P21RIK |
| B3GALTL | PTPN11 | PDCD1LG2 | MTHFD2 | LYRM1 |
| CCDC34 | PLD2 | TMEM39A | NIPA2 | D630039A03RIK |
| RAB31 | FCGR1 | MYST4 | GLIS1 | IGSF5.PCP4 |
| BIRC1F | 2610318NO2RIK | KIF24 | PLEK | ADAM8 |
| IL1RL1 | SLCO4A1 | FARS2 | ELMO2 | CSDA |
| RAB5B | 4930579G18RIK | NT5DC2 | VAMP8 | 3000002C1ORIK |
| CD200R1 | CD93 | PTPRK | PADI2 | CCDC21 |
| NPL | GFRA2 | SUDS3 | ENPP2 | NDFIP1 |
| CLEC4E | DTL | TPI1 | ANAPC4 | SDCBP2 |
| THBS1 | 11C39C | TMEM170B | BC068157 | ARHGEF9 |
| AA408396 | L0C100046560.MAGED2 | KIFC1 | ERMP1 | SAMSN1 |
| GNB5 | TMEM218 | KCTD11 | GPD2 | GZMC |
| DDEF2 | 6430537I21RIK | BCL2L15 | HIF1A | CILP2 |
| 2610024607R1K | ARG1 | RANBP9 | GNG11 | 4831426I19R1K |
| GPR84 | WNT1OB | TROVE2 | GALNT3 | TMEM184C |
| 2610027H17RIK | 9530053H05RIK | STIL | EPS8L3 | SPA17 |
| MCPT8 | D030028M11RIK | GMEB2 | TCFAP2A | AA467197 |
| GRB10 | OLFM1 | 9630060G10RIK | OBFC2A | EPAS1 |
| TMEM106A | HIGD1C.METTL7A2 | 2010111101RIK | DDX17 | 5LC22A15 |
| ZFP692 | 3100002L24RIK | PPP2R2C | XPOT | TBX21 |
| CD79A | GM14434 | ENTPD1 | RNF170 | NPHS2 |
| 4930515G01RIK | 011MU5G00000016609 | RGS8 | DCTN4 | WDR60 |
| DAB2 | CCHCR1 | CENPI | RAPH1 | NCOR2 |
| 3110082I17RIK | JAM2 | CAMK2N1 | P0MT1 | ACADSB |
| FAM129B | CDC14A.L0C100047731 | MTAP6 | CAR13 | PRF1 |
| LRFN1 | 1700029I15RIK | CCR8 | REM2 | SYNGR3 |
| RIN3 | PHF23 | BCM01 | FARP1 | 4933431E20RIK |
| DXERTD242E | TEAD1 | TACR1 | RYK | GALNTL4 |
| CCL2 | TMEM119 | 5830474E16RIK | TMBIM4 | IL15RA |
| CLEC4A2 | GPM6B | 5430439M09RIK | PPP3CB | C1QTNF6 |
| FRZB | PCYT1A | 2700008G24RIK | GABRR1 | SMPDL3B |
| DIP2A | HIST1H2AD | SLC7A3 | CRAT | GZMG |
| 2700097O09RIK | RABL5 | DAB2IP | KCTD9 | DUSP4 |
| RBP1 | ACADL | AKR1B8 | GM6194 | OSBPL3 |
| MPZL2 | ARHGAP18 | C230098O21RIK | TMEM189 | COX17 |
| 1700025K23RIK | BC010981 | NR3C1 | KLRD1 | CDKN3 |
| KIF2OB | PPP1R14A | WWC1 | CCL3 | ARPC1B |
| CLEC4D | SELM | D17ERTD165E | TBC1D2B | DSC2 |
| CCL27A.GM13306 | SLC25A13 | USP46 | FKBP7 | OSTF1 |
| PTGR1 | SH3RF1 | APLP1 | A2LD1 | ARSB |
| HMBOX1 | COL27A1 | SCCPDH | DEPDC1A | ITLN1 |
| GDA | TCTEX1D2 | RHOC | PCK2 | MRC2 |
| A1847670 | CCL4 | 5830415L20R1K | ZFP219 | ETV5 |
| PASK | 4933424G06RIK | RAB19 | BCL2A1A | SRXN1 |
| CPA2 | PHACTR3 | SLC43A3 | BCL2A1B | TMBIM1 |
| CXCL2 | ZBTB12 | AHCYL1 | BCL2A1D | GPLD1 |
| AQP11 | IGFBP7 | SGOL2 | NDC80 | 4933413G19RIK |
| APOC2 | A1836003 | COPZ2 | ZBTB32 | FOXM1 |
| PF4 | FOXD2 | ZFP760 | ERO1L | PEBP1 |
| DMXL2 | PRICKLE2 | UBE2C | RIPPLY3 | GDAP2 |
| TNFSF11 | BACE2 | DLL1 | ST6GALNAC6 | SLC25A19 |
| 8030498609RIK | ALG8 | NSMAF | HIP1 | GEM |
| A430093F15RIK | AMOTL2 | TJP1 | NFATC1 | LPXN |
| ZFP526 | SLC30A9 | KRT18 | FRMD4A | NR4A2 |
| LYZ2 | 2310039F13RIK | CTNND2 | IGF2BP2 | PPM1D |
| MSR1 | 2310031A07RIK | NPNT | MLKL | FLYWCH1 |

TABLE 4-continued

Dysfunction Signature

| | | | | |
|---|---|---|---|---|
| CXCL1 | FAM178B | L00641050 | MT2 | TOX |
| GRP | CBARA1 | UPP1 | CREB3L2 | NDFIP2 |
| 1500009L16RIK | WDSUB1 | FCER1G | KIFC3 | CASP3 |
| TPBG | TNF | PI4K2B | FAM19A3 | STARD4 |
| NEK8 | ARFGAP3 | FANCD2 | CIAPIN1 | EFHD2 |
| EPHB6 | ZEB2 | LGALS3 | MLF1 | TMEM171 |
| C4B | GH | ATG16L2 | IQGAP3 | SDF4 |
| HBB.B1.HBB.B2 | SCYL2 | 9430037013RIK | SERPINB6A | ARNT2 |
| D9ERTD26E | TRAIP | UTF1 | CENPN | TMEM159 |
| NCSTN | AA407881 | FAM64A | SLFN3.SLFN4 | POLH |
| FCGR4 | C430042M11RIK | CARHSP1 | TMCC3 | SERPINB9B |
| C3AR1 | BTBD10 | SLC35B1 | CXCR6 | SPP1 |
| MS4A7 | DPY19L4 | NUF2 | TRIP10 | EPB4.1L5 |
| ANXA1 | 2810417H13R1K | TSGA14 | L0C100048079 | ZFP511 |
| RAB27A | GM10196 | 2010002N04RIK | FZD6 | CDKN2B |
| 4930434E21RIK | GM5623 | SMPD4 | TNFSF13B | 4930448K20RIK |
| CRYZ | RPS15A | ADAM9 | LAG3 | 2900026A02R1 K |
| KNDC1 | CCR1 | LANCL3 | GSTM5 | PTTG1 |
| SLC6A9 | PLXND1 | TRAPPC1 | S100A11 | GZMD.GZME |
| ATP6V1G2 | TYMS | DCI | CDC14A | SLC16A4 |
| FHL3 | ULBP1 | NAIP2 | GPR177 | MT1 |
| ATAD5 | ZFP282 | TRAPPC4 | GSTO1 | SLC2A3 |
| 1700019E19RIK | KCNQ5 | ALDOC | IDH3A | LHFPL2 |
| FAM162A | C79607 | DENND4A | ADSSL1 | GZME |
| POPDC2 | NQ02 | CDCA3 | UBASH3B | SPIN4 |
| E130112N1ORIK | KPNA2 | MMD | SUV39H2 | RASD2 |
| GARNL1 | TCRG | LAT2 | SNAP47 | BNIP3 |
| CENPF | C530028O21RIK | UGT1A1 | CDCA2 | SERPINE2 |
| LPCAT4 | DSCAM | UGT1A10 | CCDC122 | GZMF |
| AA407331 | KDM2B | UGT1A2 | TNFRSF4 | GZMD |
| E2E3 | PRR15 | UGT1A5 | BCO23744 | HAVCR2 |
| RAB11FIP5 | BRCA2 | UGT1A6A | PPP1R3B | HTATIP2 |
| FOXF1A | C80258 | UGT1A6B | 6230409E13RIK | LIE |
| FAM20C | E2E7 | UGT1A7C | EXPH5 | SYTL3 |
| LYZ1 | TMEM29 | UGT1A9 | TTK | CNTLN |
| CX3CR1 | MPI | CD81 | TG | APOLD1 |
| SLC16A13 | BMPR2 | 4930422G04RIK | KLRE1 | TNFRSF9 |
| FCGR3 | | | | |

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of treating melanoma by reducing T cell dysfunction in a subject in need thereof comprising:
 administering to the subject one or more doses of metyrapone capable of reducing glucocorticoid signaling in the tumor microenvironment,
 wherein a dysfunctional immune state in the subject is decreased when glucocorticoid signaling is reduced,
 whereby a tumor specific immune response is enhanced.

2. The method of claim 1, wherein the one or more doses of metyrapone are administered intra-tumorally.

3. The method of claim 1, wherein the one or more doses of metyrapone are administered orally.

4. The method of claim 1, wherein the dysfunctional immune state is characterized by reduced secretion of IFN-gamma, TNF-alpha, IL-2, or combination thereof; or increased secretion of IL-10.

5. A method of treating colon cancer by reducing T cell dysfunction in a subject in need thereof comprising:
 administering to the subject one or more doses of metyrapone capable of reducing glucocorticoid signaling in the tumor microenvironment,
 wherein a dysfunctional immune state in the subject is decreased when glucocorticoid signaling is reduced,
 whereby a tumor specific immune response is enhanced.

6. The method of claim 5, wherein the one or more doses of metyrapone are administered intra-tumorally.

7. The method of claim 5, wherein the one or more doses of metyrapone are administered orally.

8. The method of claim 5, wherein the dysfunctional immune state is characterized by reduced secretion of IFN-gamma, TNF-alpha, IL-2, or combination thereof; or increased secretion of IL-10.

9. A method of treating stomach cancer by reducing T cell dysfunction in a subject in need thereof comprising:
 administering to the subject one or more doses of metyrapone capable of reducing glucocorticoid signaling in the tumor microenvironment,
 wherein a dysfunctional immune state in the subject is decreased when glucocorticoid signaling is reduced,
 whereby a tumor specific immune response is enhanced.

10. The method of claim 9, wherein the one or more doses of metyrapone are administered intra-tumorally.

11. The method of claim 9, wherein the one or more doses of metyrapone are administered orally.

12. The method of claim 9, wherein the dysfunctional immune state is characterized by reduced secretion of IFN-gamma, TNF-alpha, IL-2, or combination thereof; or increased secretion of IL-10.

* * * * *

```
                         SEQUENCE LISTING

<160> NUMBER OF SEQ ID NOS: 5

<210> SEQ ID NO 1
<211> LENGTH: 288
<212> TYPE: PRT
<213> ORGANISM: Artificial Sequence
<220> FEATURE:
<223> OTHER INFORMATION: Synthetic Peptide

<400> SEQUENCE: 1

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
```

```
                  50                  55                  60

Ser Ala Asp Ser Phe Ser Asp Leu Leu Arg Gln Phe Asp Pro Ser Leu
 65                  70                  75                  80

Phe Asn Thr Ser Leu Phe Asp Ser Leu Pro Pro Phe Gly Ala His His
                 85                  90                  95

Thr Glu Ala Ala Thr Gly Glu Trp Asp Glu Val Gln Ser Gly Leu Arg
                100                 105                 110

Ala Ala Asp Ala Pro Pro Thr Met Arg Val Ala Val Thr Ala Ala
            115                 120                 125

Arg Pro Pro Arg Ala Lys Pro Ala Pro Arg Arg Ala Ala Gln Pro
            130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
                180                 185                 190

Ile Val Ala Leu Ser Gln His Pro Ala Ala Leu Gly Thr Val Ala Val
                195                 200                 205

Lys Tyr Gln Asp Met Ile Ala Ala Leu Pro Glu Ala Thr His Glu Ala
            210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
                260                 265                 270

Glu Ala Val His Ala Trp Arg Asn Ala Leu Thr Gly Ala Pro Leu Asn
                275                 280                 285

<210> SEQ ID NO 2
<211> LENGTH: 183
<212> TYPE: PRT
<213> ORGANISM: Artificial Sequence
<220> FEATURE:
<223> OTHER INFORMATION: Synthetic Peptide

<400> SEQUENCE: 2

Arg Pro Ala Leu Glu Ser Ile Val Ala Gln Leu Ser Arg Pro Asp Pro
  1               5                  10                  15

Ala Leu Ala Ala Leu Thr Asn Asp His Leu Val Ala Leu Ala Cys Leu
                 20                  25                  30

Gly Gly Arg Pro Ala Leu Asp Ala Val Lys Lys Gly Leu Pro His Ala
             35                  40                  45

Pro Ala Leu Ile Lys Arg Thr Asn Arg Arg Ile Pro Glu Arg Thr Ser
     50                  55                  60

His Arg Val Ala Asp His Ala Gln Val Val Arg Val Leu Gly Phe Phe
 65                  70                  75                  80

Gln Cys His Ser His Pro Ala Gln Ala Phe Asp Asp Ala Met Thr Gln
                 85                  90                  95

Phe Gly Met Ser Arg His Gly Leu Leu Gln Leu Phe Arg Arg Val Gly
                100                 105                 110

Val Thr Glu Leu Glu Ala Arg Ser Gly Thr Leu Pro Pro Ala Ser Gln
            115                 120                 125

Arg Trp Asp Arg Ile Leu Gln Ala Ser Gly Met Lys Arg Ala Lys Pro
```

```
                130                 135                 140
Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 3
<211> LENGTH: 106
<212> TYPE: PRT
<213> ORGANISM: Homo sapiens

<400> SEQUENCE: 3

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg
            100                 105

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

Ile Glu Val Met Tyr Pro Pro Pro
1               5

<210> SEQ ID NO 5
<211> LENGTH: 107
<212> TYPE: PRT
<213> ORGANISM: Homo sapiens

<400> SEQUENCE: 5

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95
```

```
Ala Pro Pro Arg Asp Phe Ala Ala Tyr Arg Ser
        100                 105
```